(12) United States Patent
Beigelman et al.

(10) Patent No.: US 10,745,427 B2
(45) Date of Patent: Aug. 18, 2020

(54) ACYCLIC ANTIVIRALS

(71) Applicant: Janssen BioPharma, Inc., South San Francisco, CA (US)

(72) Inventors: Leonid Beigelman, San Mateo, CA (US); Guangyi Wang, Foster City, CA (US); Minghong Zhong, San Bruno, CA (US)

(73) Assignee: Janssen BioPharma, Inc., South San Francisco, CA (US)

( * ) Notice: Subject to any disclaimer, the term of this patent is extended or adjusted under 35 U.S.C. 154(b) by 0 days.

(21) Appl. No.: 16/090,715

(22) PCT Filed: Mar. 9, 2017

(86) PCT No.: PCT/US2017/021559
§ 371 (c)(1),
(2) Date: Oct. 2, 2018

(87) PCT Pub. No.: WO2017/156262
PCT Pub. Date: Sep. 14, 2017

(65) Prior Publication Data
US 2019/0055273 A1    Feb. 21, 2019

Related U.S. Application Data

(60) Provisional application No. 62/305,723, filed on Mar. 9, 2016.

(51) Int. Cl.
*A61K 31/683*     (2006.01)
*A61K 31/675*     (2006.01)
(Continued)

(52) U.S. Cl.
CPC .......... *C07F 9/6561* (2013.01); *A61F 13/512* (2013.01); *A61F 13/513* (2013.01);
(Continued)

(58) Field of Classification Search
CPC ... A61K 31/683; A61K 31/675; C07F 9/6561; C07D 487/04; A61P 31/18; A61P 31/20
(Continued)

(56) References Cited

U.S. PATENT DOCUMENTS

| 7,368,437 B1 | 5/2008 | Bojack et al. |
| 2010/0015094 A1 | 1/2010 | Babu et al. |

FOREIGN PATENT DOCUMENTS

| CA | 2367921 A1 * | 9/2000 | ............ A01N 43/90 |
| WO | WO-2004072078 A1 * | 8/2004 | ............ C07D 487/04 |
| WO | 2011035231 A1 | 3/2011 | |

OTHER PUBLICATIONS

Sekiya et al., "2-Amino-6-arylthio-9[2-(phosphonomethoxy)ethyl]purine Bis(2,2,2-trifluoroethyl) esters as novel HBV-specific antiviral reagents", J. Med. Chem. (2002), 45 (14), pp. 3138-3142. (Year: 2002).*

(Continued)

*Primary Examiner* — Amanda L. Aguirre
*Assistant Examiner* — Sagar Patel
(74) *Attorney, Agent, or Firm* — Knobbes Martens Olson & Bear LLP

(57) ABSTRACT

Disclosed herein are nucleotide analogs, methods of synthesizing nucleotide analogs and methods of treating diseases and/or conditions such as a HBV and/or HDV and/or HIV infection with one or more nucleotide analogs.

(Continued)

US 10,745,427 B2
Page 2

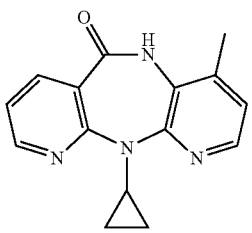

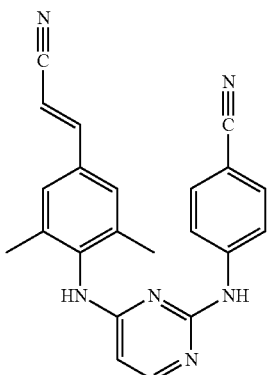

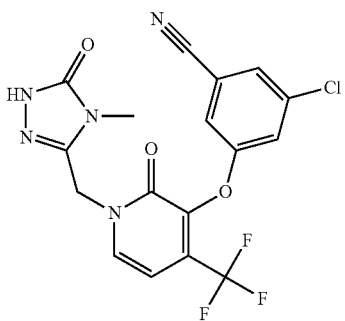

19 Claims, 62 Drawing Sheets

(51) Int. Cl.
| | |
|---|---|
| *C07F 9/6561* | (2006.01) |
| *C07D 487/04* | (2006.01) |
| *A61P 31/18* | (2006.01) |
| *A61P 31/20* | (2006.01) |
| *A61F 13/511* | (2006.01) |
| *A61F 13/513* | (2006.01) |
| *A61F 13/512* | (2006.01) |
| *A61F 13/514* | (2006.01) |
| *A61F 13/51* | (2006.01) |

(52) U.S. Cl.
CPC .. *A61F 13/51113* (2013.01); *A61F 13/51405* (2013.01); *A61P 31/18* (2018.01); *A61P 31/20* (2018.01); *A61F 2013/51026* (2013.01)

(58) Field of Classification Search
USPC .......... 514/141, 81; 562/23, 8; 544/184, 214
See application file for complete search history.

(56) References Cited

OTHER PUBLICATIONS

English translation of the claims of the WIPO Publication WO-2004072078-A1. (Year: 2020).*
English translation of the description of the WIPO Publication WO-2004072078-A1. (Year: 2020).*
Sekiya, et al., 2-Amino-6-arylthio-9-[2-(phosphonomethoxy)ethyl]purine Bis(2,2,2-trifluoroethyl)Esters as Novel HBV-Specific Antiviral Reagents, J.Med.Chem, Jan. 23, 2002, pp. 3138-3142, vol. 45 Issue 14.
International Search Report dated Jun. 2, 2017 for corresponding International Patent Application No. PCT/US2017/021559.
Supplementary European Search Report dated Sep. 5, 2019 for EP Application No. 17764089.3, filed Mar. 9, 2017.
International Preliminary Report on Patentability dated Sep. 11, 2018 for PCT Application No. PCT/US2017/021559 filed Mar. 9, 2017.
Examination Report dated Jun. 22, 2020 for AU Application No. 2017231824, filed Mar. 9, 2017.

* cited by examiner

Fig. 1 HIV Non-Nucleoside Reverse Transcriptase Inhibitors (NNRTIs)

| # | Name | IUPAC Name | Structure |
|---|---|---|---|
| 1001 | delavirdine (DLV) | N-[2-({4-[3-(propan-2-ylamino)pyridin-2-yl]piperazin-1-yl}carbonyl)-1H-indol-5-yl]methanesulfonamide | 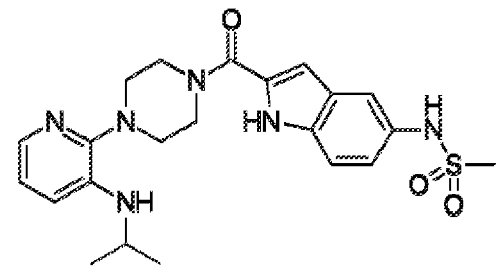 |
| 1002 | efavirenz (EFV) | (4S)-6-chloro-4-(2-cyclopropylethynyl)-4-(trifluoromethyl)-2,4-dihydro-1H-3,1-benzoxazin-2-one | 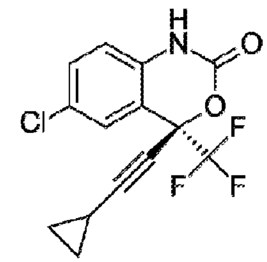 |
| 1003 | etravirine (ETR) | 4-[6-Amino-5-bromo-2-[(4-cyanophenyl)amino] pyrimidin-4-yl]oxy-3,5-dimethylbenzonitrile | 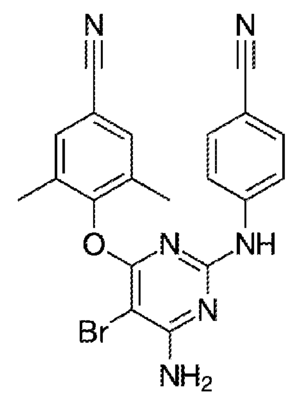 |

Fig. 1 (cont.) HIV Non-Nucleoside Reverse Transcriptase Inhibitors (NNRTIs)

| # | Name | IUPAC Name | Structure |
|---|---|---|---|
| 1004 | nevirapine (NVP) | 11-cyclopropyl-4-methyl-5,11-dihydro-6H-dipyrido[3,2-b:2',3'-e][1,4]diazepin-6-one | 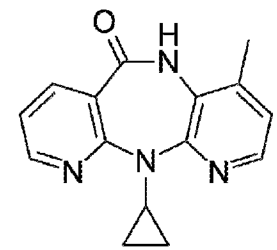 |
| 1005 | rilpivirine (TMC278) | 4-{[4-({4-[(E)-2-cyanovinyl]-2,6-dimethylphenyl}amino)pyrimidin-2-yl]amino}benzonitrile | 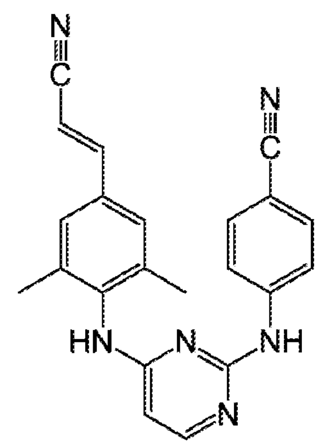 |

Fig. 1 (cont.) HIV Non-Nucleoside Reverse Transcriptase Inhibitors (NNRTIs)

| # | Name | IUPAC Name | Structure |
|---|---|---|---|
| 1006 | Doravirine (MK-1439) | 3-Chloro-5-({1-[(4-methyl-5-oxo-4,5-dihydro-1H-1,2,4-triazol-3-yl)methyl]-2-oxo-4-(trifluoromethyl)-1,2-dihydro-3-pyridinyl}oxy)benzonitrile | 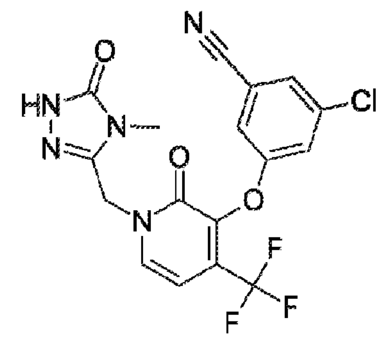 |

Fig. 2 HIV Nucleoside Reverse Transcriptase Inhibitors (NRTIs)

| # | Name | IUPAC Name | Structure |
|---|------|------------|-----------|
| 2001 | abacavir (ABC) | {(1S,4R)-4-[2-amino-6-(cyclopropylamino)-9H-purin-9-yl]cyclopent-2-en-1-yl}methanol | 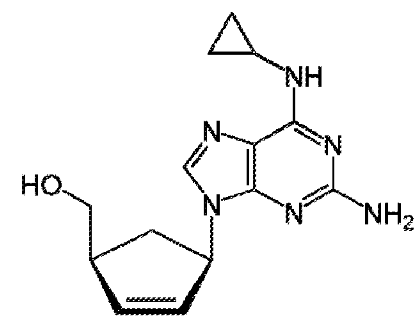 |
| 2002 | adefovir (bis-POM PMEA) | {[2-(6-amino-9H-purin-9-yl)ethoxy]methyl}phosphonic acid | 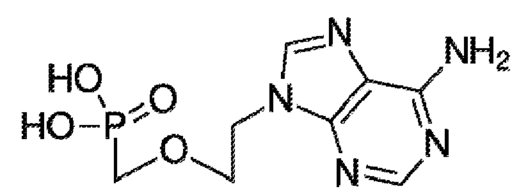 |
| 2003 | amdoxovir | [(2R,4R)-4-(2,6-diaminopurin-9-yl)-1,3-dioxolan-2-yl]methanol | 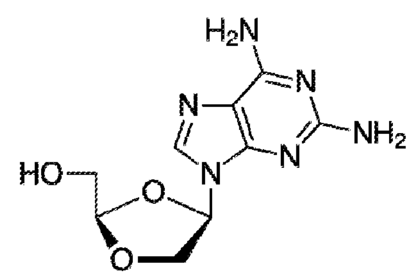 |

Fig. 2 (cont.) HIV Nucleoside Reverse Transcriptase Inhibitors (NRTIs)

| # | Name | IUPAC Name | Structure |
|---|---|---|---|
| 2004 | apricitabine (AVX754) | 4-amino-1-[(2R,4R)-2-(hydroxymethyl)-1,3-oxathiolan-4-yl]pyrimidin-2(1H)-one | 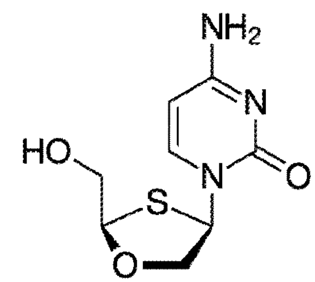 |
| 2005 | censavudine | 1-[(2R,5R)-5-ethynyl-5-(hydroxymethyl)-2H-furan-2-yl]-5-methylpyrimidine-2,4-dione | 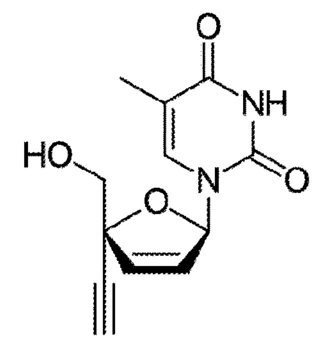 |
| 2006 | didanosine (DDI) | 9-((2R,5S)-5-(hydroxymethyl)tetrahydrofuran-2-yl)-3H-purin-6(9H)-one | 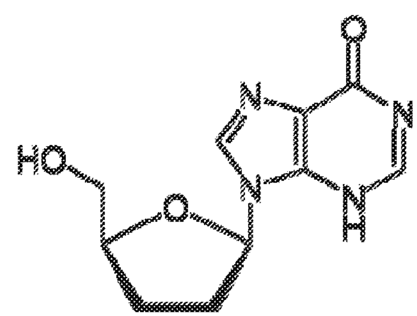 |

Fig. 2 (cont.) HIV Nucleoside Reverse Transcriptase Inhibitors (NRTIs)
| # | Name | IUPAC Name | Structure |
|---|---|---|---|
| 2007 | elvucitabine | 4-amino-5-fluoro-1-[(2S,5R)-5-(hydroxymethyl)-2,5-dihydrofuran-2-yl]pyrimidin-2-one | 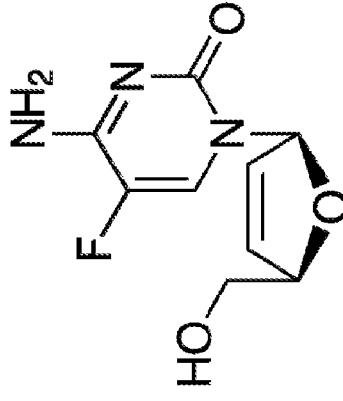 |
| 2008 | emtricitabine (FTC) | 4-amino-5-fluoro-1-[(2R,5S)-2-(hydroxymethyl)-1,3-oxathiolan-5-yl]-1,2-dihydropyrimidin-2-one | 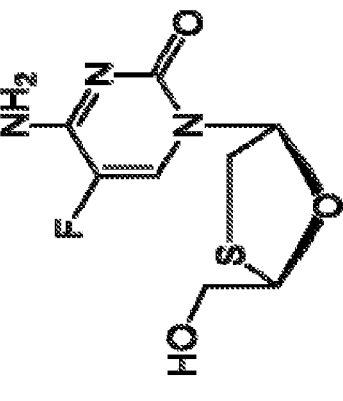 |

Fig. 2 (cont.) HIV Nucleoside Reverse Transcriptase Inhibitors (NRTIs)

| # | Name | IUPAC Name | Structure |
|---|---|---|---|
| 2009 | entecavir (ETV) | 2-Amino-9-[(1$S$,3$R$,4$S$)-4-hydroxy-3-(hydroxymethyl)-2-methylidenecyclopentyl]-6,9-dihydro-3$H$-purin-6-one | 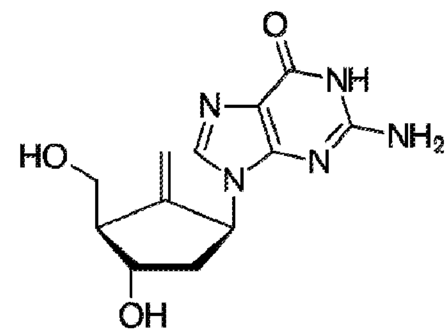 |
| 2010 | lamivudine (3TC) | 4-amino-1-[(2$R$,5$S$)-2-(hydroxymethyl)-1,3-oxathiolan-5-yl]-1,2-dihydropyrimidin-2-one | 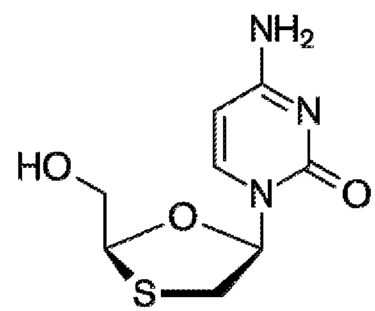 |

Fig. 2 (cont.) HIV Nucleoside Reverse Transcriptase Inhibitors (NRTIs)

| # | Name | IUPAC Name | Structure |
|---|---|---|---|
| 2011 | racivir | 4-amino-5-fluoro-1-[(2S,5R)-2-(hydroxymethyl)-1,3-oxathiolan-5-yl]-1,2-dihydropyrimidin-2-one | 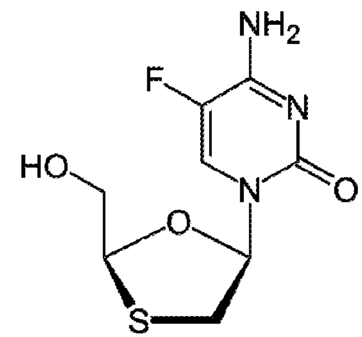 |
| 2012 | stampidine | methyl N-((4-bromophenoxy){[(2S,5R)-5-(5-methyl-2,4-dioxo-3,4-dihydropyrimidin-1(2H)-yl)-2,5-dihydrofuran-2-yl]methoxy}phosphoryl)-D-alaninate | 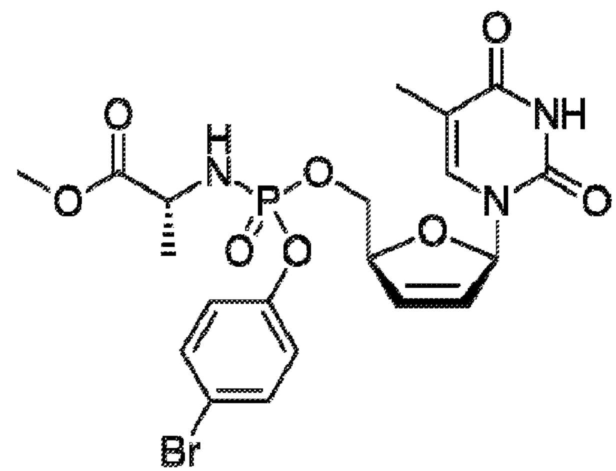 |

Fig. 2 (cont.) HIV Nucleoside Reverse Transcriptase Inhibitors (NRTIs)
| # | Name | IUPAC Name | Structure |
|---|---|---|---|
| 2013 | stavudine (d4T) | 1-[(2R,5S)-5-(hydroxymethyl)-2,5-dihydrofuran-2-yl]-5-methyl-1,2,3,4-tetrahydropyrimidine-2,4-dione | 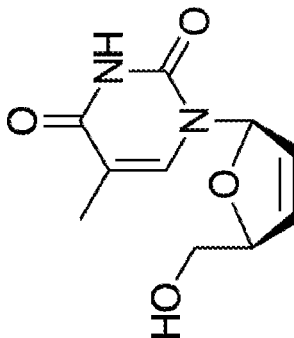 |
| 2014 | tenofovir disoproxil (TDF) | Bis{[(isopropoxycarbonyl)oxy]methyl} ({[(2R)-1-(6-amino-9H-purin-9-yl)-2-propanyl]oxy}methyl)phosphonate | 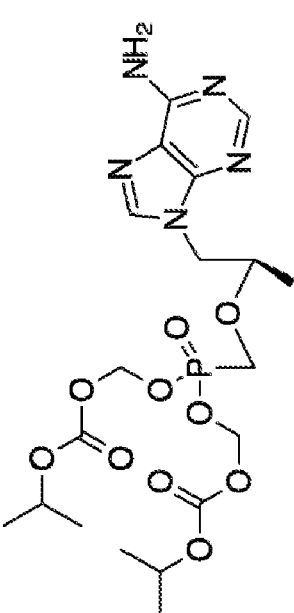 |

Fig. 2 (cont.) HIV Nucleoside Reverse Transcriptase Inhibitors (NRTIs)

| # | Name | IUPAC Name | Structure |
|---|---|---|---|
| 2015 | tenofovir alafenamide (GS-7340) | Isopropyl (2S)-2-[[[(1R)-2-(6-aminopurin-9-yl)-1-methyl-ethoxy]methyl-phenoxy-phosphoryl]amino]propanoate | 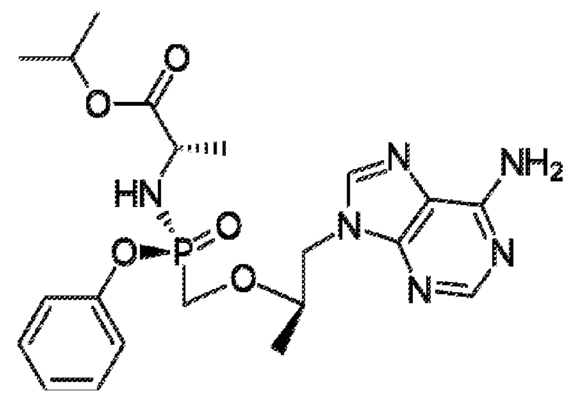 |
| 2016 | zalcitabine (ddC) | 4-amino-1-((2R,5S)-5-(hydroxymethyl)tetrahydrofuran-2-yl)pyrimidin-2(1H)-one | 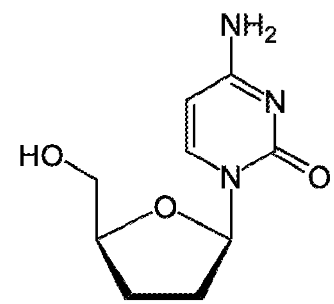 |

Fig. 2 (cont.) HIV Nucleoside Reverse Transcriptase Inhibitors (NRTIs)

| # | Name | IUPAC Name | Structure |
|---|---|---|---|
| 2017 | zidovudine (ZDV); azidothymidine (AZT) | 1-[(2R,4S,5S)-4-Azido-5-(hydroxymethyl)oxolan-2-yl]-5-methylpyrimidine-2,4-dione | 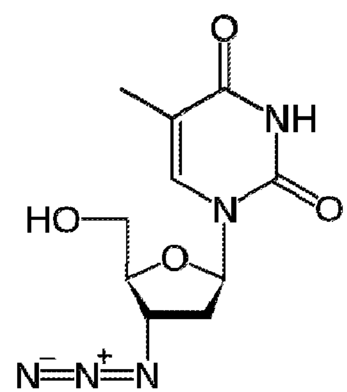 |

Fig. 3A HIV Protease Inhibitors

| # | Name | IUPAC Name | Structure |
|---|------|------------|-----------|
| 3001 | amprenavir (APV) | (3S)-oxolan-3-yl N-[(2S,3R)-3-hydroxy-4-[N-(2-methylpropyl)(4-aminobenzene)sulfonamido]-1-phenylbutan-2-yl]carbamate | 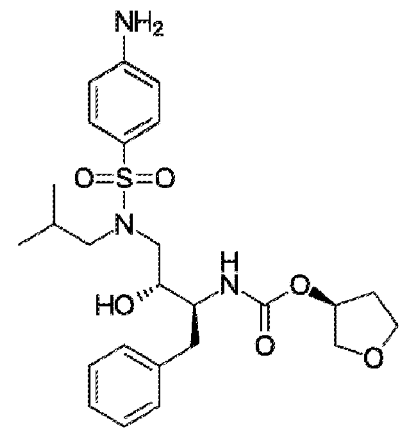 |
| 3002 | atazanavir (ATV) | methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl]carbamate | 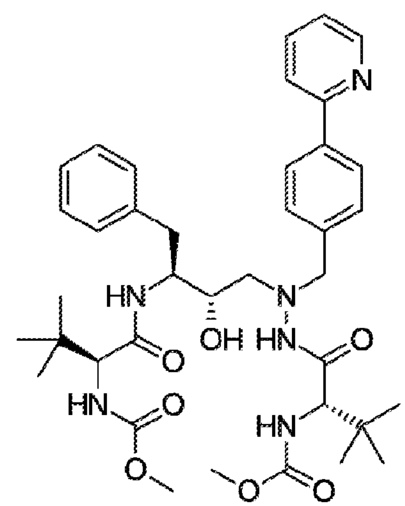 |

Fig. 3A (cont.) HIV Protease Inhibitors
| # | Name | IUPAC Name | Structure |
|---|------|------------|-----------|
| 3003 | darunavir (DRV) | [(1R,5S,6R)-2,8-dioxabicyclo[3.3.0]oct-6-yl] N-[(2S,3R)-4-[(4-aminophenyl)sulfonyl-(2-methylpropyl)amino]-3-hydroxy-1-phenyl-butan-2-yl] carbamate | 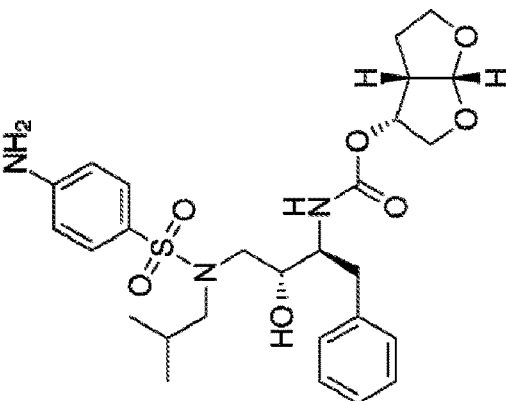 |
| 3004 | fosamprenavir (FPV) | {[[(2R,3S)-1-[N-(2-methylpropyl)(4-aminobenzene)sulfonamido]-3-({[(3S)-oxolan-3-yloxy]carbonyl}amino)-4-phenylbutan-2-yl]oxy}phosphonic acid | 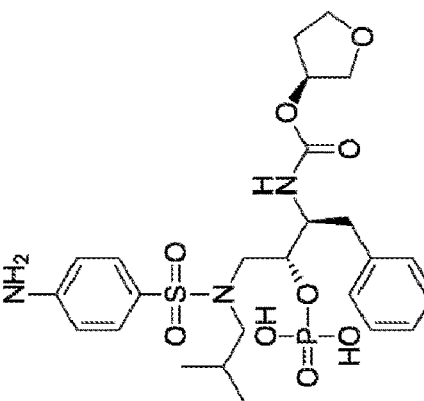 |

Fig. 3A (cont.) HIV Protease Inhibitors
| # | Name | IUPAC Name | Structure |
|---|------|------------|-----------|
| 3005 | indinavir (IDV) | (2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-ylmethyl)piperazine-2-carboxamide | 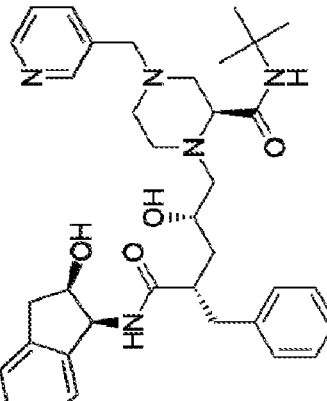 |
| 3006 | lopinavir (LPV) | (2S)-N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide | 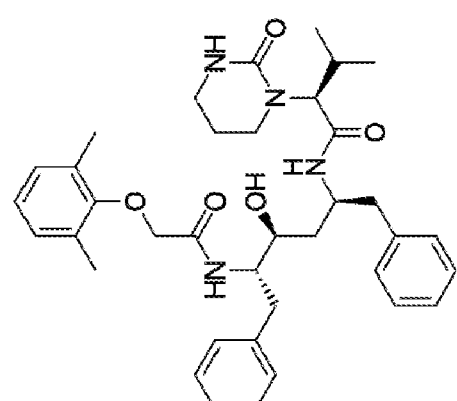 |

Fig. 3A (cont.) HIV Protease Inhibitors
| # | Name | IUPAC Name | Structure |
|---|------|------------|-----------|
| 3007 | nelfinavir (NFV) | (3S,4aS,8aS)-N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide | 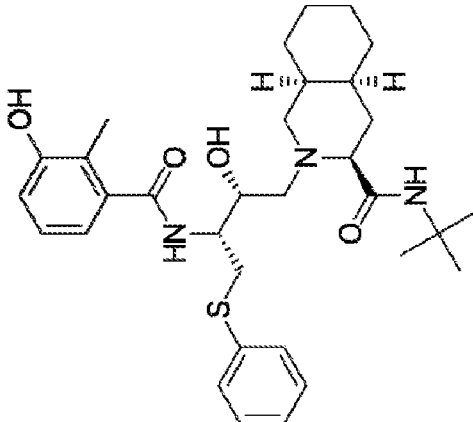 |
| 3008 | ritonavir (RTV) | 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate | 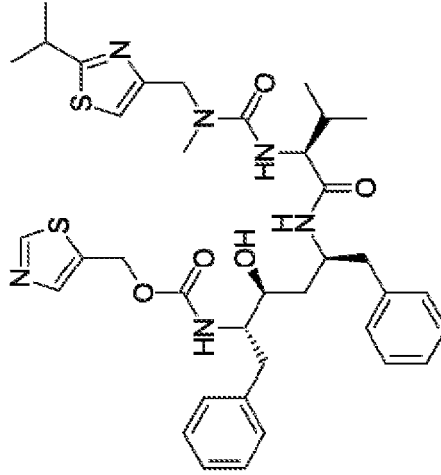 |

Fig. 3A (cont.) HIV Protease Inhibitors
| # | Name | IUPAC Name | Structure |
|---|---|---|---|
| 3009 | saquinavir (SQV) | (2S)-N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide | 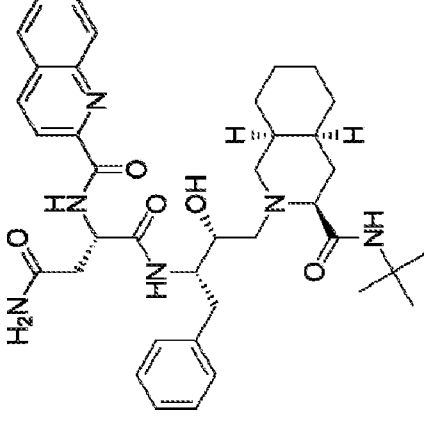 |
| 3010 | tipranavir (TPV) | N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide | 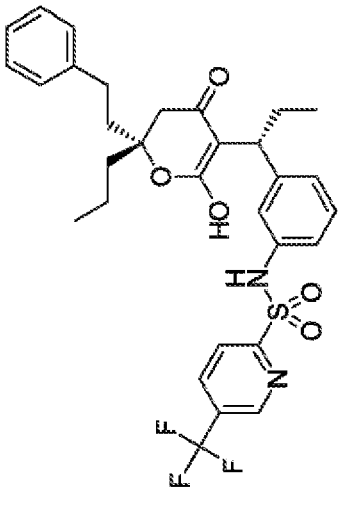 |

Fig. 3B HCV Protease Inhibitors

| # | Name | IUPAC Name | Structure |
|---|---|---|---|
| 3011 | boceprevir (Victrelis®) | (1R,5S)-N-[3-Amino-1-(cyclobutylmethyl)-2,3-dioxopropyl]-3-[2(S)-[[[(1,1-dimethylethyl)amino]carbonyl]amino]-3,3-dimethyl-1-oxobutyl]-6,6-dimethyl-3-azabicyclo[3.1.0]hexane-2(S)-carboxamide | 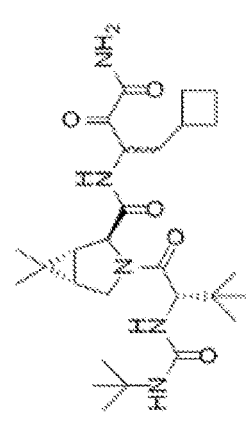 |
| 3012 | grazoprevir | (1R,18R,20R,24S,27S)-N-{(1R,2S)-1-[(cyclopropylsulfonyl)carbamoyl]-2-vinylcyclopropyl}-7-methoxy-24-(2-methyl-2-propanyl)-22,25-dioxo-2,21-dioxa-4,11,23,26-tetraazapentacyclo[24.2.1.03,12.05,10.0 18,20]nonacosa-3,5,7,9,11-pentaene-27-carboxamide | 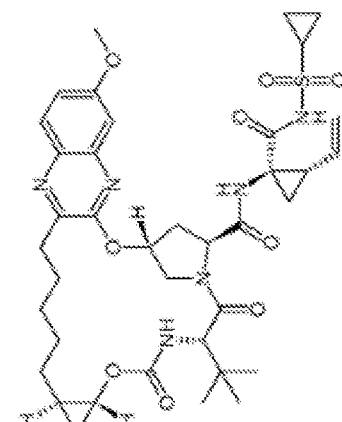 |
| 3013 | simeprevir (Olysio®) | (1R,4R,6S,7Z,15R,17R)-N-(cyclopropanesulfonyl)-2-hydroxy-17-({7-methoxy-8-methyl-2-[4-(propan-2-yl)-1,3-thiazol-2-yl]quinolin-4-yl}oxy)-13-methyl-14-oxo-3,13-diazatricyclo[13.3.0.0]octadeca-2,7-diene-4-carboximidic acid | 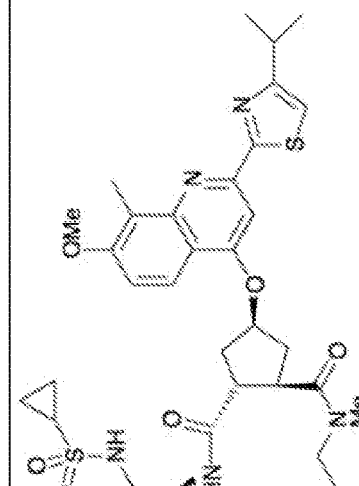 |

Fig. 3B (cont.) HIV Protease Inhibitors

| # | Name | IUPAC Name | Structure |
|---|---|---|---|
| 3014 | telaprevir (Incivek®) | (1S,3AR,6as)-(2S)-2-cyclohexyl-N-(pyrazinylcarbonyl)glycyl-3-methyl-L-valyl-N-((1S)-1-((cyclopropylamino)oxoacetyl)butyl)octahydrocyclopenta(c)pyrrole-1-carboxamide | 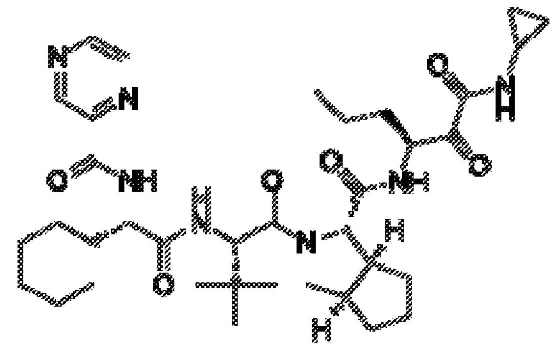 |
| 3015 | danoprevir | (2R,6S,12Z,13aS,14aR,16aS)-14a-[(Cyclopropylsulfonyl)carbamoyl]-6-({[(2-methyl-2-propanyl)oxy]carbonyl}amino)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-2-yl 4-fluoro-1,3-dihydro-2H-isoindole-2-carboxylate | 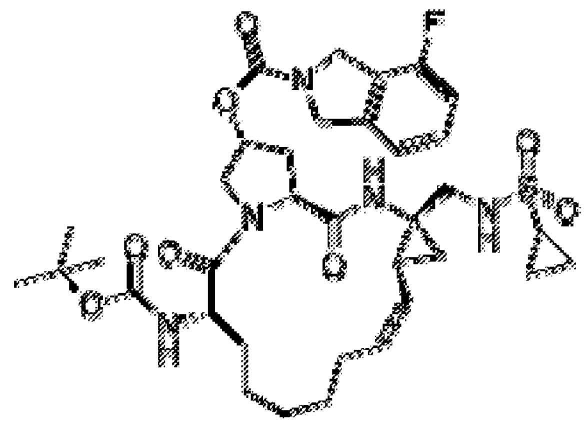 |

Fig. 3B (cont.) HIV Protease Inhibitors

| # | Name | IUPAC Name | Structure |
|---|---|---|---|
| 3016 | paritaprevir | (2R,6S,12Z,13aS,14aR,16aS)-N-(Cyclopropylsulfonyl)-6-{[(5-methyl-2-pyrazinyl)carbonyl]amino}-5,16-dioxo-2-(6-phenanthridinyloxy)-1,2,3,6,7,8,9,10,11,13a,14,15,16,16a-tetradecahydrocyclopropa[e]pyrrolo[1,2-a][1,4]diazacyclopentadecine-14a(5H)-carboxamide | 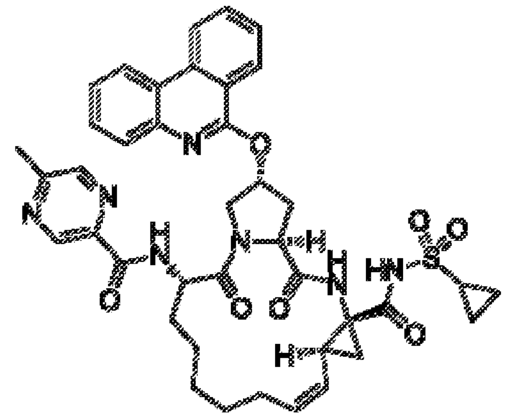 |
| 3017 | ciluprevir | (1S,4R,6S,7Z,14S,18R)-14-{[(cyclopentyloxy)carbonyl]amino}-18-[(7-methoxy-2-{2-[(propan-2-yl)amino]-1,3-thiazol-4-yl}quinolin-4-yl)oxy]-2,15-dioxo-3,16-diazatricyclo[14.3.0.0{4,6}]nonadec-7-ene-4-carboxylic acid | 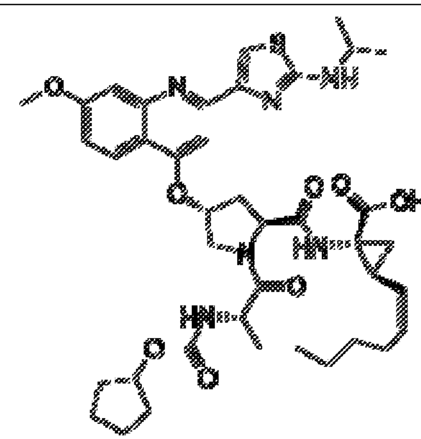 |

Fig. 3B (cont.) HIV Protease Inhibitors

| # | Name | IUPAC Name | Structure |
|---|---|---|---|
| 3018 | faldaprevir | N-[(Cyclopentyloxy)carbonyl]-3-methyl-L-valyl-(4R)-4-({8-bromo-2-[2-(isobutyrylamino)-1,3-thiazol-4-yl]-7-methoxy-4-quinolinyl}oxy)-N-[(1R,2S)-1-carboxy-2-vinylcyclopropyl]-L-prolinamide | 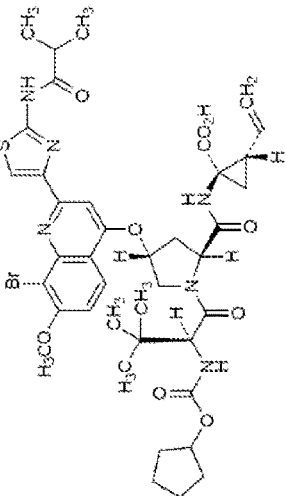 |
| 3019 | GS-9256 | N-[(2R,6S,13aR,14aS,16aS)-2-[[8-chloro-7-methoxy-2-[2-[(1-methylethyl)amino]-4-thiazolyl]-4-quinolinyl]oxy]-14a-[[(2,6-difluorophenyl)methyl]hydroxyphosphinyl]octadecahydro-5,16-dioxocyclopropa[e]pyrrolo[1,2-a][1,4]diazacyclopentadecin-6-yl]-, cyclopentyl carbamic acid ester | 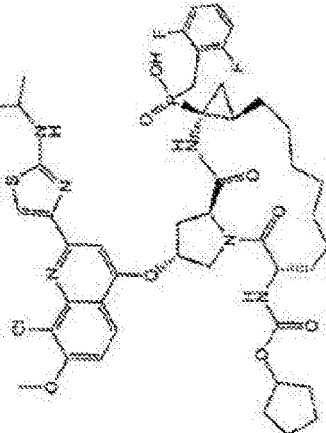 |
| 3020 | vedroprevir | N-{[(1R,3r,5S)-Bicyclo[3.1.0]hex-3-yloxy]carbonyl}-3-methyl-L-valyl-(4R)-N-[(1R,2R)-1-carboxy-2-ethylcyclopropyl]-4-({8-chloro-2-[2-(isopropylamino)-1,3-thiazol-4-yl]-7-[2-(4-morpholinyl)ethoxy]-4-quinolinyl}oxy)-L-prolinamide | 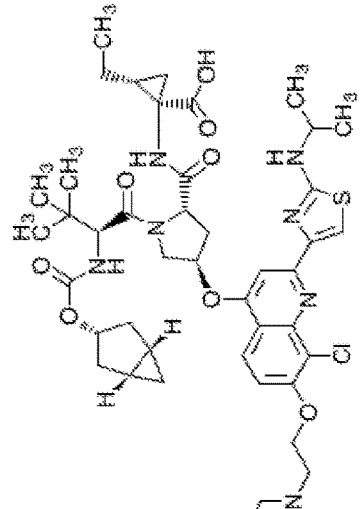 |

Fig. 3B (cont.) HCV Protease Inhibitors

| # | Name | IUPAC Name | Structure |
|---|---|---|---|
| 3021 | IDX-320 | (2S,14aR,16aS,E)-2-((7-methoxy-8-methyl-2-(4-(trifluoromethyl)thiazol-2-yl)quinolin-4-yl)oxy)-7-methyl-N-(((1-methylcyclopropyl)sulfonyl)-6,16-dioxo-1,3,4,6,7,8,9,10,11,13a,14,15,16,16a-tetradecahydrocyclopropa[g]pyrido[1,2-c][1,3,6]triazacyclotetradecine-14a(2H)-carboxamide | 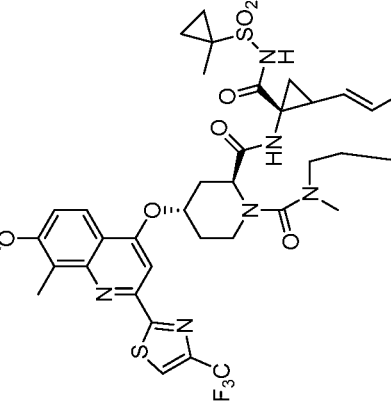 |
| 3022 | sovaprevir | (4R)-N-{(1R,2S)-1-[(Cyclopropylsulfonyl)carbamoyl]-2-vinylcyclopropyl}-1-{(2S)-3,3-dimethyl-2-[2-oxo-2-(1-piperidinyl)ethyl]butanoyl}-4-[(7-methoxy-2-phenyl-4-chinolinyl)oxy]-L-prolinamide | 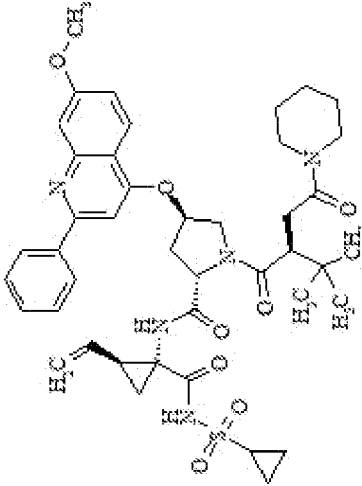 |

Fig. 3B (cont.) HIV Protease Inhibitors

| # | Name | IUPAC Name | Structure |
|---|------|------------|-----------|
| 3023 | neceprevir | (2R,6R,12Z,13aS,14aR,16aS)-N-(cyclopropylsulfonyl)-6-(2-(3,3-difluoropiperidin-1-yl)-2-oxoethyl)-2-({7-methoxy-8-methyl-2-(4-(1-methylethyl)thiazol-2-yl)quinolin-4-yl}oxy)-5,16-dioxo-1,2,3,6,7,8,9,10,11,13a,14,15,16,16a-tetradecahydrocyclo propa(e)pyrrolo(1,2-a)(1,4) diazacyclopentadecine-14a(5H)-carboxamide | 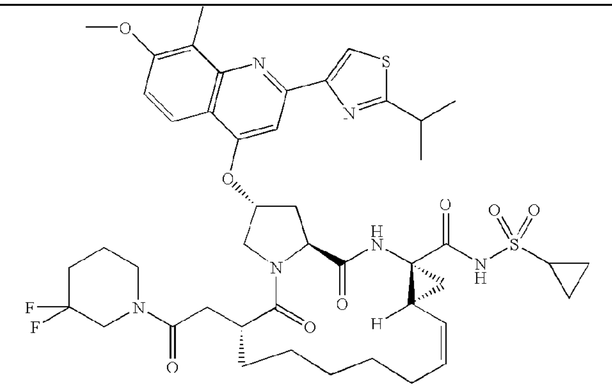 |

Fig. 4A HIV Fusion/Entry Inhibitors

| # | Name | IUPAC Name | Structure |
|---|---|---|---|
| 4001 | enfuvirtide (ENF; T20) | Ac-Tyr-Thr-Ser-Leu-Ile-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Ala-Ser-Leu-Trp-Asn-Trp-Phe-NH$_2$ | 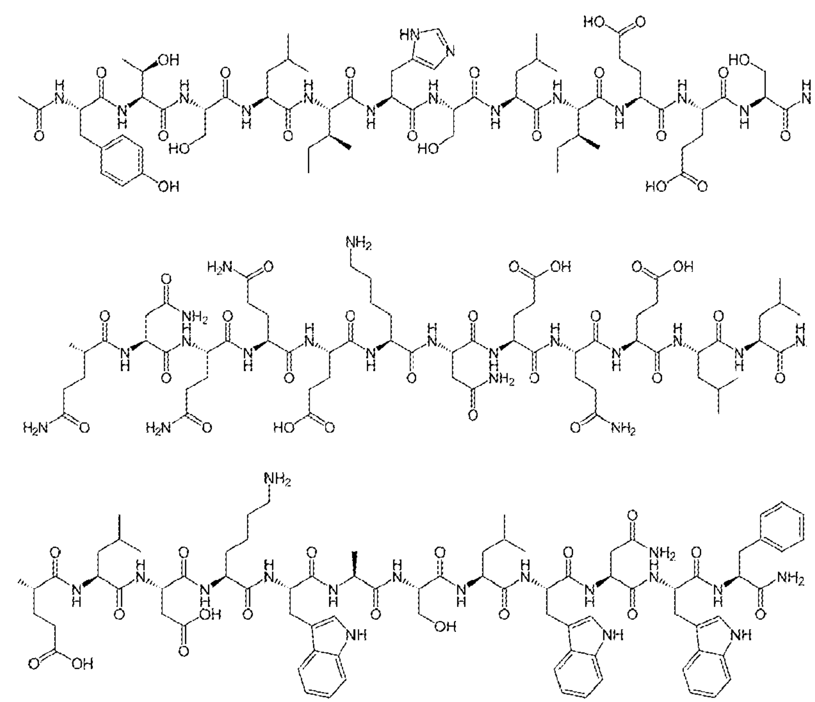 |

Fig. 4A (cont.) HIV Fusion/Entry Inhibitors
| # | Name | IUPAC Name | Structure |
|---|---|---|---|
| 4002 | maraviroc (MVC) | 4,4-difluoro-*N*-{(1*S*)-3-[3-(3-isopropyl- 5-methyl-4*H*-1,2,4-triazol-4-yl)-8-azabicyclo[3.2.1]oct-8-yl]-1-phenylpropyl}cyclohexanecarboxamide | 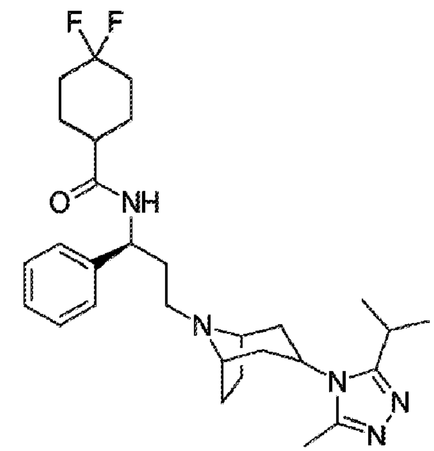 |
| 4003 | vicriviroc (SCH 417690) | 5-({4-[(3*S*)-4-{2-methoxy-1-[4-(trifluoromethyl)phenyl]eth yl}-3-methylpiperazin-1-yl]-4-methylpiperidin-1-yl}carbonyl)-4,6-dimethylpyrimidine | 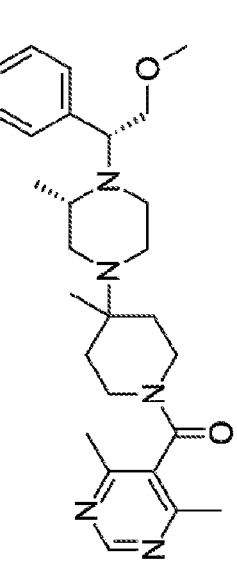 |

Fig. 4A (cont.) HIV Fusion/Entry Inhibitors

| # | Name | IUPAC Name | Structure |
|---|---|---|---|
| 4004 | cenicriviroc (TAK-652) | (S,E)-8-(4-(2-Butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide | 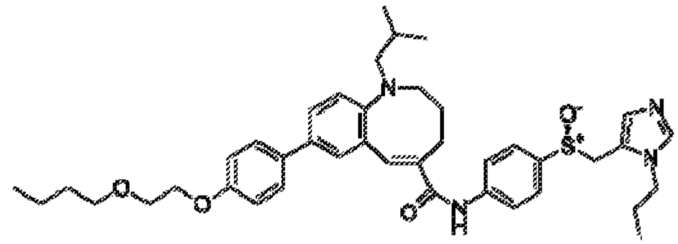 |
| 4005 | fostemsavir (BMS-663068) | {3-[(4-Benzoyl-1-piperazinyl)(oxo)acetyl]-4-methoxy-7-(3-methyl-1H-1,2,4-triazol-1-yl)-1H-pyrrolo[2,3-c]pyridin-1-yl}methyl dihydrogen phosphate | 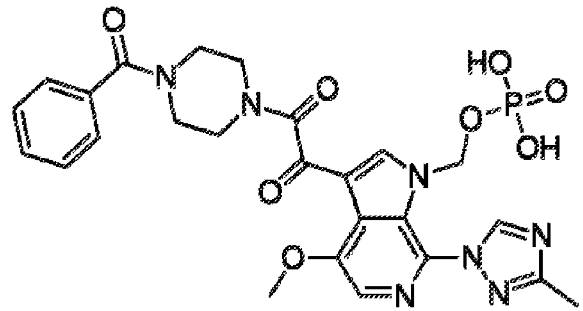 |
| 4006 | ibalizumab (TMB-355) | *humanized monoclonal antibody | |
| 4007 | PRO 140 | *humanized monoclonal antibody | |

Fig. 4B HHV Fusion/Entry Inhibitors

| # | Name | IUPAC Name | Structure |
|---|---|---|---|
| 4009 | myrcludex B | *peptide | |
| 4010 | cyclosporin A | (3S,6S,9S,12R,15S,18S,21S,24S,30S,33S)-30-ethyl-33-[(E,1R,2R)-1-hydroxy-2-methylhex-4-enyl]-1,4,7,10,12, 15,19,25,28-nonamethyl-6,9,18,24-tetrakis(2-methylpropyl)-3,21-di(propan-2-yl)-1,4,7,10,13,16,19,22, 25,28,31-undecazacyclotritriacontane-2,5,8,11,14, 17,20,23,26,29,32-undecone | 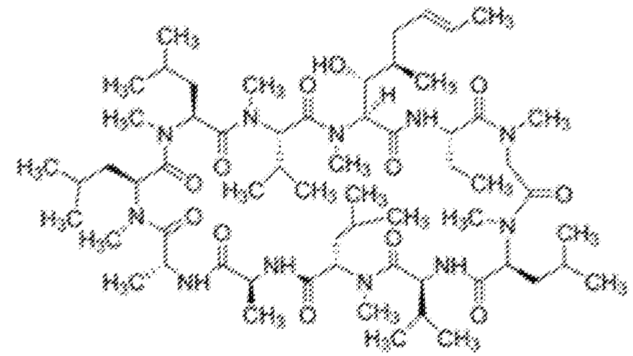 |
| 4011 | Ezetimibe (Zetia®, Ezetrol®) | (3R,4S)-1-(4-Fluorophenyl)-3-[(3S)-3-(4-fluorophenyl)-3-hydroxypropyl]-4-(4-hydroxyphenyl)-2-azetidinone | 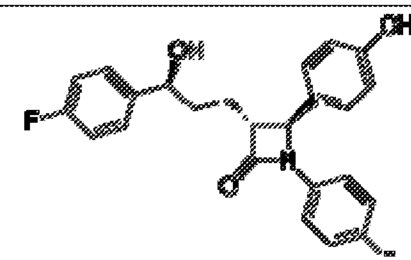 |
| 4012 | SCYX-1454139 | | |
| 4013 | HBIG | *protein | |
| 4014 | Ma18/7 | *humanized monoclonal antibody | |
| 4015 | KR127 | *humanized monoclonal antibody | |
| 4016 | 17.1.41/19.79.5 | *humanized monoclonal antibody | |

Fig. 4B (cont.) HIV Fusion/Entry Inhibitors

| # | Name | IUPAC Name | Structure |
|---|---|---|---|
| 4017 | heparin | 6-[6-[5-acetamido-4,6-dihydroxy-2-(sulfooxymethyl) oxan-3-yl]oxy-2-carboxy-4-hydroxy-5-sulfooxyoxan-3-yl]oxy-2-(hydroxymethyl)-5-(sulfoamino)-4-sulfooxyoxan-3-yl]oxy-3,4-dihydroxy-5-sulfooxyoxane-2-carboxylic acid | 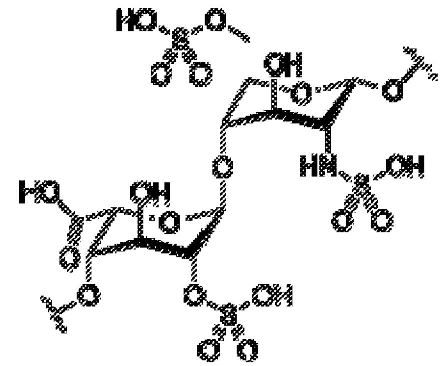 |
| 4018 | suramin | 8,8'-{carbonylbis[imino-3,1-phenylenecarbonylimino(4-methyl-3,1-phenylene)carbonylimino]}di(1,3,5-naphthalenetrisulfonate) | 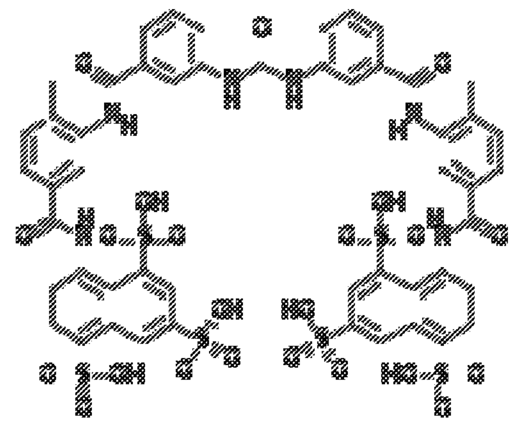 |
| 4019 | SALP | *peptide | |

Fig. 4B (cont.) HIV Fusion/Entry Inhibitors

| # | Name | IUPAC Name | Structure |
|---|---|---|---|
| 4020 | taurocholic acid (and its derivatives) | 2-{[(3α,5β,7α,12α)-3,7,12-trihydroxy-24-oxocholan-24-yl]amino}ethanesulfonic acid | 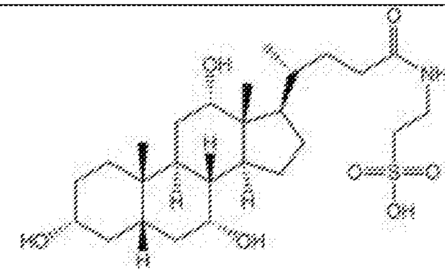 |

Fig. 5 HIV Integrase Strand Transfer Inhibitors

| # | Name | IUPAC Name | Structure |
|---|------|------------|-----------|
| 5001 | dolutegravir (DTG) | (4R,12aS)-N-(2,4-difluorobenzyl)-7-hydroxy-4-methyl-6,8-dioxo-3,4,6,8,12,12a-hexahydro-2H-pyrido[1',2':4,5]pyrazino[2,1-b][1,3]oxazine-9-carboxamide | 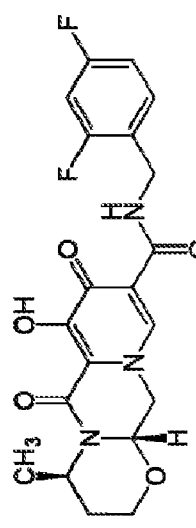 |
| 5002 | elvitegravir (EVG) | 6-[(3-Chloro-2-fluorophenyl)methyl]-1-[(2S)-1-hydroxy-3-methylbutan-2-yl]-7-methoxy-4-oxoquinoline-3-carboxylic acid | 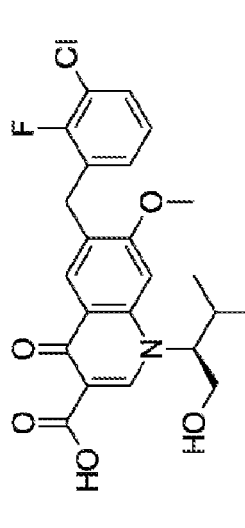 |
| 5003 | raltegravir (RAL) | N-(4-Fluorobenzyl)-5-hydroxy-1-methyl-2-(2-{[(5-methyl-1,3,4-oxadiazol-2-yl)carbonyl]amino}-2-propanyl)-6-oxo-1,6-dihydro-4-pyrimidinecarboxamide | 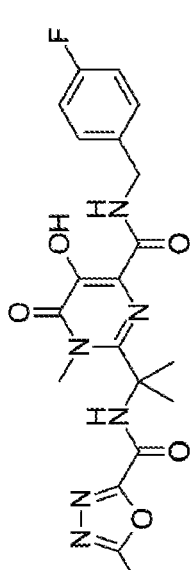 |

Fig. 5 (cont.) Other HIV Antiviral Compounds

| # | Name | IUPAC Name | Structure |
|---|---|---|---|
| 5004 | BI 224436 | (2S)-[4-(3,4-Dihydro-2H-chromen-6-yl)-3-quinolinyl][(2-methyl-2-propanyl)oxy]acetic acid | 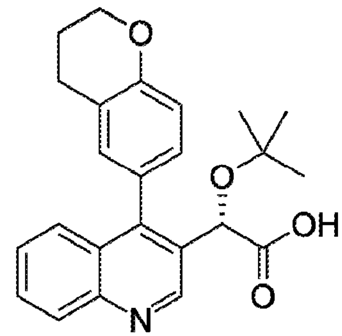 |
| 5005 | globoidnan A | (2R)-(3,4-dihydroxyphenyl)-2-{[4-(3,4-dihydroxyphenyl)-6,7-dihydroxy-2-naphthoyl]oxy}propanoic acid | 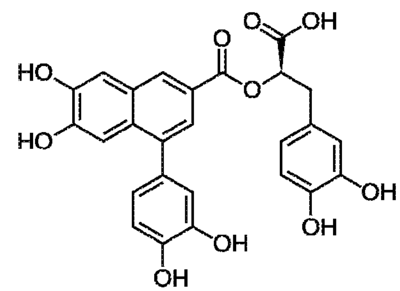 |
| 5006 | cabotegravir (GSK744) | (3S,11aR)-N-(2,4-difluorobenzyl)-6-hydroxy-3-methyl-5,7-dioxo-2,3,5,7,11,11a-hexahydrooxazolo[3,2-a]pyrido[1,2-d]pyrazine-8-carboxamide | 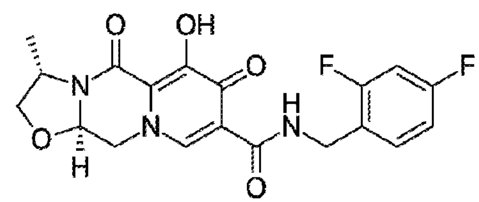 |

Fig. 5 (cont.) Other HIV Antiviral Compounds

| # | Name | IUPAC Name | Structure |
|---|---|---|---|
| 5007 | bictegravir (GS-9883) | (2R,5S,13aR)-8-hydroxy-7,9-dioxo-N-[(2,4,6-trifluorophenyl)methyl]-2,3,4,5,7,9,13,13a-octahydro-2,5-methanopyrido[1',2':4,5]pyrazino[2,1-b][1,3]oxazepine-10-carboxamide | 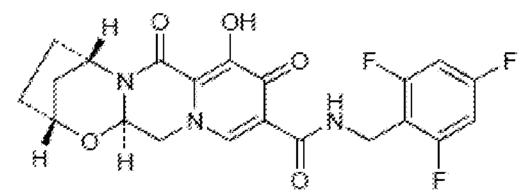 |
| 5008 | MK-2048 | (6S)-2-[(3-chloro-4-fluorophenyl)methyl]-8-ethyl-9-hydroxy-N,6-dimethyl-1,10-dioxo-6,7-dihydropyrazino[3,4]pyrrolo[3,4-b]pyridazine-4-carboxamide | 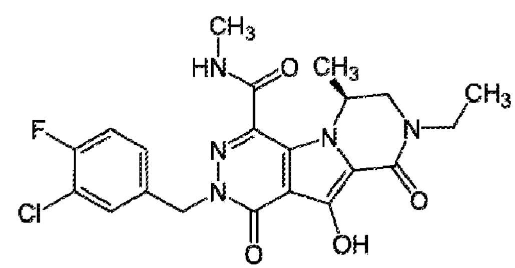 |

Fig. 6A HIV Integrase Strand Transfer Inhibitors

| # | Name | IUPAC Name | Structure |
|---|---|---|---|
| 6001 | bevirimat (MP-4326) | (1R,3aS,5aR,5bR,7aR,9S,11aR,11bR,13aR,13bR)-9-(3-carboxy-3-methylbutanoyl)oxy-5a,5b,8,8,11a-pentamethyl-1-prop-1-en-2-yl-1,2,3,4,5,6,7,7a,9,10,11,11b,12,13,13a,13b-hexadecahydrocyclopenta[a]chrysene-3a-carboxylic acid | 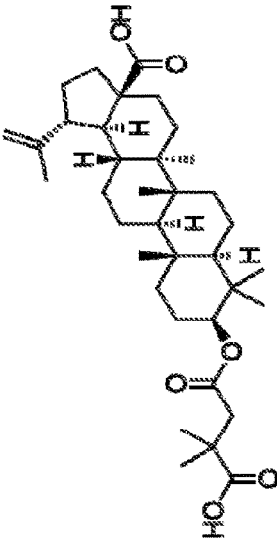 |
| 6002 | BIT225 | N-Carbamimidoyl-5-(1-methyl-1H-pyrazol-4-yl)-2-naphthamide | 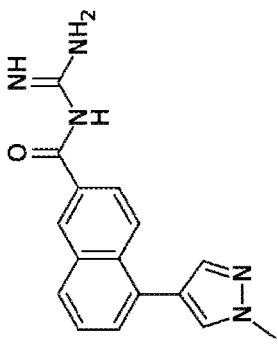 |
| 6003 | calanolide A | (+)-[10R,11S,12S]-10,11-trans-dihydro-12-hydroxy-6,6,10,11-tetramethyl-4-propyl-2H,6H-benzo[1,2-b:3,4-b':5,6-b"]tripyran-2-one | 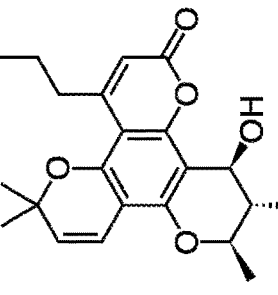 |

Fig. 6A (cont.) Other HIV Antiviral Compounds

| # | Name | IUPAC Name | Structure |
|---|---|---|---|
| 6004 | hydroxyl-carbamide | hydroxyurea | 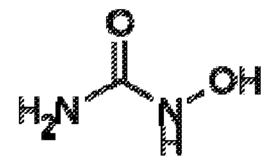 |
| 6005 | miltefosine | 2-(hexadecoxy-oxido-phosphoryl)oxyethyl-trimethyl-azanium | 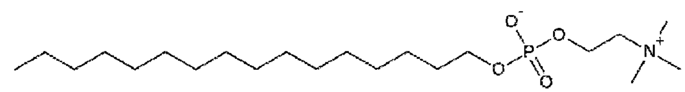 |
| 6006 | seliciclib (CYC202) | 2-(R)-(1-Ethyl-2-hydroxyethylamino)-6-benzylamino-9-isopropylpurine | 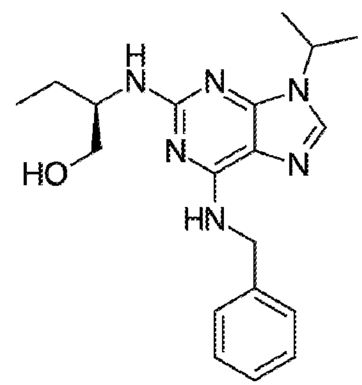 |
| 6007 | cyanovirin-N | *protein | |
| 6008 | griffithsin | *protein | |
| 6009 | scytovirin | *protein | |
| 6010 | Tre recombinase | *protein | |

Fig. 6B HIV Integrase Strand Transfer Inhibitors

| # | Name | IUPAC Name | Structure |
|---|---|---|---|
| 6011 | AT-61 | (E)-N-(1-chloro-3-oxo-1-phenyl-3-(piperidin-1-yl)prop-1-en-2-yl)benzamide | 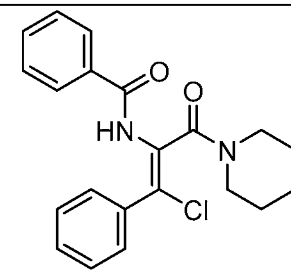 |
| 6012 | AT-130 | (E)-N-(1-bromo-1-(2-methoxyphenyl)-3-oxo-3-(piperidin-1-yl)prop-1-en-2-yl)-4-nitrobenzamide | 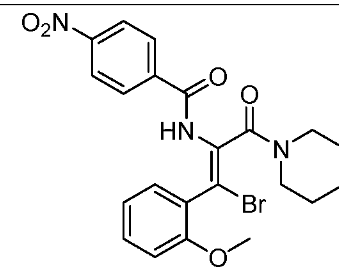 |
| 6013 | BCX4430 | (2S,3S,4R,5R)-2-(4-amino-5H-pyrrolo[3,2-d]pyrimidin-7-yl)-5-(hydroxymethyl)pyrrolidine-3,4-diol | 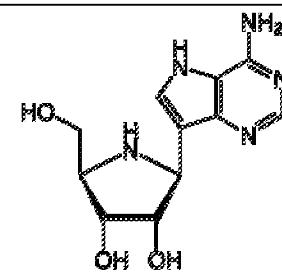 |
| 6014 | favipiravir | 5-Fluoro-2-oxo-1H-pyrazine-3-carboxamide | 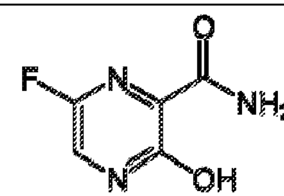 |

Fig. 6B (cont.) Other HIV Antiviral Compounds
| # | Name | IUPAC Name | Structure |
|---|---|---|---|
| 6015 | GS-5734 | (2S)-2-{(2R,3R,4S,5R)-[5-(4-aminopyrrolo[2,1-f][1,2,4]triazin-7-yl)-5-cyano-3,4-dihydroxy-tetrahydro-furan-2-yl]methoxy]phenoxy-(S)-phosphorylamino}propionic acid 2-ethyl-butyl ester | 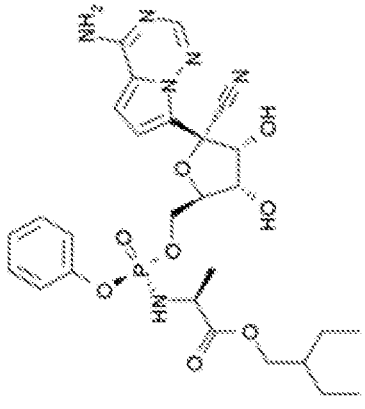 |
| 6016 | mericitabine | [(2R,3R,4R,5R)-5-(4-amino-2-oxopyrimidin-1-yl)-4-fluoro-4-methyl-3-(2-methylpropanoyloxy)oxolan-2-yl]methyl 2-methylpropanoate | 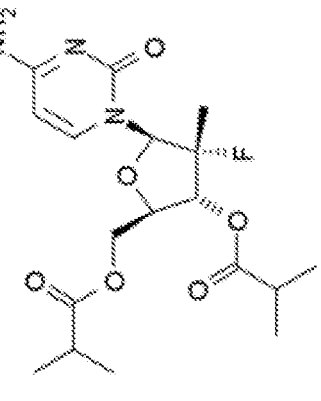 |

Fig. 6B (cont.) Other HIV Antiviral Compounds

| # | Name | IUPAC Name | Structure |
|---|---|---|---|
| 6017 | MK-608 | 7-deaza-2'-C-methyladenosine | 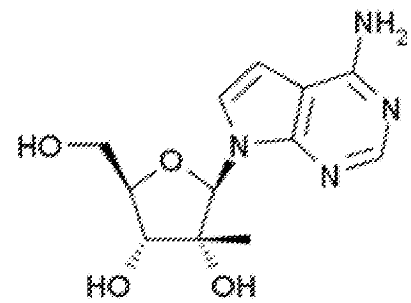 |
| 6018 | NITD008 | (2R,3R,4R,5R)-2-(4-amino-7H-pyrrolo[2,3-d]pyrimidin-7-yl)-3-ethynyl-5-(hydroxymethyl)tetrahydrofuran-3,4-diol | 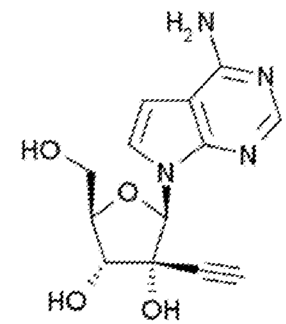 |
| 6019 | moroxydine | N-(Diaminomethylidene)morpholine-4-carboximidamide | 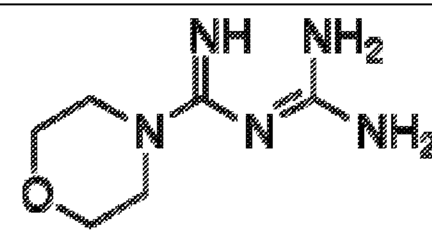 |

Fig. 6B (cont.) Other HBV Antiviral Compounds
| # | Name | IUPAC Name | Structure |
|---|---|---|---|
| 6020 | ribavirin | 1-(β-D-Ribofuranosyl)-1H-1,2,4-triazole-3-carboxamide | 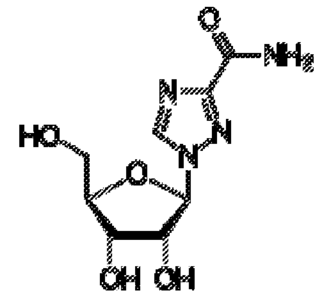 |
| 6021 | taribavirin | 1-(β-D-Ribofuranosyl)-1,2,4-triazole-3-carboximide | 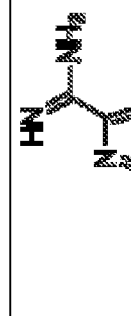 |
| 6022 | triazavirin | 2-methylsulfanyl-6-nitro[1,2,4]triazolo[5,1-c][1,2,4]triazin-7(4H)-one | 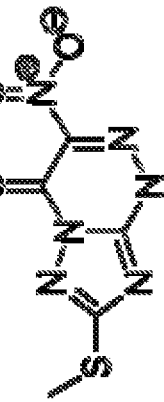 |
| 6023 | ARB-1467 | *oligonucleotide | |

Fig. 6B (cont.) Other HBV Antiviral Compounds

| # | Name | IUPAC Name | Structure |
|---|---|---|---|
| 6024 | umifenovir | 1-methyl-2-((phenylthio)methyl)-3-carbethoxy-4-((dimethylamino)methyl)-5-hydroxy-6-bromindole | 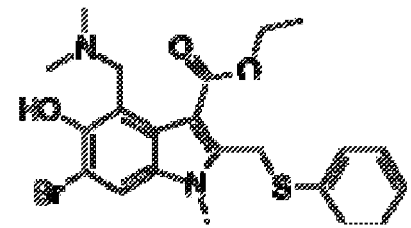 |
| 6025 | ARB-1740 | *oligonucleotide | |
| 6026 | ARC-520 | *oligonucleotide | |
| 6027 | ARC-521 | *oligonucleotide | |
| 6028 | ALN-HBV | *oligonucleotide | |
| 6029 | TG1050 | *protein | |
| 6030 | brincidofovir | 3-(Hexadecyloxy)propyl hydrogen ({[(2S)-1-(4-amino-2-oxo-1(2H)-pyrimidinyl)-3-hydroxy-2-propanyl]oxy}methyl) phosphonate | 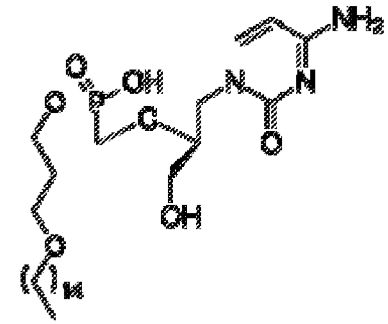 |

Fig. 6B (cont.) Other HHV Antiviral Compounds

| # | Name | IUPAC Name | Structure |
|---|---|---|---|
| 6031 | FGI-104 | 4-[(7-chloroquinolin-4-yl)amino]-2-(diethylaminomethyl)-6-[4-(hydroxymethyl)-3-methoxyphenyl]phenol | 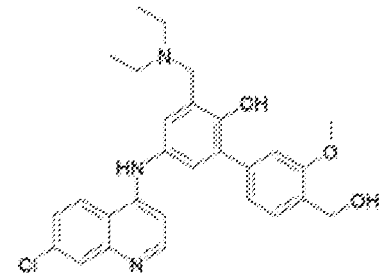 |
| 6032 | LJ-001 | (5Z)-5-[(5-phenylfuran-2-yl)methylidene]-3-prop-2-enyl-2-sulfanylidene-1,3-thiazolidin-4-one | 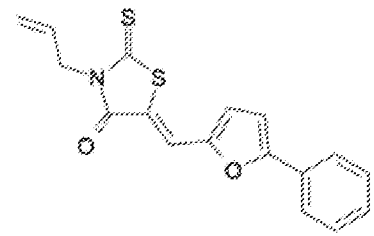 |
| 6033 | FGI-106 | 1-N,7-N-bis[3-(dimethylamino)propyl]-3,9-dimethylquinolino[8,7-h]quinoline-1,7-diamine | 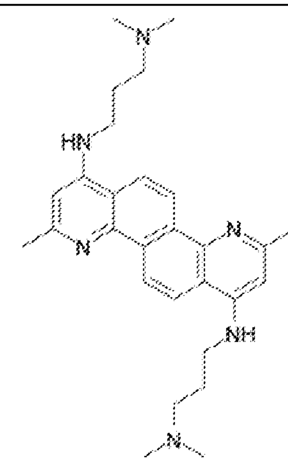 |

Fig. 7 NS5A inhibitors

| # | Name | IUPAC Name | Structure |
|---|---|---|---|
| 7001 | PPI-461 | | |
| 7002 | ACH-2928 | | |
| 7003 | ladipasvir | Methyl N-[(2S)-1-[(6S)-6-[5-[9,9-Difluoro-7-[2-[(1S,2S,4R)-3-[(2S)-2-(methoxycarbonylamino)-3-methylbutanoyl]-3-azabicyclo[2.2.1]heptan-2-yl]-3H-benzimidazol-5-yl]fluoren-2-yl]-1H-imidazol-2-yl]-5-azaspiro[2.4]heptan-5-yl]-3-methyl-1-oxobutan-2-yl]carbamate | 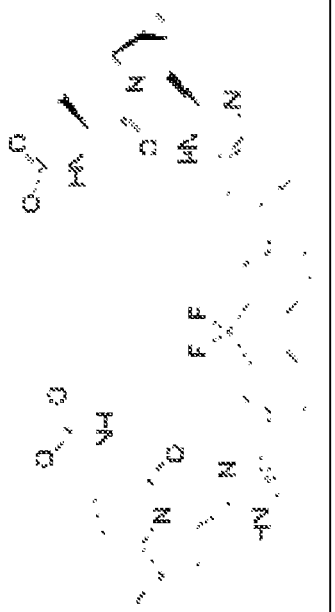 |
| 7004 | BMS-824393 | | |
| 7005 | daclatasvir | Dimethyl N,N'-([1,1'-biphenyl]-4,4'-diylbis{1H-imidazole-5,2-diyl-[(2S)-pyrrolidine-2,1-diyl][(2S)-3-methyl-1-oxobutane-1,2-diyl]})dicarbamate | 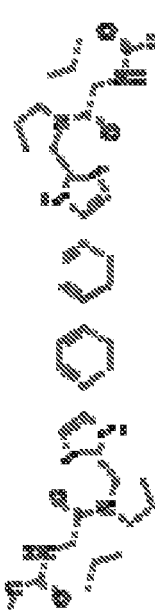 |
| 7006 | elbasvir | Dimethyl N,N'-{[(6S)-6H-indolo[1,2-c][1,3]benzoxazine-3,10-diyl]bis{1H-imidazole-5,2-diyl-(2S)-pyrrolidine-2,1-diyl[(2S)-1-oxo-3-methylbutane-1,2-diyl]}}biscarbamate | 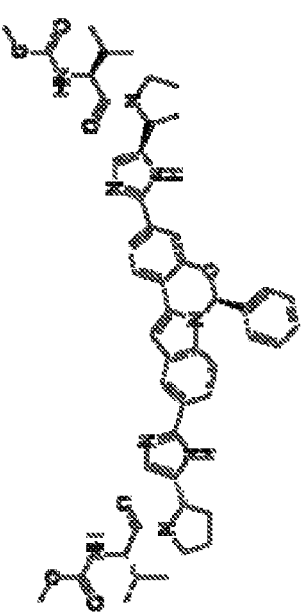 |

Fig. 7 (cont.) NS5A inhibitors

| # | Name | IUPAC Name | Structure |
|---|---|---|---|
| 7007 | ledipasvir | Methyl N-[(2S)-1-[(6S)-6-[5-[9,9-Difluoro-7-[2-[(1S,2S,4R)-3-[(2S)-2-(methoxycarbonylamino)-3-methylbutanoyl]-3-azabicyclo[2.2.1]heptan-2-yl]-3H-benzimidazol-5-yl]fluoren-2-yl]-1H-imidazol-2-yl]-5-azaspiro[2.4]heptan-5-yl]-3-methyl-1-oxobutan-2-yl]carbamate | 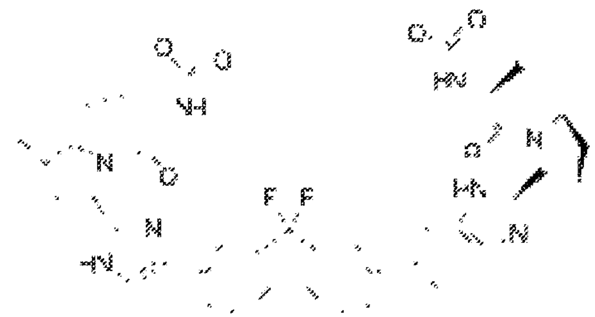 |
| 7008 | uprifosbuvir | Propan-2-yl (2R)-2-{[(R)-({(2R,3R,4R,5R)-4-chloro-5-(2,4-dioxo-3,4-dihydropyrimidin-1(2H)-yl)-3-hydroxy-4-methyloxolan-2-yl}methoxy)(phenoxy)phosphoryl]amino}propanoate | 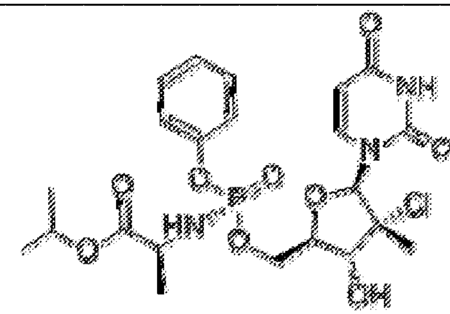 |
| 7009 | ruzasvir | Carbamic acid, N,N'-((((6S)-6-(2-cyclopropyl-5-thiazolyl)-1-fluoro-6H-indolo[1,2-C](1,3)benzoxazine-3,10-diyl)bis(1H-imidazole-5,2-diyl-(2S)-2,1-pyrrolidinediyl((1S)-1-(1-methylethyl)-2-oxo-2,1-ethanediyl)))bis-, C,C'-dimethyl ester | 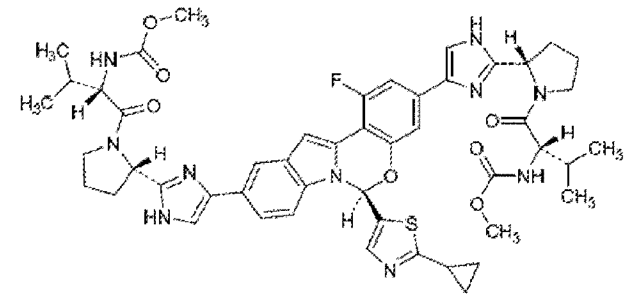 |

Fig. 7 (cont.) NS5A Inhibitors

| # | Name | IUPAC Name | Structure |
|---|---|---|---|
| 7010 | odalasvir | Dimethyl N,N'-(1,4(1,4)-dibenzenacyclohexaphane-12,42-diylbis{1H-benzimidazole-5,2-diyl[(2S,3aS,7aS)- octahydro-1H-indole-2,1-diyl]][(2S)-3-methyl-1-oxobutan- 1,2-diyl]}biscarbamate | 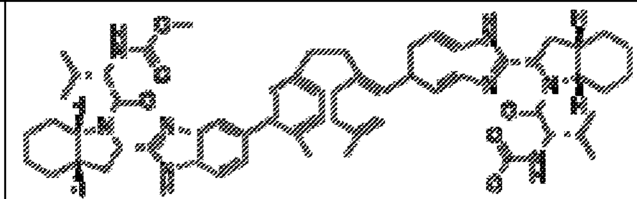 |
| 7011 | ombitasvir | Methyl ((R)-1-((S)-2-((4-((2S,5S)-1-(4-(tert-butyl)phenyl)-5-(4-((R)-1-((methoxycarbonyl)-L-valyl)pyrrolidine-2-carboxamido)phenyl)pyrrolidin-2-yl)phenyl)carbamoyl) pyrrolidin-1-yl)-3-methyl-1-oxobutan-2-yl)carbamate | 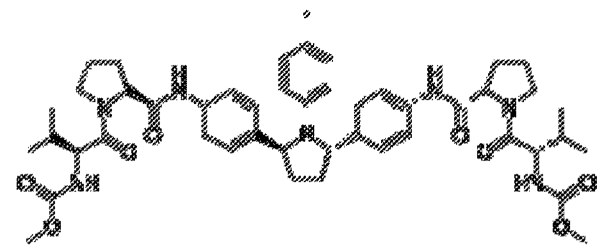 |
| 7012 | ravidasvir | (2S)-2-{[hydroxy(methoxy)methylidene]amino}-1-[(2S)-2-[5-(6-{2-[(2S)-1-[(2S)-2-{[hydroxy(methoxy) methylidene]amino}-3-methylbutanoyl]pyrrolidin-2-yl]-1H-1,3-benzodiazol-6-yl}naphthalen-2-yl)-1H-imidazol-2-yl]pyrrolidin-1-yl]-3-methylbutan-1-one | 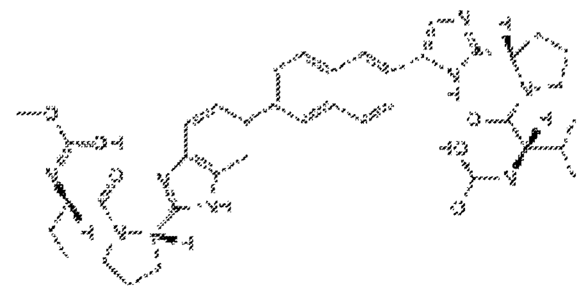 |
| 7013 | samatasvir | N-((1R)-2-((2S)-2-(5-(4-(6-(2-((2S)-1-((2S)-2-(((methoxycarbonyl)amino)-3-methylbutanoyl)pyrrolidin-2-yl)-3H-benzimidazol-5-yl)thieno(3,2-b)thiophen-3-yl)phenyl)-1H-imidazol-2-yl)pyrrolidin-1-yl)-2-oxo-1-phenylethyl)carbamate | 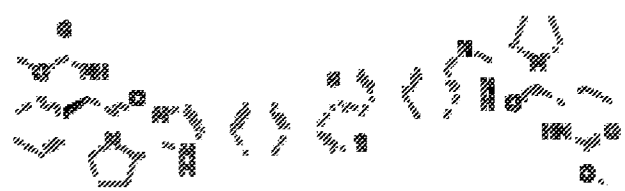 |

Fig. 7 (cont.) NS5A inhibitors
| # | Name | IUPAC Name | Structure |
|---|---|---|---|
| 7014 | velpatasvir | Methyl {(2S)-1-[(2S,5S)-2-(9-{2-[(2S,4S)-1-{(2R)-2-[(methoxycarbonyl)amino]-2-phenylacetyl}-4-(methoxymethyl)-2-pyrrolidinyl]-1H-imidazol-4-yl}-1,11-dihydroisochromeno[4',3':6,7]naphtho[1,2-d]imidazol-2-yl)-5-methyl-1-pyrrolidinyl]-3-methyl-1-oxo-2-butanyl}carbamate | 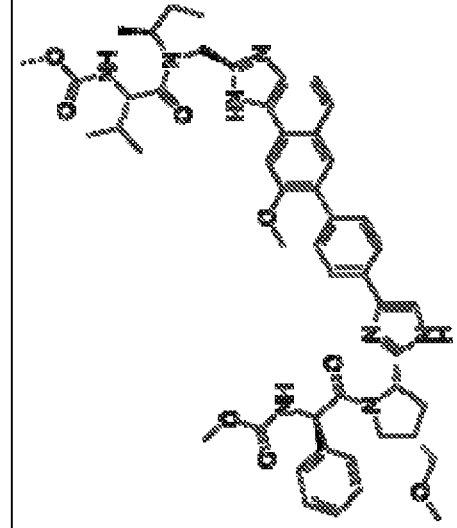 |

Figure 8: Viral Maturation Inhibitors

| # | Name | IUPAC Name | Structure |
|---|---|---|---|
| 8001 | Bevirimat | (1R,3aS,5aR,5bR,7aR,9S,11aR,11bR,13aR,13bR)-9-(3-carboxy-3-methylbutanoyl)oxy-5a,5b,8,8,11a-pentamethyl-1-prop-1-en-2-yl-1,2,3,4,5,6,7,7a,9,10,11,11b,12,13,13a,13b-hexadecahydrocyclopenta[a]chrysene-3a-carboxylic acid | 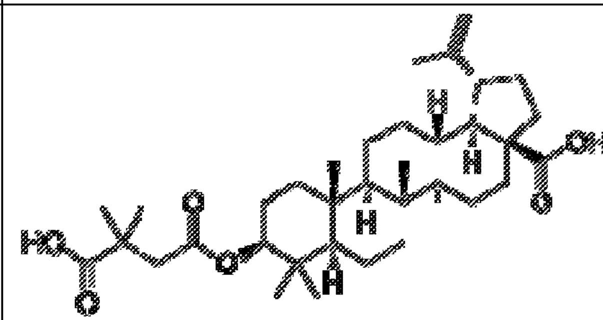 |
| 8002 | BMS-955176 | 4-[(1R,3aS,5aR,5bR,7aR,11aS,11bR,13aR,13bR)-3a-[[2-(1,1-dioxido-4-thiomorpholinyl)ethyl]amino]-2,3,3a,4,5,5a,5b,6,7,7a,8,11,11a,11b,12,13,13a,13b-octadecahydro-5a,5b,8,8,11a-pentamethyl-1-(1-methylethenyl)-1H-cyclopenta[a]chrysen-9-yl]-benzoic acid | 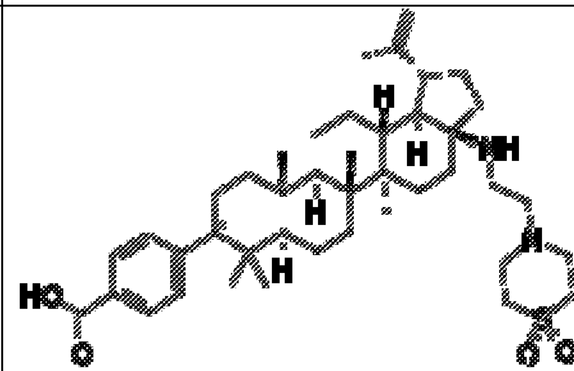 |
| 8003 | MPC-9055 | | |

Fig. 9 Capsid Assembly Modulators

| # | Name | IUPAC Name | Structure |
|---|---|---|---|
| 9001 | NVR-3-778 | | |
| 9002 | AB-423 | | |
| 9003 | GLS-4 | ethyl 4-(2-bromo-4-fluorophenyl)-6-(morpholinomethyl)-2-(thiazol-2-yl)-1,4-dihydropyrimidine-5-carboxylate | 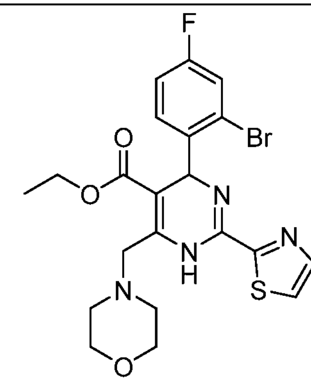 |
| 9004 | Bayer 41-4109 | methyl (R)-4-(2-chloro-4-fluorophenyl)-2-(3,5-difluoropyridin-2-yl)-6-methyl-1,4-dihydropyrimidine-5-carboxylate | 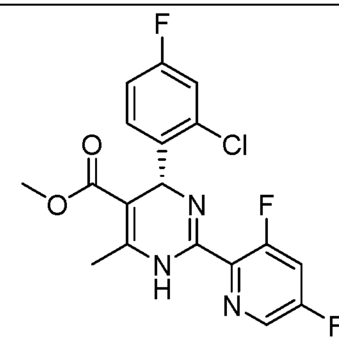 |

Fig. 9 (cont.) Capsid Assembly Modulators
| # | Name | IUPAC Name | Structure |
|---|---|---|---|
| 9005 | HAP-1 | methyl 4-(2-chloro-4-fluorophenyl)-6-methyl-2-(pyridin-2-yl)-1,4-dihydropyrimidine-5-carboxylate | 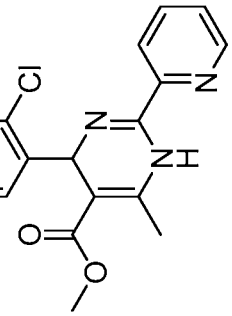 |
| 9006 | AT-1 | | |

Fig. 10 FXR Agonists

| # | Name | IUPAC Name | Structure |
|---|---|---|---|
| 10001 | cafestol | (3bS,5aS,7R,8R,10aR,10bS)-3b,4,5,6,7,8,9,10,10a,10b,11,12-Dodecahydro-7-hydroxy-10b-methyl-5a,8-methano-5aH-cyclohepta[5,6]naphtho[2,1-b]furan-7-methanol | 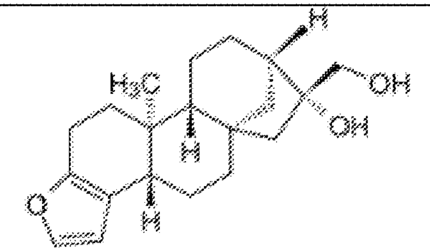 |
| 10002 | chenodeoxycholic acid | (R)-((3R,5S,7R,8R,9S,10S, 13R,14S,17R)-3,7-dihydroxy-10,13-dimethylhexadecahydro-1H-cyclopenta[a] phenanthren-17-yl)pentanoic acid | 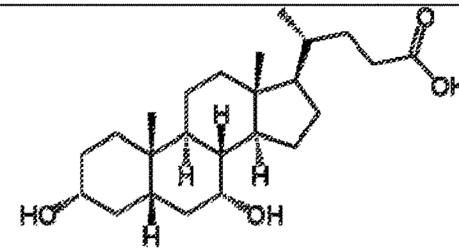 |
| 10003 | cholic acid | (R)-4-((3R,5S,7R,8R,9S,10S,12S,13R,14S,17R)-3,7,12-Trihydroxy-10,13-dimethylhexadecahydro-1H-cyclopenta[a]phenanthren-17-yl)pentanoic acid | 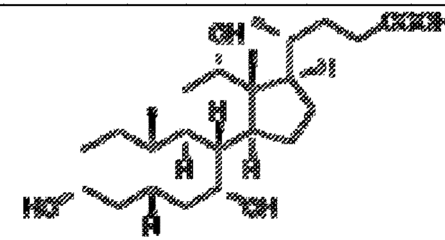 |
| 10004 | obeticholic acid | (4R)-4-[(3R,5S,6R,7R,8S,9S,10S,13R,14S,17R)-6-ethyl-3,7-dihydroxy-10,13-dimethyl-2,3,4,5,6,7,8,9,11,12,14,15,16,17-tetradecahydro-1H-cyclopenta[a] phenanthren-17-yl]pentanoic acid | 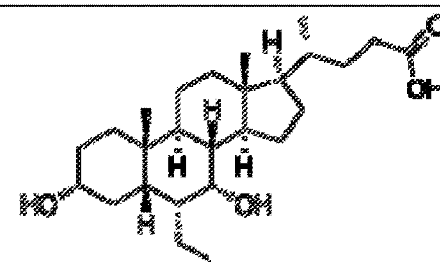 |

Fig. 10 (cont.): FXR Agonists

| # | Name | IUPAC Name | Structure |
|---|---|---|---|
| 10005 | ursodeoxycholic acid | (R)-4-((3R,5S,7S,8R,9S,10S,13R,14S,17R)-3,7-dihydroxy-10,13-dimethylhexadeca hydro-1H-cyclopenta[a]phenanthren-17-yl)pentanoic acid | 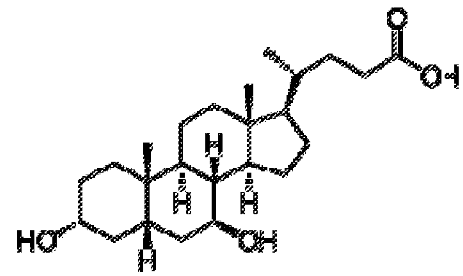 |
| 10006 | fexaramine | Methyl (E)-3-[3-[cyclohexanecarbonyl-[[4-[4-(dimethylamino)phenyl]phenyl]methyl]amino]phenyl]prop-2-enoate | 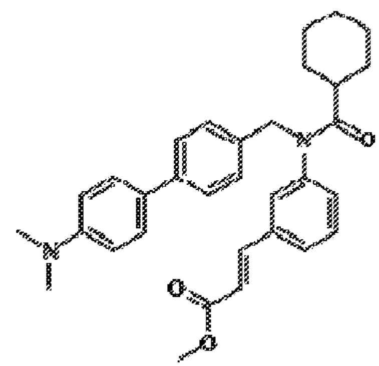 |

Fig. 11 Cyclophilin/TNF Inhibitors

| # | Name | IUPAC Name | Structure |
|---|---|---|---|
| 11001 | infliximab (Remicade®) | *humanized monoclonal antibody | |
| 11002 | adalimumab (Humira®) | *humanized monoclonal antibody | |
| 11003 | certolizumab pegol (Cimzia®) | *humanized monoclonal antibody | |
| 11004 | golimumab (Simponi®) | *humanized monoclonal antibody | |
| 11005 | etanercept (Enbrel®) | *humanized monoclonal antibody | |
| 11006 | thalidomide (Immunoprin®) | 2-(2,6-dioxopiperidin-3-yl)-1H-isoindole-1,3(2H)-dione | 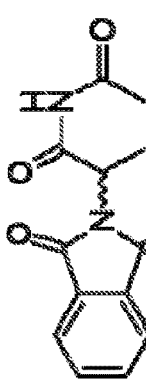 |
| 11007 | lenalidomide (Revlimid®) | 3-(4-Amino-1-oxoisoindolin-2-yl)piperidine-2,6-dione | 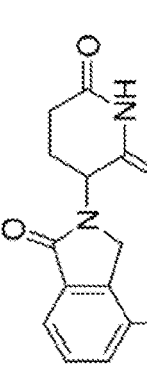 |
| 11008 | pomalidomide (Pomalyst®, Imnovid®) | 4-amino-2-(2,6-dioxopiperidin-3-yl)isoindole-1,3-dione | 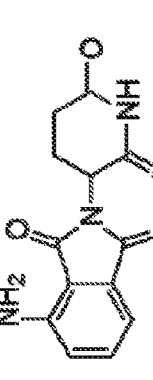 |

Fig. 11 (cont.): Cyclophilin/TNF Inhibitors

| # | Name | IUPAC Name | Structure |
|---|---|---|---|
| 11009 | cyclosporin A | (3S,6S,9S,12R,15S,18S,21S,24S,30S,33S)-30-ethyl-33-[(E,1R,2R)-1-hydroxy-2-methylhex-4-enyl]-1,4,7,10, 12,15,19,25,28-nonamethyl-6,9,18,24-tetrakis(2-methylpropyl)-3,21-di(propan-2-yl)-1,4,7,10,13,16,19, 22,25,28,31-undecazacyclotritriacontane-2,5,8,11,14, 17,20,23,26,29,32-undecone | 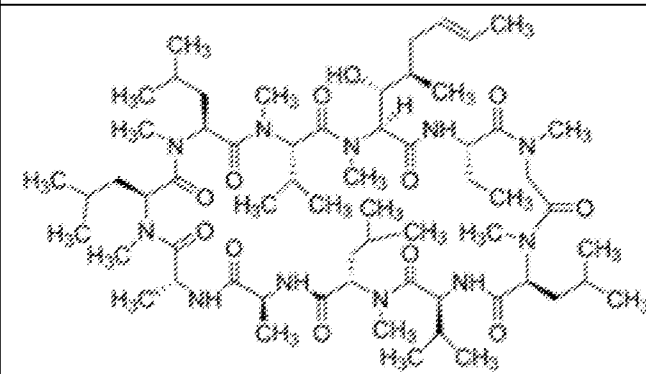 |
| 11010 | NIM811 | *cyclic peptide | |
| 11011 | Alisporivir (DEB-025) | *cyclic peptide | |
| 11012 | SCY-635 | *cyclic peptide | |
| 11013 | DEB-064 | | |
| 11014 | CRV-431 | | |

Fig.12 TLR Agonists

| #     | Name              | IUPAC Name                                                                                                                                                          | Structure |
|-------|-------------------|---------------------------------------------------------------------------------------------------------------------------------------------------------------------|-----------|
| 12001 | GS-9620           |                                                                                                                                                                     |           |
| 12002 | ARB-1598          |                                                                                                                                                                     |           |
| 12003 | ANA-975           | (2R,3R,4R,5R)-2-(5-amino-2-oxothiazolo[4,5-d]pyrimidin-3(2H)-yl)-5-(hydroxymethyl)tetrahydrofuran-3,4-diyl diacetate                                                 | 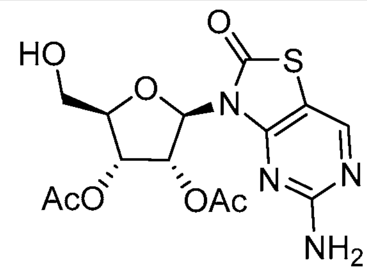          |
| 12004 | RG-7795 (ANA-773) |                                                                                                                                                                     |           |
| 12005 | MEDI-9197         |                                                                                                                                                                     |           |
| 12006 | PF-3512676        |                                                                                                                                                                     |           |
| 12007 | IMO-2055          | *oligodeoxynucleotide                                                                                                                                               |           |
| 12008 | SM360320          | 9-benzyl-8-hydroxy-2-(2-methoxyethoxy)adenine                                                                                                                       | 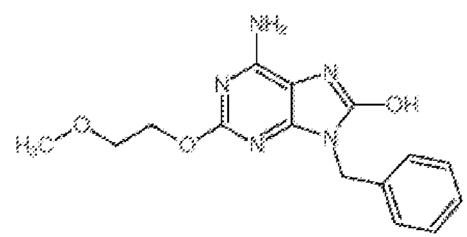          |

Fig. 12 (cont.): TLR Agonist
| # | Name | IUPAC Name | Structure |
|---|---|---|---|
| 12009 | AZD 8848 | Methyl[3-({[3-(6-amino-2-butoxy-8-oxo-7,8-dihydro-9H-purin-9-yl)propyl][3-(4-morpholinyl)propyl]amino}methyl)phenyl]acetate | 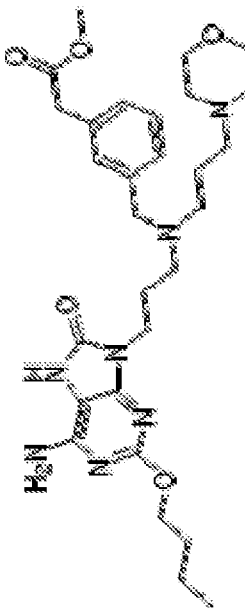 |
| 12010 | Isatoribine | 5-Amino-3-(β-D-ribofuranosyl)[1,3]thiazolo[4,5-d]pyrimidine-2,7(3H,4H)-dione | 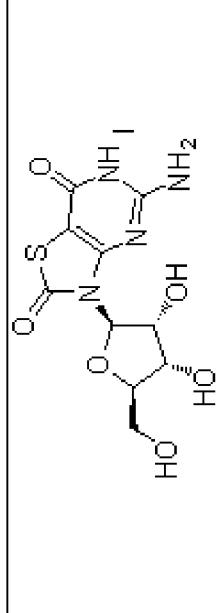 |
| 12011 | Tremelimumab | *oligodeoxynucleotide | |
| 12012 | SM360320 | 9-benzyl-8-hydroxy-2-(2-methoxy-ethoxy)adenine | 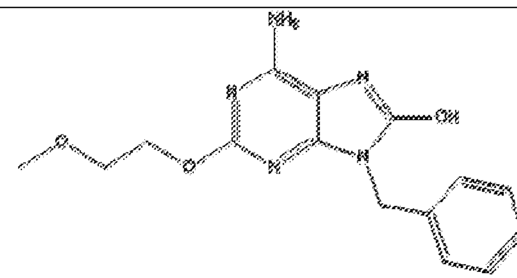 |

Fig. 12 (cont.): TLR Agonist

| # | Name | IUPAC Name | Structure |
|---|------|------------|-----------|
| 12013 | AZD-8848 | methyl[3-({[3-(6-amino-2-butoxy-8-oxo-7,8-dihydro-9H-purin-9-yl)propyl][3-(4-morpholinyl)propyl]amino}methyl)phenyl]acetate | 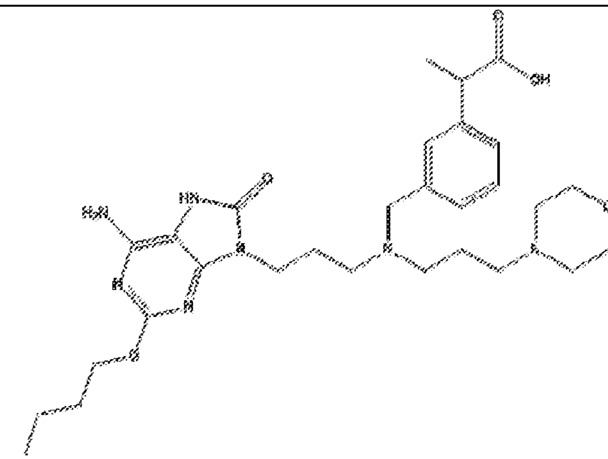 |

Fig. 13 Polymerase Inhibitors

| # | Name | IUPAC Name | Structure |
|---|---|---|---|
| 13001 | telbivudine | 1-(2-deoxy-β-L-erythro-pentofuranosyl)-5-methylpyrimidine-2,4(1H,3H)-dione | 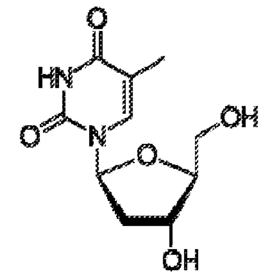 |
| 13002 | beclabuvir | (1aR,12bS)-8-Cyclohexyl-N-(dimethylsulfamoyl)-11-methoxy-1a-{[(1R,5S)-3-methyl-3,8-diazabicyclo[3.2.1]oct-8-yl]carbonyl}-1,1a,2,12b-tetrahydrocyclopropa[d]indolo[2,1-a][2]benzazepine-5-carboxamide | 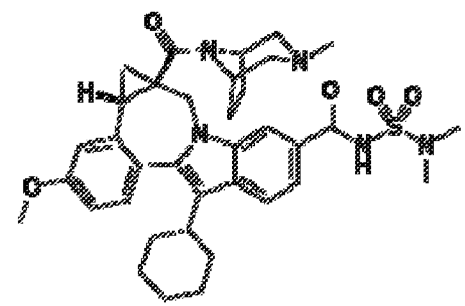 |
| 13003 | dasabuvir | N-{6-[5-(2,4-Dioxo-3,4-dihydro-1(2H)-pyrimidinyl)-2-methoxy-3-(2-methyl-2-propanyl)phenyl]-2-naphthyl}methanesulfonamide | 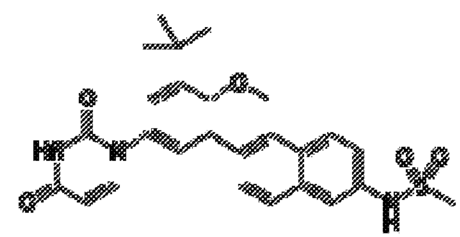 |

Fig. 13 (cont.): Polymerase Inhibitors

| # | Name | IUPAC Name | Structure |
|---|---|---|---|
| 13004 | deleobuvir | (2E)-3-(2-{1-[2-(5-Bromopyrimidin-2-yl)-3-cyclopentyl-1-methyl-1H-indole-6-carboxamido]cyclobutyl}-1-methyl-1H-benzimidazol-6-yl)prop-2-enoic acid | 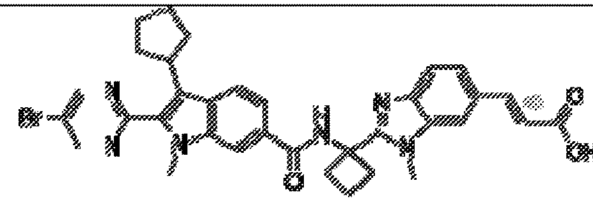 |
| 13005 | filibuvir | (2R)-2-cyclopentyl-2-[2-(2,6-diethylpyridin-4-yl)ethyl]-5-[(5,7-dimethyl-[1,2,4]triazolo[1,5-a]pyrimidin-2-yl)methyl]-4-hydroxy-3H-pyran-6-one | 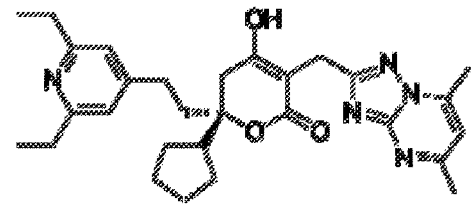 |
| 13006 | setrobuvir | N-(3-{(4aR,5S,8R,8aS)-1-[(4-fluorophenyl)methyl]-4-hydroxy-2-oxo-1,2,4a,5,6,7,8,8a-octahydro-5,8-methanoquinolin-3-yl}-1,1-dioxo-1,4-dihydro-1λ6,2,4-benzothiadiazin-7-yl)methanesulfonamide | 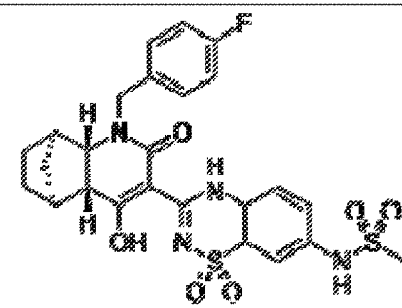 |
| 13007 | sofosbuvir | Isopropyl (2S)-2-[[[(2R,3R,4R,5R)-5-(2,4-dioxopyrimidin-1-yl)-4-fluoro-3-hydroxy-4-methyl-tetrahydrofuran-2-yl]methoxy-phenoxy-phosphoryl]amino]propanoate | 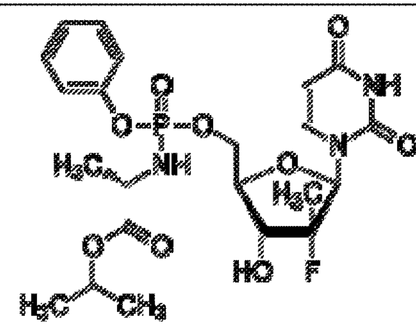 |

Fig. 13 (cont.): Polymerase Inhibitors

| # | Name | IUPAC Name | Structure |
|---|---|---|---|
| 130008 | radalbuvir | 5-(3,3-Dimethylbut-1-yn-1-yl)-3-{(1R)-N-[(1s,4s)-4-hydroxy-4-({[(3S)-oxolan-3-yl]oxy}methyl)cyclohexyl]-4-methylcyclohex-3-ene-1-carboxamido}thiophene-2-carboxylic acid | 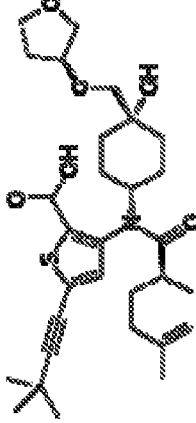 |
| 13009 | mericitabine | [(2R,3R,4R,5R)-5-(4-amino-2-oxopyrimidin-1-yl)-4-fluoro-4-methyl-3-(2-methylpropanoyloxy)oxolan-2-yl]methyl 2-methylpropanoate | 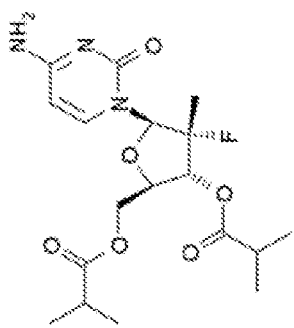 |
| 13010 | PSI-7851 | Propan-2-yl (2S)-2-[[[(2R,3R, 4R,5R)-5-(2,4-dioxopyrimidin-1-yl)-4-fluoro-3-hydroxy-4-methyloxolan-2-yl]methoxy-phenoxyphosphoryl]amino]propanoate | 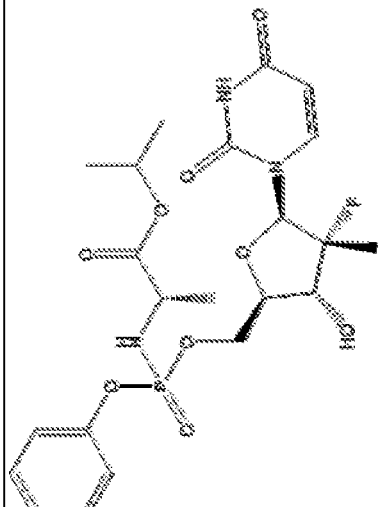 |

Fig. 13 (cont.): Polymerase Inhibitors

| # | Name | IUPAC Name | Structure |
|---|---|---|---|
| 13011 | INX-189 | 2,2-dimethylpropyl (2S)-2-[[[(2R,3R,4R,5R)-5-(2-amino-6-methoxypurin-9-yl)-3,4-dihydroxy-4-methyloxolan-2-yl]methoxy-naphthalen-1-yloxyphosphoryl] amino]propanoate | 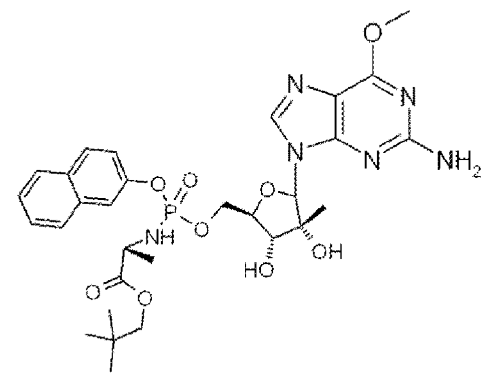 |
| 13012 | PSI-352938 | (2R,4aR,6R,7R,7aR)-6-(2-amino-6-ethoxy-9H-purin-9-yl)-7-fluoro-2-isopropoxy-7-methyltetrahydro-4H-furo[3,2-d][1,3,2]dioxaphosphinine 2-oxide | 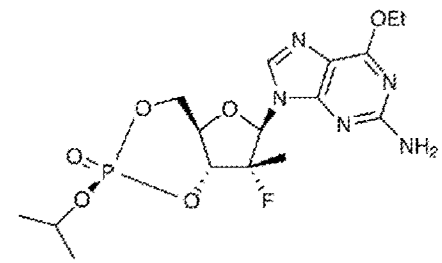 |
| 13013 | PSI-661 | | |
| 13014 | GS-6620 | (2R,3R,4S,5S)-5-(4-aminopyrrolo[2,1-f][1,2,4]triazin-7-yl)-4-cyano-4-hydroxy-2-((((S)-(((S)-1-isopropoxy-1-oxopropan-2-yl)amino)(phenoxy)phosphoryl)oxy)methyl)tetrahydrofuran-3-yl isobutyrate | 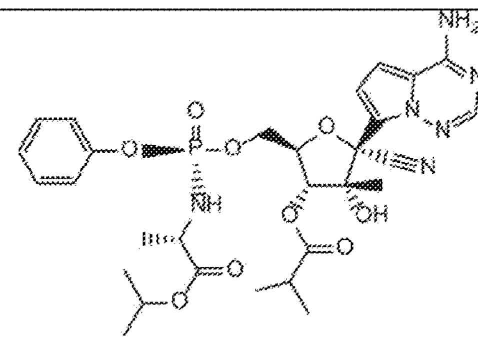 |

Fig. 13 (cont.): Polymerase Inhibitors

| # | Name | IUPAC Name | Structure |
|---|---|---|---|
| 13015 | IDX-184 | 2'-C-Methylguanosine 5'-[2-[(3-hydroxy-2,2-dimethyl-1-oxopropyl)thio]ethyl N-(phenylmethyl)phosphoramidate] | 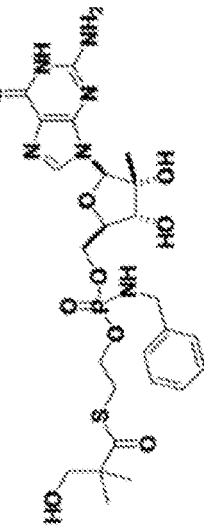 |
| 13016 | TMC649128 | (2R,3S,4S,5R)-5-(4-amino-2-oxopyrimidin-1(2H)-yl)-2-azido-2-((isobutyryloxy)methyl)-4-methyltetrahydrofuran-3-yl isobutyrate | 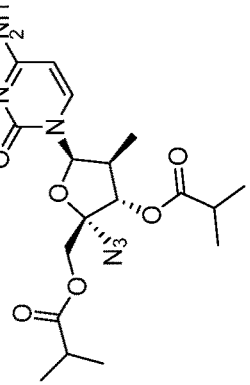 |
| 13017 | setrobuvir | N-(3-{(4aR,5S,8R,8aS)-1-[(4-fluorophenyl)methyl]-4-hydroxy-2-oxo-1,2,4a,5,6,7,8,8a-octahydro-5,8-methanoquinolin-3-yl}-1,1-dioxo-1,4-dihydro-1λ6,2,4-benzothiadiazin-7-yl)methanesulfonamide | 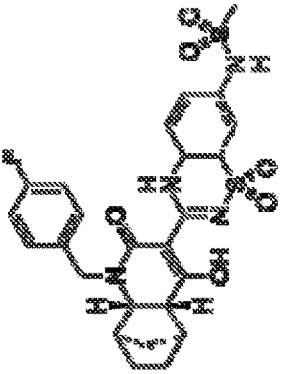 |
| 13018 | lomibuvir | 5-(3,3-dimethylbut-1-ynyl)-3-[(4-hydroxycyclohexyl)-(4-methylcyclohexanecarbonyl)amino]thiophene-2-carboxylic acid | 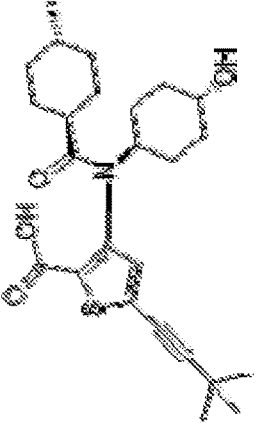 |

Fig. 13 (cont.): Polymerase Inhibitors

| # | Name | IUPAC Name | Structure |
|---|---|---|---|
| 13019 | nesbuvir | 5-cyclopropyl-2-(4-fluorophenyl)-6-[2-hydroxyethyl (methylsulfonyl)amino]-N-methyl-1-benzofuran-3-carboxamide | 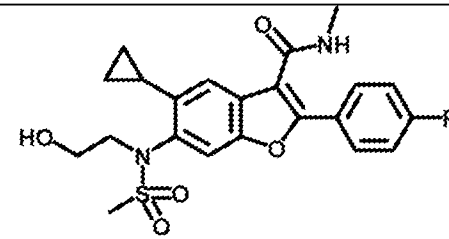 |
| 13020 | tegobuvir | 5-({6-[2,4-Bis(trifluoromethyl)phenyl]-3-pyridazinyl} methyl)-2-(2-fluorophenyl)-5H-imidazo[4,5-c]pyridine | 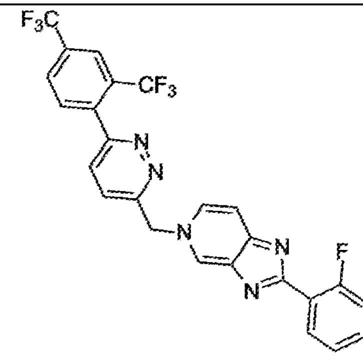 |
| 13021 | merimepodib | N-3-(3-[3-methoxy-4-(oxazol-5-yl)phenyl]ureido) benzylcarbamic acid-(S)-tetrahydrofuran-3-yl-ester | 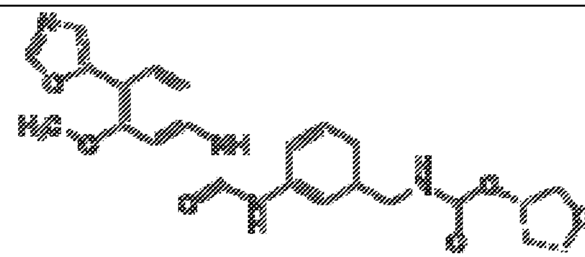 |

Fig. 13 (cont.): Polymerase Inhibitors

| # | Name | IUPAC Name | Structure |
|---|---|---|---|
| 13022 | ribavirin | 1-(β-D-Ribofuranosyl)-1H-1,2,4-triazole-3-carboxamide | 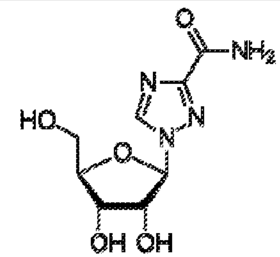 |
| 13023 | acyclovir | 1-((2-Hydroxyethoxy)methyl)guanine | 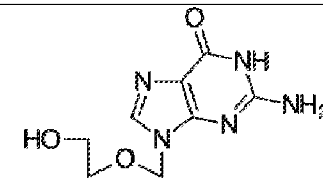 |
| 13024 | atevirapine | | |
| 13025 | famciclovir | 2-[(acetyloxy)methyl]-4-(2-amino-9H-purin-9-yl)butyl acetate | 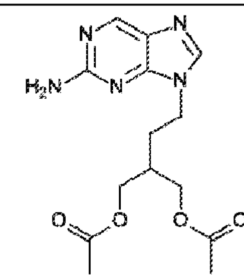 |
| 13026 | valacyclovir | (S)-2-[(2-amino-6-oxo-6,9-dihydro-3H-purin-9-yl)methoxy]ethyl-2-amino-3-methylbutanoate | 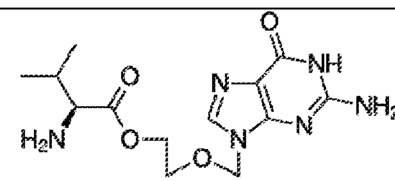 |

Fig. 13 (cont.): Polymerase Inhibitors

| # | Name | IUPAC Name | Structure |
|---|---|---|---|
| 13027 | ganciclovir | 9-(1,3-dihydroxy-2-propoxymethyl)guanine | 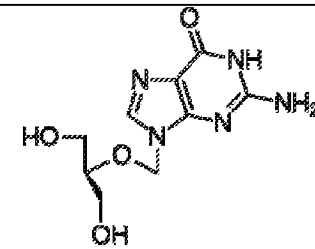 |
| 13028 | valganciclovir | 2-[(2-amino-6-oxo-6,9-dihydro-3H-purin-9-yl)methoxy]-3-hydroxypropyl-(2S)-2-amino-3-methylbutanoate | 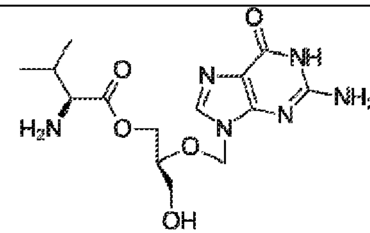 |
| 13029 | cidofovir | ({[(S)-1-(4-amino-2-oxo-1,2-dihydropyrimidin-1-yl)-3-hydroxypropan-2-yl]oxy}methyl)phosphonic acid | 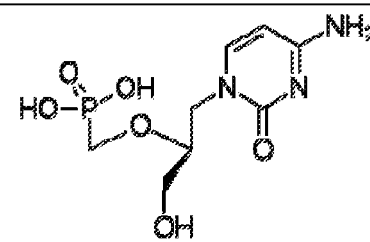 |
| 13030 | JK-05 | | |

Figure 14: Vaccines

| # | Name | IUPAC Name | Structure |
|---|---|---|---|
| 14001 | Heplislav® | *protein | |
| 14002 | ABX-203 | *protein | |
| 14003 | INO-1800 | *protein | |

ACYCLIC ANTIVIRALS

CROSS-REFERENCE TO RELATED APPLICATIONS

This application is a national phase entry of International Application No. PCT/US2017/021559, filed on Mar. 9, 2017, which claims priority to U.S. Provisional Patent Application No. 62/305,723, filed Mar. 9, 2016, each of which is incorporated herein in its entirety.

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

BACKGROUND

Field

The present application relates to the fields of chemistry, biochemistry and medicine. More particularly, disclosed herein are nucleotide analogs, pharmaceutical compositions that include one or more nucleotide analogs and methods of synthesizing the same. Also disclosed herein are methods of treating diseases and/or conditions with a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I), or a pharmaceutically acceptable salt thereof.

Some embodiments disclosed herein relate to a method of ameliorating and/or treating a human immunodeficiency virus (HIV) infection, a hepatitis B virus (HBV) infection, and/or a hepatitis D virus infection (HDV), that can include administering to a subject identified as suffering from the HIV, HBV, and/or HDV infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a HIV, HBV, and/or HDV infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a HIV, HBV, and/or HDV infection. In some embodiments, the infection can be caused by HIV. In some embodiments, the infection can be caused by HBV. In some embodiments, the infection can be caused by HDV. In some embodiments, the infection can be caused by two or more of HIV, HBV, and HDV.

Some embodiments disclosed herein relate to a method of ameliorating and/or treating a HIV, HBV, and/or HDV infection that can include contacting a cell infected with the HIV, HBV, and/or HDV virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for ameliorating and/or treating a HIV, HBV, and/or HDV infection that can include contacting a cell infected with the HIV, HBV, and/or HDV virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for ameliorating and/or treating a HIV, HBV, and/or HDV infection by contacting a cell infected with the HIV, HBV, and/or HDV virus with an effective amount of said compound(s). In some embodiments, the infection can be caused by HIV. In some embodiments, the infection can be caused by HBV. In some embodiments, the infection can be caused by HDV. In some embodiments, the infection can be caused by two or more of HIV, HBV, and HDV.

Some embodiments disclosed herein relate to a method of inhibiting replication of a HIV, HBV, and/or HDV virus that can include contacting a cell infected with the HIV, HBV, and/or HDV virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for inhibiting replication of a HIV, HBV, and/or HDV virus that can include contacting a cell infected with the HIV, HBV, and/or HDV virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for inhibiting replication of a HIV, HBV, and/or HDV virus by contacting a cell infected with the HIV, HBV, and/or HDV virus with an effective amount of said compound(s). In some embodiments, the virus can be HIV. In some embodiments, the virus can be HBV. In some embodiments, the virus can be HDV. In some embodiments, the virus can be two or more of HIV, HBV, and HDV.

Some embodiments disclosed herein relate to a method of ameliorating and/or treating a HIV, HBV, and/or HDV infection that can include administering to a subject identified as suffering from the HIV, HBV, and/or HDV infection an effective amount of a compound described herein or a pharmaceutically acceptable salt thereof (for example, one or more compounds of Formula (I), or a pharmaceutically acceptable salt thereof), or a pharmaceutical composition that includes a compound described herein, or a pharmaceutically acceptable salt thereof, in combination with one or more additional therapeutic agents, or a pharmaceutically acceptable salt thereof. Some embodiments disclosed herein relate to a method of ameliorating and/or treating a HIV, HBV, and/or HDV infection that can include contacting a cell infected with the HIV, HBV, and/or HDV infection with an effective amount of a compound described herein or a pharmaceutically acceptable salt thereof (for example, one or more compounds of Formula (I), or a pharmaceutically acceptable salt thereof), or a pharmaceutical composition that includes a compound described herein, or a pharmaceutically acceptable salt thereof, in combination with one or more additional therapeutic agents, or a pharmaceutically acceptable salt thereof. Some embodiments disclosed herein relate to a method of inhibiting replication of a HIV, HBV, and/or HDV virus that can include administering to a subject identified as suffering from a HIV, HBV, and/or HDV infection an effective amount of a compound described herein or a pharmaceutically acceptable salt thereof (for example, a compound of Formula (I), or a pharmaceutically acceptable salt thereof), or a pharmaceutical composition that includes a compound described herein, or a pharmaceutically acceptable salt thereof, in combination with one or more additional therapeutic agents, or a pharmaceutically acceptable salt thereof. In some embodiments, the infection can be caused by HIV. In some embodiments, the infection can be caused by HBV. In some embodiments, the infection can be caused by HDV. In some embodiments, the infection can be caused by two or more of HIV, HBV, and HDV.

BRIEF DESCRIPTION OF THE DRAWINGS

FIG. 1 shows example non-nucleoside reverse transcriptase inhibitors (NNRTI's).

FIG. 2 shows example nucleoside reverse transcriptase inhibitor (NRTI's).

FIG. 3A shows example HIV protease inhibitors. FIG. 3B shows additional HIV, HBV and/or HDV protease inhibitors.

FIG. 4A shows HIV fusion/entry inhibitors. FIG. 4B shows HBV and/or HDV fusion/entry inhibitors.

FIG. 5 shows HIV integrase strand transfer inhibitor (INSTI's).

FIG. 6A shows additional HIV antiviral compounds. FIG. 6B shows additional antiviral compounds.

FIG. 7 shows examples HBV and/or HDV NS5A inhibitors.

FIG. 8 shows example HIV, HBV and/or HDV viral maturation inhibitors.

FIG. 9 shows example HIV, HBV and/or HDV capsid assembly modulators.

FIG. 10 shows example anti-HBV and/or anti-HDV farnesoid X receptor (FXR) agonists.

FIG. 11 shows example anti-HBV and/or anti-HDV tumor necrosis factor (TNF)/cyclophilin inhibitors.

FIG. 12 shows example anti-HBV and/or anti-HDV toll-like receptor (TLR) agonists.

FIG. 13 shows example HBV and/or HDV polymerase inhibitors.

FIG. 14 shows example HBV and/or HDV vaccines.

DETAILED DESCRIPTION

The Hepadnavirus family is a family of enveloped viruses utilizing partially double-stranded, partially single-stranded circular DNA genomes. This family includes a group of viruses that cause liver disease in various organisms, and is divided between two genera: the Avihepadnaviruses, affecting birds, and the Orthohepdnaviruses, affecting mammals. Hepatitis B is a causative agent of acute/chronic hepatitis, and has a partially double-stranded 3.2 kb circular DNA from which four proteins are synthesized: the core, polymerase, surface antigen and X-gene product.

During hepatitis infection, HBV virions enter hepatocytes through a receptor-mediated process. Viral replication occurs through a multi-step mechanism. First, the circular, partially double-stranded DNA genome is transcribed by the host cell machinery, and then the full length RNA transcript is packaged into viral procapsids. The transcript is then reverse-transcribed within the capsid by the P protein, utilizing the P protein's intrinsic protein priming activity. The RNA component is then degraded by an intrinsic RNase H activity of the P protein, to yield a full-length minus-strand circular DNA. Finally, a subsequent partial plus-strand DNA is synthesized to yield the final viral genome assembly.

Viral capsids also may release the circular, partially double stranded genome into the nucleus of host cells, where synthesis of the complementary strand to the single stranded region is completed and the remaining viral ends are ligated to form the covalently closed circular DNA (cccDNA), which persists in host cell nuclei and can be passed on to daughter cells during cell division. The presence of the cccDNA gives rise to the risk of viral reemergence throughout the life of the host organism. Additionally, HBV carriers can transmit the disease for many years. Immunosuppressed individuals are especially at risk for the establishment of persistent (chronic) or latent HBV infection.

HDV is a subviral satellite of HBV, and thus, may only propagate in the presence of HBV. See, e.g., Shieh, et al., Nature, 329(6137), pp. 343-346 (1987). Replication of the single-stranded circular RNA HDV genome produces two forms of a RNA-binding protein known as the long and small delta antigens (Ag). After entering a hepatocyte, the virus is uncoated and the nucleocapsid translocated to the nucleus. The virus then uses the host cell's RNA polymerases, which treat the RNA genome as dsDNA due to its tertiary structure. Three forms of RNA are produced during replication: circular genomic RNA, circular complementary antigenomic RNA and a linear polyadenylated antigenomic RNA.

HBV and HDV are primarily transmitted by blood or mucosal contact, including by sexual activity. Infection with HBV and/or HDV leads to a wide spectrum of liver disease ranging from acute (including fulminant hepatic failure) to chronic hepatitis, cirrhosis and hepatocellular carcinoma. Acute HBV and/or HDV infection can be asymptomatic, or present with symptomatic acute effects, including fever, headaches, joint aches, and diarrhea, leading to the more severe symptoms of liver enlargement and/or jaundice associated with conjugated hyperbilirubinemia and cholestasis. Most adults infected with the virus recover, but 5%-10% are unable to clear the virus and become chronically infected. Many chronically infected individuals have persistent mild liver disease (latent HBV and/or HDV), presenting with lymphoid aggregates and bile duct damage, steatosis and/or increased fibrosis that may lead to cirrhosis. Others with chronic HBV and/or HDV infection develop active disease, which can lead to life-threatening conditions such as cirrhosis and liver cancer. Some subjects with latent HBV and/or HDV may relapse and develop acute hepatitis.

HIV is a lentivirus that belongs to the Retroviridae family. HIV is an enveloped virus with a core consisting of two copies of a positive single-stranded RNA. HIV relies upon reverse transcriptase for reverse transcription of RNA into DNA, which becomes incorporated into host genome as a provirus. HIV uses viral glycoprotein 120 (gp 120) to bind to and infect CD4+T lymphocytes. An increase in viral plasma load corresponds to a decrease in CD4+T lymphocyte counts. Normal CD4+T lymphocyte levels are from about 500 to 1,200 cells/mL. Two types of HIV have been characterized, HIV-1 and HIV-2. HIV-1 is more virulent and more infective, and has a global prevalence, whereas HIV-2 is less virulent and is geographically confined.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

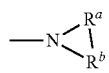

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl) and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), (heteroaryl)alkyl or (heterocyclyl)alkyl is defined herein. A non-limiting list of alkoxys is methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an —O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl (alkyl), (heteroaryl)alkyl or (heterocyclyl)alkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl.

The term "amino" as used herein refers to a —NH$_2$ group.

The term "mono-substituted amino group" refers to an amino group where one hydrogen has been replaced with an R group, for example, "—NHR$_A$," in which R$_A$ can be alkyl, alkenyl, alkynyl, cycloalkyl, cycloalkenyl, aryl, heteroaryl, heterocyclyl, aryl(alkyl), (heteroaryl)alkyl or (heterocyclyl) alkyl. The R$_A$ can be substituted or unsubstituted.

The term "di-substituted amino group" refers to an amino group where both hydrogens have been replaced with R groups, for example, an "—NR$_A$R$_B$." group in which R$_A$ and R$_B$ can be independently alkyl, alkenyl, alkynyl, cycloalkyl, cycloalkenyl, aryl, heteroaryl, heterocyclyl, aryl(alkyl), (heteroaryl)alkyl or (heterocyclyl)alkyl. R$_A$ and R$_B$ can independently be substituted or unsubstituted.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-sulfonamido may be substituted or unsubstituted.

An "O-carbamyl" group refers to a "—OC(=O)N (R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An O-carbamyl may be substituted or unsubstituted.

An "N-carbamyl" group refers to an "ROC(=O)N (R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-carbamyl may be substituted or unsubstituted.

An "O-thiocarbamyl" group refers to a "—OC(=S)—N (R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An O-thiocarbamyl may be substituted or unsubstituted.

An "N-thiocarbamyl" group refers to an "ROC(=S)N (R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom.

A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "acyclic nucleoside" is used herein in its ordinary sense as understood by those skilled in the art, and refers to a nucleoside having an acyclic moiety that replaces the pentose moiety of nucleoside.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4$,$N^4$-ethanocytosin, $N^6$,$N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

As used herein, a "C-linked" group refers to a group that is attached to the indicated moiety via a carbon atom. For example, a C-linked heterocyclic base refers to a heterocyclic base as defined herein that can be attached to an optionally substituted pentose moiety or modified pentose moiety via a carbon atom of the heterocyclic base. As used herein, an "N-linked" group refers to a heterocyclic base as defined herein that can be attached to an optionally substituted pentose moiety or modified pentose moiety via a nitrogen atom of the heterocyclic base. For example, an N-linked heterocyclic base refers to an optionally substituted nitrogen-containing heterocyclyl that can be attached to an optionally substituted pentose moiety or modified pentose moiety via a nitrogen atom.

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

As used herein, the term "phosphate" is used in its ordinary sense as understood by those skilled in the art, and includes its protonated forms (for example,

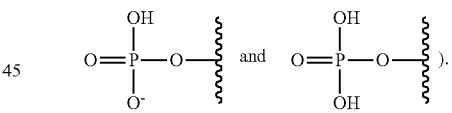

As used herein, the terms monophosphate, diphosphate and triphosphate are used in their ordinary sense as understood by those skilled in the art, and include protonated forms.

Likewise, the term "phosphonate" is also used in its ordinary sense as understood by those skilled in the art, and includes its protonated forms (for example,

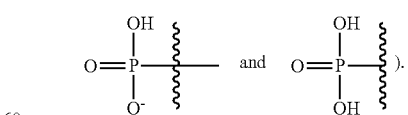

As used herein, the terms "monophosphonate," "diphosphonate" and "triphosphonate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propyl silyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

The term "interferon" is used herein as is commonly understood by one of ordinary skill in the art. Several types of interferons are known to those skilled in the art, such as Type I interferons, Type 2 interferons and Type 3 interferons. A non-limiting list of examples include: alpha-interferons, beta-interferons, delta-interferons, gamma interferons, lambda interferons, omega-interferons, tau-interferons, x-interferons, consensus interferons and asialo-interferons. Interferons can be pegylated. Examples of type 1 interferons include interferon alpha 1A, interferon alpha 1B, interferon alpha 2A, interferon alpha 2B, pegylated-interferon alpha 2a (PEGASYS, Roche), recombinant interferon alpha 2a (ROFERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical). Examples of type 2 interferons include interferon gamma 1, interferon gamma 2 and pegylated interferon gamma; and examples of type 3 interferons include interferon lambda 1, interferon lambda 2 and interferon lambda 3.

The term "FXR agonist" refers to compounds that function by targeting and selectively binding FXR and which activate FXR by at least 40% above background in the assay described in Maloney et al., *J. Med. Chem.*, Vol. 43, pp. 2971-2974 (2000).

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may be independently of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may be independently E or Z, or a mixture thereof.

Likewise, it is understood that, in any compound described, all tautomeric forms are also intended to be included. For example all tautomers of a phosphate and a phosphonate groups are intended to be included. Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

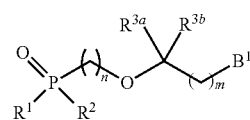

(I)

wherein: $B^1$ can be an optionally substituted C-linked bicyclic heteroaryl containing 9 atoms in the rings and 3, 4 or 5 nitrogens or an optionally substituted C-linked bicyclic heterocyclyl containing 9 atoms in the rings and 3, 4 or 5 nitrogens; $R^1$ and $R^2$ can be independently selected from $O^-$, —OH, an optionally substituted —O—$C_{1-24}$ alkyl, an optionally substituted —O—$C_{2-24}$ alkenyl, an optionally substituted —O—$C_{2-24}$ alkynyl, an optionally substituted —O—$C_{3-6}$ cycloalkyl, an optionally substituted —O—$C_{3-6}$ cycloalkenyl, an optionally substituted —O-aryl, an optionally substituted —O-heteroaryl, an optionally substituted —O-aryl($C_{1-6}$ alkyl), an optionally substituted *—O—$(CR^4R^5)_p$—O—$C_{1-24}$ alkyl, an optionally substituted *—O—$(CR^6R^7)_q$—O—$C_{1-24}$ alkenyl,

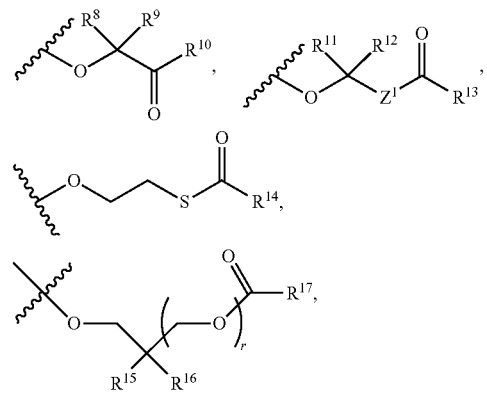

an optionally substituted N-linked amino acid and an optionally substituted N-linked amino acid ester derivative; or $R^1$ can be

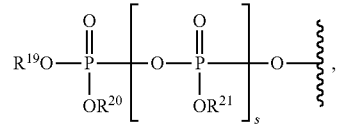

and $R^2$ can be $O^-$ or OH; or $R^1$ and $R^2$ can be taken together to form a moiety selected from an optionally substituted

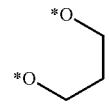

and an optionally substituted

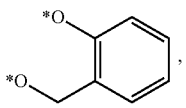, wherein the phosphorus and the moiety form a six-membered to ten-membered ring system; $R^{3a}$ and $R^{3b}$ can be independently selected from hydrogen, fluoro, an unsubstituted $C_{1-4}$ alkyl, an unsubstituted $C_{3-6}$ cycloalkyl, cyano, halogen($C_{1-4}$ alkyl), hydroxy($C_{1-4}$ alkyl), alkoxy($C_{1-4}$ alkyl), acyl($C_{1-4}$ alkyl) and cyano($C_{1-4}$ alkyl); or $R^{3a}$ and $R^{3b}$ can be taken together with the carbon to which they are connected to form an optionally substituted $C_{3-6}$ cycloalkyl; each $R^4$, each $R^5$, each $R^6$ and each $R^7$ can be independently hydrogen, an optionally substituted $C_{1-24}$ alkyl or alkoxy; $R^8$, $R^9$, $R^{11}$ and $R^{12}$ can be independently selected from hydrogen, an optionally substituted $C_{1-24}$ alkyl and an optionally substituted aryl; $R^{10}$ and $R^{13}$ can be independently selected from hydrogen, an optionally substituted $C_{1-24}$ alkyl, an optionally substituted aryl, an optionally substituted —O—$C_{1-24}$ alkyl, an optionally substituted —O-heteroaryl and an optionally substituted —O-monocyclic heterocyclyl; $R^{14}$ can be selected from hydrogen, an optionally substituted $C_{1-24}$ alkyl and an optionally substituted aryl; $R^{15}$ and $R^{16}$ can be independently selected from —C≡N, an optionally substituted $C_{2-8}$ organylcarbonyl, an optionally substituted $C_{2-8}$ alkoxycarbonyl and an optionally substituted $C_{2-8}$ organylaminocarbonyl; $R^{17}$ can be selected from can be hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{19}$, $R^{20}$ and $R^{21}$ can be independently absent or hydrogen; m can be 0 or 1; n can be 1 or 2; p and q can be independently selected from 1, 2 and 3; r can be 1 or 2; s can be 0 or 1; and $Z^1$ can be oxygen (O) or sulfur (S). In some embodiments, at least one of $R^{3a}$ and $R^{3b}$ is hydrogen.

A variety of $R^1$ and $R^2$ groups can be attached to the phosphorus atom of Formula (I).

In some embodiments, one of $R^1$ and $R^2$ can be O⁻ or —OH, and the other of $R^1$ and $R^2$ can be selected from an optionally substituted —O—$C_{1-24}$ alkyl, an optionally substituted —O—$C_{2-24}$ alkenyl, an optionally substituted —O—$C_{2-24}$ alkynyl, an optionally substituted —O—$C_{3-6}$ cycloalkyl, an optionally substituted —O—O—$C_{3-6}$ cycloalkenyl, an optionally substituted —O-aryl, an optionally substituted —O-heteroaryl and an optionally substituted —O-aryl($C_{1-6}$ alkyl). In some embodiments, one of $R^1$ and $R^2$ can be O⁻ or —OH, and the other of $R^1$ and $R^2$ can be an optionally substituted —O—$C_{1-24}$ alkyl. In other embodiments, both $R^1$ and $R^2$ can be independently selected from an optionally substituted —O—$C_{1-24}$ alkyl, an optionally substituted —O—$C_{2-24}$ alkenyl, an optionally substituted —O—$C_{2-24}$ alkynyl, an optionally substituted —O—$C_{3-6}$ cycloalkyl, an optionally substituted —O—$C_{3-6}$ cycloalkenyl, an optionally substituted —O-aryl, an optionally substituted —O-heteroaryl and an optionally substituted —O-aryl($C_{1-6}$ alkyl). In some embodiments, both $R^1$ and $R^2$ can be an optionally substituted —O—$C_{1-24}$ alkyl. In other embodiments, both $R^1$ and $R^2$ can be an optionally substituted —O—$C_{2-24}$ alkenyl. In some embodiments, $R^1$ and $R^2$ can be independently an optionally substituted group selected from the following: —O-myristoleyl, —O-myristyl, —O-palmitoleyl, —O-palmityl, —O-sapienyl, —O-oleyl, —O-elaidyl, —O-vaccenyl, —O-linoleyl, —O-α-linolenyl, —O-arachidonyl, —O-eicosapentaenyl, —O-erucyl, —O— docosahexaenyl, —O-caprylyl, —O-capryl, —O-lauryl, —O-stearyl, —O-arachidyl, —O-behenyl, —O-lignoceryl and —O-cerotyl.

In some embodiments, at least one of $R^1$ and $R^2$ can be an optionally substituted *—O—$(CR^4R^5)_p$—O—$C_{1-24}$ alkyl. In other embodiments, $R^1$ and $R^2$ can be both an optionally substituted *—O—$(CR^4R^5)_p$—O—$C_{1-24}$ alkyl. In some embodiments, each $R^4$ and each $R^5$ can be hydrogen. In other embodiments, at least one of $R^4$ and $R^5$ can be an optionally substituted $C_{1-24}$ alkyl. In other embodiments, at least one of $R^4$ and $R^5$ can be an alkoxy (for example, benzoxy). In some embodiments, p can be 1. In other embodiments, p can be 2. In still other embodiments, p can be 3.

In some embodiments, at least one of $R^1$ and $R^2$ can be an optionally substituted *—O—$(CR^6R^7)_q$—O—$C_{1-24}$ alkenyl. In other embodiments, $R^1$ and $R^2$ can be both an optionally substituted *—O—$(CR^6R^7)_q$—O—$C_{1-24}$ alkenyl. In some embodiments, each $R^6$ and each $R^7$ can be hydrogen. In other embodiments, at least one of $R^6$ and $R^7$ can be an optionally substituted $C_{1-24}$ alkyl. In some embodiments, q can be 1. In other embodiments, q can be 2. In still other embodiments, q can be 3. When at least one of $R^1$ and $R^2$ is *—O—$(CR^4R^5)_p$—O—$C_{1-24}$ alkyl or an optionally substituted *—O—$(CR^6R^7)_q$—O—$C_{1-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, at least one of $R^1$ and $R^2$ can be selected from

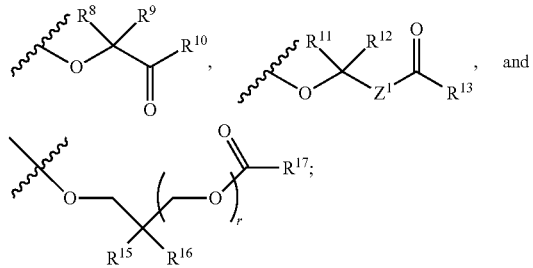

and the other of $R^1$ and $R^2$ can be selected from O⁻, —OH, an optionally substituted —O—$C_{1-24}$ alkyl, an optionally substituted —O—$C_{2-24}$ alkenyl, an optionally substituted —O—$C_{2-24}$ alkynyl, an optionally substituted —O—$C_{3-6}$ cycloalkyl, an optionally substituted —O—$C_{3-6}$ cycloalkenyl, an optionally substituted —O-aryl, an optionally substituted —O-heteroaryl and an optionally substituted —O-aryl($C_{1-6}$ alkyl).

In some embodiments, at least one of $R^1$ and $R^2$ can be

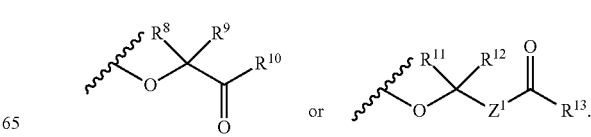

In some embodiments, both $R^1$ and $R^2$ can be

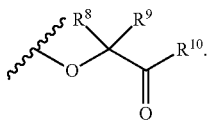

When one or both of $R^1$ and $R^2$ are

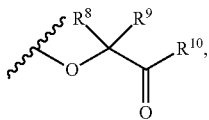

$R^8$ and $R^9$ can be independently selected from hydrogen, an optionally substituted $C_{1-24}$ alkyl and an optionally substituted aryl; and $R^{10}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl. In some embodiments, $R^8$ and $R^9$ can be hydrogen. In other embodiments, at least one of $R^8$ and $R^9$ can be an optionally substituted $C_{1-24}$ alkyl or an optionally substituted aryl. In some embodiments, $R^{10}$ can be an optionally substituted $C_{1-24}$ alkyl. In some embodiments, $R^{10}$ can be an unsubstituted $C_{1-4}$ alkyl. In other embodiments, $R^{10}$ can be an optionally substituted aryl. In still other embodiments, $R^{10}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{10}$ can be an unsubstituted —O—$C_{1-4}$ alkyl.

In some embodiments, both $R^1$ and $R^2$ can be

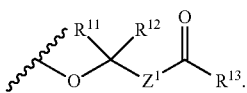

When one or both of $R^1$ and $R^2$ are

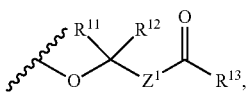

$R^{11}$ and $R^{12}$ can be independently selected from hydrogen, an optionally substituted $C_{1-24}$ alkyl and an optionally substituted aryl; $R^{13}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl; and $Z^1$ can be independently O (oxygen) or S (sulfur). In some embodiments, $R^{11}$ and $R^{12}$ can be hydrogen. In other embodiments, at least one of $R^{11}$ and $R^{12}$ can be an optionally substituted $C_{1-24}$ alkyl or an optionally substituted aryl. In some embodiments, $R^{13}$ can be an optionally substituted $C_{1-24}$ alkyl. In some embodiments, $R^{13}$ can be an unsubstituted $C_{1-4}$ alkyl. In other embodiments, $R^{13}$ can be an optionally substituted aryl. In still other embodiments, $R^{13}$ can be an optionally substituted —O—$C_{1-24}$ alkyl, an optionally substituted —O-aryl, an optionally substituted —O-heteroaryl or an optionally substituted —O-monocyclic heterocyclyl. In some embodiments, $R^{13}$ can be an unsubstituted —O—$C_{1-4}$ alkyl. In some embodiments, $Z^1$ can be O (oxygen). In other embodiments, $Z^1$ can be or S (sulfur). In some embodiments, one or both of $R^1$ and $R^2$ can be an optionally substituted isopropyloxycarbonyloxymethoxy (POC). In some embodiments, $R^1$ and $R^2$ each can be an optionally substituted isopropyloxycarbonyloxymethoxy (POC) group, and form an optionally substituted bis(isopropyloxycarbonyloxymethyl) (bis(POC)) prodrug. In other embodiments, one or both of $R^1$ and $R^2$ can be an optionally substituted pivaloyloxymethoxy (POM). In some embodiments, $R^1$ and $R^2$ each can be an optionally substituted pivaloyloxymethoxy (POM) group, and form an optionally substituted bis(pivaloyloxymethyl) (bis(POM)) prodrug.

In some embodiments, at least one of $R^1$ and $R^2$ can be

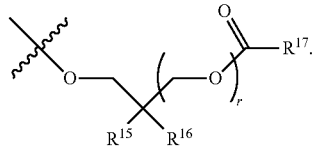

In some embodiments, both $R^1$ and $R^2$ can be

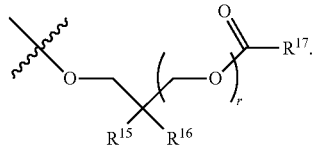

When one or both of $R^1$ and $R^2$ are

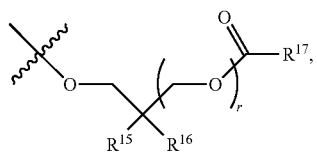

$R^{15}$ and $R^{16}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{17}$ can be selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and r can be 1 or 2. In some embodiments, $R^{15}$ can be —C≡N and $R^{16}$ can be an optionally substituted $C_{2-8}$ alkoxycarbonyl, such as —C(=O)OCH$_3$. In other embodiments, $R^{15}$ can be —C≡N and $R^{16}$ can be an optionally substituted $C_{2-8}$ organylaminocarbonyl, for example, —C(=O)NHCH$_2$CH$_3$ and —C(=O)NHCH$_2$CH$_2$phenyl. In some embodiments, both $R^{15}$ and $R^{16}$ can be an optionally substituted $C_{2-8}$ organylcarbonyl, such as —C(=O)CH$_3$. In some embodiments, both $R^{15}$ and $R^{16}$ can be an optionally substituted $C_{1-8}$ alkoxycarbonyl, for example, —C(=O)OCH$_2$CH$_3$ and —C(=O)OCH$_3$. In some embodiments, including those described in this paragraph, $R^{17}$ can be an optionally substituted $C_{1-4}$ alkyl. In some embodiment, $R^{17}$ can be methyl or tert-butyl. In some embodiments, r can be 1. In other embodiments, r can be 2.

In some embodiments, $R^1$ and $R^2$ can be both an optionally substituted —O-aryl. In some embodiments, at least one of $R^1$ and $R^2$ can be an optionally substituted —O-aryl. For example, both $R^1$ and $R^2$ can be an optionally substituted —O-phenyl or an optionally substituted —O-naphthyl. When substituted, the substituted —O-aryl can be substituted with 1, 2, 3 or more than 3 substituents. When more than two substituents are present, the substituents can be the same or different. In some embodiments, when at least one of $R^1$ and $R^2$ is a substituted —O-phenyl, the substituted —O-phenyl can be a para, ortho- or meta-substituted.

In some embodiments, $R^1$ and $R^2$ can be both an optionally substituted —O-aryl($C_{1-6}$ alkyl). In some embodiments, at least one of $R^1$ and $R^2$ can be an optionally substituted —O-aryl($C_{1-6}$ alkyl). For example, both $R^1$ and $R^2$ can be an optionally substituted —O-benzyl. When substituted, the substituted —O-benzyl group can be substituted with 1, 2, 3 or more than 3 substituents. When more than two substituents are present, the substituents can be the same or different. In some embodiments, the —O-aryl group of the aryl($C_{1-6}$ alkyl) can be a para-, ortho- or meta-substituted phenyl.

In some embodiments, at least one of $R^1$ and $R^2$ can be

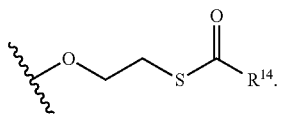

In some embodiments, $R^1$ and $R^2$ can be both

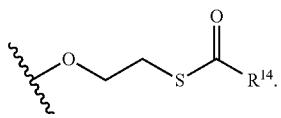

In some embodiments, at least one of $R^1$ and $R^2$ can be

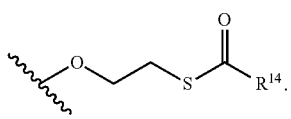

In some embodiments, $R^{14}$ can be hydrogen. In other embodiments, $R^{14}$ can be an optionally substituted $C_{1-24}$ alkyl. In still other embodiments, $R^{14}$ can be an optionally substituted aryl (for example, an optionally substituted phenyl). In some embodiments, $R^{14}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, $R^1$ and $R^2$ can be both an optionally substituted S-acylthioethoxy (SATE) group and form an optionally substituted SATE ester prodrug.

In some embodiments, $R^1$ and $R^2$ can be taken together to form an optionally substituted

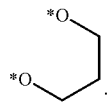

For example, when $R^1$ and $R^2$ can be taken together, the resulting moiety can be an optionally substituted

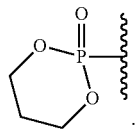

When substituted, the ring can be substituted 1, 2, 3 or 3 or more times. When substituted with multiple substituents, the substituents can be the same or different. In some embodiments, the ring

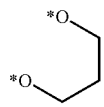

can be substituted with an optionally substituted aryl group and/or an optionally substituted heteroaryl. An example of a suitable heteroaryl is pyridinyl. In some embodiments, $R^1$ and $R^2$ can be taken together to form an optionally substituted

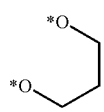

such as

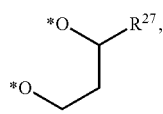

wherein $R^{27}$ can be an optionally substituted aryl, an optionally substituted heteroaryl or an optionally substituted heterocyclyl. In some embodiments, $R^1$ and $R^2$ can form an optionally substituted cyclic 1-aryl-1,3-propanyl ester (HepDirect) prodrug moiety.

In some embodiments, $R^1$ and $R^2$ can be taken together to form an optionally substituted

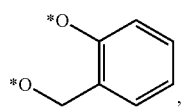

wherein the phosphorus and the moiety form a six-membered to ten-membered ring system. Example of an optionally substituted include

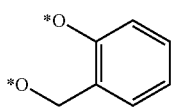

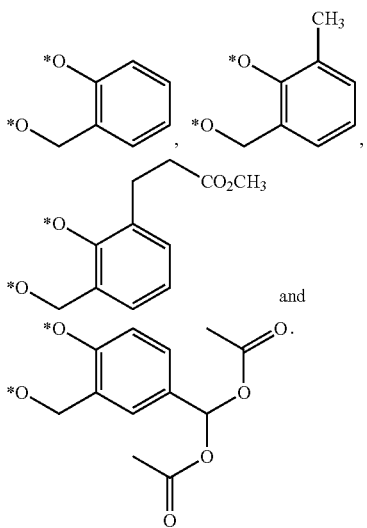

In some embodiments, $R^1$ and $R^2$ can form an optionally substituted cyclosaligenyl (cycloSal) prodrug.

In other embodiments, $R^1$ can be an optionally substituted —O-aryl; and $R^2$ can be an optionally substituted N-linked amino acid or an optionally substituted N-linked amino acid ester derivative. In still other embodiments, $R^1$ can be an optionally substituted —O-heteroaryl; and $R^2$ can be an optionally substituted N-linked amino acid or an optionally substituted N-linked amino acid ester derivative.

In some embodiments, when $R^1$ can be an optionally substituted —O-aryl, $R^1$ can be an optionally substituted —O-phenyl. When the phenyl is substituted, the ring can be substituted 1, 2, 3 or more than 3 times. When substituted, the phenyl can be substituted at one or both ortho positions, one or both meta positions and/or the para position. In some embodiments, $R^1$ can be an unsubstituted —O-aryl. In some embodiments, $R^1$ can be an optionally substituted —O-naphthyl. In some embodiments, $R^1$ can be an unsubstituted —O— phenyl. In some embodiments, $R^1$ can be an unsubstituted —O-naphthyl.

In some embodiments, when $R^2$ can be an optionally substituted N-linked amino acid or an optionally substituted N-linked amino acid ester derivative. Various amino acids are suitable, including those described herein. Examples of suitable amino acids include α-amino acids such as alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. In other embodiments, $R^2$ can be an optionally substituted N-linked amino acid ester derivative, for example, optionally substituted N-linked α-amino acid ester derivatives. Examples of suitable amino acid ester derivatives include, but are not limited to, an ester derivative of any of the following amino acids, alanine, asparagine, aspartate, cysteine, glutamate, glycine, proline, serine, tyrosine, arginine, histidine, isoleucine, leucine, lysine, methionine, phenylalanine, threonine, tryptophan, and valine. Examples of suitable ester moieties are described herein and include $C_{1-6}$ alkyl, $C_{3-6}$ cycloalkyl, phenyl ester or benzyl ester (each of which can be substituted or unsubstituted) Additional examples of N-linked amino acid ester derivatives include, but are not limited to, an ester derivative of any of the following amino acids: alpha-ethyl-glycine, alpha-propyl-glycine and beta-alanine. In some embodiments, the N-linked amino acid ester derivative can be selected from N-alanine isopropyl ester, N-alanine cyclohexyl ester, N-alanine neopentyl ester, N-valine isopropyl ester and N-leucine isopropyl ester.

In some embodiments, $R^2$ can be

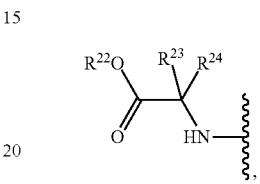

wherein $R^{22}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{23}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{24}$ can be hydrogen or an optionally substituted $C_{1-4}$-alkyl; or $R^{23}$ and $R^{24}$ can be taken together to form an optionally substituted $C_{3-6}$ cycloalkyl.

In some embodiments, $R^{23}$ can be substituted by a variety of substituents. Suitable examples of substituents include, but are not limited to, N-amido, mercapto, alkylthio, an optionally substituted aryl, hydroxyl, an optionally substituted heteroaryl, O-carboxy and amino. In some embodiments $R^{23}$ can be hydrogen. In some embodiments, $R^{23}$ can be an optionally substituted $C_{1-6}$-alkyl. In some embodiments, $R^{24}$ can be hydrogen. In some embodiments $R^{24}$ can be an optionally substituted $C_{1-4}$ alkyl, such as methyl, ethyl, n-propyl, isopropyl, n-butyl, isobutyl or tert-butyl. In some embodiments $R^{24}$ can be methyl. In some embodiments, $R^{22}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{22}$ can be methyl or isopropyl. In some embodiments, $R^{22}$ can be ethyl or neopentyl. In some embodiments, $R^{22}$ can be an optionally substituted $C_{3-6}$ cycloalkyl. Examples of optionally substituted $C_{3-6}$ cycloalkyls include optionally substituted variants of the following: cyclopropyl, cyclobutyl, cyclopentyl and cyclohexyl. Depending on the groups that are selected for $R^{23}$ and $R^{24}$, the carbon to which $R^{23}$ and $R^{24}$ are attached may be a chiral center. In some embodiments, the carbon to which $R^{23}$ and $R^{24}$ are attached may be a (R)-chiral center. In other embodiments, the carbon to which $R^{23}$ and $R^{24}$ are attached may be a (S)-chiral center.

Examples of suitable

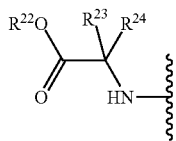

groups include the following

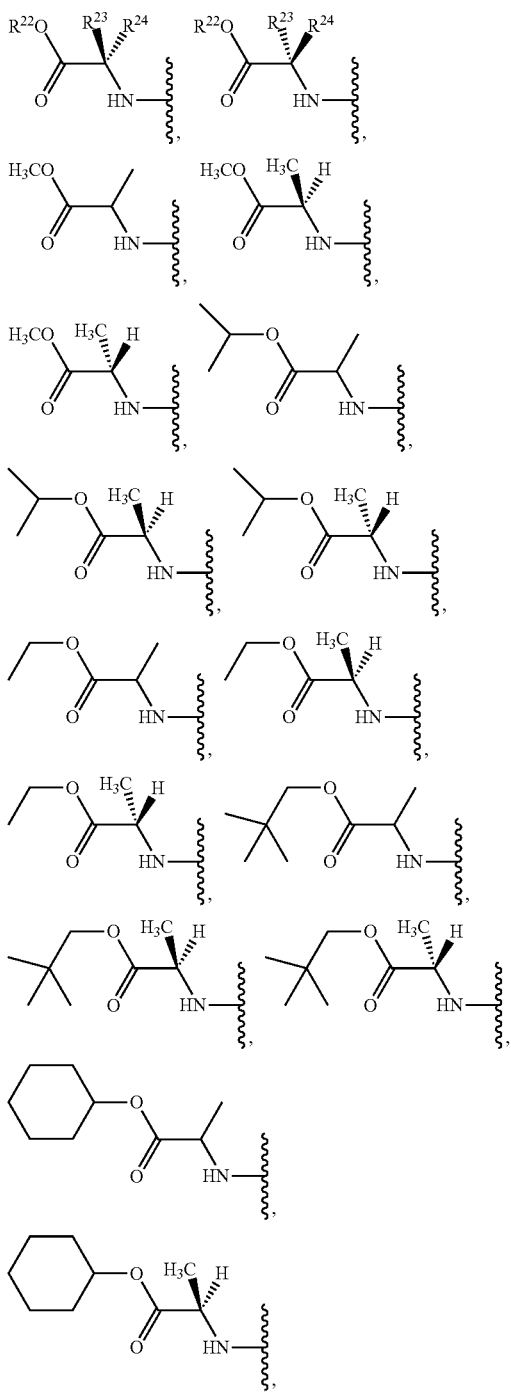

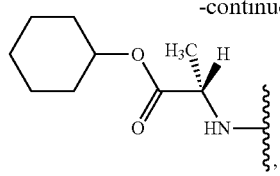

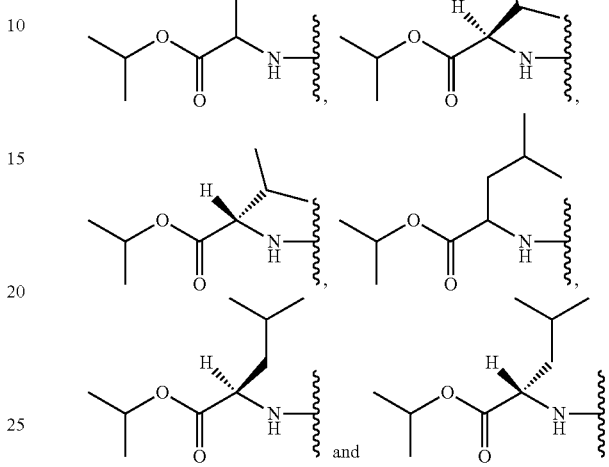

In some embodiments, $R^1$ and $R^2$ can form a phosphoroamidate prodrug, such as an optionally substituted aryl phosphoroamidate prodrug. For example, $R^1$ can be an —O-optionally substituted aryl (for example, optionally substituted phenyl or optionally substituted naphthyl), and $R^2$ can be an optionally substituted N-linked amino acid or an optionally substituted N-linked amino acid ester derivative.

In some embodiments, both $R^1$ and $R^2$ can be independently an optionally substituted N-linked amino acid or an optionally substituted N-linked amino acid ester derivative. Various amino acids are suitable, including those described herein. Examples of suitable amino acids include α-amino acids such as alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. In other embodiments, both $R^1$ and $R^2$ can be independently an optionally substituted N-linked amino acid ester derivative. Examples of suitable amino acid ester derivative, for example, optionally substituted N-linked α-amino acid ester derivatives. Examples of suitable amino acid ester derivatives include, but are not limited to, an ester derivative of any of the following amino acids, alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. Examples of suitable ester moieties are described herein and include $C_{1-6}$ alkyl, $C_{3-6}$ cycloalkyl, phenyl ester or benzyl ester (each of which can be substituted or unsubstituted) Additional examples of N-linked amino acid ester derivatives include, but are not limited to, an ester derivative of any of the following amino acids: alpha-ethyl-glycine, alpha-propyl-glycine and beta-alanine. In some embodiments, the N-linked amino acid ester derivative can be selected from N-alanine isopropyl ester, N-alanine cyclohexyl ester, N-alanine neopentyl ester, N-valine isopropyl ester and N-leucine isopropyl ester. In some embodiments, $R^1$ and $R^2$ can form an optionally substituted phosphonic diamide prodrug.

In some embodiments, both $R^1$ and $R^2$ can be independently

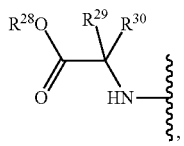

wherein $R^{28}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{29}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{30}$ can be hydrogen or an optionally substituted $C_{1-4}$-alkyl; or $R^{29}$ and $R^{30}$ can be taken together to form an optionally substituted $C_{3-6}$ cycloalkyl.

In some embodiments, $R^{29}$ can be substituted by a variety of substituents. Suitable examples of substituents include, but are not limited to, N-amido, mercapto, alkylthio, an optionally substituted aryl, hydroxyl, an optionally substituted heteroaryl, O-carboxy and amino. In some embodiments $R^{29}$ can be hydrogen. In some embodiments, $R^{29}$ can be an optionally substituted $C_{1-6}$-alkyl. In some embodiments, $R^{30}$ can be hydrogen. In some embodiments $R^{30}$ can be an optionally substituted $C_{1-4}$ alkyl, such as methyl, ethyl, n-propyl, isopropyl, n-butyl, isobutyl or tert-butyl. In some embodiments $R^{30}$ can be methyl. In some embodiments, $R^{28}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{28}$ can be methyl or isopropyl. In some embodiments, $R^{28}$ can be ethyl or neopentyl. In some embodiments, $R^{28}$ can be an optionally substituted $C_{3-6}$ cycloalkyl. Examples of optionally substituted $C_{3-6}$ cycloalkyls include optionally substituted variants of the following: cyclopropyl, cyclobutyl, cyclopentyl and cyclohexyl. Depending on the groups that are selected for $R^{29}$ and $R^{30}$, the carbon to which $R^{29}$ and $R^{30}$ are attached may be a chiral center. In some embodiments, the carbon to which $R^{29}$ and $R^{30}$ are attached may be a (R)-chiral center. In other embodiments, the carbon to which $R^{29}$ and $R^{30}$ are attached may be a (S)-chiral center.

Examples of suitable

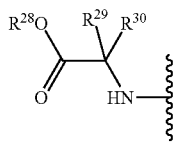

groups include the following

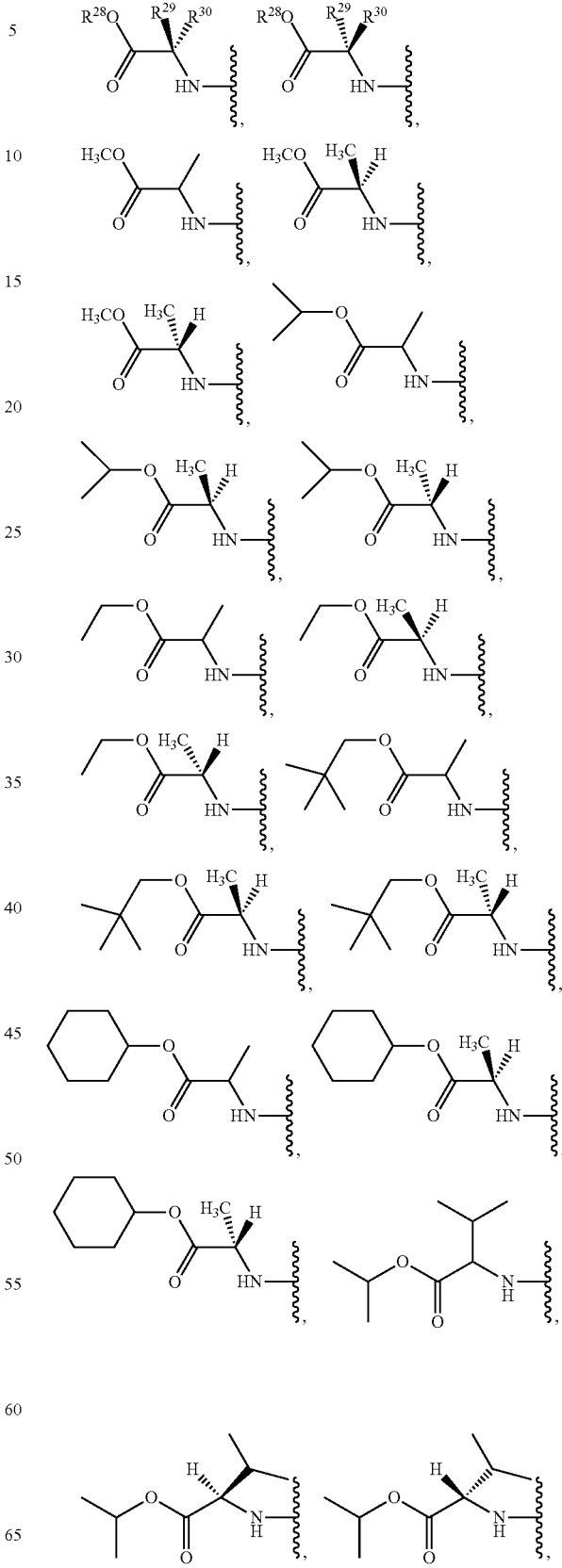

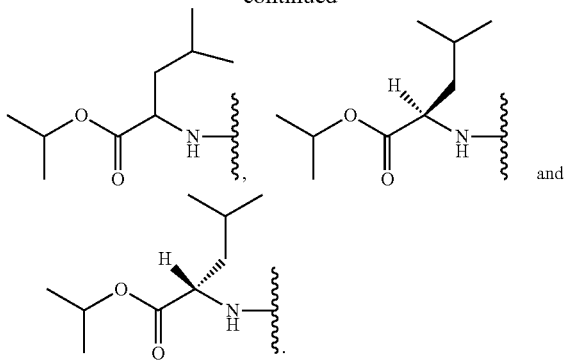

In some embodiments, $R^1$ and $R^2$ can be the same. In some embodiments, $R^1$ and $R^2$ can be different.

In some embodiments, $R^1$ and $R^2$ can be independently $O^-$ or —OH. In other embodiments, $R^1$ can be

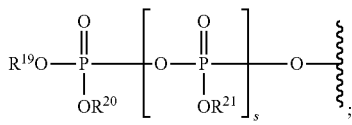

wherein s can be 0; $R^{19}$ and $R^{20}$ can be independently absent or hydrogen; and $R^2$ can be $O^-$ or —OH. Those skilled in the art understand that when $R^{19}$, $R^{20}$ and $R^{21}$ are absent, the associated oxygen can have a negative charge. For example, when $R^{20}$ is absent, then the associated oxygen can have a negative charge, such that $R^1$ can be

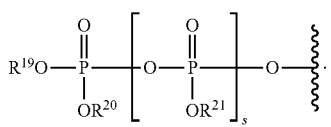

When $R^1$ is

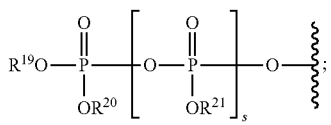

$R^{19}$ and $R^{20}$ are independently absent or hydrogen, s is 0 and $R^2$ is $O^-$ or —OH, a compound of Formula (I), or a pharmaceutically acceptable salt thereof, can be a monophosphonate. In yet other embodiments $R^1$ can be

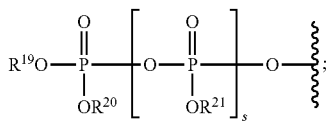

wherein s can be 1; $R^{19}$, $R^{20}$ and $R^{21}$ can be independently absent or hydrogen; and $R^2$ can be $O^-$ or —OH. When $R^1$ is

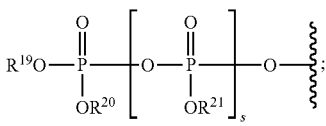

$R^{19}$, $R^{20}$ and $R^{21}$ are independently absent or hydrogen, s is 1 and $R^2$ is $O^-$ or —OH, a compound of Formula (I), or a pharmaceutically acceptable salt thereof, can be a diphosphonate.

In some embodiments, $R^{3a}$ and $R^{3b}$ can be independently selected from hydrogen, halogen (for example, fluoro, chloro, bromo, iodo), an unsubstituted $C_{1-4}$ alkyl, an unsubstituted $C_{3-6}$ cycloalkyl, cyano, halogen($C_{1-4}$ alkyl), hydroxy($C_{1-4}$ alkyl), alkoxy($C_{1-4}$ alkyl), acyl($C_{1-4}$ alkyl) and cyano($C_{1-4}$ alkyl). In some embodiments, $R^{3a}$ and $R^{3b}$ can each be hydrogen. In some embodiments, at least one of $R^{3a}$ and $R^{3b}$ is hydrogen. In some embodiments, at least one of $R^{3a}$ and $R^{3b}$ is halogen. In some embodiments, at least one of $R^{3a}$ and $R^{3b}$ is fluoro. In some embodiments, $R^{3a}$ and $R^{3b}$ can each be an unsubstituted $C_{1-4}$ alkyl. In some embodiments, $R^{3a}$ and $R^{3b}$ can each be an unsubstituted methyl. In other embodiments, one of $R^{3a}$ and $R^{3b}$ can be hydrogen, and other of $R^{3a}$ and $R^{3b}$ can be an unsubstituted $C_{1-4}$ alkyl (such as methyl, ethyl, n-propyl, iso-propyl, n-butyl, iso-butyl and tert-butyl). In some embodiments, one of $R^{3a}$ and $R^{3b}$ can be hydrogen, and other of $R^{3a}$ and $R^{3b}$ can be methyl. In still other embodiments, one of $R^{3a}$ and $R^{3b}$ can be hydrogen, and other of $R^{3a}$ and $R^{3b}$ can be halogen($C_{1-4}$ alkyl). For example, one of $R^{3a}$ and $R^{3b}$ can be hydrogen, and other of $R^{3a}$ and $R^{3b}$ can be $CH_2F$; one of $R^{3a}$ and $R^{3b}$ can be hydrogen, and other of $R^{3a}$ and $R^{3b}$ can be $CHF_2$; one of $R^{3a}$ and $R^{3b}$ can be hydrogen, and other of $R^{3a}$ and $R^{3b}$ can be $CF_3$. In yet still other embodiments, one of $R^{3a}$ and $R^{3b}$ can be hydrogen, and other of $R^{3a}$ and $R^{3b}$ can be hydroxy($C_{1-4}$ alkyl) (including —$CH_2OH$). In some embodiments, one of $R^{3a}$ and $R^{3b}$ can be hydrogen, and other of $R^{3a}$ and $R^{3b}$ can be alkoxy($C_{1-4}$ alkyl) (for example, —$CH_2OCH_3$). In other embodiments, one of $R^{3a}$ and $R^{3b}$ can be hydrogen, and other of $R^{3a}$ and $R^{3b}$ can be acyl($C_{1-4}$ alkyl). In some embodiments, one of $R^{3a}$ and $R^{3b}$ can be hydrogen, and other of $R^{3a}$ and $R^{3b}$ can be —$CH_2C(=O)$ (an unsubstituted $C_{1-4}$ alkyl), such as —$CH_2C(=O)CH_3$. In still other embodiments, one of $R^{3a}$ and $R^{3b}$ can be hydrogen, and other of $R^{3a}$ and $R^{3b}$ can be an unsubstituted $C_{3-6}$ cycloalkyl. In yet still other embodiments, one of $R^{3a}$ and $R^{3b}$ can be hydrogen, and other of $R^{3a}$ and $R^{3b}$ can be cyano. In some embodiments, one of $R^{3a}$ and $R^{3b}$ can be hydrogen, and other of $R^{3a}$ and $R^{3b}$ can be cyano($C_{1-4}$ alkyl). In other embodiments, one of $R^{3a}$ and $R^{3b}$ can be hydrogen, and other of $R^{3a}$ and $R^{3b}$ can be fluoro. In some embodiments, $R^{3a}$ and $R^{3b}$ can be taken together with the carbon to which they are connected to form an optionally substituted $C_{3-6}$ cycloalkyl group. In some embodiments, $R^{3a}$ and $R^{3b}$ can be taken together with the carbon to which they are connected to form an optionally substituted $C_{3-4}$ cycloalkyl group. In some embodiments, $R^{3a}$ and $R^{3b}$ can be taken together with the carbon to which they are connected to form an optionally substituted cyclopropyl group, an optionally substituted cyclobutyl group, an optionally substituted cyclopentyl group, or an optionally substituted cyclohexyl group.

In some embodiments, m can be 0. In other embodiments, m can be 1. In some embodiments, n can be 1. In other embodiments, n can be 2. In some embodiments, m can be 0 and n can be 1. In other embodiments, m can be 0 and n can be 2. In some embodiments, m can be 1 and n can be 1. In other embodiments, m can be 1 and n can be 2.

The nucleobase of a compound described herein can vary. In some embodiments, $B^1$ can be an optionally substituted C-linked bicyclic heteroaryl containing 9 atoms in the rings and 3 nitrogens. In other embodiments, $B^1$ can be an optionally substituted C-linked-bicyclic heteroaryl containing 9 atoms in the rings and 4 nitrogens. In still other embodiments, $B^1$ can be an optionally substituted C-linked bicyclic heteroaryl containing 9 atoms in the rings and 5 nitrogens. In some embodiments, $B^1$ can be an optionally substituted C-linked bicyclic heterocyclyl containing 9 atoms in the rings and 3 nitrogens. In some embodiments, $B^1$ can be an optionally substituted C-linked bicyclic heterocyclyl containing 9 atoms in the rings and 4 nitrogens. In some embodiments, $B^1$ can be an optionally substituted C-linked bicyclic heterocyclyl containing 9 atoms in the rings and 5 nitrogens.

In some embodiments, $B^1$ can have the structure

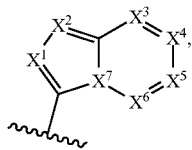

wherein $X^1$, $X^2$, $X^3$, $X^4$, $X^5$, $X^6$ and $X^7$ are independently selected from N and $CR^{25}$, and each $R^{25}$ can be independently selected from hydrogen, halogen, $-NH_2$, $-OH$, an optionally substituted $C_{1-6}$-alkyl and an optionally substituted $(C_{1-6})$alkoxy. In other embodiments, $B^1$ can have the structure

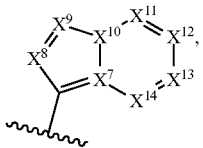

wherein $X^8$, $X^9$, $X^{10}$, $X^{11}$, $X^{12}$, $X^{13}$ and $X^{14}$ are independently selected from N and $CR^{25}$, and each $R^{25}$ can be independently selected from hydrogen, halogen, $-NH_2$, $-OH$, an optionally substituted $C_{1-6}$-alkyl and an optionally substituted $(C_{1-6})$alkoxy.

In some embodiments, $B^1$ can have the structure

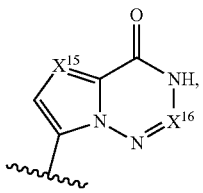

wherein $X^{15}$ and $X^{16}$ can be independently selected from N and $CR^{25}$, and each $R^{25}$ can be independently selected from hydrogen, halogen, $-NH_2$, $-OH$, an optionally substituted $C_{1-6}$-alkyl and an optionally substituted $(C_{1-6})$alkoxy.

Examples of suitable $B^1$ moieties include the following: an optionally substituted

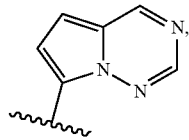 [SMILES: *c1ccc2cncnn12]

an optionally substituted

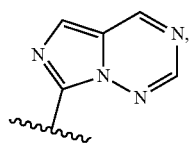 [SMILES: *c1ncc2cncnn12]

an optionally substituted

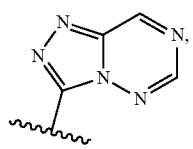 [SMILES: *c1nnc2cncnn12]

an optionally substituted

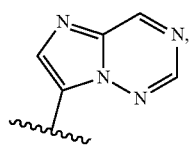 [SMILES: *c1cnc2cncnn12]

an optionally substituted

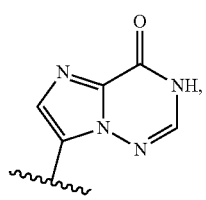 [SMILES: *c1cnc2c(=O)[nH]cnn12]

an optionally substituted

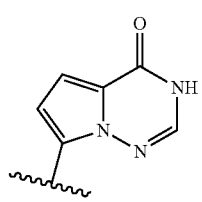 [SMILES: *c1ccc2c(=O)[nH]cnn12]

and an optionally substituted

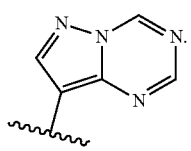

In some embodiments of this paragraph, B¹ can be substituted with —NH₂. In some embodiments of this paragraph, B¹ can be substituted with halo (for example, F). For example, B¹ can be an optionally substituted

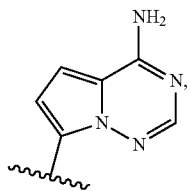 [SMILES: *c1ccc2c(N)ncnn12]

an optionally substituted

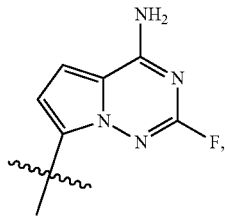 [SMILES: *c1ccc2c(N)nc(F)nn12]

an optionally substituted

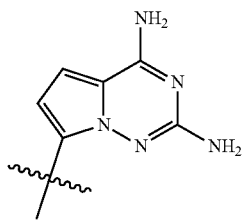 [SMILES: *c1ccc2c(N)nc(N)nn12]

or an optionally substituted

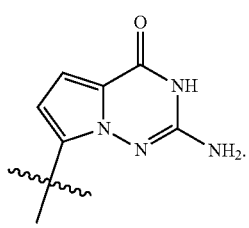 [SMILES: *c1ccc2c(=O)[nH]c(N)nn12]

Examples of a compound of Formula (I), or a pharmaceutically acceptable salt thereof, include:

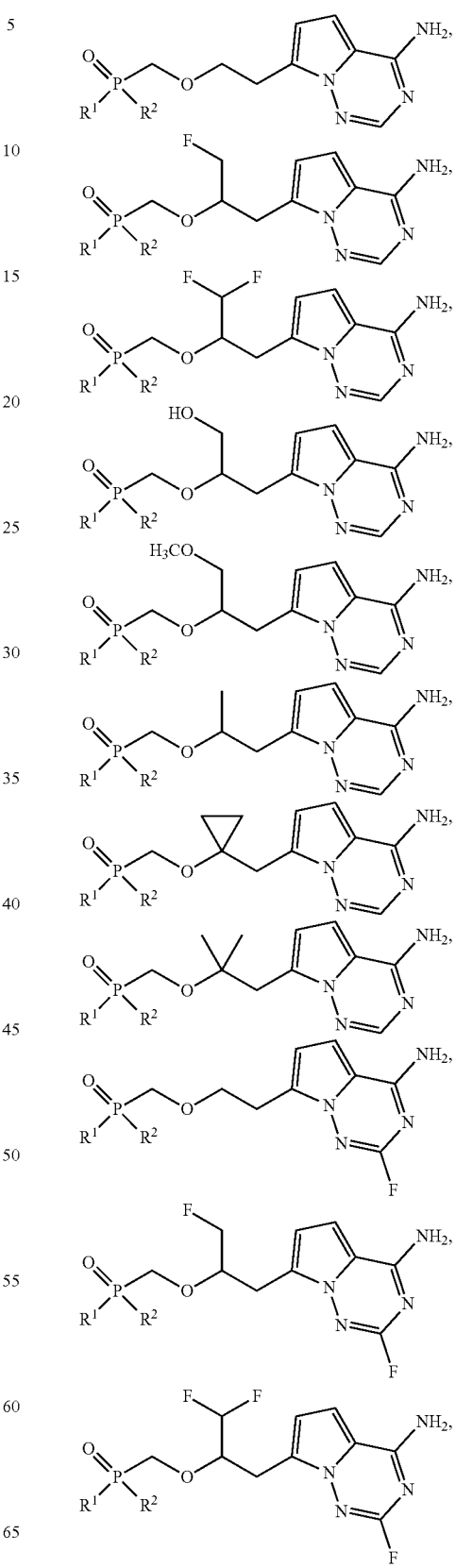

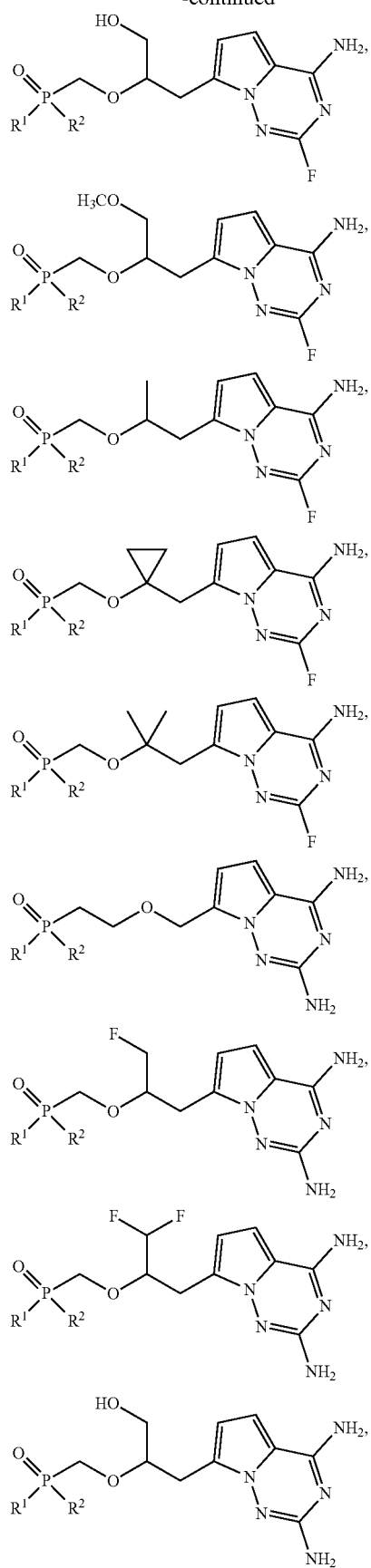
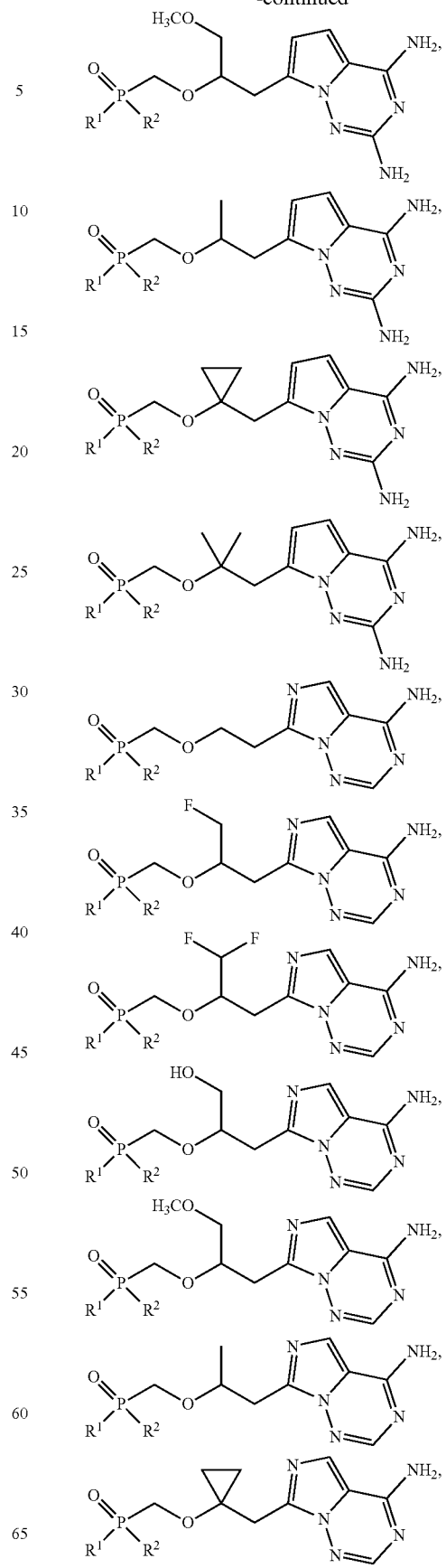

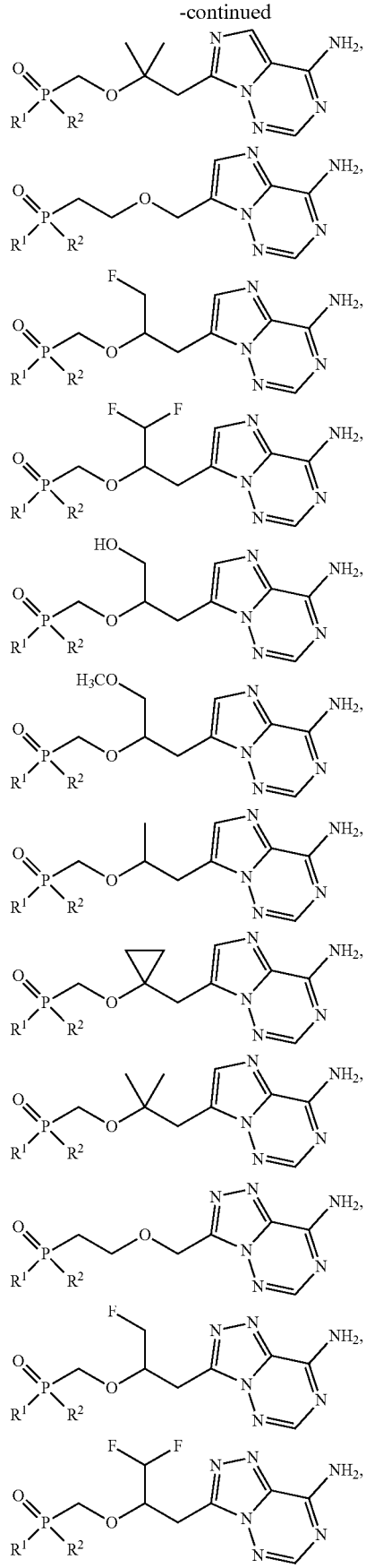
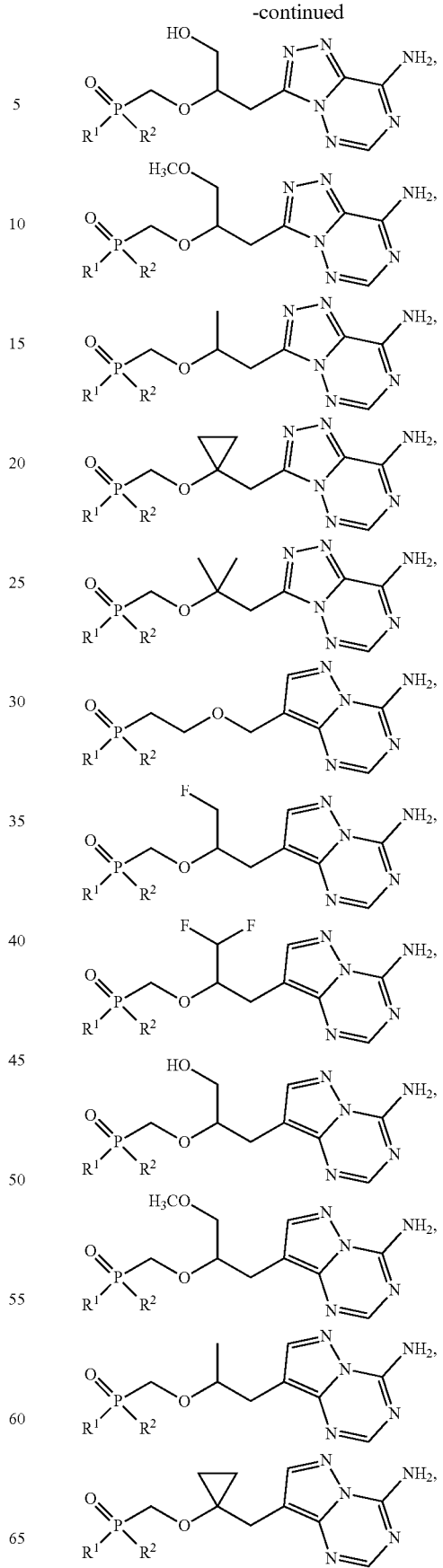

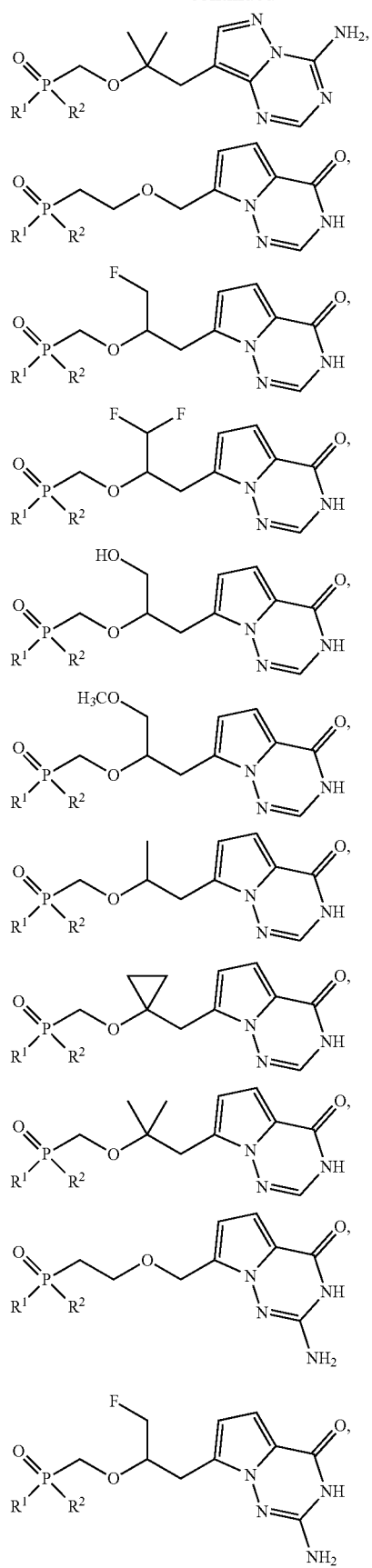
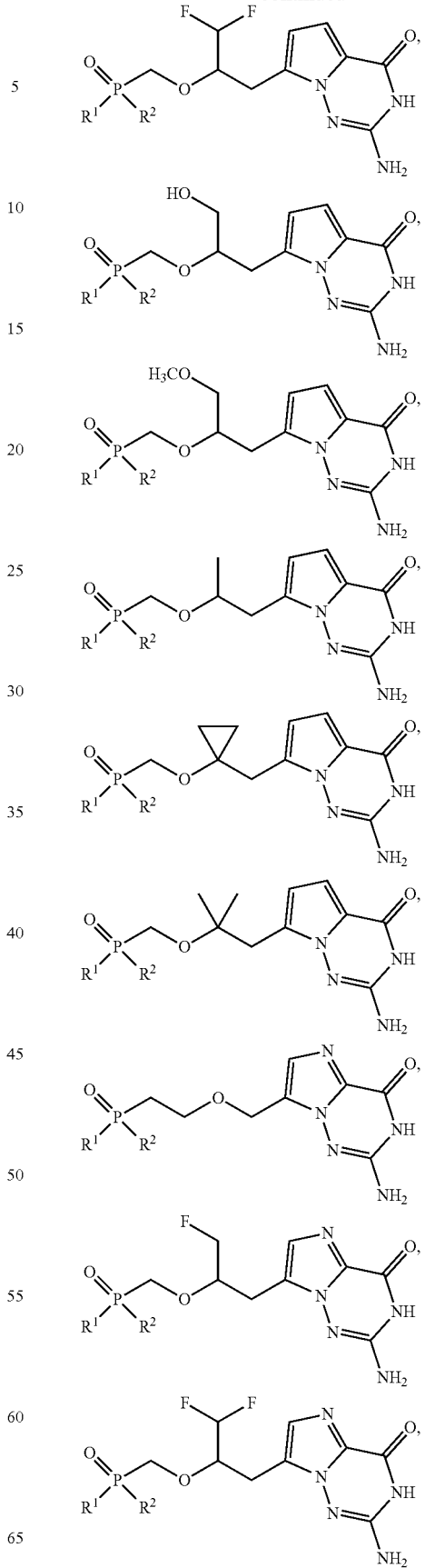

-continued

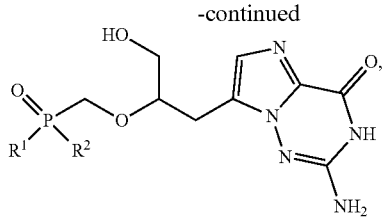

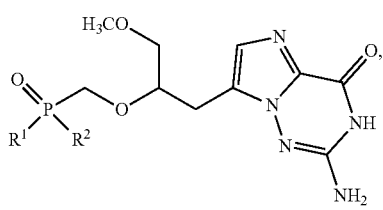

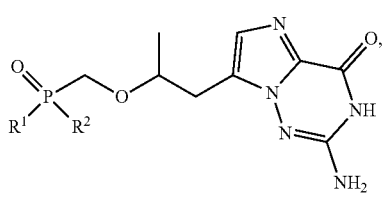

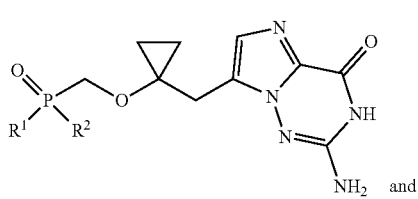

and

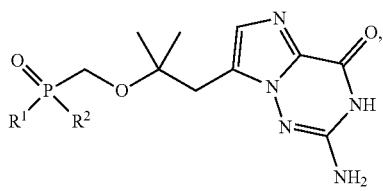

or a pharmaceutically acceptable salt of any of the foregoing. In some embodiments of this paragraph, $R^1$ and $R^2$ each can be an optionally substituted isopropyloxycarbonyloxymethoxy (POC) group, and form an optionally substituted bis(isopropyloxycarbonyloxymethyl) (bis(POC)) prodrug. In some embodiments of this paragraph, $R^1$ and $R^2$ each can be an optionally substituted pivaloyloxymethoxy (POM) group, and form an optionally substituted bis(pivaloyloxymethyl) (bis(POM)) prodrug. In some embodiments of this paragraph, $R^1$ and $R^2$ can form a phosphoroamidate prodrug, such as an optionally substituted aryl phosphoroamidate prodrug. In some embodiments of this paragraph, $R^1$ and $R^2$ can be both an optionally substituted S-acylthioethoxy (SATE) group and form an optionally substituted SATE ester prodrug. In some embodiments of this paragraph, $R^1$ and $R^2$ can form an optionally substituted cyclic 1-aryl-1,3-propanyl ester (HepDirect) prodrug moiety. In some embodiments of this paragraph, $R^1$ and $R^2$ can form an optionally substituted cyclosaligenyl (cycloSal) prodrug. In some embodiments of this paragraph, $R^1$ and $R^2$ can form an optionally substituted phosphonic diamide prodrug. In some embodiments of this paragraph, $R^1$ can be

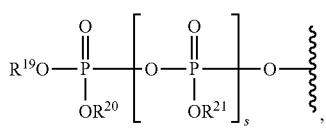

$R^2$ can be O⁻ or OH, and $R^{19}$, $R^{20}$ and $R^{21}$ can be hydrogen.

Additional examples of a compound of Formula (I), or a pharmaceutically acceptable salt thereof, include:

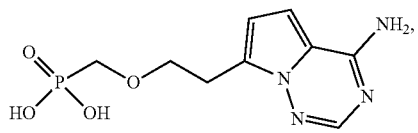

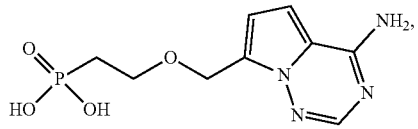

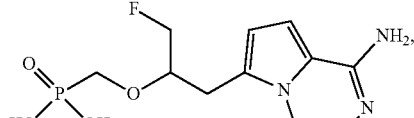

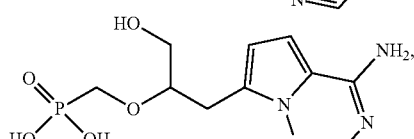

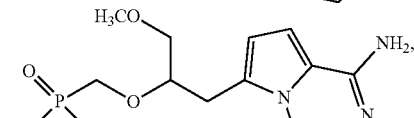

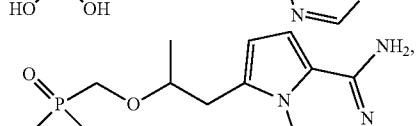

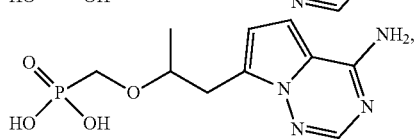

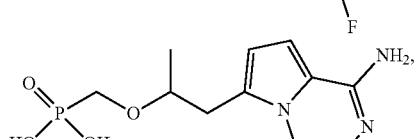

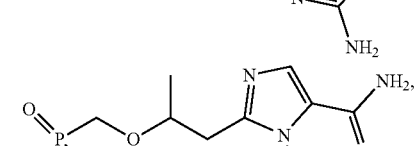

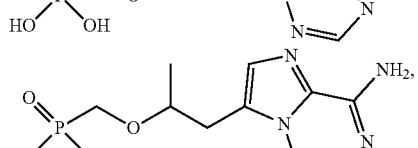

-continued
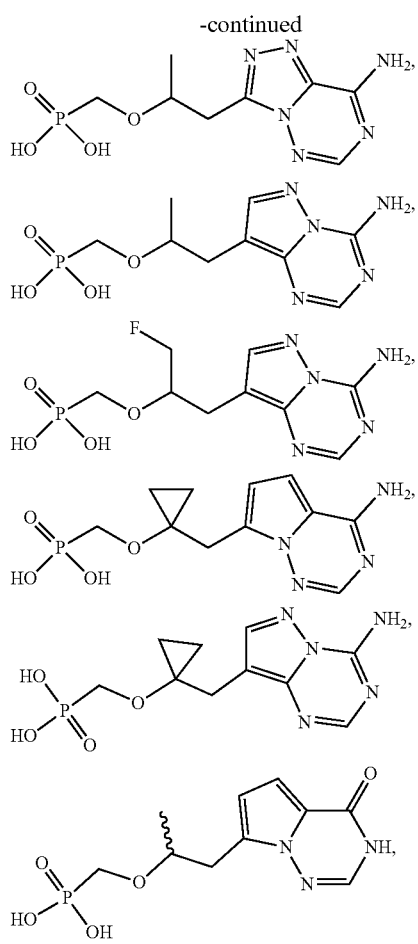
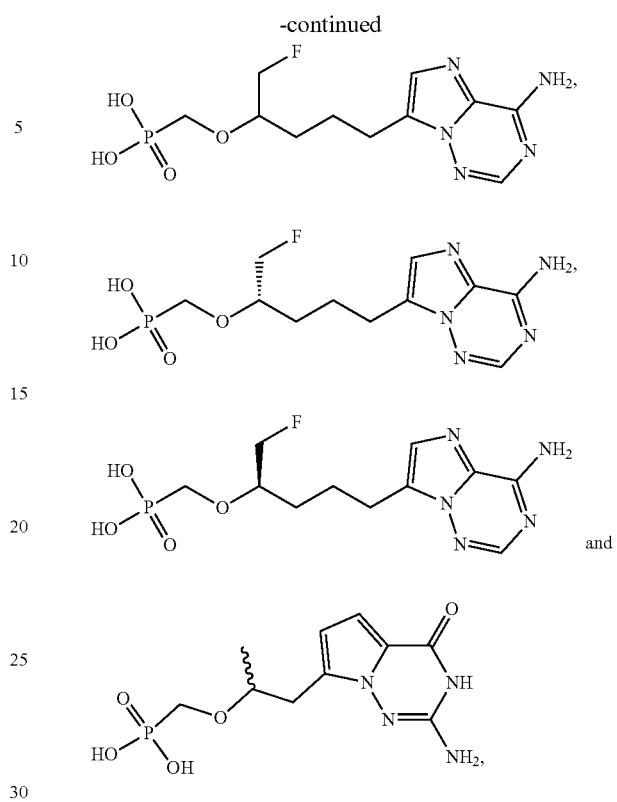
or a pharmaceutically acceptable salt of any of the foregoing.
Further examples of a compound of Formula (I), or a pharmaceutically acceptable salt thereof, include:
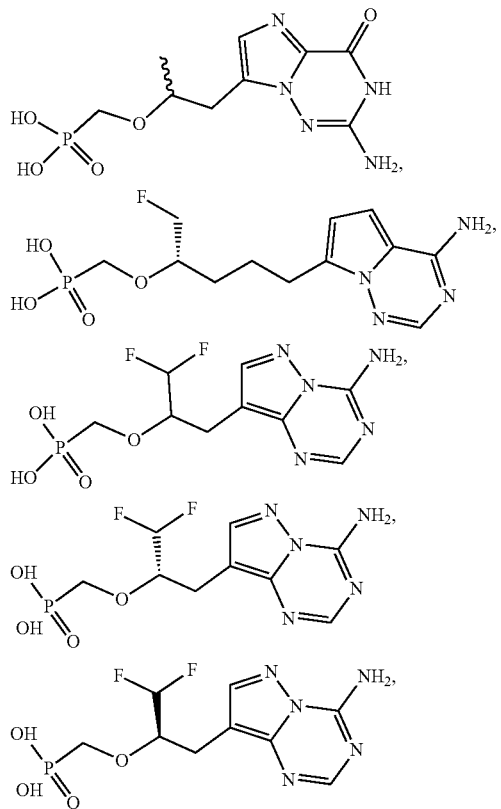
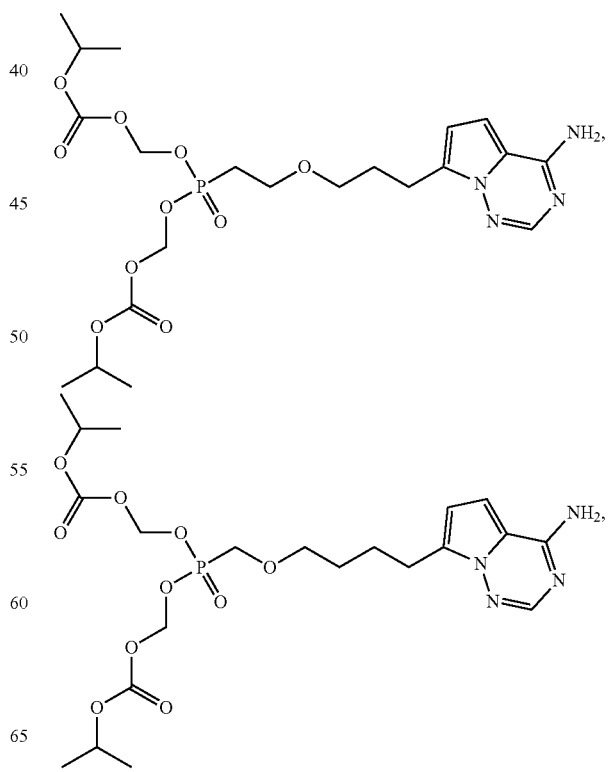

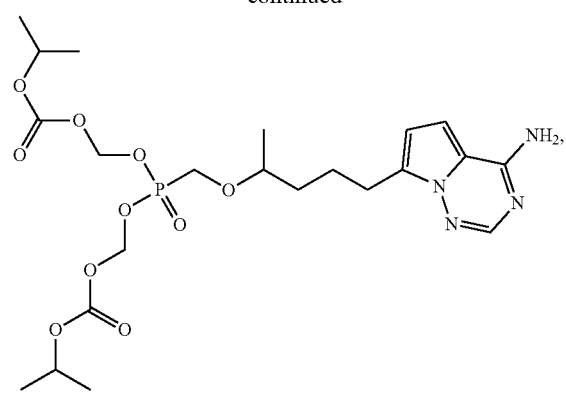
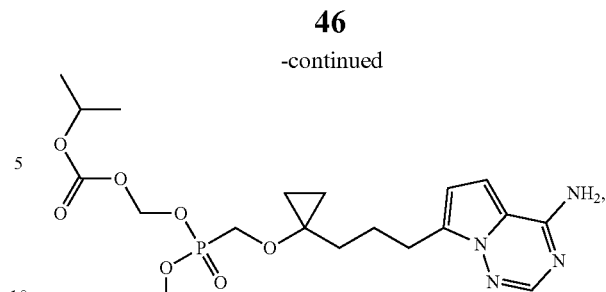
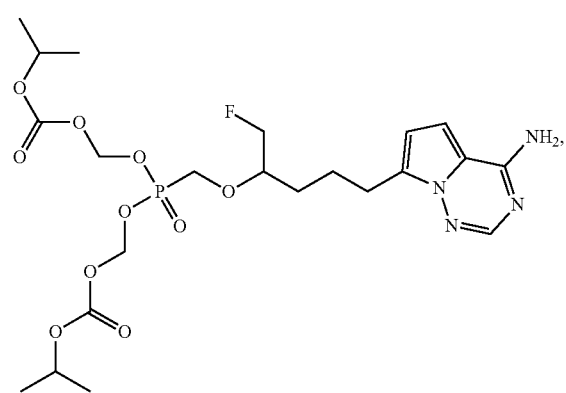
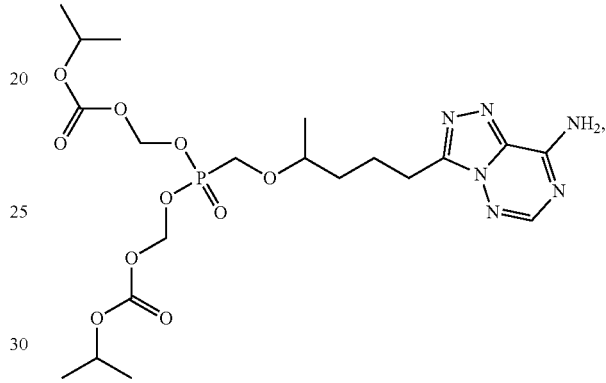
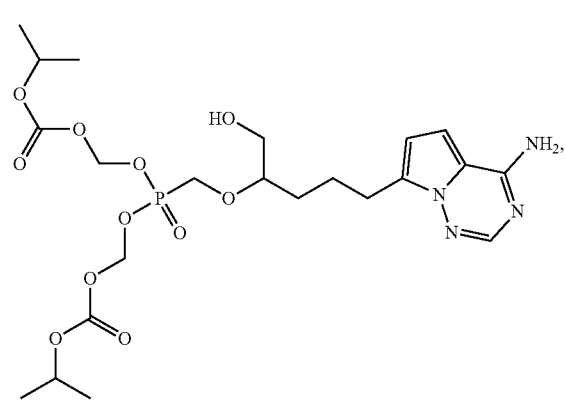
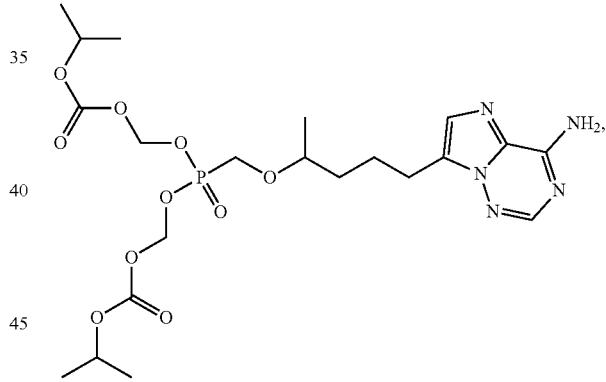
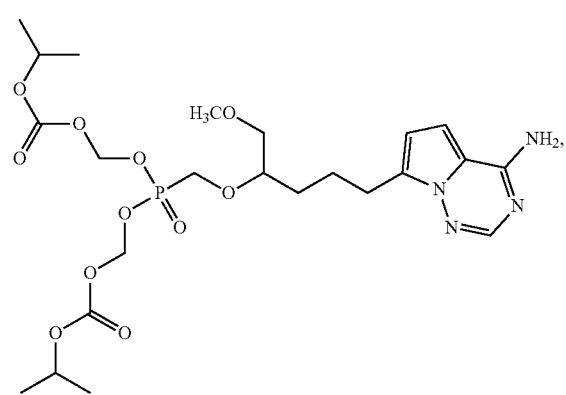
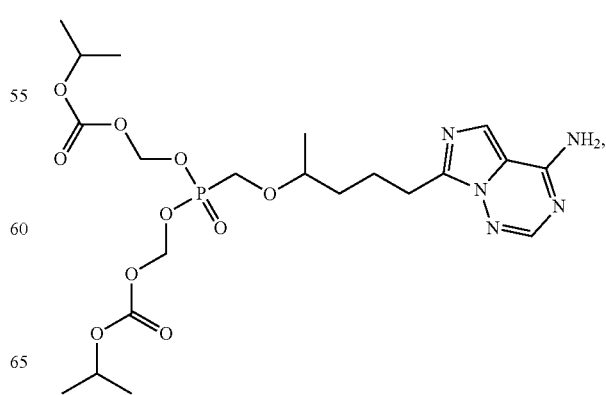

47
-continued
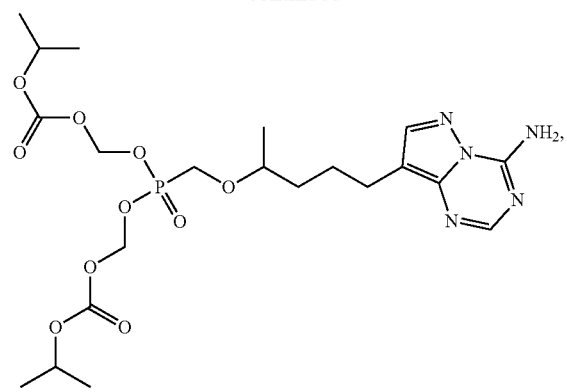
48
-continued
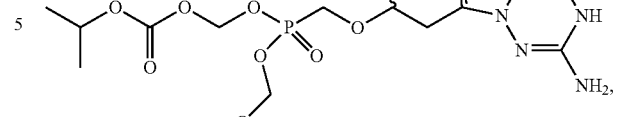
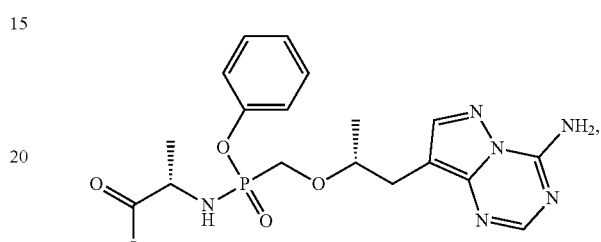
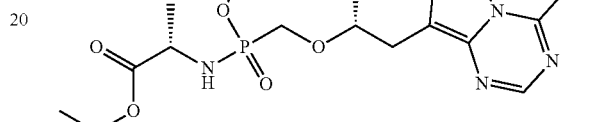
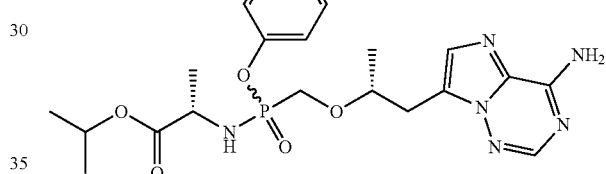
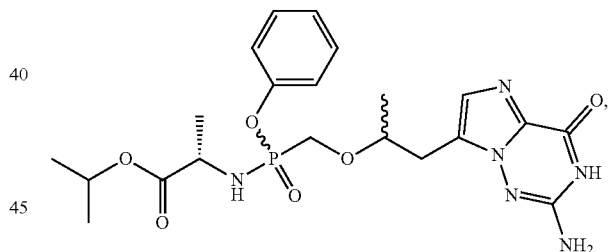
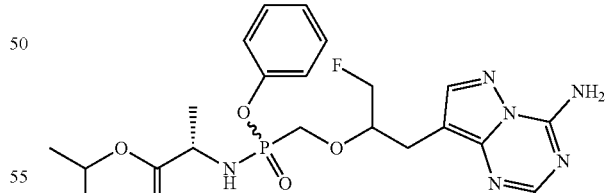
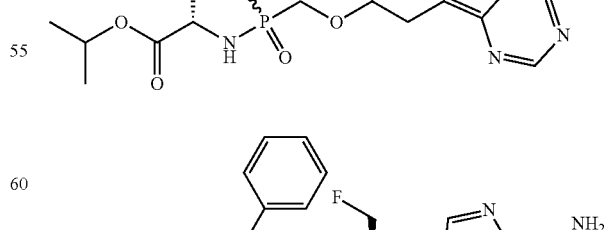

-continued
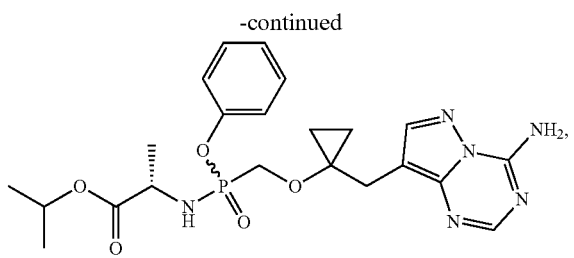
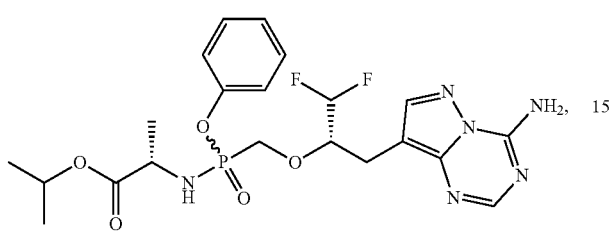
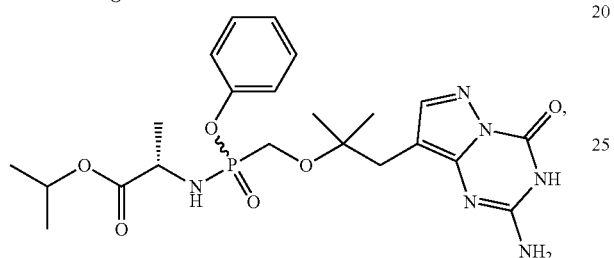
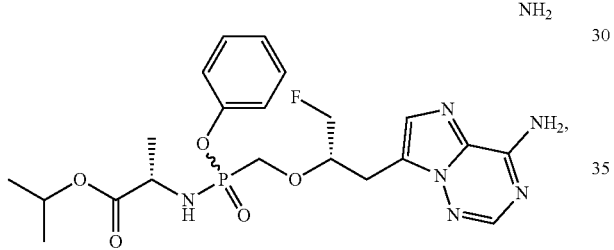
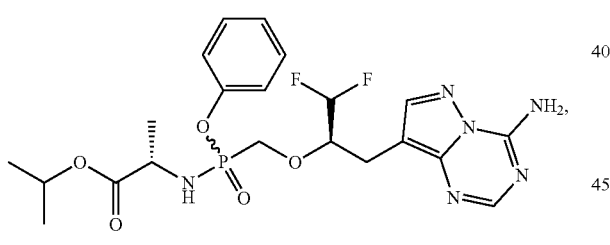
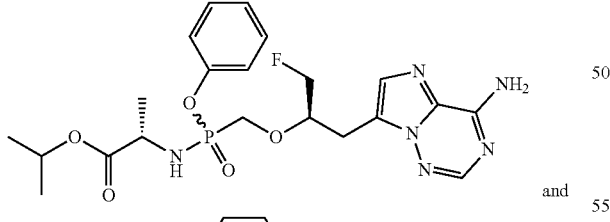
and
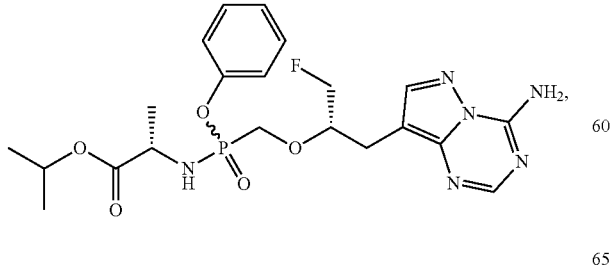
or a pharmaceutically acceptable salt of any of the foregoing.
Examples of a compound of Formula (I), or a pharmaceutically acceptable salt thereof, include:
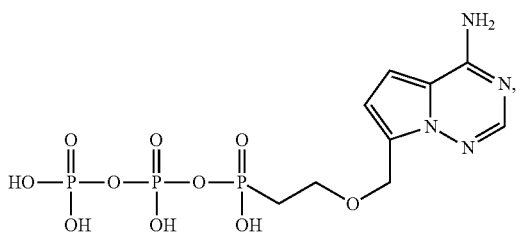
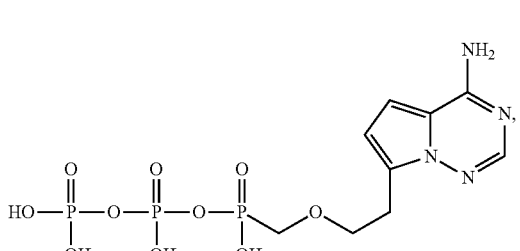
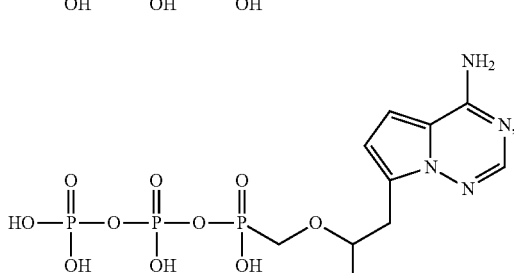
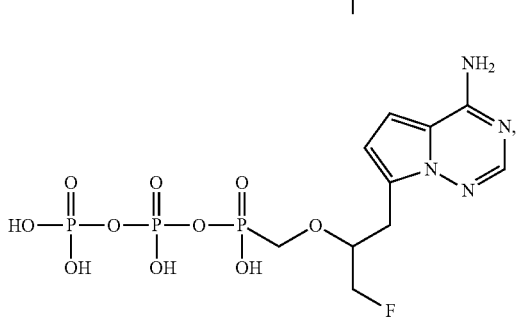
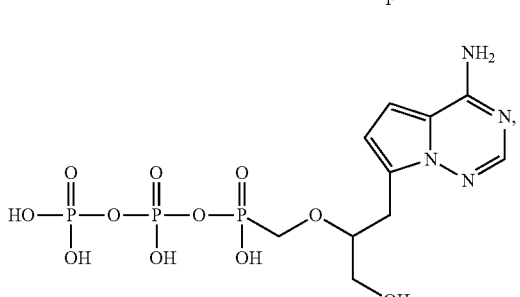
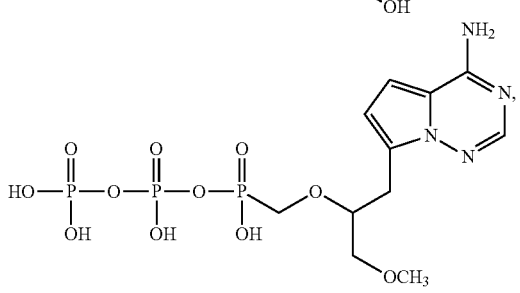

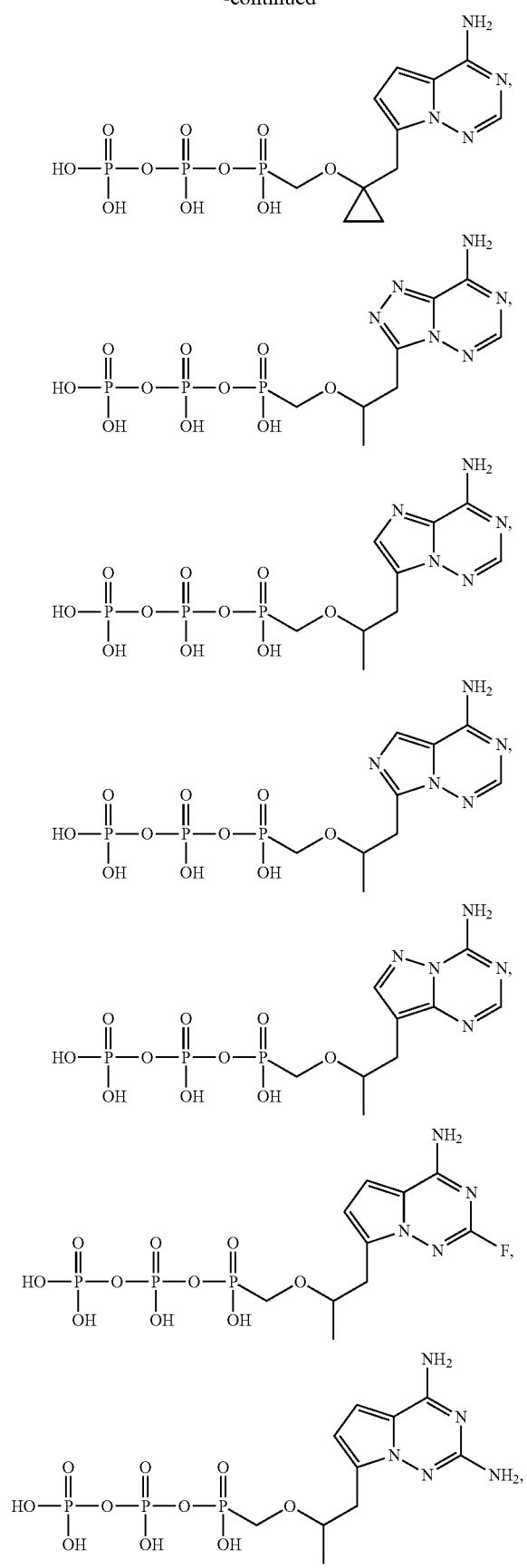

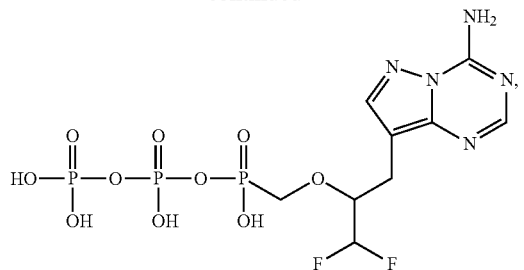

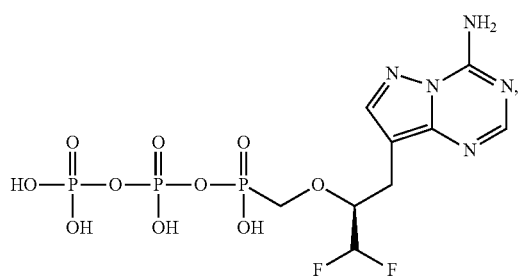

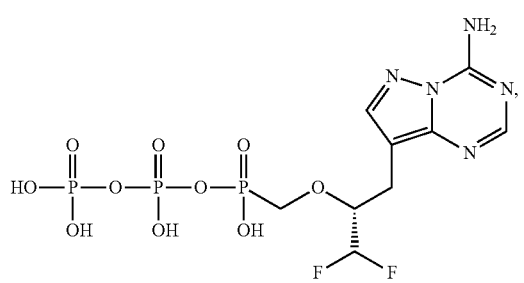

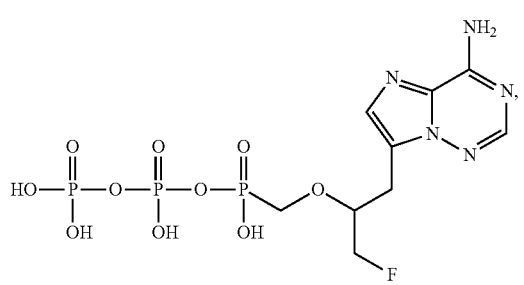

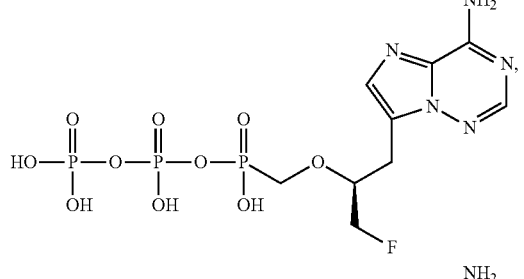

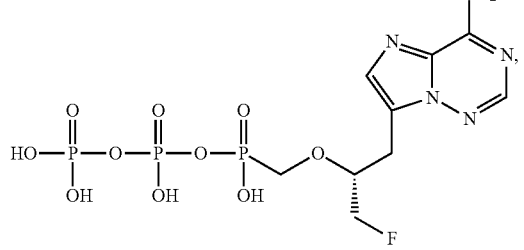

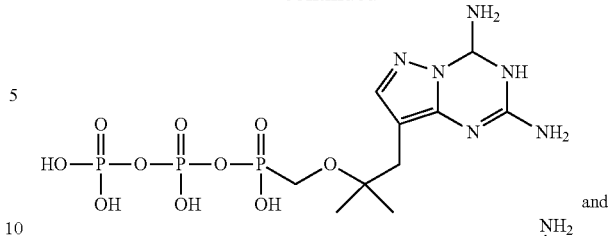

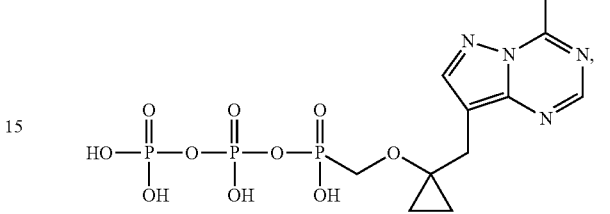

or a pharmaceutically acceptable salt of any of the foregoing.

In some embodiments, the compound of Formula (I) can be PMEA (9-(2-phosphonylmethoxyethyl)adenine), wherein the adenine is replaced with a $B^1$ moiety as described herein. In other embodiments, the compound of Formula (I) can be HPMPA ((S)-9-(3-hydroxy-2-phosphonylmethoxypropyl)adenine), wherein the adenine is replaced with a $B^1$ moiety as described herein. In still other embodiments, the compound of Formula (I) can be FPMPA ((S)-9-(3-fluoro-2-phosphonylmethoxypropyl)adenine), wherein the adenine is replaced with a $B^1$ moiety as described herein. In yet still other embodiments, the compound of Formula (I) can be PMPA ((R)-9-(2-phosphonylmethoxypropyl)adenine), wherein the adenine is replaced with a $B^1$ moiety as described herein.

By neutralizing the charge on the phosphonate moiety of Formula (I), or a pharmaceutically acceptable salt thereof, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphonate thus released may then be metabolized by cellular enzymes to the monophosphonate or the active diphosphonate (for example, a phosphono diphosphate). Furthermore, in some embodiments, varying the substituents on a compound described herein, such as a compound of Formula (I), or a pharmaceutically acceptable salt thereof, can help maintain the efficacy of the compound by reducing undesirable effects.

In some embodiments, varying the substituents on a compound described herein, such as a compound of Formula (I), or a pharmaceutically acceptable salt thereof, can result in the phosphorous being a chiral center. In some embodiments, the phosphorous can be in the (R)-configuration. In some embodiments, the phosphorous can be in the (S)-configuration. Examples of the two configurations are:

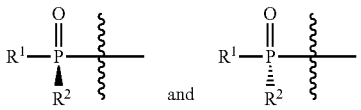

In some embodiments, a compound of Formula (I), or a pharmaceutically acceptable salt thereof, can be enriched in (R) or (S) configuration with respect to the phosphorous. For example, one of the (R) and (S) configuration with respect to the phosphorous atom can be present in an amount >50%, ≥75%, ≥90%, ≥95% or ≥99% compared to the amount of the other of the (R) or (S) configuration with respect to the phosphorous atom.

In some embodiments, a compound of Formula (I), or a pharmaceutically acceptable salt thereof, can act as a chain terminator of a virus and inhibit the virus' replication, wherein the virus can be HBV, HDV and/or HIV. For example, compounds of Formula (I), or a pharmaceutically acceptable salt thereof, can be incorporated into a DNA chain of the virus (such as HBV, HDV and/or HIV) and then no further elongation is observed to occur.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis. In some embodiments, a compound of Formula (I), or a pharmaceutically acceptable salt thereof, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in plasma viral load, increase CD4+T lymphocyte counts, reduction in time to seroconversion (i.e., the virus becomes undetectable in patient serum), increased sustained viral response, a reduction of morbidity or mortality in clinical outcomes, decrease in or prevention of opportunistic infections, increased subject compliance, and compatibility with other medications. In some embodiments, a compound of Formula (I), or a pharmaceutically acceptable salt thereof, can have a biological half-life of greater than 24 hours. In some embodiments, a compound of Formula (I), or a pharmaceutically acceptable salt thereof, can have more potent antiviral activity (for example, a lower $EC_{50}$ in an HIV, HBV and/or HDV replicon assay) as compared to the current standard of care.

Synthesis

Compounds of Formula (I) or a pharmaceutically acceptable salt thereof, and those described herein may be prepared in various ways. General synthetic routes to the compound of Formula (I), or a pharmaceutically acceptable salt thereof, and some examples of starting materials used to synthesize the compounds of Formula (I) or a pharmaceutically acceptable salt thereof, are shown in Scheme 1, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) or a pharmaceutically acceptable salt thereof, can be prepared using various methods known to those skilled in the art. Examples of methods are shown in Scheme 1.

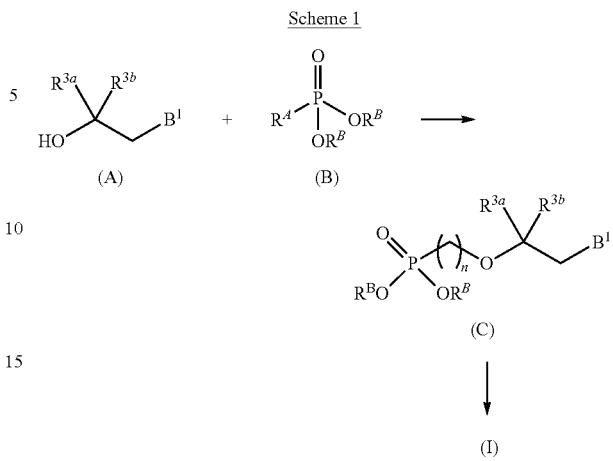

Compound (A) can be formed using methods known to those skilled in the art. Similarly, Compound (B) can be formed using methods known to those skilled in the art or commercially obtained. As shown in Scheme 1, Compound (B) can be a phosphonate, wherein $R^A$ can be a suitable carbon linked moiety (such as ethenyl or ethyl trifluoromethanesulfonate) and each $R^B$ can be independently an unsubstituted $C_{1-4}$ alkyl (such as methyl or ethyl).

Compound (C) can be obtained via an ether formation reaction. Examples include nucleophilic addition (such as a Michael-type addition) or nucleophilic substitution (such as a Williamson ether type synthesis). The $R^B$ groups of Compound (C) can be removed using methods and reagents known to those skilled in the art. For example, Compound (C) can be dealkylated using TMSBr or TMSOTf.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments disclosed herein relate to a method of treating and/or ameliorating a disease or condition that can include administering to a subject an effective amount of one or more compounds described herein, such as a compound of Formula (I), or a pharmaceutically acceptable salt thereof, or a pharmaceutical composition that includes a compound described herein, or a pharmaceutically acceptable salt thereof. Other embodiments disclosed herein relate to a method of treating and/or ameliorating a disease or condition that can include administering to a subject identified as suffering from the disease or condition an effective amount of one or more compounds described herein, such as a compound of Formula (I), or a pharmaceutically acceptable salt thereof, or a pharmaceutical composition that includes a compound described herein, or a pharmaceutically acceptable salt thereof.

Some embodiments described herein relate to a method of inhibiting HBV and/or HDV activity that can include contacting a cell infected with HBV and/or HDV with an effective amount of a compound of Formula (I), or a pharmaceutically acceptable salt thereof. Some embodiments described herein relate to a method of inhibiting HBV and/or HDV activity that can include administering to a subject infected with HBV and/or HDV an effective amount of a compound of Formula (I), or a pharmaceutically acceptable salt thereof. It should be appreciated that inhibiting replication of HBV may also inhibit replication of HDV which is a subviral satellite of HBV.

Some embodiments disclosed herein relate to methods of inhibiting replication of an HBV and/or HDV virus that can include contacting a cell infected with the HBV and/or HDV virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a HBV and/or HDV virus that can include contacting a cell infected with the HBV and/or HDV virus with an effective amount of said compound(s). Still other embodiments described herein relate to a compound described herein, or a pharmaceutically acceptable salt of a compound described herein, that can be used for inhibiting replication of a HBV and/or HDV virus by contacting a cell infected with the HBV and/or HDV virus with an effective amount of said compound(s). As HDV is a subviral satellite of HBV, inhibiting replication of HBV may also inhibit replication of HDV.

Some embodiments disclosed herein relate to a method for treating an HBV and/or HDV infection that can include administering to a subject in need thereof an effective amount of one or more compounds described herein (for example, a compound of Formula (I)), or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for treating a HBV and/or HDV infection that can include administering to a subject in need thereof an effective amount of one or more compounds described herein. Still other embodiments described herein relate to one or more compounds described herein, or a pharmaceutically acceptable salt of a compound described herein, that can be used for treating a HBV and/or HDV infection by administering to a subject in need thereof an effective amount of one or more compounds described herein. As HDV is a subviral satellite of HBV, it should be appreciated that treating an HBV infection may also treat an HDV infection.

Some embodiments disclosed herein relate to methods for treating an HBV and/or HDV infection that can include contacting a cell infected with the HBV and/or HDV virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for treating a HBV and/or HDV infection that can include contacting a cell infected with the HBV and/or HDV virus with an effective amount of said compound(s). Still other embodiments described herein relate to one or more compounds described herein, or a pharmaceutically acceptable salt of a compound described herein, that can be used for treating a HBV and/or HDV infection by contacting a cell infected with the HBV and/or HDV virus with an effective amount of said compound(s). As HDV is a subviral satellite of HBV it should be appreciated that treating an HBV infection may also treat an HDV infection.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

In some embodiments, an effective amount of a compound of Formula (I), or a pharmaceutically acceptable salt thereof, is an amount that is effective to reduce HBV and/or HDV viral load to undetectable levels, for example, to about 10 to about 50, or to about 15 to about 25 international units/mL serum, or to less than about 20 international units/mL serum. In some embodiments, an effective amount of a compound of Formula (I), or a pharmaceutically acceptable salt thereof, is an amount that is effective to reduce HBV and/or HDV viral load compared to the HBV and/or HDV viral load before being provided the compound of Formula (I), or a pharmaceutically acceptable salt thereof. For example, wherein the HBV and/or HDV viral load is measured before being provided the compound of Formula (I), or a pharmaceutically acceptable salt thereof, and again after completion of, or completion of at least a portion of, the treatment regime with the compound of Formula (I), or a pharmaceutically acceptable salt thereof (for example, 1 month after completion). In some embodiments, an effective amount of a compound of Formula (I), or a pharmaceutically acceptable salt thereof, can be an amount that is effective to reduce HBV and/or HDV viral load to lower than about 20 international units/mL serum. In some embodiments, an effective amount of a compound of Formula (I), or a pharmaceutically acceptable salt thereof, is an amount that is effective to achieve a reduction in HBV and/or HDV viral load in the serum of the subject to an undetectable level and/or in the range of about 1.5-log to about a 2.5-log reduction, about a 3-log to about a 4-log reduction, or a greater than about 5-log reduction compared to the viral load before being provided the compound of Formula (I), or a pharmaceutically acceptable salt thereof. For example, the HBV and/or HDV viral load can be measured before being provided the compound of Formula (I), or a pharmaceutically acceptable salt thereof, and again after completion of at least a portion of the treatment regime with the compound of Formula (I), or a pharmaceutically acceptable salt thereof (for example, 1 month after initiation or completion). As HDV is a subviral satellite of HBV, lowering of HBV load to undetectable levels may also lower HDV viral load to an undetectable level.

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of HBV and/or HDV relative to pre-treatment levels in a subject, as determined after completion of, or completion of at least a portion of, the treatment regime (for example, 1 month after initiation or completion). In some embodiments, a compound of Formula (I), or a pharmaceutically acceptable salt thereof, can result in a reduction of the replication of HBV and/or HDV relative to pre-treatment levels in the range of more than 1 fold, about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of HBV and/or HDV replication in the range of more than 0.5 log, 1 to 1.5 log, 1.5 log to 2 log, 2 log to 2.5 log, 2.5 to 3 log, 3 log to 3.5 log or 3.5 to 4 log more reduction of HBV and/or HDV replication compared to the reduction of HBV and/or HDV replication achieved by the standard of care of HBV and/or HDV, administered according to the standard of care, or may achieve the same reduction as that standard of care therapy in a shorter period of time, for example, in one month, two months, or three months, as compared to the reduction achieved after six months of standard of care therapy. As HDV is a subviral satellite of HBV, reduction of HBV replication may also reduce HDV replication.

In some embodiments, an effective amount of a compound of Formula (I), or a pharmaceutically acceptable salt thereof, is an amount that is effective to achieve a sustained virologic response, for example, non-detectable or substantially non-detectable HBV and/or HDV DNA load (e.g., less than about 25, or less than about 15 international units per milliliter serum) is found in the subject's serum for a period of at least about one month, at least about two months, at least about three months, at least about four months, at least about five months, or at least about six months following cessation of therapy. As HDV is a subviral satellite of HBV, achievement of a sustained viral responses against HBV may also produce a sustained viral response against HDV.

In some embodiments, an effective amount of a compound of Formula (I), or a pharmaceutically acceptable salt thereof, can reduce the HBV and/or HDV viral load by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the viral load a subject treated with standard of care, in an untreated subject, or a placebo-treated subject. Methods of detecting HBV and/or HDV viral load are known to those skilled in the art and include immunological-based methods, e.g., enzyme-linked immunosorbent assays (ELISA), radioimmunoassays, and the like, that detect HBV and/or HDV antibodies and other markers indicative of HBV and/or HDV viral load, and combinations thereof. As HDV is a subviral satellite of HBV, reduction of the HBV viral load may also reduce the HDV viral load.

Subjects who are clinically diagnosed with HBV and/or HDV infection include "naïve" subjects (e.g., subjects not previously treated for HBV and/or HDV), individuals who have failed prior treatment for HBV and/or HDV ("treatment failure" subjects), subjects with acute HBV and/or HDV infection, individuals with chronic HBV and/or HDV, and subjects who were previously treated for HBV and/or HDV (or were asymptomatic), but currently present with increased viral load and/or symptoms of acute hepatitis ("relapsers"). Treatment failure subjects include "non-responders" (i.e., subjects in whom the HBV and/or HDV load was not significantly or sufficiently reduced by a previous treatment for HBV and/or HDV, for example, by administration of the standard of care for HBV and/or HDV, or other therapy.

In some embodiments, a compound of Formula (I), or a pharmaceutically acceptable salt thereof, can be provided to a treatment failure subject suffering from HBV and/or HDV. In some embodiments, a compound of Formula (I), or a pharmaceutically acceptable salt thereof, can be provided to a non-responder subject suffering from HBV and/or HDV. In some embodiments, a compound of Formula (I), or a pharmaceutically acceptable salt thereof, can be provided to a relapsed subject suffering from HBV and/or HDV. In some embodiments, a compound of Formula (I), or a pharmaceutically acceptable salt thereof, can be provided to a subject suffering from chronic HBV and/or HDV. In some embodiments, a compound of Formula (I), or a pharmaceutically acceptable salt thereof, can be provided to a subject suffering from acute HBV and/or HDV. In some embodiments, the subject can be asymptomatic. In some embodiments, the subject can be immunocompromised. In some embodiments, the subject is suffering from at least one of HIV, HBV and/or HDV.

After a period of time, infectious agents can develop resistance to one or more therapeutic agents. The term "resistance" as used herein refers to a viral strain displaying a delayed, lessened and/or null response to a therapeutic agent(s). In some instances, the virus sometimes mutates or produces variations that are resistant or partially resistant to certain drugs. For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be provided to a subject infected with an HBV and/or HDV strain that is resistant to one or more different anti-HBV and/or anti-HDV agents (for example, an agent used in a conventional standard of care). In some embodiments, development of resistant HBV and/or HDV strains is delayed when a subject is treated with a compound of Formula (I), or a pharmaceutically acceptable salt thereof, compared to the development of HBV and/or HDV strains resistant to other HBV and/or HDV drugs (such as an agent used in a conventional standard of care).

In some embodiments, an effective amount of a compound of Formula (I), or a pharmaceutically acceptable salt thereof, can be provided to a subject for whom other anti-HBV and/or anti-HDV medications are contraindicated. In some embodiments, a compound of Formula (I), or a pharmaceutically acceptable salt thereof, can be provided to a subject that is hypersensitive to an antiretroviral therapy agent.

Some subjects being treated for HBV and/or HDV experience a viral load rebound. The term "viral load rebound" as used herein refers to a sustained increase of viral load before the end of treatment, above any decrease below baseline which may have been achieved during treatment, or nadir. In some embodiments, a compound of Formula (I), or a pharmaceutically acceptable salt thereof, can be provided to a subject experiencing viral load rebound, or can prevent such viral load rebound when used to treat the subject.

The standard of care for treating HBV and/or HDV has been associated with several side effects (adverse events). In some embodiments, a compound of Formula (I), or a pharmaceutically acceptable salt thereof, can decrease the number and/or severity of side effects that can be observed in HBV and/or HDV patients being treated with the standard of care for HBV and/or HDV. Examples of side effects include, but are not limited to dyspepsia, neuropathy, cough, loss of appetite, lactic acidosis, lipodystrophy, diarrhea, fatigue, insomnia, rash, fever, malaise, tachycardia, chills, headache, arthralgias, myalgias, apathy, nausea, vomiting, cognitive changes, asthenia, and drowsiness. In some embodiments, a compound of Formula (I), or a pharmaceutically acceptable salt thereof, can be provided to a subject that discontinued a HBV and/or HDV therapy because of one or more adverse effects or side effects associated with one or more other anti-HBV and/or anti-HDV agents (for example, an agent used in the standard of care).

Table 1 provides some embodiments of the percentage improvement obtained using a compound of Formula (I), or a pharmaceutically acceptable salt thereof, as compared to the standard of care for HBV and/or HDV. Examples include the following: in some embodiments, a compound of Formula (I), or a pharmaceutically acceptable salt thereof, results in a percentage of non-responders that is 10% less than the percentage of non-responders receiving the standard of care. In some embodiments, a compound of Formula (I), or a pharmaceutically acceptable salt thereof, results in a number of side effects that is in the range of about 10% to about 30% less than compared to the number of side effects experienced by a subject receiving the standard of care; and in some embodiments, a compound of Formula (I), or a pharmaceutically acceptable salt thereof, results in a severity of a side effect (such as one of those described herein) that is 25% less than compared to the severity of the same side effect experienced by a subject receiving the standard of care. Methods of quantifying the severity of a side effect are known to those skilled in the art.

TABLE 1

| Percentage of non-responders | Percentage of relapsers | Percentage of resistance | Percentage of viral load rebound | Number of side effects | Severity of side effects |
|---|---|---|---|---|---|
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

Some embodiments described herein relate to a method of inhibiting HIV activity that can include contacting a cell infected with HIV with an effective amount of a compound of Formula (I), or a pharmaceutically acceptable salt thereof. Some embodiments described herein relate to a method of inhibiting HIV activity that can include administering to a subject infected with HIV an effective amount of a compound of Formula (I), or a pharmaceutically acceptable salt thereof. In some embodiments, a compound of Formula (I), or a pharmaceutically acceptable salt thereof, can inhibit a viral reverse transcriptase, and thus, inhibit the transcription of HIV RNA to DNA. In some embodiments, a compound of Formula (I), or a pharmaceutically acceptable salt thereof, can inhibit an HIV integrase. In some embodiments, a compound of Formula (I), or a pharmaceutically acceptable salt thereof, can inhibit viral envelop glycoprotein 120 (gp 120).

Some embodiments disclosed herein relate to methods of inhibiting replication of an HIV virus that can include contacting a cell infected with the HIV virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a HIV virus that can include contacting a cell infected with the HIV virus with an effective amount of said compound(s). Still other embodiments described herein relate to a compound described herein, or a pharmaceutically acceptable salt of a compound described herein, that can be used for inhibiting replication of a HIV virus by contacting a cell infected with the HIV virus with an effective amount of said compound(s).

Some embodiments disclosed herein relate to a method of ameliorating and/or treating a HIV infection that can include administering to a subject identified as suffering from a HIV infection an effective amount of one or more compounds described herein (for example, a compound of Formula (I)), or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HIV infection that can include administering to a subject identified as suffering from a HIV infection an effective amount of one or more compounds described herein. Still other embodiments described herein relate to one or more compounds described herein, or a pharmaceutically acceptable salt of a compound described herein, that can be used for ameliorating and/or treating a HIV infection by administering to a subject identified as suffering from a HIV infection an effective amount of one or more compounds described herein.

Some embodiments disclosed herein relate to methods of ameliorating and/or treating a HIV infection that can include contacting a cell infected with the HIV virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HIV infection that can include contacting a cell infected with the HIV virus with an effective amount of said compound(s). Still other embodiments described herein relate to one or more compounds described herein, or a pharmaceutically acceptable salt of a compound described herein, that can be used for ameliorating and/or treating a HIV infection by contacting a cell infected with the HIV virus with an effective amount of said compound(s).

In some embodiments described herein, when the infection is caused by HIV, and/or the virus is HIV, the subject suffers from an opportunistic infection (OI). OIs take advantage of the subjects weakened immune system. In some embodiments described herein, a subject having a CD4+T lymphocyte count of less than about 200 cells/mL is an at increased risk of developing an OI. In some embodiments, OIs occur when the CD4+T lymphocyte count is less than about 500 cells/mL. In some embodiments, an OI occurs when an HIV viral load is greater than about 100,000 copies/mL. In some embodiments, HIV viral loads and/or CD4+T lymphocyte counts can be determined by conventional standard of care methodologies, for example, through HIV immunoassay detection assays for the detection of HIV antibodies and/or HIV p24 antigen.

Some embodiments described herein relate to a method of treating an OI selected from candidiasis, bronchitis, pneumonitis, esophagitis, invasive cervical cancer, coccidioidomycosis, cryptococcosis, chronic intestinal cryptosporidiosis, cytomegalovirus disease, encephalopathy, herpes simplex, histoplasmosis, chronic intestinal isosporiasis, Kaposi's sarcoma, lymphoma, *Mycobacterium avium* complex, tuberculosis, *Pneumocystis carinii* pneumonia, progressive multifocal leukoencephalopathy, *Salmonella* septicemia, toxoplasmosis of brain, and wasting syndrome in a subject suffering from one or more of the aforementioned conditions that can include providing to the subject an effective amount of a compound or a pharmaceutical composition described herein (for example, a compound of Formula (I), or a pharmaceutically acceptable salt thereof). In some embodiments, the OI is caused by a HIV infection. Some embodiments described herein relate to a method of preventing and/or treating one or more OI in a subject having a HIV infection that can include providing to the subject an effective amount of a compound or a pharmaceutical composition described herein (for example, a compound of Formula (I), or a pharmaceutically acceptable salt thereof). Also contemplated is a method for reducing or eliminating one or more OI in a subject having an HIV infection by providing to the subject an effective amount of a compound or a pharmaceutical composition described herein (for example, a compound of Formula (I), or a pharmaceutically acceptable salt thereof). In some embodiments, this method can include slowing or halting the progression of an OI. In other embodiments, the course of the OI can be reversed, and stasis or improvement in the infection is contemplated. In some embodiments, one or more of candidiasis, bronchitis, pneumonitis, esophagitis, invasive cervical cancer, coccidioidomycosis, cryptococcosis, chronic intestinal cryptosporidiosis, cytomegalovirus disease, encephalopathy, herpes simplex, histoplasmosis, chronic intestinal isosporiasis, Kaposi's sarcoma, lymphoma, *Mycobacterium avium* complex, tuberculosis, *Pneumocystis carinii* pneumonia, progressive multifocal leukoencephalopathy, *Salmonella* septicemia, toxoplasmosis of brain, and wasting syndrome can be treated by contacting a cell infected with HIV with an effective amount of a compound described herein (for example, a compound of Formula (I), or a pharmaceutically acceptable salt thereof.)

Two types of HIV have been characterized, HIV-1 and HIV-2. HIV-1 is more virulent and more infective, and has a global prevalence, whereas HIV-2 is less virulent and is geographically confined. In some embodiments, an effective amount of a compound of Formula (I), or a pharmaceutically acceptable salt thereof, or a pharmaceutical composition that includes an effective amount of a compound of Formula (I), or a pharmaceutically acceptable salt thereof, can be effective to treat HIV-1. In some embodiments, an effective amount of a compound of Formula (I), or a pharmaceutically acceptable salt thereof, or a pharmaceutical composition that includes an effective amount of a compound of Formula (I), or a pharmaceutically acceptable salt thereof, can be effective to treat HIV-2. In some embodiments, a compound described herein (for example, a compound of Formula (I), or a pharmaceutically acceptable salt thereof) can be effective to treat both genotypes of HIV (HIV-1 and HIV-2).

Various indicators for determining the effectiveness of a method for treating an HIV infection are known to those skilled in the art. Examples of suitable indicators include, but are not limited to, a reduction in viral load, a reduction in plasma viral load, an increase CD4+T lymphocyte counts, a reduction in viral replication, a reduction in time to seroconversion (virus undetectable in patient serum), an increase in the rate of sustained viral response to therapy, a reduction of morbidity or mortality in clinical outcomes and/or a reduction in the rate of opportunistic infections. Similarly, successful therapy with an effective amount of a compound or a pharmaceutical composition described herein (for example, a compound of Formula (I), or a pharmaceutically acceptable salt thereof) can reduce the incidence of opportunistic infections in HIV infected subjects.

In some embodiments, an effective amount of a compound of Formula (I), or a pharmaceutically acceptable salt thereof, is an amount that is effective to reduce HIV viral titers to undetectable levels, for example, to about 10 to about 50, or to about 15 to about 25 international units/mL serum, or to less than about 20 international units/mL serum. In some embodiments, an effective amount of a compound of Formula (I), or a pharmaceutically acceptable salt thereof, is an amount that is effective to reduce HIV viral load compared to the HIV viral load before being provided the compound of Formula (I), or a pharmaceutically acceptable salt thereof. For example, wherein the HIV viral load is measured before being provided the compound of Formula (I), or a pharmaceutically acceptable salt thereof, and again after completion of the treatment regime with the compound of Formula (I), or a pharmaceutically acceptable salt thereof (for example, 1 month after completion). In some embodiments, an effective amount of a compound of Formula (I), or a pharmaceutically acceptable salt thereof, can be an amount that is effective to reduce HIV viral load to lower than about 20 international units/mL serum. In some embodiments, an effective amount of a compound of Formula (I), or a pharmaceutically acceptable salt thereof, is an amount that is effective to achieve a reduction in HIV viral titer in the serum of the subject in the range of about 1.5-log to about a 2.5-log reduction, about a 3-log to about a 4-log reduction, or a greater than about 5-log reduction compared to the viral load before being provided the compound of Formula (I), or a pharmaceutically acceptable salt thereof. For example, the HIV viral load can be measured before being provided the compound of Formula (I), or a pharmaceutically acceptable salt thereof, and again after completion of the treatment regime with the compound of Formula (I), or a pharmaceutically acceptable salt thereof (for example, 1 month after completion).

In some embodiments, an effective amount of a compound of Formula (I), or a pharmaceutically acceptable salt thereof, is an amount that is effective to increase CD4+T lymphocyte counts from less than about 200 cells/mL to greater than about 1,200 cells/mL. In some embodiments, an effective amount of a compound of Formula (I), or a pharmaceutically acceptable salt thereof, is an amount that is effective to increase CD4+T lymphocyte counts from less than about 200 cells/mL to greater than about 500 cells/mL.

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of the human immunodeficiency virus relative to pre-treatment levels in a subject, as determined after completion of the treatment regime (for example, 1 month after completion). In some embodiments, a compound of Formula (I), or a pharmaceutically acceptable salt thereof, can result in a reduction of the replication of the human immunodeficiency virus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of the human immunodeficiency virus replication in the range of 1 to 1.5 log, 1.5 log to 2 log, 2 log to 2.5 log, 2.5 to 3 log, 3 log to 3.5 log or 3.5 to 4 log more reduction of the human immunodeficiency virus replication compared to the reduction of the human immunodeficiency virus reduction achieved by standard of care therapy, such as therapy including ritonavir in combination with etravirine, or may achieve the same reduction as that standard of care therapy in a shorter period of time, for example, in one month, two months, or three months, as compared to the reduction achieved after six months of standard of care therapy.

In some embodiments, an effective amount of a compound of Formula (I), or a pharmaceutically acceptable salt thereof, is an amount that is effective to achieve a sustained viral response, for example, non-detectable or substantially non-detectable HIV RNA (e.g., less than about 25, or less than about 15 international units per milliliter serum) is found in the subject's serum for a period of at least about one month, at least about two months, at least about three months, at least about four months, at least about five months, or at least about six months following cessation of therapy.

In some embodiments, an effective amount of a compound of Formula (I), or a pharmaceutically acceptable salt thereof, can reduce the HIV viral load by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the viral load in an untreated subject, or to a placebo-treated subject. Methods of detecting HIV viral load are known to those skilled in the art and include immunological-based methods, e.g., enzyme-linked immunosorbent assays (ELISA), radioimmunoassays, and the like, that detect HIV-1 and/or HIV-2 antibodies, HIV-1 p24 antigen, and other markers indicative of HIV viral load, and combinations thereof.

Subjects who are clinically diagnosed with HIV infection include "naïve" subjects (e.g., subjects not previously treated for HIV, particularly those who have not previously received ART, including ritonavir-based therapy) and individuals who have failed prior treatment for HIV ("treatment failure" subjects). Treatment failure subjects include "non-responders" (i.e., subjects in whom the HIV titer was not significantly or sufficiently reduced by a previous treatment for HIV (≤0.5 log IU/mL), for example, a previous ART, including ritonavir or other therapy; and "relapsers" (i.e., subjects who were previously treated for HIV, for example, who received a previous ART whose HIV titer decreased, and subsequently increased).

In some embodiments, a compound of Formula (I), or a pharmaceutically acceptable salt thereof, can be provided to a treatment failure subject suffering from HIV. In some embodiments, a compound of Formula (I), or a pharmaceutically acceptable salt thereof, can be provided to a non-responder subject suffering from HIV. In some embodiments, a compound of Formula (I), or a pharmaceutically acceptable salt thereof, can be provided to a relapsed subject suffering from HIV.

After a period of time, infectious agents can develop resistance to one or more therapeutic agents. The term "resistance" as used herein refers to a viral strain displaying a delayed, lessened and/or null response to a therapeutic agent(s). In some instances, the virus sometimes mutates or produces variations that are resistant or partially resistant to certain drugs. For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be provided to a subject infected with an HIV strain that is resistant to one or more different anti-HIV agents (for example, an agent used in a conventional standard of care). In some embodiments, development of resistant HIV strains is delayed when a subject is treated with a compound of Formula (I), or a pharmaceutically acceptable salt thereof, compared to the development of HIV strains resistant to other HIV drugs (such as an agent used in a conventional standard of care).

In some embodiments, an effective amount of a compound of Formula (I), or a pharmaceutically acceptable salt thereof, can be provided to a subject for whom other anti-HIV medications are contraindicated. In some embodiments, a compound of Formula (I), or a pharmaceutically acceptable salt thereof, can be provided to a subject that is hypersensitive to an antiretroviral therapy agent.

Some subjects being treated for HIV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formula (I), or a pharmaceutically acceptable salt thereof, can be provided to a subject experiencing viral load rebound, or can prevent such viral load rebound when used to treat the subject.

The standard of care for treating HIV has been associated with several side effects (adverse events). In some embodiments, a compound of Formula (I), or a pharmaceutically acceptable salt thereof, can decrease the number and/or severity of side effects that can be observed in HIV patients being treated with an ART according to the standard of care. Examples of side effects include, but are not limited to loss of appetite, lipodystrophy, diarrhea, fatigue, elevated cholesterol and triglycerides, rash, insomnia, fever, malaise, tachycardia, chills, headache, arthralgias, myalgias, apathy, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formula (I), or a pharmaceutically acceptable salt thereof, can be provided to a subject that discontinued a HIV therapy because of one or more adverse effects or side effects associated with one or more other anti-HIV agents (for example, an agent used in a conventional standard of care).

Table 2 provides some embodiments of the percentage improvement obtained using a compound of Formula (I), or a pharmaceutically acceptable salt thereof, as compared to the standard of care. Examples include the following: in some embodiments, a compound of Formula (I), or a pharmaceutically acceptable salt thereof, results in a percentage of non-responders that is 10% less than the percentage of non-responders receiving the standard of care. In some embodiments, a compound of Formula (I), or a pharmaceutically acceptable salt thereof, results in a number of side effects that is in the range of about 10% to about 30% less than compared to the number of side effects experienced by a subject receiving the standard of care; and in some embodiments, a compound of Formula (I), or a pharmaceutically acceptable salt thereof, results in a severity of a side effect (such as one of those described herein) that is 25% less than compared to the severity of the same side effect experienced by a subject receiving the standard of care. Methods of quantifying the severity of a side effect are known to those skilled in the art.

TABLE 2

| Percentage of non-responders | Percentage of relapsers | Percentage of resistance | Percentage of viral load rebound | Number of side effects | Severity of side effects |
|---|---|---|---|---|---|
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |

TABLE 2-continued

| Percentage of non-responders | Percentage of relapsers | Percentage of resistance | Percentage of viral load rebound | Number of side effects | Severity of side effects |
|---|---|---|---|---|---|
| 90% less about 10% to about 30% less | 90% less about 10% to about 30% less | 90% less about 10% to about 30% less | 90% less about 10% to about 30% less | 90% less about 10% to about 30% less | 90% less about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively, dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a HIV infection. In some embodiments, the total time of the treatment regime with a compound of Formula (I), or a pharmaceutically acceptable salt thereof, can be less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s). Examples of additional agents that can be used in combination with a compound of Formula (I), or a pharmaceutically acceptable salt thereof, or a pharmaceutical composition that includes a compound of Formula (I), or a pharmaceutically acceptable salt thereof, can be agents currently used in a conventional standard of care for treating HIV, HBV, and/or HDV. In some embodiments, a compound of Formula (I), or a pharmaceutically acceptable salt thereof, or a pharmaceutical composition that includes a compound of Formula (I), or a pharmaceutically acceptable salt thereof, can be used with one, two, three or more additional agents described herein.

In some embodiments, when the infection is caused by HBV, and/or the virus is HBV, the additional therapeutic agent can be an antiretroviral therapy (ART) agent such as a non-nucleoside reverse transcriptase inhibitor (NNRTI), a nucleoside reverse transcriptase inhibitor (NRTI), a polymerase inhibitor, a protease inhibitor (PI), a NS5A inhibitor, a fusion/entry inhibitor, an interferon, a viral maturation inhibitor, a capsid assembly modulator, a FXR agonist, a TNF/cyclophilin inhibitor, a TLR agonist, a vaccine, an siRNA or ASO covalently closed circular DNA (cccDNA) inhibitor, a gene silencing agent, an HBx inhibitor, a surface antigen (sAg) secretion inhibitor (for example, HBsAg), and/or an HBV other antiviral compound, or a pharmaceutically acceptable salt of any of the foregoing. In some embodiments, when the infection is caused by HDV, and/or the virus is HDV, the additional therapeutic agent can be an antiretroviral therapy (ART) agent such as a non-nucleoside reverse transcriptase inhibitor (NNRTI), a nucleoside reverse transcriptase inhibitor (NRTI), a polymerase inhibitor, a protease inhibitor (PI), a NS5A inhibitor, a fusion/entry inhibitor, an interferon, a viral maturation inhibitor, a capsid assembly modulator, a FXR agonist, a TNF/cyclophilin inhibitor, a TLR agonist, a vaccine, an siRNA or ASO cccDNA inhibitor, a gene silencing agent, an HBx inhibitor, an sAg secretion inhibitor, and/or an HDV other antiviral compound, or a pharmaceutically acceptable salt of any of the foregoing. In some embodiments, including those described herein, a compound or compounds, or a pharmaceutically acceptable salt thereof, can be used for treating and/or ameliorating HIV and/or inhibiting replication of HIV, can be used for treating and/or ameliorating HBV and/or HDV, and/or inhibiting the replication of HBV and/or HDV.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HBV and/or HDV, a compound disclosed herein can be used in combination with an interferon therapy.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HIV, a compound of Formula (I), or a pharmaceutically acceptable salt thereof, or a pharmaceutical composition that includes a compound of Formula (I), or a pharmaceutically acceptable salt thereof, can be used in place of a conventional polymerase inhibitor.

In some embodiments, a compound of Formula (I), or a pharmaceutically acceptable salt thereof, or a pharmaceutical composition that includes a compound of Formula (I), or a pharmaceutically acceptable salt thereof, can be used in combination with a non-nucleoside reverse transcriptase inhibitor (NNRTI). In some embodiments, the NNRTI can inhibit a HBV and/or HDV reverse transcriptase. Examples of suitable NNRTIs include, but are not limited to, delavirdine (Rescriptor®), efavirenz (Sustiva®), etravirine (Intelence®), nevirapine (Viramune®), rilpivirine (Edurant®), doravirine, and pharmaceutically acceptable salts of any of the foregoing, and/or a combination thereof. A non-limiting list of example NNRTIs includes compounds numbered 1001-1006 in FIG. 1.

In some embodiments, a compound of Formula (I), or a pharmaceutically acceptable salt thereof, or a pharmaceutical composition that includes a compound of Formula (I), or a pharmaceutically acceptable salt thereof, can be used in combination with a nucleoside reverse transcriptase inhibitor (NRTI). In some embodiments, the NRTI can inhibit a HBV and/or HDV reverse transcriptase. Examples of suitable NRTIs include, but are not limited to, abacavir (Ziagen®), adefovir (Hepsera®), amdoxovir, apricitabine, censavudine, didanosine (Videx®), elvucitabine, emtricitabine (Emtriva®), entecavir (Baraclude®), lamivudine (Epivir®), racivir, stampidine, stavudine (Zerit®), tenofovir disoproxil (including Viread®), tenofovir alafenamide, zalcitabine (Hivid®), zidovudine (Retrovir®), and pharmaceutically acceptable salts of any of the foregoing, and/or a combination thereof. A non-limiting list of example NRTIs includes compounds numbered 2001-2017 in FIG. 2.

In some embodiments, a compound of Formula (I), or a pharmaceutically acceptable salt thereof, or a pharmaceutical composition that includes a compound of Formula (I), or a pharmaceutically acceptable salt thereof, can be used in combination with a protease inhibitor. In some embodiments, the protease inhibitor can inhibit a HBV and/or HDV protease, for example NS3/4A. A non-limiting list of example protease inhibitors include the following: amprenavir (Agenerase®), asunaprevir (Sunvepra®), atazanavir (Reyataz®), boceprevir (Victrelis®), darunavir (Prezista®), fosamprenavir (Lexiva®; Telzir®), grazoprevir, indinavir (Crixivan®), lopinavir (Kaletra®), nelfinavir (Viracept®), ritonavir (Norvir®), saquinavir (Fortovase®; Invirase®), simeprevir (Olysio®), telaprevir (Incivek®), danoprevir, tipranavir (Aptivus®), ABT-450 (paritaprevir), BILN-2061 (ciluprevir), BI-201335 (faldaprevir), GS-9256, vedroprevir (GS-9451), IDX-320, ACH-1625 (sovaprevir), ACH-2684, and pharmaceutically acceptable salts of any of the foregoing, and/or combinations thereof. A non-limiting list of example protease inhibitors includes compounds numbered 3001-3010 in FIG. 3A and 3011-3023 in FIG. 3B.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HBV and/or HDV fusion/entry inhibitor. In some embodiments, the fusion/entry inhibitors can block HBV and/or HDV from entering hepatocytes. In some embodiments, the HBV and/or HDV fusion/entry inhibitors can block proteins on the hepatocytes that are required for HBV and/or HDV cellular entry. In some embodiments, the HBV and/or HDV fusion/entry inhibitors can bind to sodium-taurocholate cotransporting polypeptides. Examples of suitable HBV and/or HDV fusion/entry inhibitors include, but are not limited to, myrcludex B, cyclosporin A, ezetimibe, and SCYX1454139, HBIG, Ma18/7, KR127, 17.1.41/19.79.5, heparin, suramin, SALP, taurocholic acid derivatives, and pharmaceutically acceptable salts of any of the foregoing, and/or combinations thereof. A non-limiting list of example HBV and/or HDV fusion/entry inhibitors includes compounds numbered 4008-4020 in FIG. 4B.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, bevirimat, BIT225, calanolide A, hydroxycarbamide, miltefosine, seliciclib, cyanovirin-N, griffithsin, scytovirin, BCX4430, favipiravir, GS-5734, mericitabine, MK-608, NITD008, moroxydine, ribavirin, taribavirin, triazavirin, ARB-1467, ARB-1740, ARC-520, ARC-521, ALN-HBV, TG1050, Tre recombinase, AT-61, AT-130, BCX4430, favipiravir, GS-5734, mericitabine, MK-608 (7-deaza-2'-C-methyladenosine), NITD008, moroxydine, ribavirin, taribavirin, triazavirin, ARB-1467, umifenovir, ARB-1740, ARC-520, ARC-521, ALN-HBV, TG1050 brincidofovir, FGI-104, LJ-001, FGI-106, and pharmaceutically acceptable salts of any of the foregoing, and/or combinations thereof. A non-limiting list of example other antiviral compounds includes the compounds numbered 6001-6010 in FIG. 6A and 6011-6033 in FIG. 6B. Additional examples of other antiviral compounds include, but are not limited to, an abzyme, an enzyme, a protein, or an antibody. Additional examples of other antiviral compounds include, but are not limited to, ceragenins, including CSA-54, diarylpyrimidines, synergistic enhancers, and zinc finger protein transcription factors, and pharmaceutically acceptable salts of any of the foregoing, and/or combinations thereof.

In some embodiments, a compound of Formula (I), or a pharmaceutically acceptable salt thereof, or a pharmaceutical composition that includes a compound of Formula (I), or a pharmaceutically acceptable salt thereof, can be used in combination with a polymerase inhibitor. Examples of polymerase inhibitors include, but are not limited to, telbivudine, beclabuvir, dasabuvir, deleobuvir, filibuvir, setrobuvir, sofosbuvir, radalbuvir, RG7128 (mericitabine), PSI-7851, INX-189, PSI-352938, PSI-661, GS-6620, IDX-184, TMC649128, setrobuvir, lomibuvir, nesbuvir, GS-9190 (tegobuvir), VX-497 (merimepodib), ribavirin, acyclovir, atevirapine, famciclovir, valacyclovir, ganciclovir, valganciclovir, cidofovir, JK-05, and pharmaceutically acceptable salts of any of the foregoing, and/or combinations thereof. A non-limiting list of example polymerase inhibitors includes the compounds numbered 13001-13030 in FIG. 13.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon. Examples of interferons include, but are not limited to alpha-interferons, beta-interferons, delta-interferons, omega-interferons, tau-interferons, x-interferons, consensus interferons, and asialo-interferons. Specific non-limiting examples include: interferon alpha 1A, interferon alpha 1B, interferon alpha 2A, interferon alpha 2B, pegylated-interferon alpha 2a (PEGASYS®, Roche), recombinant interferon alpha 2a (ROFERON®, Roche), inhaled interferon alpha 2b (AERX®, Aradigm), pegylated-interferon alpha 2b (ALBUFERON®, Human Genome Sciences/Novartis, PEGINTRON®, Schering), recombinant interferon alpha 2b (INTRON A®, Schering), pegylated interferon alpha 2b (PEG-INTRON®, Schering, VIRAFERONPEG®, Schering), interferon beta-1a (REBIF®, Serono, Inc. and Pfizer), consensus interferon alpha (INFERGEN®, Valeant Pharmaceutical).

In some embodiments, a compound of Formula (I), or a pharmaceutically acceptable salt thereof, or a pharmaceutical composition that includes a compound of Formula (I), or a pharmaceutically acceptable salt thereof, can be used in combination with a NS5A inhibitor. Examples of NS5A inhibitors include, but are not limited to PPI-461, ACH-2928, GS-5885, BMS-824393, daclatasvir, elbasvir, ledipasvir, uprifosbuvir, MK-8408, odalasvir, ombitasvir, ravidasvir, samatasvir, velpatasvir, and pharmaceutically acceptable salts of any of the foregoing, and/or combinations thereof. A non-limiting list of example NS5A inhibitors includes the compounds numbered 7001-7014 in FIG. 7.

In some embodiments, a compound of Formula (I), or a pharmaceutically acceptable salt thereof, or a pharmaceutical composition that includes a compound of Formula (I), or a pharmaceutically acceptable salt thereof, can be used in combination with a FXR agonist. Examples of FXR agonists include, but are not limited to cafestol; chenodeoxychoic acid; cholic acid; obeticholic acid; ursodeoxycholic acid; fexaramine;

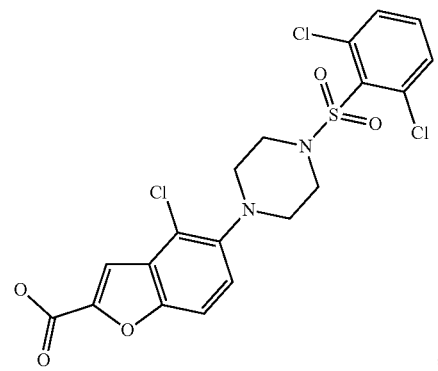

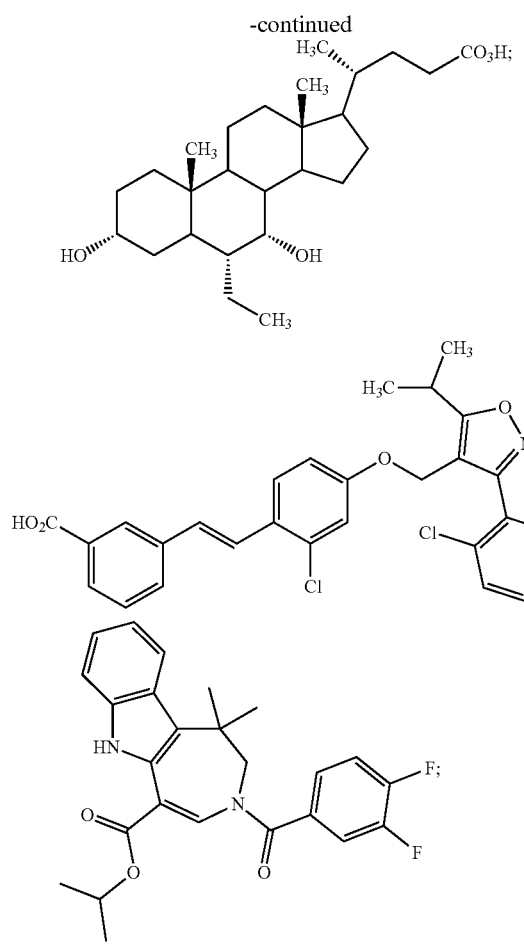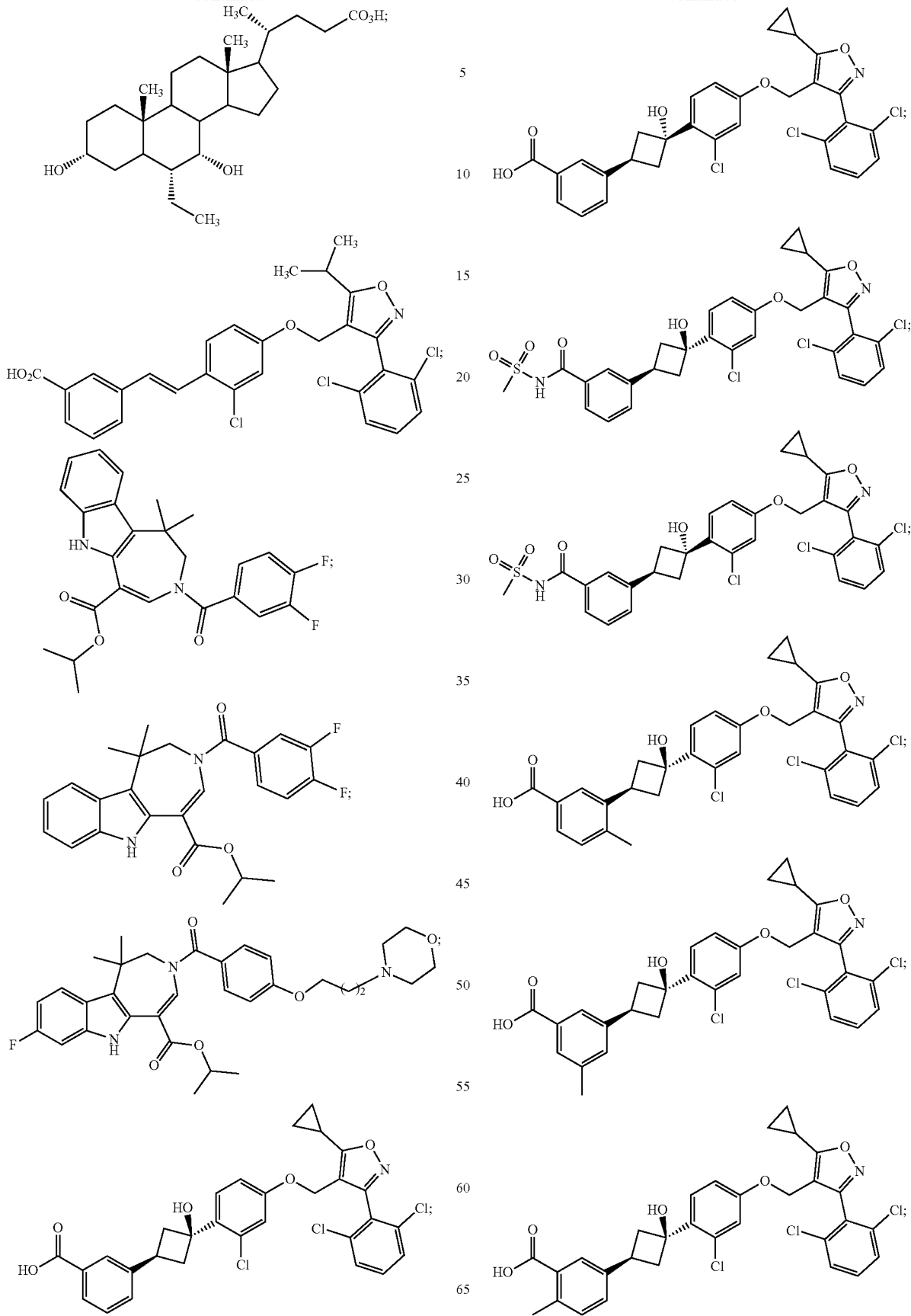

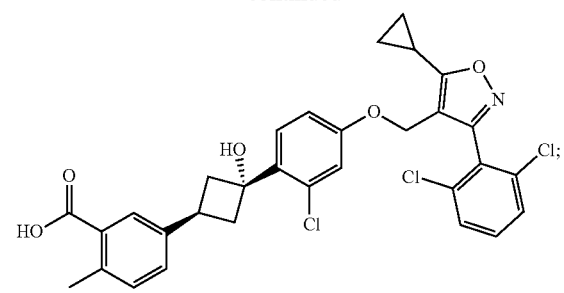
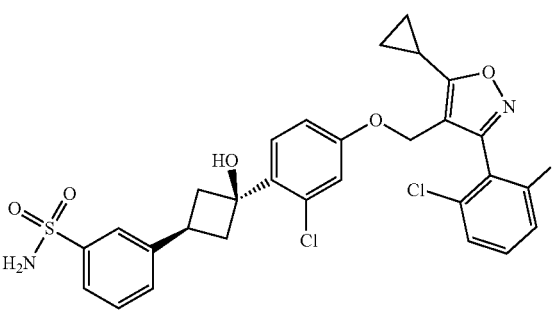
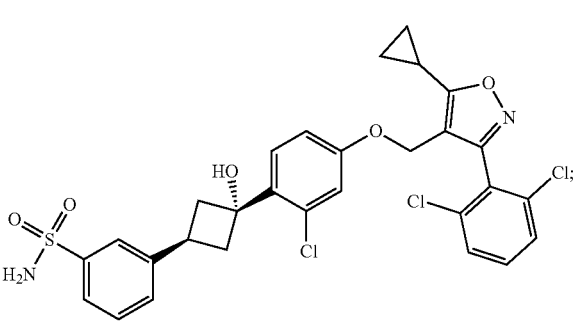
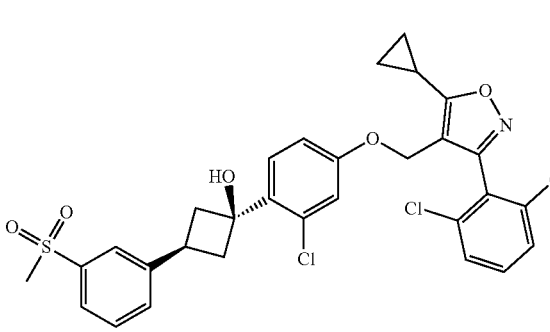
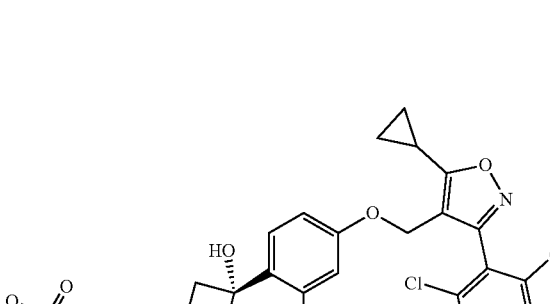
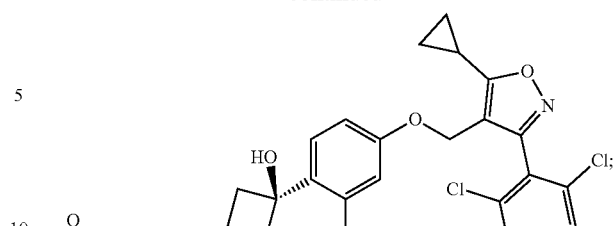
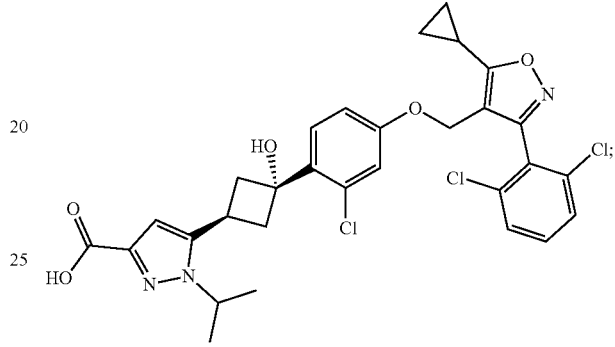
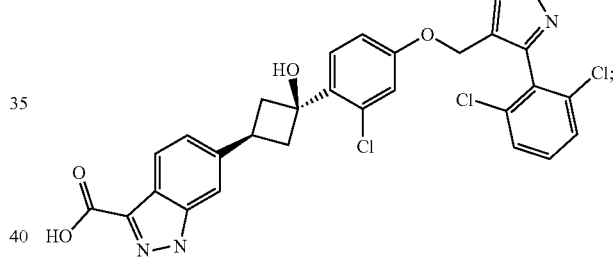
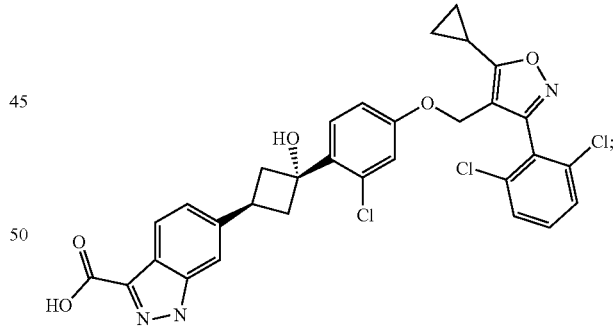
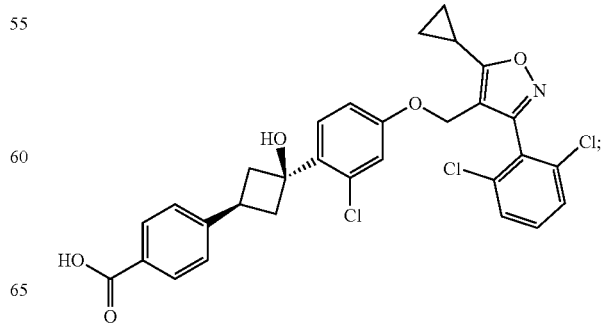

-continued

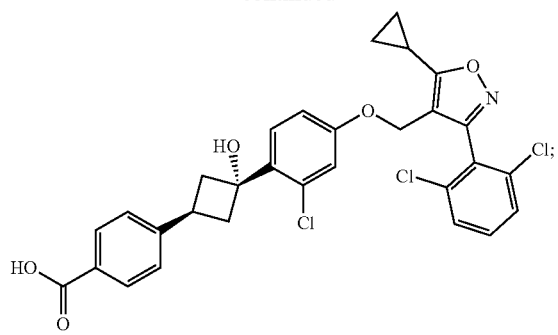

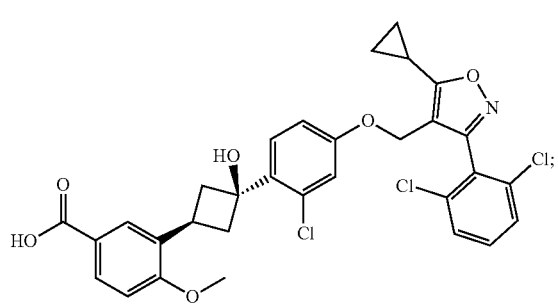

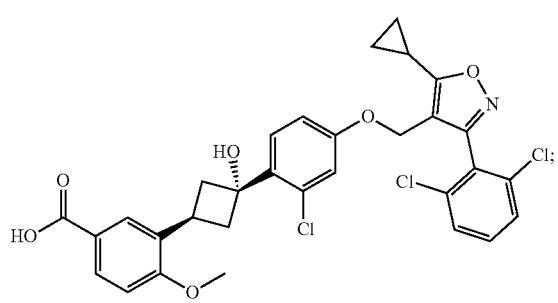

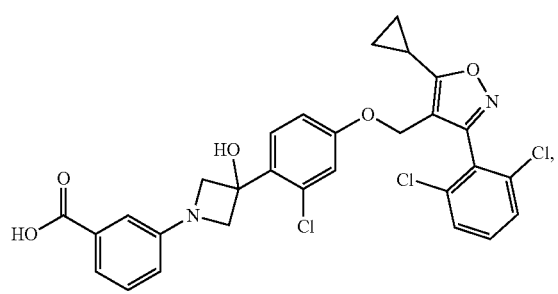

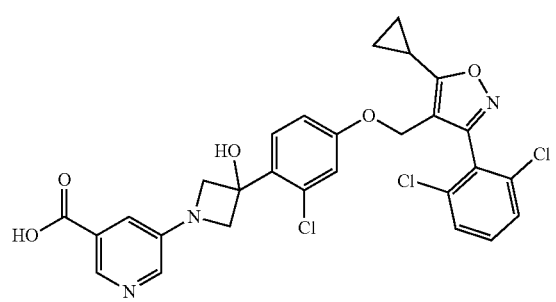

or

-continued

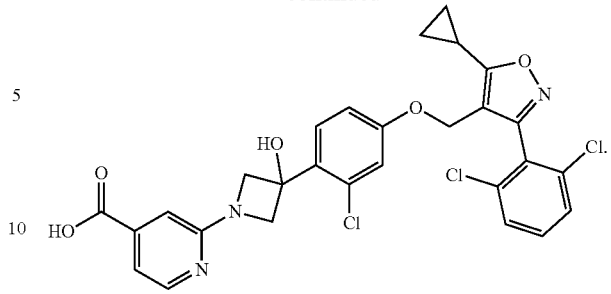

and pharmaceutically acceptable salts of any of the foregoing, and/or combinations thereof. A non-limiting list of additional example FXR agonists includes the compounds numbered 10001-10006 in FIG. 10.

In some embodiments, a compound of Formula (I), or a pharmaceutically acceptable salt thereof, or a pharmaceutical composition that includes a compound of Formula (I), or a pharmaceutically acceptable salt thereof, can be used in combination with a viral maturation inhibitor. In some embodiments, the viral maturation inhibitor can inhibit maturation of HBV and/or HDV. Examples of viral maturation inhibitors include, but are not limited to bevimirat, BMS-955176, MPC-9055, and pharmaceutically acceptable salts of any of the foregoing, and/or combinations thereof. A non-limiting list of example viral maturation inhibitors includes the compounds numbered 8001-8003 in FIG. 8.

In some embodiments, a compound of Formula (I), or a pharmaceutically acceptable salt thereof, or a pharmaceutical composition that includes a compound of Formula (I), or a pharmaceutically acceptable salt thereof, can be used in combination with an siRNA or ASO cccDNA inhibitor. In some embodiments, the an siRNA or ASO cccDNA inhibitor can prevent cccDNA formation, eliminate existing cccDNA, destabilizing existing cccDNA, and/or silence cccDNA transcription.

In some embodiments, a compound of Formula (I), or a pharmaceutically acceptable salt thereof, or a pharmaceutical composition that includes a compound of Formula (I), or a pharmaceutically acceptable salt thereof, can be used in combination with a gene silencing agent. In some embodiments, the gene silencing agent decreases transcription of a target gene or genes. In some embodiments, the gene silencing agent decreases translation of a target gene or genes. In some embodiments, the gene silencing agent can be an oligodeoxynucleotide, a ribozyme, siRNA, a morpholino, or a combination of any of the foregoing.

In some embodiments, a compound of Formula (I), or a pharmaceutically acceptable salt thereof, or a pharmaceutical composition that includes a compound of Formula (I), or a pharmaceutically acceptable salt thereof, can be used in combination with an HBx inhibitor. HBx is a polypeptide encoded by hepadnaviruses that contributes to viral infectivity. In some embodiments, the HBx inhibitor decreases HBx transactivation activity. In some embodiments, the HBx inhibitor blocks or decreasing HBx binding to mammalian cellular proteins. In some embodiments, the HBx inhibitor decreases HBx blocks or decreases recruitment of kinases.

In some embodiments, a compound of Formula (I), or a pharmaceutically acceptable salt thereof, or a pharmaceutical composition that includes a compound of Formula (I), or a pharmaceutically acceptable salt thereof, can be used in combination with an HBsAg secretion inhibitor. HBV and HDV surface antigens are proteins found on both new HBV particle and subviral particles. The subviral particles are non-infectious and are secreted in significant excess to infectious virus, potentially exhausting a subject's immune system. In some embodiments, the HBsAg secretion inhibitor can reduce a subject's immune exhaustion due to the surface antigen. In some embodiments, the HBsAg secretion inhibitor can promote a subject's immune response to HBV and/or HDV.

In some embodiments, a compound of Formula (I), or a pharmaceutically acceptable salt thereof, or a pharmaceutical composition that includes a compound of Formula (I), or a pharmaceutically acceptable salt thereof, can be used in combination with a capsid assembly modulator. In some embodiments, the capsid assembly modulator can stabilize the capsid. In some embodiments, the capsid assembly modulator can promote excess capsid assembly. In some embodiments, the capsid assembly modulator can induce formation of non-capsid polymers of capsid peptides. In some embodiments, the capsid assembly modulator can misdirect capsid assembly (e.g., decreasing capsid stability). In some embodiments, the capsid assembly modulator can bind to the HBV and/or HDV core protein. Examples of capsid assembly modulators include, but are not limited to NVR-3-778, AB-423, GLS-4, Bayer 41-4109, HAP-1, AT-1, and pharmaceutically acceptable salts of any of the foregoing, and/or combinations thereof. A non-limiting list of example capsid assembly modulators includes the compounds numbered 9001-9006 in FIG. 9.

In some embodiments, a compound of Formula (I), or a pharmaceutically acceptable salt thereof, or a pharmaceutical composition that includes a compound of Formula (I), or a pharmaceutically acceptable salt thereof, can be used in combination with a cyclophilin/TNF inhibitor. Examples of cyclophilin/TNF inhibitors include, but are not limited to infliximab (Remicade®), adalimumab (Humira®), certolizumab pegol (Cimzia®), golimumab (Simponi®), etanercept (Enbrel®), thalidomide (Immunoprin®), lenalidomide (Revlimid®), pomalidomide (Pomalyst®, Imnovid®), cyclosporin A, NIM811, Alisporivir (DEB-025), SCY-635, DEB-064, CRV-431, and pharmaceutically acceptable salts of any of the foregoing, and/or combinations thereof. A non-limiting list of example TNF/cyclophilin inhibitors includes the compounds numbered 11001-11014 in FIG. 11.

In some embodiments, a compound of Formula (I), or a pharmaceutically acceptable salt thereof, or a pharmaceutical composition that includes a compound of Formula (I), or a pharmaceutically acceptable salt thereof, can be used in combination with a TLR agonist. Examples of TLR agonists include, but are not limited to GS-9620, ARB-1598, ANA-975, RG-7795 (ANA-773), MEDI-9197, PF-3512676, IMO-2055, isatoribine, tremelimumab, SM360320, AZD-8848, and pharmaceutically acceptable salts of any of the foregoing, and/or combinations thereof. A non-limiting list of example TLR agonists includes the compounds numbered 12001-12013 in FIG. 12.

In some embodiments, a compound of Formula (I), or a pharmaceutically acceptable salt thereof, or a pharmaceutical composition that includes a compound of Formula (I), or a pharmaceutically acceptable salt thereof, can be used in combination with a vaccine. Examples of vaccines include, but are not limited to Heplislav®, ABX-203, INO-1800, and pharmaceutically acceptable salts of any of the foregoing, and/or combinations thereof. A non-limiting list of example vaccines includes those numbered 14001-14003 in FIG. 14.

In some embodiments, a compound of Formula (I), or a pharmaceutically acceptable salt thereof, or a pharmaceutical composition that includes a compound of Formula (I), or a pharmaceutically acceptable salt thereof, can be used in combination with a covalently closed circular DNA (cccDNA) inhibitor. In some embodiments, the cccDNA inhibitor can directly bind cccDNA, can inhibit conversion of relaxed circular DNA (rcDNA) to cccDNA, can reduce or silence transcription of cccDNA, and/or can promote elimination of existing cccDNA.

Some embodiments described herein relate to a method of ameliorating or treating a HBV and/or HDV infection that can include contacting a cell infected with the HBV and/or HDV infection with an effective amount of a compound of Formula (I), or a pharmaceutically acceptable salt thereof, in combination with one or more antiviral agents, such as those described herein, for example, a polymerase inhibitor, a NS5A inhibitor, a protease inhibitor (PI), a fusion/entry inhibitor, an interferon, a FXR agonist, a TLR agonist, a viral maturation inhibitor, a capsid assembly modulator, a cyclophilin/TNF inhibitor, an siRNA or ASO cccDNA inhibitor, a gene silencing agent, an HBx inhibitor, an HBsAg secretion inhibitor, and another antiviral compound, or a pharmaceutically acceptable salt of any of the foregoing.

Some embodiments described herein relate to a method of ameliorating or treating a HBV and/or HDV infection that can include administering to a subject suffering from the HBV and/or HDV infection an effective amount of a compound of Formula (I), or a pharmaceutically acceptable salt thereof, in combination with one or more antiviral agents, such as those described herein, for example, a polymerase inhibitor, a NS5A inhibitor, a protease inhibitor (PI), a fusion/entry inhibitor, an interferon, a FXR agonist, a TLR agonist, a viral maturation inhibitor, a capsid assembly modulator, a cyclophilin/TNF inhibitor, a vaccine, an siRNA or ASO cccDNA inhibitor, a gene silencing agent, an HBx inhibitor, an HBsAg secretion inhibitor, and another antiviral compound, or a pharmaceutically acceptable salt of any of the foregoing.

Some embodiments described herein relate to a method of inhibiting the replication of a HBV and/or HDV virus that can include contacting a cell infected with the HBV and/or HDV virus with an effective amount of a compound of Formula (I), or a pharmaceutically acceptable salt thereof, in combination with one or more antiviral agents, such as those described herein, for example, a polymerase inhibitor, a NS5A inhibitor, a protease inhibitor (PI), a fusion/entry inhibitor, an interferon, a FXR agonist, a TLR agonist, a viral maturation inhibitor, a capsid assembly modulator, a cyclophilin/TNF inhibitor, a vaccine, an siRNA or ASO cccDNA inhibitor, a gene silencing agent, an HBx inhibitor, an HBsAg secretion inhibitor, and another antiviral compound, or a pharmaceutically acceptable salt of any of the foregoing.

Some embodiments described herein relate to a method of inhibiting the replication of a HBV and/or HDV virus that can include administering to a subject infected with the HBV and/or HDV virus an effective amount of a compound of Formula (I), or a pharmaceutically acceptable salt thereof, in combination with one or more antiviral agents, such as those described herein, for example, a polymerase inhibitor, a NS5A inhibitor, a protease inhibitor (PI), a fusion/entry inhibitor, an interferon, a FXR agonist, a TLR agonist, a viral maturation inhibitor, a capsid assembly modulator, a cyclophilin/TNF inhibitor, a vaccine, an siRNA or ASO cccDNA inhibitor, a gene silencing agent, an HBx inhibitor, an HBsAg secretion inhibitor, and another antiviral compound, or a pharmaceutically acceptable salt of any of the foregoing.

In some embodiments, when the infection is caused by HIV, and/or the virus is HIV, the additional therapeutic agent can be an antiretroviral therapy (ART) agent such as a non-nucleoside reverse transcriptase inhibitor (NNRTI), a nucleoside reverse transcriptase inhibitor (NRTI), a protease inhibitor (PI), a fusion/entry inhibitor (also called a CCR5 antagonist), an integrase strand transfer inhibitor (INSTI), an interferon, a viral maturation inhibitor, a capsid assembly modulator, a vaccine, and an HIV other antiretroviral therapy compound, or a pharmaceutically acceptable salt of any of the foregoing. In some embodiments, the method of inhibiting replication of the HIV virus, the additional therapeutic agent can be an antiretroviral therapy (ART) agent such as a non-nucleoside reverse transcriptase inhibitor (NNRTI), a nucleoside reverse transcriptase inhibitor (NRTI), a protease inhibitor (PI), a fusion/entry inhibitor (for HIV, also called a CCR5 antagonist), an integrase strand transfer inhibitor (INSTI), an interferon, a viral maturation inhibitor, a capsid assembly modulator, a vaccine, and an HIV other antiretroviral therapy compound, or a pharmaceutically acceptable salt of any of the foregoing.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HIV, a compound disclosed herein, or a pharmaceutically acceptable salt thereof, can be used in combination with antiretroviral therapies. In some instances, a compound or compounds used for treating and/or ameliorating HBV and/or HDV, and/or inhibiting replication of HBV and/or HDV, may be used for treating and/or ameliorating HIV and/or inhibiting the replication of HIV.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HIV, a compound of Formula (I), or a pharmaceutically acceptable salt thereof, or a pharmaceutical composition that includes a compound of Formula (I), or a pharmaceutically acceptable salt thereof, can be used in place of a conventional ART agent.

In some embodiments, a compound of Formula (I), or a pharmaceutically acceptable salt thereof, or a pharmaceutical composition that includes a compound of Formula (I), or a pharmaceutically acceptable salt thereof, can be used in combination with a non-nucleoside reverse transcriptase inhibitor (NNRTI). In some embodiments, the NNRTI can inhibit a HIV reverse transcriptase. Examples of suitable NNRTIs include, but are not limited to, delavirdine (Rescriptor®), efavirenz (Sustiva®), etravirine (Intelence®), nevirapine (Viramune®), rilpivirine (Edurant®), doravirine, and pharmaceutically acceptable salts of any of the foregoing, and/or a combination thereof. A non-limiting list of example NNRTIs includes compounds numbered 1001-1006 in FIG. 1.

In some embodiments, a compound of Formula (I), or a pharmaceutically acceptable salt thereof, or a pharmaceutical composition that includes a compound of Formula (I), or a pharmaceutically acceptable salt thereof, can be used in combination with a nucleoside reverse transcriptase inhibitor (NRTI). In some embodiments, the NRTI can inhibit a HIV reverse transcriptase. Examples of suitable NRTIs include, but are not limited to, abacavir (Ziagen®), adefovir (Hepsera®), amdoxovir, apricitabine, censavudine, didanosine (Videx®), elvucitabine, emtricitabine (Emtriva®), entecavir (Baraclude®), lamivudine (Epivir®), racivir, stampidine, stavudine (Zerit®), tenofovir disoproxil (including Viread®), tenofovir alafenamide, zalcitabine (Hivid®), zidovudine (Retrovir®), and pharmaceutically acceptable salts of any of the foregoing, and/or a combination thereof. A non-limiting list of example NRTIs includes compounds numbered 2001-2017 in FIG. 2.

In some embodiments, a compound of Formula (I), or a pharmaceutically acceptable salt thereof, or a pharmaceutical composition that includes a compound of Formula (I), or a pharmaceutically acceptable salt thereof, can be used in combination with a protease inhibitor. In some embodiments, the protease inhibitor can block HIV protease. A non-limiting list of example protease inhibitors include the following: amprenavir (Agenerase®), asunaprevir (Sunvepra®), atazanavir (Reyataz®), boceprevir (Victrelis®), darunavir (Prezista®), fosamprenavir (Lexiva®; Telzir®), grazoprevir, indinavir (Crixivan®), lopinavir (Kaletra®), nelfinavir (Viracept®), ritonavir (Norvir®), saquinavir (Fortovase®; Invirase®), simeprevir (Olysio®), telaprevir (Incivek®), danoprevir, tipranavir (Aptivus®), ABT-450 (paritaprevir), BILN-2061 (ciluprevir), BI-201335 (faldaprevir), GS-9256, vedroprevir, IDX-320, ACH-1625 (sovaprevir), ACH-2684, and pharmaceutically acceptable salts of any of the foregoing, and/or a combination thereof. A non-limiting list of example protease inhibitors includes the compounds numbered 3001-3010 in FIG. 3A and compounds numbered 3011-3023 in FIG. 3B.

In some embodiments, a compound of Formula (I), or a pharmaceutically acceptable salt thereof, or a pharmaceutical composition that includes a compound of Formula (I), or a pharmaceutically acceptable salt thereof, can be used in combination with an HIV fusion/entry inhibitor. In some embodiments, the HIV fusion/entry inhibitors can block HIV from entering the CD4+T lymphocytes. In some embodiments, the fusion/entry inhibitors, which are also known as CCR5 antagonists, can block proteins on the CD4+T lymphocyte cells that are required for HIV cellular entry. Examples of suitable fusion/entry inhibitors include, but are not limited to, enfuvirtide (Fuzeon®), maraviroc (Selzentry®), vicriviroc, cenicriviroc, fostemsavir, ibalizumab, PRO 140, and pharmaceutically acceptable salts of any of the foregoing, and/or combinations thereof. A non-limiting list of example HIV fusion/entry inhibitors includes compounds numbered 4001-4007 in FIG. 4A.

In some embodiments, a compound of Formula (I), or a pharmaceutically acceptable salt thereof, or a pharmaceutical composition that includes a compound of Formula (I), or a pharmaceutically acceptable salt thereof, can be used in combination with an HIV integrase strand transfer inhibitor (INSTI). In some embodiments, the INSTI can block HIV integrase. Examples of INSTIs include, but are not limited to, dolutegravir (Tivicay®), elvitegravir (Strivild®; Vitekta®), raltegravir (Isentress®), BI 224436, globoidnan A, cabotegravir, bictegravir, MK-2048, and pharmaceutically acceptable salts of any of the foregoing, and/or a combination thereof. A non-limiting list of example HIV INSTIs includes compounds numbered 5001-5008 in FIG. 5.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, bevirimat, BIT225, calanolide A, hydroxycarbamide, miltefosine, seliciclib, cyanovirin-N, griffithsin, scytovirin, BCX4430, favipiravir, GS-5734, mericitabine, MK-608, NITD008, moroxydine, ribavirin, taribavirin, triazavirin, ARB-1467, ARB-1740, ARC-520, ARC-521, ALN-HBV, TG1050, Tre recombinase, AT-61, AT-130, BCX4430, favipiravir, GS-5734, mericitabine, MK-608 (7-deaza-2'-C-methyladenosine), NITD008, moroxydine, ribavirin, taribavirin, triazavirin, ARB-1467, umifenovir, ARB-1740, ARC-520, ARC-521, ALN-HBV, TG1050 brincidofovir, FGI-104, LJ-001, FGI-106, and pharmaceutically acceptable salts of any of the foregoing, and/or combinations thereof. A non-limiting list of example other antiviral compounds includes the compounds numbered 6001-6010 in FIG. 6A and 6011-6033 in FIG. 6B. Additional examples of other antiviral compounds include, but are not limited to, an abzyme, an enzyme, a protein, or an antibody. Additional examples of other antiviral compounds include, but are not limited to, ceragenins, including CSA-54, diarylpyrimidines, synergistic enhancers, and zinc finger protein transcription factors, and/or combinations thereof.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon. Examples of interferons include, but are not limited to alpha-interferons, beta-interferons, delta-interferons, omega-interferons, tau-interferons, x-interferons, consensus interferons, and asialo-interferons. Specific non-limiting examples include: interferon alpha 1A, interferon alpha 1B, interferon alpha 2A, interferon alpha 2B, pegylated-interferon alpha 2a (PEGASYS®, Roche), recombinant interferon alpha 2a (ROFERON®, Roche), inhaled interferon alpha 2b (AERX®, Aradigm), pegylated-interferon alpha 2b (ALBUFERON®, Human Genome Sciences/Novartis, PEGINTRON®, Schering), recombinant interferon alpha 2b (INTRON A®, Schering), pegylated interferon alpha 2b (PEG-INTRON®, Schering, VIRAFERONPEG®, Schering), interferon beta-1a (REBIF®, Serono, Inc. and Pfizer), consensus interferon alpha (INFERGEN®, Valeant Pharmaceutical), and/or combinations of any of the foregoing.

In some embodiments, a compound of Formula (I), or a pharmaceutically acceptable salt thereof, or a pharmaceutical composition that includes a compound of Formula (I), or a pharmaceutically acceptable salt thereof, can be used in combination with a viral maturation inhibitor. Examples of viral maturation inhibitors include, but are not limited to bevirimat, BMS-955176, MPC-9055, and pharmaceutically acceptable salts of any of the foregoing, and/or combinations thereof. A non-limiting list of example viral maturation inhibitors includes the compounds numbered 8001-8003 in FIG. 8.

In some embodiments, a compound of Formula (I), or a pharmaceutically acceptable salt thereof, or a pharmaceutical composition that includes a compound of Formula (I), or a pharmaceutically acceptable salt thereof, can be used in combination with a capsid assembly modulator. In some embodiments, the capsid assembly modulator can inhibit assembly of the HIV capsid. Examples of capsid assembly modulators include, but are not limited to NVR-3-778, AB-423, GLS-4, Bayer 41-4109, HAP-1, AT-1 and combinations thereof, and pharmaceutically acceptable salts of any of the foregoing, and/or combinations thereof. A non-limiting list of example capsid assembly modulators includes the compounds numbered 9001-9006 in FIG. 9.

Some embodiments described herein relate to a method of ameliorating or treating a HIV infection that can include contacting a cell infected with the HIV infection with an effective amount of a compound of Formula (I), or a pharmaceutically acceptable salt thereof, in combination with one or more antiretroviral therapy (ART) agents, such as a non-nucleoside reverse transcriptase inhibitor (NNRTI), a nucleoside reverse transcriptase inhibitor (NRTI), a protease inhibitor (PI), a fusion/entry inhibitor (also called a CCR5 antagonist), an integrase strand transfer inhibitor (INSTI), and an HIV other antiretroviral therapy compound, or a pharmaceutically acceptable salt of any of the foregoing.

Some embodiments described herein relate to a method of ameliorating or treating a HIV infection that can include administering to a subject suffering from the HIV infection an effective amount of a compound of Formula (I), or a pharmaceutically acceptable salt thereof, in combination with one or more antiretroviral therapy (ART) agents, such as a non-nucleoside reverse transcriptase inhibitor (NNRTI), a nucleoside reverse transcriptase inhibitor (NRTI), a protease inhibitor (PI), a fusion/entry inhibitor (also called a CCR5 antagonist), an integrase strand transfer inhibitor (INSTI), and another antiviral compound, or a pharmaceutically acceptable salt of any of the foregoing.

Some embodiments described herein relate to a method of inhibiting the replication of a HIV virus that can include contacting a cell infected with the HIV virus with an effective amount of a compound of Formula (I), or a pharmaceutically acceptable salt thereof, in combination with one or more antiretroviral therapy (ART) agents, such as a non-nucleoside reverse transcriptase inhibitor (NNRTI), a nucleoside reverse transcriptase inhibitor (NRTI), a protease inhibitor (PI), a fusion/entry inhibitor (also called a CCR5 antagonist), an integrase strand transfer inhibitor (INSTI), and another antiviral compound, or a pharmaceutically acceptable salt of any of the foregoing.

Some embodiments described herein relate to a method of inhibiting the replication of a HIV virus that can include administering to a subject infected with the HIV virus an effective amount of a compound of Formula (I), or a pharmaceutically acceptable salt thereof, in combination with one or more antiretroviral therapy (ART) agents, such as a non-nucleoside reverse transcriptase inhibitor (NNRTI), a nucleoside reverse transcriptase inhibitor (NRTI), a protease inhibitor (PI), a fusion/entry inhibitor (also called a CCR5 antagonist), an integrase strand transfer inhibitor (INSTI), and another antiviral compound, or a pharmaceutically acceptable salt of any of the foregoing.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt the thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) in FIGS. 1-14 (including pharmaceutically acceptable salts and prodrugs of any of the foregoing) can result in an additive effect. In some embodiments, the combination of a compound of Formula (I), or a pharmaceutically acceptable salt thereof, in combination with one or more additional agent(s) in FIGS. 1-14 (including pharmaceutically acceptable salts and prodrugs of any of the foregoing) can result in a synergistic effect. In some embodiments, the combination of a compound of Formula (I), or a pharmaceutically acceptable salt thereof, in combination with one or more additional agent(s) in FIGS. 1-14 (including pharmaceutically acceptable salts and prodrugs of any of the foregoing) can result in a strongly synergistic effect. In some embodiments, the combination of a compound of Formula (I), or a pharmaceutically acceptable salt thereof, in combination with one or more additional agent(s) in FIGS. 1-14 (including pharmaceutically acceptable salts and prodrugs of any of the foregoing) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) in FIGS. 1-14 (including pharmaceutically acceptable salts of any of the foregoing) may be a reduction in the required amount(s) of one or more compounds of FIGS. 1-14 (including pharmaceutically acceptable salts of any of the foregoing) that is effective in treating a disease condition disclosed herein (for example, HBV), as compared to the amount required to achieve same therapeutic result when one or more compounds of FIGS. 1-14 (including pharmaceutically acceptable salts of any of the foregoing) are administered without a compound of Formula (I), or a pharmaceutically acceptable salt thereof. For example, the amount of a compound in FIGS. 1-14 (including a pharmaceutically acceptable salt of any of the foregoing), can be less compared to the amount of the compound in FIGS. 1-14 (including a pharmaceutically acceptable salt of any of the foregoing), needed to achieve the same viral load reduction when administered as a monotherapy. Another potential advantage of utilizing a compound of Formula (I), or a pharmaceutically acceptable salt thereof, in combination with one or more additional agent(s) in FIGS. 1-14 (including pharmaceutically acceptable salts of any of the foregoing) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) in FIGS. 1-14 (including pharmaceutically acceptable salts of any of the foregoing) may include little to no cross resistance between a compound of Formula (I), or a pharmaceutically acceptable salt thereof, and one or more additional agent(s) in FIGS. 1-14 (including pharmaceutically acceptable salts of any of the foregoing) thereof; different routes for elimination of a compound of Formula (I), or a pharmaceutically acceptable salt thereof, and one or more additional agent(s) in FIGS. 1-14 (including pharmaceutically acceptable salts of any of the foregoing); little to no overlapping toxicities between a compound of Formula (I), or a pharmaceutically acceptable salt thereof, and one or more additional agent(s) in FIGS. 1-14 (including pharmaceutically acceptable salts of any of the foregoing); little to no significant effects on cytochrome P450; little to no pharmacokinetic interactions between a compound of Formula (I), or a pharmaceutically acceptable salt thereof, and one or more additional agent(s) in FIGS. 1-14 (including pharmaceutically acceptable salts of any of the foregoing); greater percentage of subjects achieving a sustained viral response compared to when a compound is administered as monotherapy and/or a decrease in treatment time to achieve a sustained viral response compared to when a compound is administered as monotherapy.

EXAMPLES

Additional embodiments are disclosed in further detail in the following examples, which are not in any way intended to limit the scope of the claims.

Example 1

(2-((4-aminopyrrolo[2,1-f][1,2,4]triazin-7-yl)methoxy)ethyl)phosphonic acid (Compound 1)

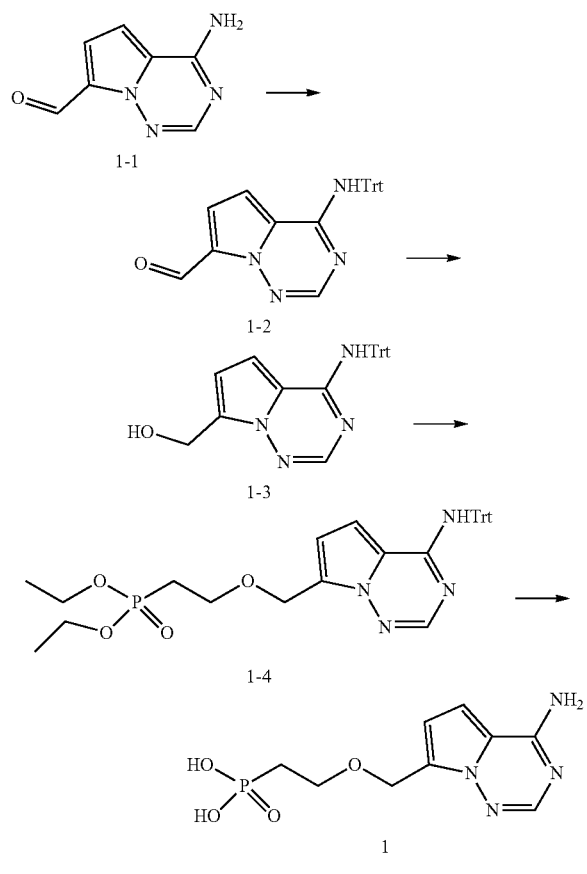

To a solution of 1-1 (300 mg, 1.85 mmol, WO 2013/124316, published Aug. 29, 2013) in DCM (5 mL) was added triphenylmethyl chloride (TrtCl) (670 mg, 2.4 mmol), silver nitrate (AgNO$_3$) (406 mg, 2.4 mmol) and 2,4,6-Trimethly pyridine (0.7 mL, 5.6 mmol) sequentially. The mixture was stirred at room temperature (RT) for 15 h. After filtration, water (100 mL) was added to the filtrate, and the mixture was extracted with ethyl acetate (3×100 mL3). The combined organic phase was concentrated in vacuo to give a residue which was further purified by silica gel column (Petroleum ether (PE):ethyl acetate (EA)=3:1) to give 1-2 (390 mg, 52%) as a white solid. ESI-LCMS: m/z 405.1 [M+H]$^+$.

To a solution of 1-2 (340 mg, 0.8 mmol) in MeOH (4 mL) was added NaBH$_4$ (80 mg, 2.1 mmol). The mixture was stirred at RT for 1 h. Water (10 mL) was added to quench the reaction. The mixture was extracted with EA (3×20 mL), and the organic phase was concentrated in vacuo to give a residue. The residue was further purified with silica gel column to give 1-3 (285 mg, 81%) as a white solid. ESI-LCMS: m/z 407.1 [M+H]$^+$.

To a suspension of NaH (43 mg, 1.8 mmol) in anhydrous THF (1 mL) was added 1-3 (240 mg, 0.6 mmol) under N$_2$ at 0° C. The mixture was stirred at 0° C. for 0.5 h. Diethyl vinylphosphonate (1.23 g, 5.0 mmol) was added. The mixture was warmed to RT, and stirred for 3 h. Water was added to quench the reaction. The mixture was extracted with EA (3×20 mL). The organic layer was dried over Na$_2$SO$_4$, concentrated and purified by silica gel column to give 1-4 (200 mg, 43%). ESI-LCMS: m/z 571.1 [M+H]$^+$.

To a solution of 1-4 (170 mg, 0.30 mmol) in DCM (1 mL) was added TMSBr (0.98 mL, 7.5 mmol) at 0° C. The mixture was stirred at RT for 1 h. The mixture was removed in vacuo to produce a yellow residue. Saturated aqueous Na$_2$CO$_3$ was added, and the pH was adjusted to 9. The aqueous solution was extracted with EA (3×30 mL). The pH of the aqueous layer was adjusted to 4-5 with 2M HCl, and then then extracted with EA (3×30 mL). The combined organic phase was concentrated in vacuo to give crude product which was used directly for the next step. To a solution of the above crude product in DCM (0.5 mL) was added TFA (0.5 mL). The reaction was stirred at 40° C. for 2.5 h. TFA was removed in vacuo, and the remaining residue was further purified by RP-HPLC to give 1 (39 mg, 48%) as a white solid. ESI-LCMS: m/z 273.1 [M+H]$^+$.

Example 2

(R)-(((1-(4-aminopyrrolo[2,1-f][1,2,4]triazin-7-yl)propan-2-yl)oxy)methyl)phosphonic acid (Compound 2)

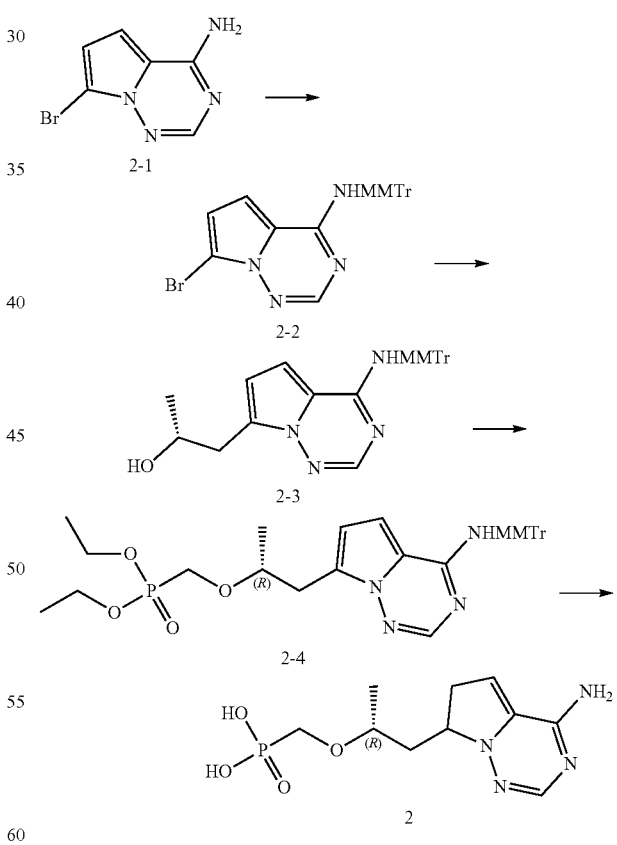

To a solution of 2-1 (3.85 g, 18.1 mmol, WO 2007/64931, published Jun. 7, 2007) in anhydrous DMF (30 mL) was added NaH (1.08 g, 27.1 mmol) at 0° C. The reaction was stirred under N$_2$ for 0.5 h. MMTrCl (6.14 g, 19.9 mmol) was added. The mixture was stirred at RT for 2 h. Water was added to quench the reaction. The mixture was extracted with EA (3×100 mL). The organic phase was combined and then dried over Na$_2$SO$_4$. After filtration, the solution was concentrated in vacuo to give a residue which was further purified by column chromatograph (PE:EA=20:1) to give 2-2 (3.8 g, 45%) as a white solid. ESI-LCMS: m/z 485.2 [M+H]$^+$.

To a solution of 2-2 (3.80 g, 7.83 mmol) in THF (36 mL) was added n-BuLi (540 mg, 23.5 mmol) dropwise at −78° C. The mixture was stirred for 20 mins at −78° C. (R)-2-methyloxirane (4.55 g, 78.3 mmol) was added slowly at −78° C. over 15 mins. The reaction was warmed to RT slowly and then stirred at RT for 2 h. After the reaction was quenched with sat. NH$_4$Cl solution, the mixture was extracted with EA (3×100 mL). The organic phase was concentrated in vacuo to give the crude product which was further purified by silica gel column (PE:EA=2:1) to give 2-3 (1.4 g, 38%) as a white solid. ESI-LCMS: m/z 465.3 [M+H]$^+$.

To a suspension of NaH (832 mg, 21 mmol) in THF (5 mL) was added 2-3 (225 mg, 0.5 mmol) under N$_2$ at 0° C. The mixture was stirred at 0° C. for 1 h. (Diethoxyphosphoryl)methyl trifluoromethanesulfonate (3.12 g, 10.4 mmol) was added. The mixture was stirred at RT for 3 h. Water was added to quench the reaction, and the mixture was extracted with EA (3×20 mL). The organic layer was dried over Na$_2$SO$_4$, concentrated and purified by silica gel column to give 2-4 (694 mg, 42%). ESI-LCMS: m/z 615.4 [M+H]$^+$.

To a solution of 2-4 (700 mg, 1.14 mmol) in anhydrous CH$_3$CN (4 mL) was added TMSBr (3.8 mL, 28.5 mmol) dropwise at 0° C. The reaction was then stirred at 50° C. for 1 h. The mixture was then concentrated in vacuo to give a residue which was further purified by RP-HPLC to give 2 (89 mg, 27%) as a white solid. ESI-LCMS: m/z 287.1 [M+H]$^+$.

Example 3

((2-(4-aminopyrrolo[2,1-f][1,2,4]triazin-7-yl)ethoxy)methyl)phosphonic acid (Compound 3)

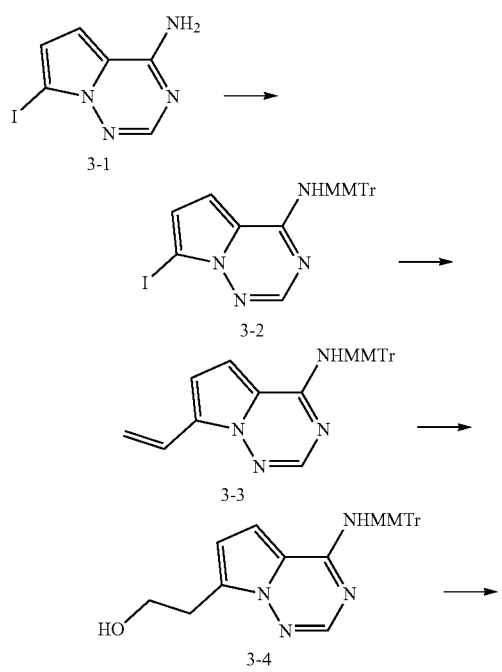

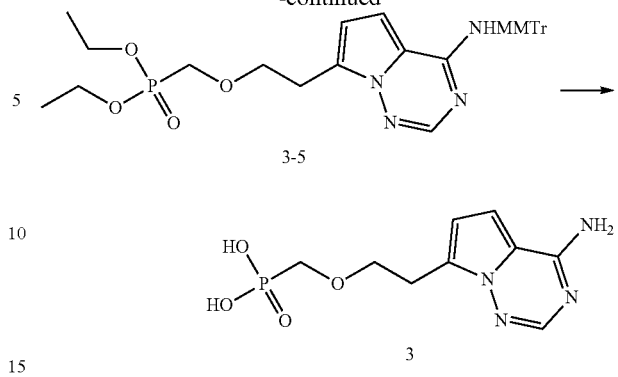

To a solution of 3-1 (2.08 g, 8.0 mmol, WO 2015/133395, published Sep. 11, 2015) in anhydrous DMF (20 mL) was added NaH (0.29 g, 12 mmol) at 0° C. The reaction was stirred under N$_2$ for 0.5 h. MMTrCl (2.71 g, 8.8 mmol) was added under N$_2$. The mixture was stirred at RT for 2 h. Water was added to quench the reaction. The mixture was extracted with EA (3×100 mL). The organic phase was combined and then dried over Na$_2$SO$_4$. After filtration, the solution was concentrated in vacuo to give a residue which was further purified by column chromatograph (PE:EA=20:1) to give 3-2 (3.5 g, 82%). ESI-LCMS: m/z 533.1 [M+H]$^+$.

To a solution of 3-2 (3.02 g, 5.7 mmol) in mixed solvent (acetonitrile:H$_2$O=9:1, 35 mL) were added potassium vinyltrifluoroborate (1 g, 7.4 mmol), Pd(PPh$_3$)$_4$ (0.66 g, 0.6 mmol), and Cs$_2$CO$_3$ (5.56 g, 17 mmol). The mixture was stirred at 65° C. overnight under N$_2$. Water was added, and the mixture was extracted with DCM (3×100 mL). The organic lay was concentrated and purified by column chromatograph (PE:EA=20:1) to give 3-3 (1.19 g, 48%). ESI-LCMS: m/z 433.2 [M+H]$^+$.

To the solution of 3-3 (2.13 g, 4.9 mmol) in THF (12.4 mL) was added 2M BH$_3$-THF solution (12.4 mL, 24.8 mmol) at 0° C. under N$_2$. The mixture was stirred at 0° C. for 1 h and then at RT overnight. The mixture was then cooled to 0° C., and 1M aqueous NaOH solution (3 mL) and 30% H$_2$O$_2$ (3 mL) was added. The mixture was stirred at RT for 6 h. The mixture was then extracted with EA (3×50 mL). The organic layer was dried over anhydrous Na$_2$SO$_4$. After concentration in vacuo, the residue was further purified by column chromatograph (PE:EA=2:1) to give product 3-4 (0.62 g, 28%). ESI-LCMS: m/z 451.0 [M+H]$^+$.

To a suspension of NaH (0.2 g, 5 mmol) in THF (1.5 mL) was added 3-4 (225 mg, 0.5 mmol) under N$_2$ at −20 OC. The mixture was stirred at −20 OC for 0.5 h. (Diethoxyphosphoryl)methyl trifluoromethanesulfonate (1.23 g, 5 mmol) was added, and the mixture was stirred at −20° C. to RT for 3 h. Water was added to quench the reaction, and the mixture was extracted with EA (3×20 mL). The organic layer was dried over Na$_2$SO$_4$, concentrated and purified by silica gel column to give 3-5 (250 mg, 83%). ESI-LCMS: m/z 601.4 [M+H]$^+$.

To the solution of 3-5 (300 mg, 0.5 mmol) in anhydrous acetonitrile (1.65 mL) was added TMSBr (1.65 mL, 12.5 mmol) at 0° C. The mixture was then stirred at 50° C. for 1.0 h. The mixture was concentrated in vacuo and then purified by pre-HPLC to give 3 (30.8 mg, 23%). ESI-LCMS: m/z 273.1 [M+H]$^+$.

Example 4

(R)-(((1-(8-amino-[1,2,4]triazolo[3,4-f][1,2,4]triazin-3-yl)propan-2-yl)oxy)methyl)phosphonic acid (Compound 4)

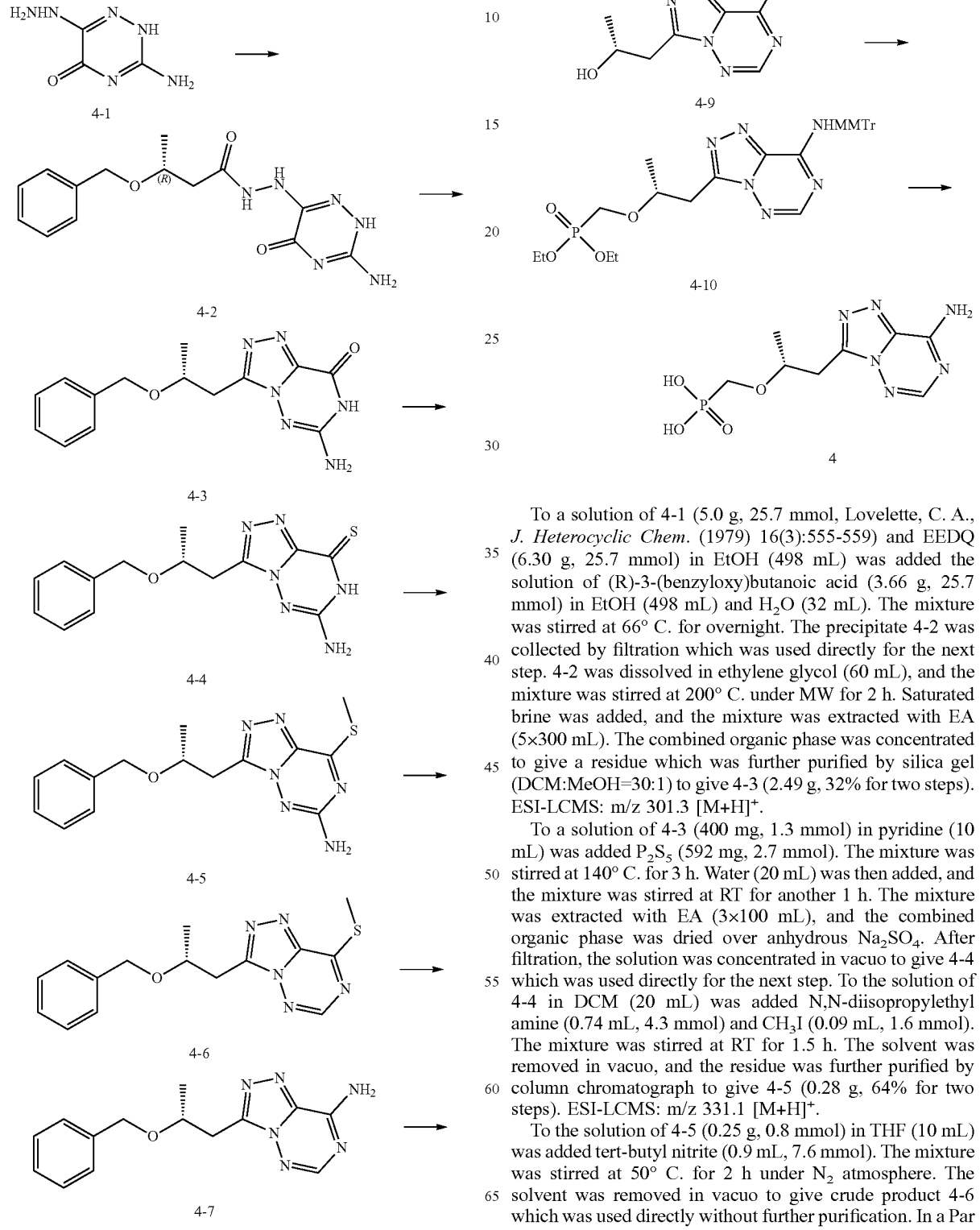

To a solution of 4-1 (5.0 g, 25.7 mmol, Lovelette, C. A., *J. Heterocyclic Chem.* (1979) 16(3):555-559) and EEDQ (6.30 g, 25.7 mmol) in EtOH (498 mL) was added the solution of (R)-3-(benzyloxy)butanoic acid (3.66 g, 25.7 mmol) in EtOH (498 mL) and H$_2$O (32 mL). The mixture was stirred at 66° C. for overnight. The precipitate 4-2 was collected by filtration which was used directly for the next step. 4-2 was dissolved in ethylene glycol (60 mL), and the mixture was stirred at 200° C. under MW for 2 h. Saturated brine was added, and the mixture was extracted with EA (5×300 mL). The combined organic phase was concentrated to give a residue which was further purified by silica gel (DCM:MeOH=30:1) to give 4-3 (2.49 g, 32% for two steps). ESI-LCMS: m/z 301.3 [M+H]$^+$.

To a solution of 4-3 (400 mg, 1.3 mmol) in pyridine (10 mL) was added P$_2$S$_5$ (592 mg, 2.7 mmol). The mixture was stirred at 140° C. for 3 h. Water (20 mL) was then added, and the mixture was stirred at RT for another 1 h. The mixture was extracted with EA (3×100 mL), and the combined organic phase was dried over anhydrous Na$_2$SO$_4$. After filtration, the solution was concentrated in vacuo to give 4-4 which was used directly for the next step. To the solution of 4-4 in DCM (20 mL) was added N,N-diisopropylethyl amine (0.74 mL, 4.3 mmol) and CH$_3$I (0.09 mL, 1.6 mmol). The mixture was stirred at RT for 1.5 h. The solvent was removed in vacuo, and the residue was further purified by column chromatograph to give 4-5 (0.28 g, 64% for two steps). ESI-LCMS: m/z 331.1 [M+H]$^+$.

To the solution of 4-5 (0.25 g, 0.8 mmol) in THF (10 mL) was added tert-butyl nitrite (0.9 mL, 7.6 mmol). The mixture was stirred at 50° C. for 2 h under N$_2$ atmosphere. The solvent was removed in vacuo to give crude product 4-6 which was used directly without further purification. In a Par reactor, 4-6 was dissolved in 2 M solution of ammonium in methanol (10 mL). The mixture was stirred at 80° C. overnight. The solvent was removed in vacuo, and the residue was further purified by column chromatograph to give 4-7 (86 mg, 40% yield for two steps). ESI-LCMS: m/z 285.1 [M+H]⁺.

To the solution of 4-7 (1.00 g, 3.5 mmol) in DCM (20 mL) was added 1M BCl₃ DCM solution (6.4 mL) dropwise at −78° C. The reaction was stirred at −78° C. for 2 h and then at 0° C. for 0.5 h. 2M NH₃ methanol solution was added to adjust the pH to 10. The mixture was concentrated in vacuo and then purified by column chromatograph to give 4-8 (680 mg, 98%). ESI-LCMS: m/z 195.1[M+H]⁺.

To a solution of 4-8 (50 mg, 0.3 mmol) in anhydrous DMF (1 mL) was added NaH (26 mg, 0.6 mmol) at 0° C. The reaction was stirred under N₂ for 0.5 h. MMTrCl (79 mg, 0.3 mmol) was then added under N₂. The mixture was stirred at RT for 2.0 h. Water was added to quench the reaction. The mixture was extracted with EA (3×20 mL). The organic phase was combined and dried over Na₂SO₄. After filtration, the solution was concentrated in vacuo to give a residue which was further purified by column chromatograph (PE: EA=20:1) to give 4-9 (80 mg, 60%) as a white solid. ESI-LCMS: m/z 467.2 [M+H]⁺.

To a suspension of NaH (189 mg, 4.7 mmol) in THF (1 mL) was added 4-9 (220 mg, 0.5 mmol) under N₂ at 0° C. The mixture was stirred at 0° C. for 1 h. (Diethoxyphosphoryl)methyl trifluoromethanesulfonate (708 mg, 2.4 mmol) was added, and the mixture was stirred at RT for 5 h. Water was added to quench the reaction. The mixture was extracted with EA (3×20 mL). The organic layer was dried over Na₂SO₄, concentrated and purified by silica gel column to give 4-10 (119 mg, 43%). ESI-LCMS: m/z 589.4 [M+H]⁺.

To a solution of 4-10 (300 mg, 0.5 mmol) in anhydrous CH₃CN (3 mL) was added TMSBr (1.7 mL, 12.7 mmol) dropwise at 0° C. The reaction was stirred at RT for 6 h. The mixture was then concentrated in vacuo to give a residue which was further purified by prep-HPLC to give 4 (43.2 mg, 30%) as a white solid. ESI-LCMS: m/z 289.2 [M+H]⁺.

Example 5

(R)-(((1-(4-aminoimidazo[2,1-f][1,2,4]triazin-7-yl)propan-2-yl)oxy)methyl)phosphonic acid (Compound 5)

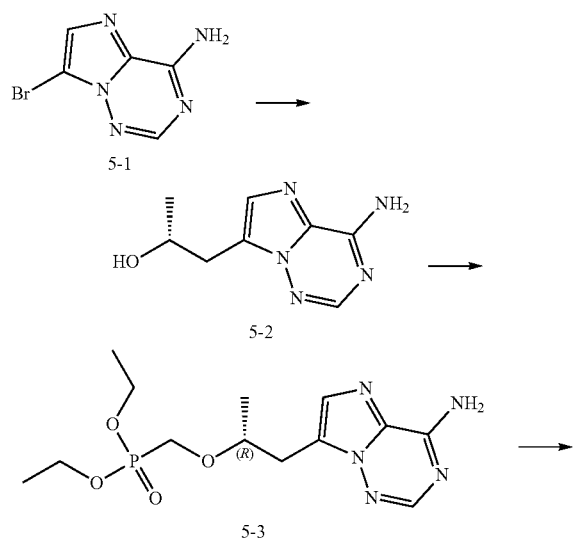

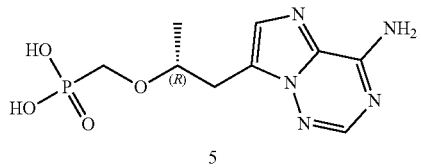

To a solution of 5-1 (1.00 g, 4.7 mmol, Lindell et al., *ACS Med. Chem. Lett.* (2010) 1(6):286-289) and 1,3-dichloro-1,1,3,3-tetraisopropyldisiloxane (2.21 g, 7 mmol) in THF (20 mL) was stirred at RT for 3 h. The mixture was cooled to −78° C. n-BuLi (28.0 mmol, 1.8 mL) was added dropwise and stirred at −78° C. for 1 h. (R)-2-methyloxirane (2.71 g, 46.7 mmol) was added dropwise, and the mixture was warmed to RT and stirred for 2 h. Water (0.5 mL) was added to quench the reaction, and the mixture was extracted with DCM (3×20 mL). The organic phase was concentrated and purified by flash column to give 5-2 (0.50 g, 55%). ESI-LCMS: m/z 194.1 [M+H]⁺.

A solution of 5-2 (100 mg, 0.5 mmol) and (t-BuO)₂Mg (264 mg, 1.55 mmol) in NMP (1 mL) was stirred at 70° C. for 10 mins. Diethyl p-tolylsulfonyloxymethyl phosphonate (250 mg, 0.8 mmol) was added, and the mixture stirred at 70° C. overnight. Water was added, and the mixture was extracted with EA (3×100 mL). The organic layer was dried over Na₂SO₄, and then concentrated to give a residue which was purified by prep-TLC to give 5-3 (81 mg, 45%) as a colorless oil. ESI-LCMS: m/z 344.1 [M+H]⁺.

To a solution of 5-3 (0.21 g, 0.6 mmol) in CH₃CN (2.30 mL) was added TMSBr (1.92 mL, 14.6 mmol) dropwise at 0° C. The mixture was stirred at RT for 3 h. The mixture was concentrated under reduced pressure and purified by RP-HPLC to give 5 (80.0 mg, 48%) as a white solid. ESI-LCMS: m/z 288.2 (M+H)⁺.

Example 6

(R)-(((1-(4-aminoimidazo[5,1-f][1,2,4]triazin-7-yl)propan-2-yl)oxy)methyl)phosphonic acid (Compound 6)

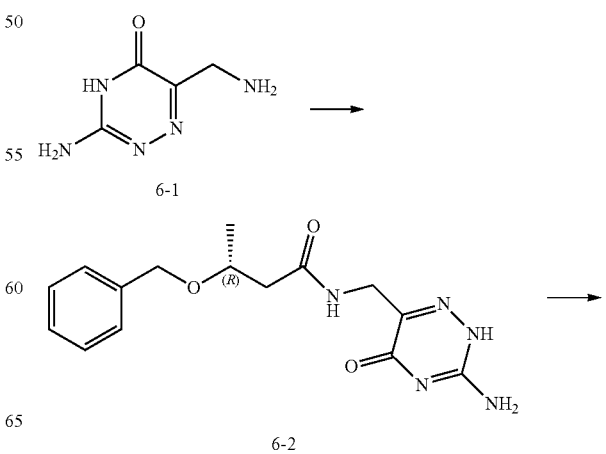

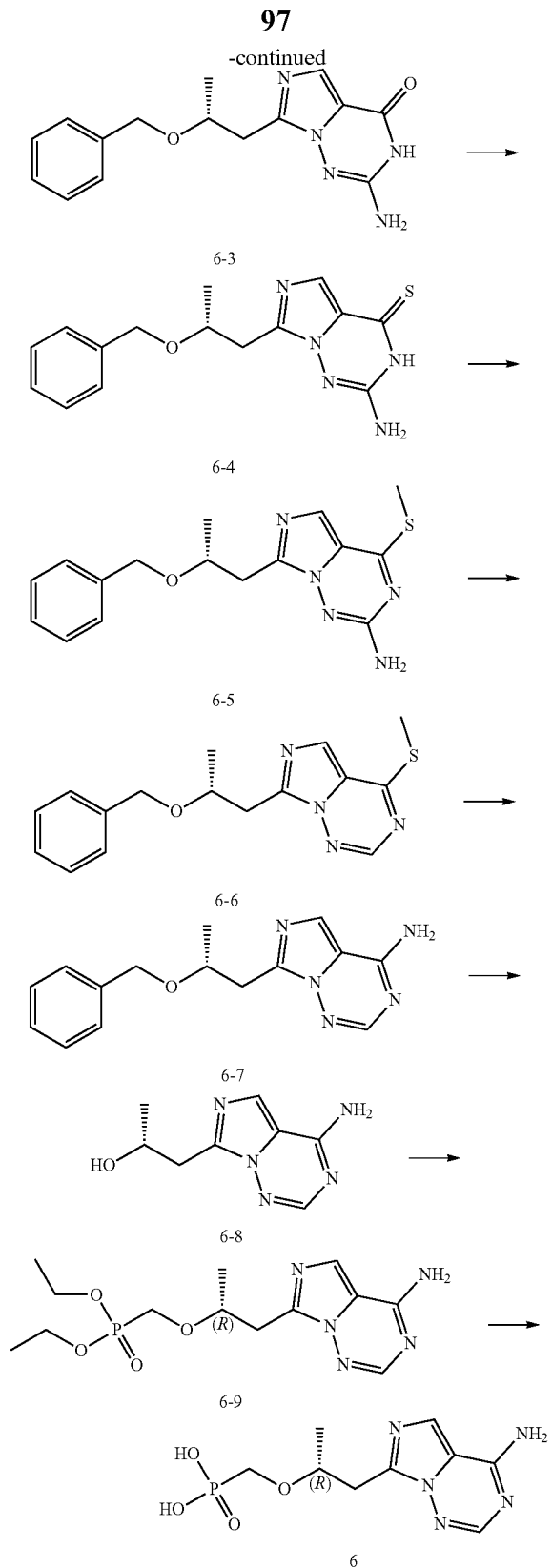

To the solution of 6-1 (1.77 g, 10 mmol, Mitchell et al., J. Heterocyclic Chem. (1984) 21(3):697-699) in mixed EtOH and water solvent (EtOH:H₂O=10:2, 48 mL) was added (R)-3-(benzyloxy)butanoic acid (2.14 g, 11 mmol), EEDQ (2.72 g, 11 mmol) and N,N-diisopropylethyl amine (2.09 mL, 12 mmol). The reaction was stirred at 85° C. overnight under N₂ atmosphere. The solvent was removed in vacuo to give 6-2 as a residue, which was purified by column chromatograph (2.51 g, 79%). ESI-LCMS: m/z 318.3 [M+H]⁺.

To a solution of 6-2 (6.97 g, 22 mmol) in acetonitrile (70 mL) was added POCl₃ (6.73 g, 44 mmol) dropwise. The reaction was stirred at 80° C. for 5 h under N₂ atmosphere. The reaction was quenched by adding a sat. aq. Na₂CO₃ solution to adjust the pH to 10. The mixture was extracted with EA (3×200 mL). The organic phase was concentrated to give crude 6-3 which was used directly for next step. To a solution of 6-3 in pyridine (60 mL) was added P₂S₅ (7.67 g, 36.2 mmol). The reaction was stirred at 100° C. overnight under N₂ atmosphere. Pyridine was removed in vacuo. Water (100 mL) was then added and the mixture was stirred at RT for 1 h. The precipitate was filtered to give crude 6-4 which was used directly for the next step. To the solution of 6-4 in DCM (60 mL) was added N,N-diisopropylethyl amine (6.27 mL, 36 mmol) and CH₃I (1.35 mL, 21.6 mmol). The mixture was stirred at RT for 2 h. The solvent was removed in vacuo, and the residue was further purified by column chromatograph to give 6-5 (1.98 g, 27% for three steps). ESI-LCMS: m/z 330.2 [M+H]⁺.

To the solution of 6-5 (1.98 g, 6 mmol) in THF (20 mL) was added tert-butyl nitrite (6.18 g, 60 mmol). The mixture was stirred at 60° C. for 2 h under N₂ atmosphere. The solvent was removed in vacuo to give crude 6-6 without further purification. In a Par reactor, 6-6 was dissolved in 2M solution of ammonium in methanol (20 mL). The mixture was stirred at 80° C. overnight. The solvent was removed in vacuo, and the residue was further purified by column chromatograph to give 6-7 (724 mg, 42% for two steps). ESI-LCMS: m/z=284.3 [M+H]⁺.

To the solution of 6-7 (724 mg, 2.55 mmol) in DCM (10 mL) was added a solution of 1M BCl₃ (6.4 mL, 6.4 mmol) in DCM dropwise at −78° C. The reaction was stirred at −78° C. for 1.5 h and then at 0° C. for 0.5 h. 2M NH₃ methanol solution was added to adjust the pH to 10. The mixture was concentrated in vacuo and then purified by column chromatograph to give 6-8 (380 mg, 78%). ESI-LCMS: m/z 194.2 [M+H]⁺.

To the solution of 6-8 (380 mg, 1.97 mmol) in DCM (2 mL) was added Mg(O^tBu)₂ (1.02 g, 6.0 mmol). The mixture was stirred at 70° C. for 30 mins under N₂ atmosphere. Diethyl p-tolylsulfonyloxymethyl phosphonate (510 mg, 3 mmol) in NMP (2 mL) was added under N₂ atmosphere. The mixture was stirred at 70° C. overnight. The reaction was quenched by adding water. The mixture was extracted by EA (3×30 mL). The organic layer was concentrated and then purified by column chromatograph to give 6-9 (180 mg, 27%). ESI-LCMS: m/z 344.3 [M+H]⁺.

To the solution of 6-9 (45 mg, 0.1 mmol) in acetonitrile (0.5 mL) was added TMSBr (0.31 mL, 3.3 mmol) dropwise at 0° C. The mixture was stirred at RT for 5 h. Another portion of TMSBr (0.15 mL) was added, and the mixture was stirred at RT for 1 h. The mixture was concentrated and purification by prep-HPLC to give 6 (18 mg, 48%). ESI-LCMS: m/z 288.2 [M+1]⁺.

Example 7

(1-(4-aminopyrazolo[1,5-a][1,3,5]triazin-8-yl)propan-2-yloxy)methylphosphonic acid (Compound 7)

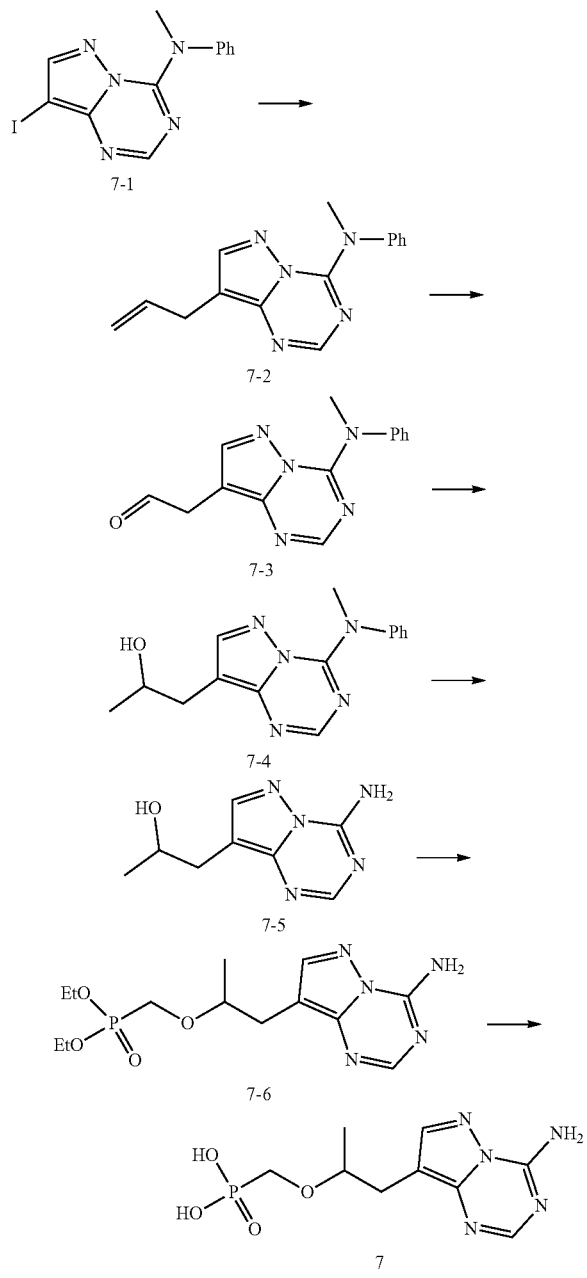

To a solution of 7-1 (12 g, 34.2 mmol, Lefoix et al., *J. Org. Chem.* (2014) 79:3221-3227) in anhydrous DMF (100 mL) was added LiCl (1.88 g, 44.4 mmol) and Pd(PPh$_3$)$_4$ (7.9 g, 6.8 mmol). Allyltributyltin (13.58 g, 41 mmol) was added dropwise at RT, and the mixture was stirred at 100° C. for 2 h. The reaction was quenched with water, and the mixture was extracted with EA (3×50 mL). The combined organic phase was washed with brine and dried over Na$_2$SO$_4$. After filtration, the filtrate was concentrated in vacuo to give a residue which was further purified by silica gel column (PE:EA=5:1) to give 7-2 (6.06 g, 67%) as a yellow oil. ESI-LCMS: m/z 266 [M+H]$^+$.

To the solution of 7-2 (6.06 g, 22.8 mmol) in dioxane (50 mL) was added NMO (2.12 g, 68.5 mmol) and K$_2$OsO$_4$.2H$_2$O (252 mg, 690 µmol). The mixture was stirred at RT for 1 h. The reaction was quenched with aq. sat. Na$_2$S$_2$O$_3$, and then extracted with EA (4×50 mL). The combined organic phase was dried over anhydrous Na$_2$SO$_4$. After filtration, the filtrate was concentrated in vacuo to give the diol product which was used directly for the next step. To the solution of the diol in dioxane:H$_2$O=10:1 (55 mL) was added NaIO$_4$ (9.77 g, 45.7 mmol). The mixture was stirred at RT for 1 h. Water (10 mL) was added, and the mixture was extracted with EA (3×20 mL). The combined organic phase was dried over Na$_2$SO$_4$. After filtration, the filtrate was concentrated in vacuo to give 7-3 as a yellow oil which was used directly for the next step. 7-3 was dissolved in dry-THF (50 mL), and MeMgBr (3.78 g, 36.3 mmol) was added dropwise at 0° C. After stirring at RT for 1 h, the reaction was quenched with sat. aq. NH$_4$Cl aq. The mixture was extracted with EA (3×20 mL). The combined organic phase was dried over anhydrous Na$_2$SO$_4$. After filtration, the filtrate was concentrated in vacuo to give a residue which was further purified by silica gel column (PE:EA=1:1) to give 7-4 (1.6 g, 22% yield) as a white solid. ESI-LCMS: m/z 284 [M+H]$^+$.

To a solution of 7-4 (130 mg, 0.5 mmol) in MeOH (20 mL) in Par reactor was added 7M solution of ammonium in methanol (0.77 mL, 5.4 mmol). The mixture was stirred at 100° C. for overnight. After concentration in vacuo, the mixture was purified by a gel silica gel column (DCM:MeOH=10:1) to give 7-5 as a white powder. ESI-LCMS: m/z 194 [M+H]$^+$.

To a solution of 7-5 (130 mg, 0.7 mmol) in anhydrous NMP (500 µL) under N$_2$ was added (t-BuO)$_2$Mg (456 mg, 2.7 mmol). The mixture was stirred at 80° C. for 10 mins. Diethyl (tosyloxy)methylphosphonate (432 mg, 1.3 mmol) in NMP (300 µL) was added, and the mixture was stirred at 90° C. for 1 h. Water (5 mL) was added, and the mixture was extracted with EtOAc (6×10 mL). The combined organic phase was then dried over anhydrous Na$_2$SO$_4$. After filtration, the filtrate was concentrated in vacuo to give a residue which was further purified by silica gel column (DCM:MeOH=10:1) to give 7-6 (117 mg, 51%) as a colorless solid. ESI-LCMS: m/z 344 [M+H]$^+$.

To a solution of 7-6 (117 mg, 0.3 mmol) in anhydrous CH$_3$CN (1.2 mL) under N$_2$ was added TMSBr (1.1 mL, 8.5 mmol) at 0° C. The mixture was stirred at RT for 5 h. After concentration in vacuo, the mixture was purified through prep-HPLC to give 7 (48.2 mg, 49%) as a white powder. ESI-LCMS: m/z 288 [M+H]$^+$.

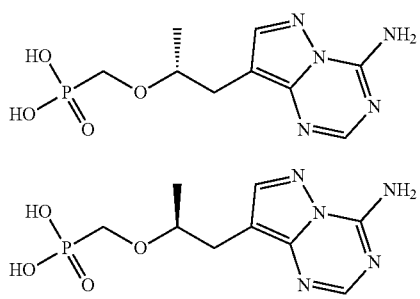

Racemic 7 was separated by SFC to give enantiomers 29 and 30. Compounds 29 and 30 are shown above with relative stereochemistry arbitrarily assigned.

Example 8

(((1-(4-amino-2-fluoropyrrolo[2,1-f][1,2,4]triazin-7-yl)propan-2-yl)oxy)methyl)phosphonic acid (Compound 8)

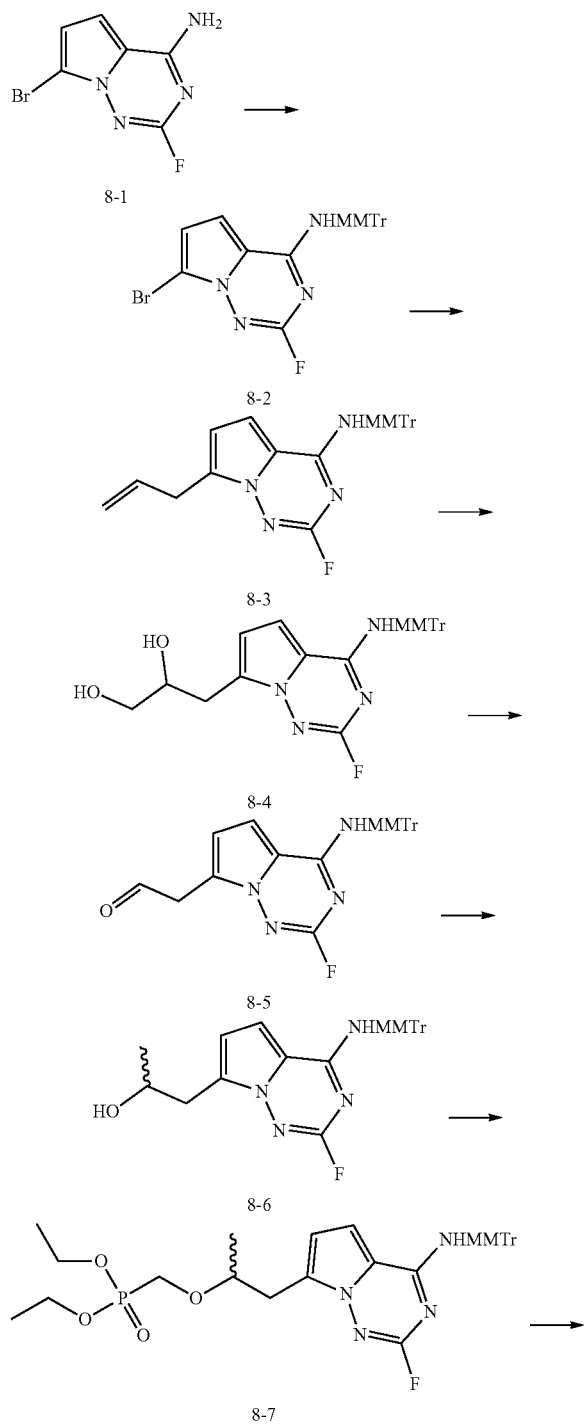

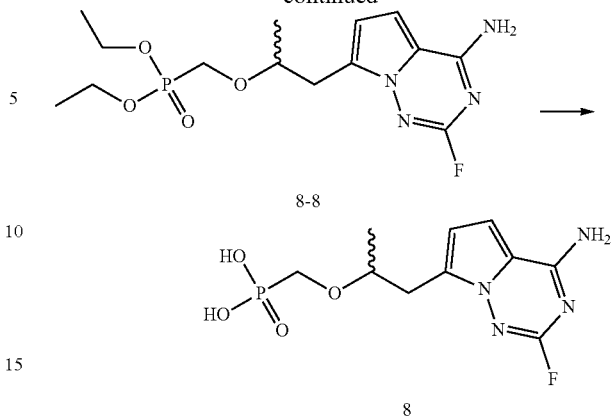

To a solution of 8-1 (9.9 g, 42.9 mmol, prepared according to procedures provided in U.S. 2015/133395) in DMF (100 mL) was added NaH (2.06 g, 85.7 mmol) at 0° C. The mixture was stirred at 0° C. for 30 mins. MMTrCl (13.2 g, 42.9 mmol) was added, and the mixture was stirred at RT for 2 h. Water was added, and the mixture was extracted with EA (3×400 mL). The organic layer was washed with brine, dried over $Na_2SO_4$ and concentrated in vacuo. The obtained mixture was purified by silica gel column (PE:EA=20:1) to give 8-2 (19.6 g, 91%) as a white solid. ESI-LCMS: m/z=503.1 [M+H]$^+$.

A solution of 8-2 (19.6 g, 38.9 mmol), allyltributyltin (16.8 g, 50.6 mmol), Pd(PPh$_3$)$_4$ (8.99 g, 7.8 mmol) and LiCl (2.15 g, 50.6 mmol) in DMF (200 mL) was stirred under $N_2$ atmosphere at 100° C. for 1 h. The mixture was cooled to RT, and water was added. The mixture was extracted with EA (3×400 mL). The combined organic layer was washed with brine, dried over $Na_2SO_4$ and concentrated in vacuo to give a residue. The residue was purified by silica gel column (PE:EA=60:1) to give 8-3 (13.8 g, 76%) as a white solid. ESI-LCMS: m/z=465.2 [M+H]$^+$.

A solution of 8-3 (13.8 g, 29.7 mmol), $K_2OsO_4 \cdot 2H_2O$ (328 mg, 0.9 mmol) and 50% NMO aq (20.9 g, 89.1 mmol) in dioxane (200 mL) was stirred at RT for 2 h. Water was added, and the mixture was extracted with EA (3×400 mL). The organic layer was washed by brine, dried over $Na_2SO_4$ and concentrated in vacuo to give a residue. The residue was purified by silica gel column (DCM:MeOH=50:1) to give 8-4 (14.6 g, 98%) as a white solid. ESI-LCMS: m/z=499.2 [M+H]$^+$.

A solution of 8-4 (3.0 g, 6 mmol) and NaIO$_4$ (2.58 g, 12.0 mmol) in dioxane (90 mL) and $H_2O$ (9 mL) was stirred at RT for 2 h. Water was added, and the mixture was extracted with EA (3×200 mL). The organic layer was washed with brine, dried over $Na_2SO_4$ and concentrated in vacuo to give 8-5 which was used for next step without the future purification. To a solution of 8-5 in anhydrous THF (20 mL) was added methyl magnesium bromide (6.0 mmol, 6 mL) at 0° C. The mixture was stirred at 0° C. for 2 h. Water was added, and the mixture was extracted with EA (3×100 mL). The organic layer was washed with brine, dried over $Na_2SO_4$ and concentrated in vacuo to give a residue. The residue was purified by silica gel column (PE:EA=5:1) to give 8-6 (1.02 g, 36%) as a yellow solid. ESI-LCMS: m/z=483.2 [M+H]$^+$.

A solution of 8-6 (1.25 g, 2.6 mmol) and Mg(t-BuO)$_2$ (1.32 g, 7.8 mmol) in NMP (6 mL) was stirred at 80° C. for 10 mins. Diethyl(tosyloxy)methylphosphonate (1.25 g, 3.9 mmol) was added, and the solution was stirred at 80° C.

overnight. Water was added, and the mixture was extracted with EA (3×100 mL). The organic layer was washed with brine, dried over Na₂SO₄ and concentrated in vacuo to give a residue. The residue was purified by silica gel column (PE:EA=3:1) to give 8-7 (1.3 g, 79%) as a brown oil. ESI-LCMS: m/z=633.2 [M+H]⁺.

A solution of 8-7 (400 mg, 0.6 mmol) in 80% AcOH (10 mL) was stirred at 70° C. overnight. The mixture was concentrated in vacuo to give a residue. The residue was dissolved in MeOH (10 mL), and sat. Na₂CO₃ was added to adjust pH to 7. The mixture was concentrated in vacuo and purified by silica gel column (DCM:MeOH=70:1) to give 8-8 (120 mg, 52%) as a yellow oil. ESI-LCMS m/z=361.1 [M+H]⁺.

To a solution of 8-8 (100 mg, 0.27 mmol) in ACN (1.1 mL) was added TMSBr (1.06 g, 6.9 mmol). The mixture was stirred at RT for 6 h. The mixture was concentrated in vacuo to give a residue. The residue was purified by RP-HPLC to give 8 (24 mg, 28%) as a white solid. ³¹P NMR (162 MHz, DMSO-d₆): δ 17.13 (s). ESI-LCMS: m/z=305.1 [M+H]⁺.

Example 9

((((1-(2,4-diaminopyrrolo[2,1-f][1,2,4]triazin-7-yl)propan-2-yl)oxy)methyl) phosphonic acid (Compound 9)

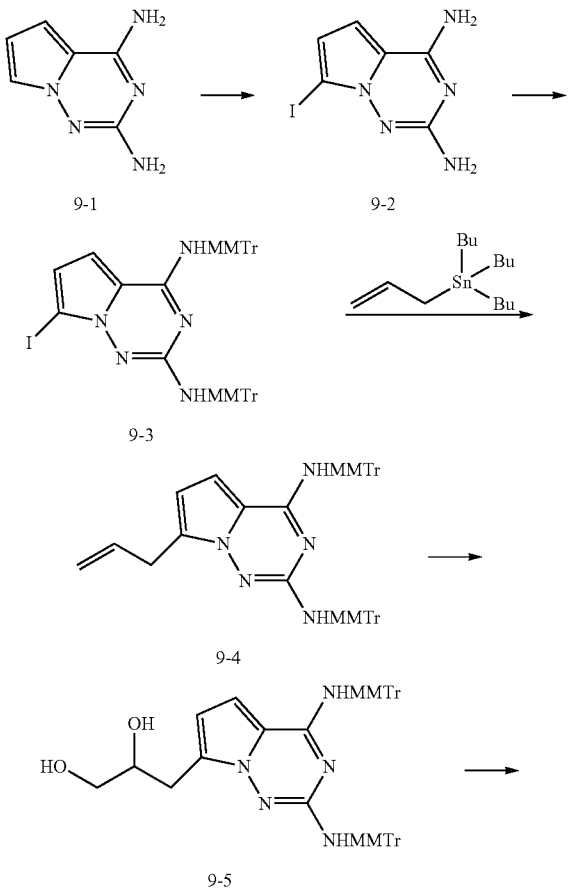

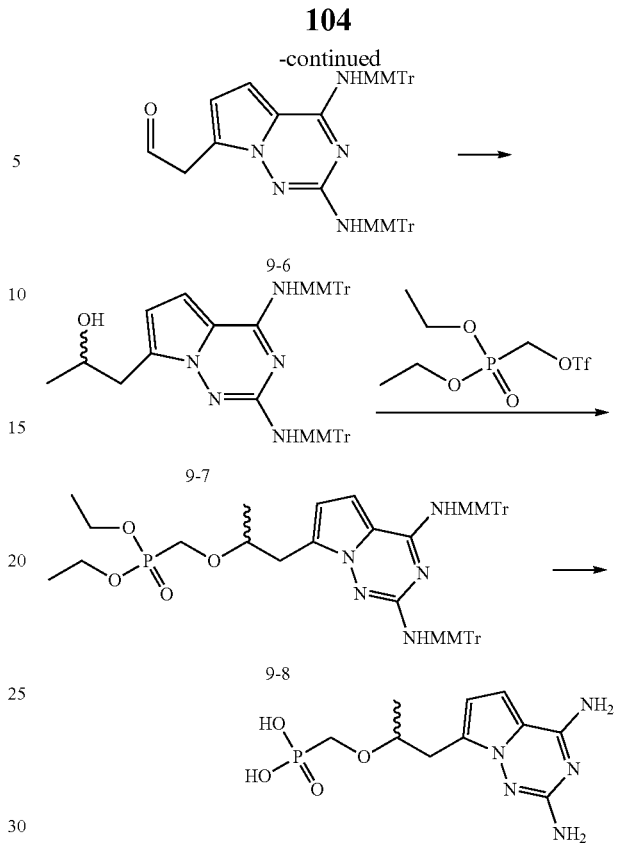

To a solution of 9-1 (5.0 g, 33.5 mmol, prepared as provided in Patil et al., *J. Heterocyclic Chem.* (1994) 31(4): 781-1186) in DMF (50 mL) was added the solution of NIS (6.8 g, 30 mmol) in DMF (10 mL) dropwise at 0° C. The mixture was stirred at RT for 1.5 h. After completion, water (100 mL) and EA (200 mL) was added. The mixture was extracted, and the combined organic phase was dried over anhydrous Na₂SO₄. The organic solution was concentrated to give 9-2 (7.5 g, 81%) as a white solid. ESI-LCMS: m/z=276.0 [M+H]⁺.

To a solution of 9-2 (10.3 g, 37 mmol) in DMF (150 mL) was added NaH (3.6 g, 150 mmol, 60%) under N₂ at 0° C. The mixture was stirred at 0° C. for 30 mins. MMTrCl (2.8 g, 79 mmol) was added, and the mixture was stirred at RT for 2 h. Water (100 mL) was added, and the mixture was extracted with EA (3×400 mL). The combined organic solution was dried with Na₂SO₄, and then concentrated to give a residue. The residue was further purified by silica gel column (PE:EA=20:1) to give 9-3 (21.0 g, 68%) as a white solid.

To a solution of 9-3 (600 mg, 0.7 mmol) and allyltributyltin (315 mg, 950 µmol) in DMF (5 mL) was added Pd(Ph₃)₄ (170 mg, 150 µmol) and LiCl (40 mg, 950 µmol) under N₂. The mixture was stirred at 100° C. for 1 h. Water was added, and the mixture was extracted with EA (3×100 mL). The organic solution was dried with Na₂SO₄ and concentrated to get a residue, which was further purified by silica gel column (PE:EA=40:1) to give 9-4 (500 mg, 93%) as a white solid. ¹H NMR (400 MHz, DMSO-d₆) δ 8.07 (s, 1H), 7.40-7.19 (m, 16H), 7.18-7.08 (m, 6H), 7.01 (d, J=8.9 Hz, 2H), 6.92 (d, J=4.4 Hz, 1H), 6.86 (d, J=9.0 Hz, 2H), 6.79 (d, J=9.0 Hz, 2H), 6.02 (d, J=4.4 Hz, 1H), 5.44 (dd, J=17.0, 10.0 Hz, 1H), 4.86-4.67 (m, 3H), 3.70 (s, 6H), 2.92 (d, J=6.8 Hz, 2H).

To a solution of 9-4 (500 mg, 0.7 mmol) in dioxane (10 mL) was added K$_2$OsO$_4$ (7.5 mg, 20 µmol) and 50% NMO aq. (2 mmol). The mixture was stirred at RT for 75 mins. The reaction was quenched with Na$_2$SO$_3$ (aq). The mixture was then extracted with EA (3×150 mL). The combined organic solution was dried with Na$_2$SO$_4$ and then concentrated to give a residue. The residue was further purified by silica gel column (PE:EA=2:1) to give 9-5 (350 mg, 67%) as a white solid. $^1$H NMR (400 MHz, DMSO-d$_6$) δ 8.01 (s, 1H), 7.37-7.17 (m, 16H), 7.17-7.06 (m, 6H), 7.00 (d, J=8.9 Hz, 2H), 6.93-6.83 (m, 3H), 6.78 (d, J=9.0 Hz, 2H), 6.08 (d, J=4.3 Hz, 1H), 4.72 (s, 1H), 4.27 (t, J=5.6 Hz, 1H), 4.12 (d, J=5.5 Hz, 1H), 3.70 (s, 6H), 3.27 (s, 1H), 2.99 (ddt, J=35.2, 11.0, 5.6 Hz, 2H), 2.34-2.17 (m, 2H).

To a solution of 9-5 (300 mg, 0.4 mmol) in dioxane (6 mL) and H$_2$O (0.5 mL) was added NaIO$_4$ (167 mg, 0.8 mmol). The mixture was stirred at RT for 2 h. Water (10 mL) was added, and the mixture was extracted with EA (3×50 mL). The combined organic solution was dried over anhydrous Na$_2$SO$_4$, and concentrated to give a residue. The residue was further purified by silica gel column (PE: EA=12:1) to give 9-6 (110 mg, 38%) as a light yellow solid. $^1$H NMR (400 MHz, DMSO-d$_6$) δ 8.97 (t, J=1.6 Hz, 1H), 8.22 (s, 1H), 7.34-7.20 (m, 16H), 7.15 (d, J=7.2 Hz, 2H), 7.07-7.01 (m, 4H), 6.98 (d, J=4.4 Hz, 1H), 6.94 (d, J=8.9 Hz, 2H), 6.86 (d, J=9.0 Hz, 2H), 6.78 (d, J=9.0 Hz, 2H), 6.17 (d, J=4.4 Hz, 1H), 4.78 (s, 1H), 3.70 (s, 6H), 3.26 (s, 2H).

To a solution of 9-6 (420 mg, 0.57 mmol) in anhydrous THF (4 mL) was added MeMgBr (2 mL, 2 mmol, 1M) dropwise at 0° C. The solution was stirred at 0° C. for 2 h. The reaction was then quenched with water, and the mixture was extracted with EA (3×50 mL). The combined organic solution was then dried over anhydrous Na$_2$SO$_4$, and concentrated to get a residue. The residue was further purified by silica gel column (PE:EA=10:1) to give 9-7 (210 mg, 49%) as a light yellow solid. ESI-LCMS: m/z=480.4.4 [M+H-MMTr]$^+$.

To a solution of 9-7 (200 mg, 0.3 mmol) in THF (0.8 mL) was added NaH (64 mg, 2.7 mmol) at 0° C. under N$_2$. After 0.5 h, (diethoxyphosphoryl)methyl trifluoromethanesulfonate (798 mg, 2.7 mmol) was added, and the mixture was stirred at RT for overnight. The reaction was quenched with H$_2$O, and the mixture was extracted with EA (3×50 mL). The combined organic solution was dried over anhydrous Na$_2$SO$_4$ and concentrated to get a residue. The residue was further purified by silica gel column (PE:EA:DCM=5:1:1) to give 9-8 (100 mg, 42%) as a light yellow solid. ESI-LCMS: m/z=630.5 [M+H-MMTr]$^+$.

To a solution of 9-8 (400 mg, 0.4 mmol) in DCM (3 mL) was added TMSBr (1.8 mL, 22.2 mmol) dropwise. The mixture was stirred at RT for 1 h. The reaction was concentrated to give a crude which was further purified by RP-HPLC to give 9 (40 mg, 30%) as a white solid. ESI-LCMS: m/z=302.2 [M+H]$^+$.

Example 10

(1-(4-aminopyrazolo[1,5-a][1,3,5]triazin-8-yl)-3-fluoropropan-2-yloxy)methylphosphonic acid (Compound 10)

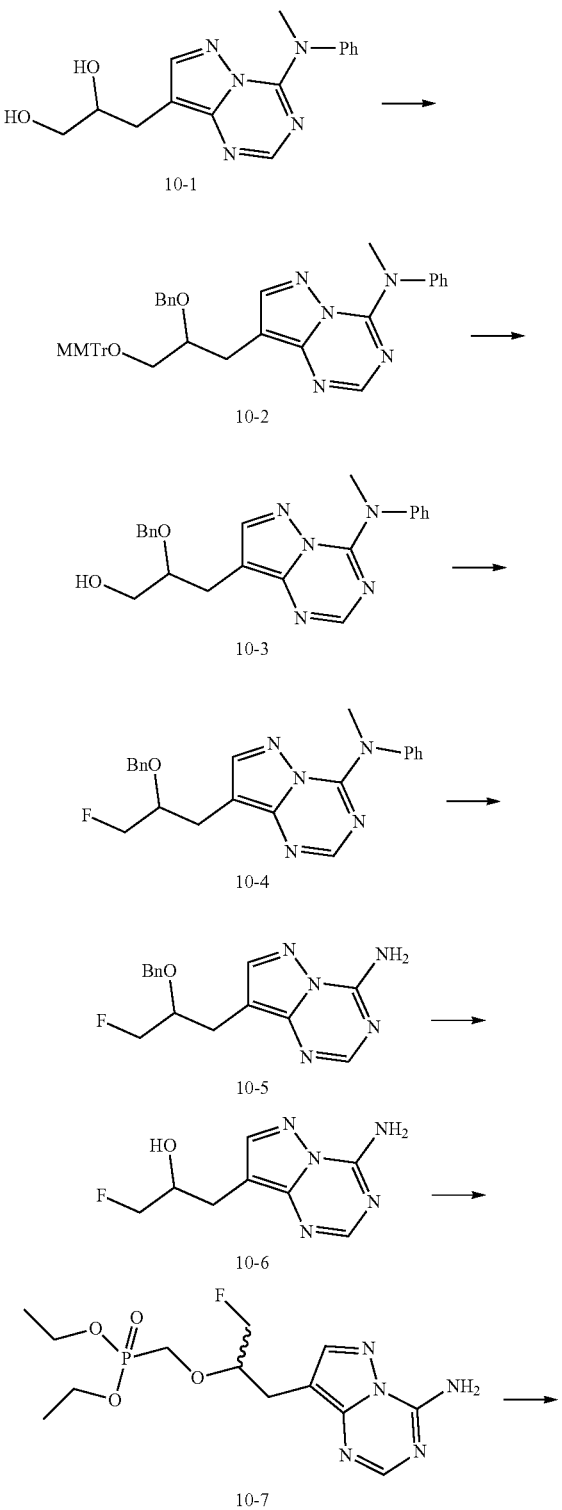

-continued

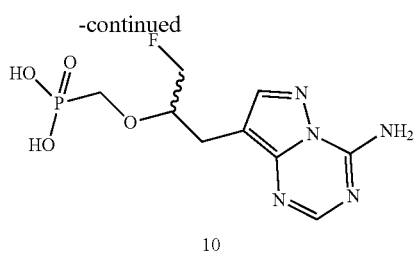

10

To a solution of 10-1 (14.6 g, 48.8 mmol) in DCM (100 mL) was added TEA (14.8 g, 146.3 mmol, 21 mL), DMAP (1.19 g, 9.8 mmol) and MMTr-Cl (2.6 g, 73.2 mmol) at 0° C. The mixture was stirred at RT overnight. Water (50 mL) was added. The mixture was extracted with DCM (3×20 mL) and dried over Na$_2$SO$_4$. The organic solvent was removed in vacuo to get crude product which was purified by a gel silica column (PE:EA=10:1) to give the product as a white powder (13.5 g). To a solution of MMTr protected product (13.5 g, 23.6 mmol) in DMF (100 mL) was added NaH (850 mg, 35.4 mmol) at 0° C. The mixture was stirred at 0° C. for 30 mins. BnBr (6.1 g, 35.43 mmol) was added, and the mixture was stirred at RT for 1 h. The mixture was then cooled to 0° C., and the reaction was quenched with ice-water (200 mL). The mixture was extracted with EA (3×50 mL) and dried over Na$_2$SO$_4$. The organic solvent was combined and removed in vacuo to give 10-2 (14.6 g, 46%). ESI-LCMS: m/z 684 [M+Na]$^+$.

To a solution of 10-2 (3.5 g, 5.3 mmol) in DCM (25 mL) was added TFA (1.5 mL), and the mixture was stirred at RT for 2 h. The solvent was removed in vacuo, and sat. Na$_2$CO$_3$ was added to adjust pH to 7-8. The mixture was extracted with EA (3×10 mL), and dried over Na$_2$SO$_4$. The solvent was removed in vacuo to get crude product which was purified by a gel silica column (PE:EA=1:1) to give 10-3 as a colorless oil (1.4 g, 52%). ESI-LCMS: m/z 390 [M+H]$^+$.

To a solution of 10-3 (4.3 g, 11 mmol) in THF (30 mL) was added DBU (6.7 g, 44.2 mmol) and CF$_3$(CF$_2$)$_3$SO$_2$F (13.3 g, 44.2 mmol) at 0° C. under N$_2$ atmosphere. The mixture was stirred at RT for overnight. Water (10 mL) was added. The mixture was extracted with EA (3×30 mL), and dried over Na$_2$SO$_4$. The organic solvent was removed in vacuo to get crude product which was purified by a gel silica column (PE:EA=1:1) to give 10-4 as a yellow powder (2.8 g, 65%). ESI-LCMS: m/z 392 [M+H]$^+$.

To a solution of 10-4 (2.8 g, 7.2 mmol) in MeOH (5 mL) in Par reactor was added 7M solution of ammonium in MeOH (12 mL, 84 mmol). The mixture was stirred at 100° C. for overnight. After being concentrated in vacuo, the mixture was purified by a gel silica column (DCM: MeOH=10:1) to give 10-5 as a white powder (430 mg, 20%). ESI-LCMS: m/z 302 [M+H]$^+$.

To a solution of 10-5 (430 mg, 1.4 mmol) in DCM (2 mL) was added BCl3 (4.3 mL, 4.3 mmol, 1M in DCM) at −50° C. under N$_2$ atmosphere. The mixture was stirred at this temperature for 1 h. MeOH (2 mL) was added to quench the reaction, and sat. Na$_2$CO$_3$ was added to adjust pH to 7-8. The solvent was removed in vacuo to give a crude product which was purified by a gel silica column (DCM:MeOH=10:1) to give 10-6 as a white powder (313 mg, 98%). ESI-LCMS: m/z 212 [M+H]$^+$.

To a solution of 10-6 (145 mg, 0.7 mmol) in anhydrous NMP (500 μL) under N$_2$ was added (t-BuO)$_2$Mg (456 mg, 2.7 mmol). The mixture was stirred at 70° C. for 10 mins. Diethyl (tosyloxy)methylphosphonate (432 mg, 1.3 mmol) in NMP (300 μL) was added, and the mixture was stirred at 80° C. for 1 h. Water (5 mL) was added, and the mixture was extracted with EtOAc (6×10 mL). The combined organic phase was then dried over anhydrous Na$_2$SO$_4$. After filtration, the filtrate was concentrated in vacuo to give a residue which was further purified by silica gel column (DCM: MeOH=10:1) to give 10-7 (184 mg, 75%) as a colorless oil. ESI-LCMS: m/z 362 [M+H]$^+$.

To a solution of 10-7 (160 mg, 0.4 mmol) in anhydrous CH$_3$CN (1.2 mL) under N$_2$ was added TMSBr (1.2 mL, 11 mmol) at 0° C. The mixture was stirred at RT for 5 h. After concentration in vacuo, the mixture was purified by prep-HPLC to give 10 (29 mg, 22%) as a white powder. $^{31}$P NMR (162 MHz, DMSO-d$_6$) δ ppm 15.34 (s). ESI-LCMS: m/z 306 [M+H]$^+$.

Compound 10 may be separated into two enantiomers through supercritical fluid chromatography to give compound 10a (343 mg, retention time: 1.454 min) and compound 10b (321 mg, retention time: 1.92 min). (SFC, CHIRALPAK AD-H column, Column size: 0.46 cm I.D.×15 cm L, Injection: 1.0 ul, Mobile phase: Hexane/IPA=60/40 (V/V), Flow rate: 1.0 mL/min, retention time: 1.454 min, 1.924 min).

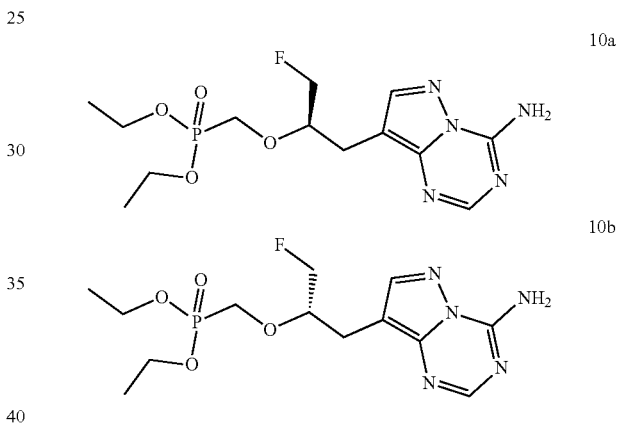

10-1 may be obtained by adding 8-allyl-N-methyl-N-phenylpyrazolo[1,5-a][1,3,5]triazin-4-amine (16.8 g, 63.4 mmol) to dioxane (150 mL) followed by NMO (22.3 g, 190.2 mmol) and K$_2$OsO$_4$.2H$_2$O (700 mg, 1.9 mmol). The mixture was stirred at room temperature for 1 h, quenched with aqueous saturated Na$_2$S$_2$O$_3$, and then extracted with ethyl acetate. The combined organic phase is then dried over anhydrous Na$_2$SO$_4$ and filtered, followed by concentration under reduced pressure. The resulting residue may be further purified by silica gel chromatography (DCM:MeOH=10:1) to give 10-1 (14.6 g, 76.9% yield) as a yellow oil. ESI-LCMS: m/z 300 [M+H]$^+$.

Example 11

(1-(4-aminopyrazolo[1,5-a][1,3,5]triazin-8-yl)propan-2-yloxy)methylphosphonic acid (Compound 11)

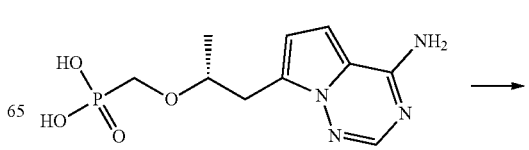

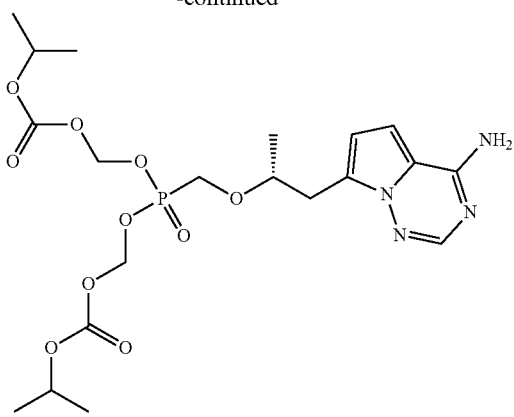

11

To a stirred mixture of 2 (14 mg, 0.05 mmol) and tetrabutylammonium bromide (16 mg, 0.05 mmol) in NMP (1 mL) RT under argon were added trimethylamine (20 mg, 28 µL, 0.2 mmol) and chloromethyl isopropyl carbonate (POC—Cl) (38 mg, 33 µL, 0.25 mmol) sequentially. The mixture was warmed to 50° C., and stirred at that temperature for 15 h. The reaction was then cooled to RT, diluted with water (10 mL), and extracted with EA (2×10 mL). The combined organic phase was washed with water (2×10 mL), dried over anhydrous magnesium sulfate, and concentrated in vacuo to give a residue, which was purified on silica gel column (MeOH:DCM, 0 to 10%) to give 11 as a colorless glassy gel. $^{31}$P NMR: 21.57. ESI-LCMS: m/z 519.00 [M+H]$^+$.

Example 12

The following compounds in Table 3 were prepared in a similar manner as 11.

TABLE 3

| # | Compound | $^{31}$P NMR | MS [M + H]$^+$ |
|---|---|---|---|
| 12 | | | 520.00 |
| 13 | | | 520.15 |

TABLE 3-continued

| # | Compound | $^{31}$P NMR | MS [M + H]$^+$ |
|---|---|---|---|
| 14 | | — | 520.15 |
| 15 | | 21.24 | 505.00 |
| 16 | | 20.81 (d, J = 3.2 Hz) | 538.10 |

TABLE 3-continued

| # | Compound | ³¹P NMR | MS [M + H]⁺ |
|---|---|---|---|
| 17 | | 21.50 | 537.05 |
| 18 | | 21.73 | 534.10 |
| 51 | | 22.33 | 535.00 |
| 11 | | 21.57 | 519.00 |

TABLE 3-continued

| # | Compound | ³¹P NMR | MS [M + H]⁺ |
|---|----------|---------|-------------|
| 12 | | — | 520.00 |
| 13 | | — | 520.15 |
| 14 | | — | 520.15 |

TABLE 3-continued
| # | Compound | $^{31}$P NMR | MS [M + H]$^+$ |
|---|---|---|---|
| 15 | 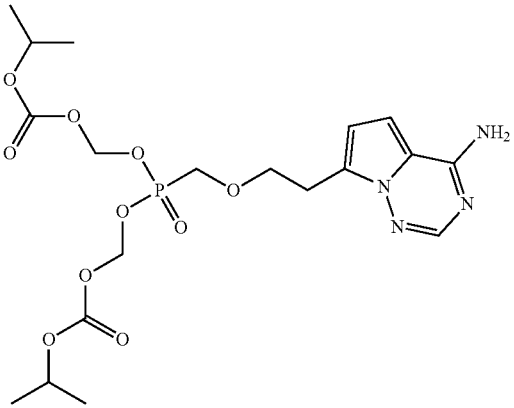 [SMILES: CC(C)OC(=O)OCOP(=O)(COCCc1ccc2c(N)ncnn12)OCOC(=O)OC(C)C] | 21.24 | 505.00 |
| 16 | 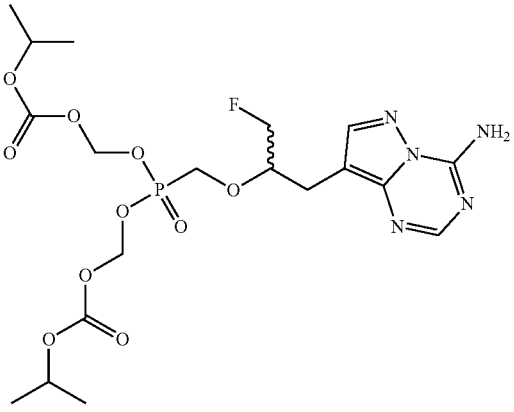 [SMILES: CC(C)OC(=O)OCOP(=O)(COC(CF)Cc1cnn2c(N)ncnc12)OCOC(=O)OC(C)C] | 20.81 (d, J = 3.2 Hz) | 538.10 |
| 17 | 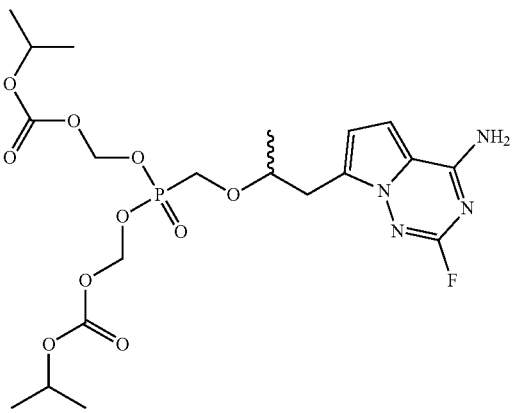 [SMILES: CC(C)OC(=O)OCOP(=O)(COC(C)Cc1ccc2c(N)nc(F)nn12)OCOC(=O)OC(C)C] | 21.50 | 537.05 |

TABLE 3-continued
| # | Compound | $^{31}$P NMR | MS [M + H]$^+$ |
|---|---|---|---|
| 18 | | 21.73 | 534.10 |
| 51 | | 22.33 | 535.00 |
Example 13
((((1-(4-oxo-3,4-dihydropyrrolo[2,1-f][1,2,4]triazin-7-yl)propan-2-yl)oxy)methyl)phosphonic acid (Compound 47)
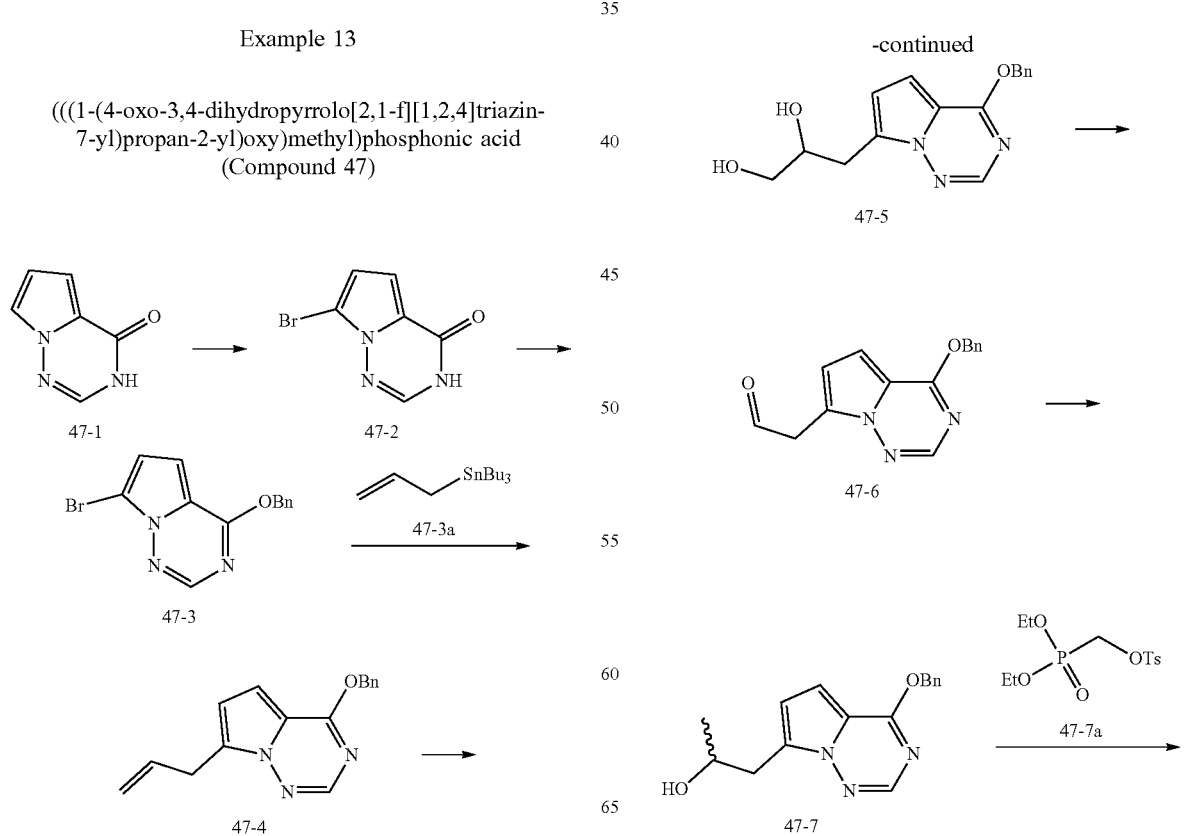

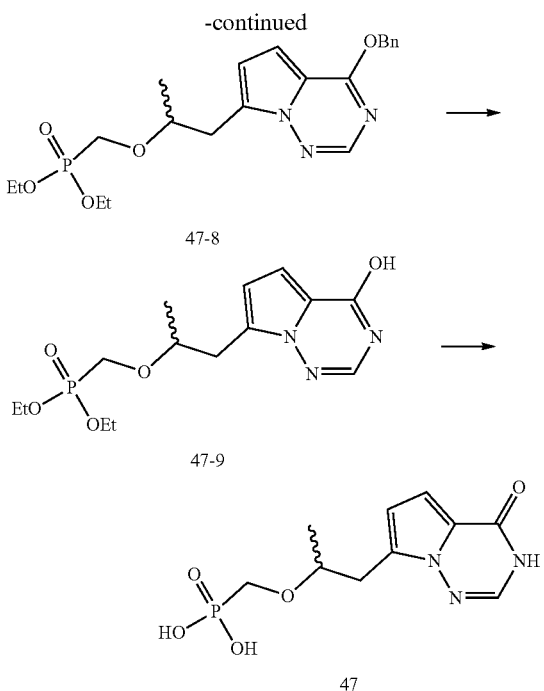

To a solution of 47-1 (8.5 g, 62.9 mmol, prepared according to the procedures provided in WO 2009/117157 A1) in DCM (80.4 mL) at 0° C. was added TFA (39.6 mL), then NBS (9.52 g, 53.5 mmol) in portions over 5 mins. The mixture was stirred at 0° C. for 1 h. The solvent was concentrated and NaHCO₃ (aq.) was added. The mixture was stirred for 10 mins, filtered, washed with water and then washed with petroleum ether to give 47-2 as a white solid (11.2 g, 52.3 mmol, 83.2%).

To a solution of 47-2 (120 mg, 560 μmol), was added K₂CO₃ (155 mg, 1.1 mmol) and BnBr (91 mg, 840 μmol) in DMF (2.0 mL). The mixture was stirred at 80° C. overnight. The mixture was then diluted with water and extracted with EA (3×50 mL). The organic layer was dried with Na₂SO₄ and concentrated to give the crude product. The crude was purified by silica gel (PE:EA=20:1) to give 47-3 (90 mg, 295 μmol, 52.78%) as a white solid.

To a solution of 47-3 (1.90 g, 6.3 mmol) and 47-3a (2.69 g, 8.1 mmol) in DMF (20 mL), LiCl (344 mg, 8.1 mmol) and Pd(PPh₃)₄ (1.3 mmol) were added. The mixture was stirred at 100° C. for 1 h., and then cooled to RT. The mixture was then diluted with water and extracted with EA (3×100 mL). The organic phase was dried over Na₂SO₄, and then concentrated to give the crude product. The crude was purified by silica gel (PE:EA=20:1) to give 47-4 (900 mg, 3.4 mmol, 54.3%) as a white solid.

To a solution of 47-4 (1.10 g, 4.2 mmol) in 1,4-dioxane (10 mL) and H₂O (990 μL), K₂OsO₄·2H₂O (125 μmol), NMO (386 mg, 12.5 mmol) were added. The mixture was stirred at RT for 1.5 h, and then water was added. The mixture was extracted with EA (3×100 mL), dried over Na₂SO₄ and concentrated to give the crude product. The crude was purified by silica gel (DCM:MeOH=150:1 to 80:1) to give 47-5 (620 mg, 2.1 mmol, 49.9% yield).

To a solution of 47-5 (300 mg, 1 mmol) in 1,4-dioxane (3 mL) and H₂O (300 μL), NaIO₄ (428 mg, 2 mmol) was added at 0° C. The mixture was stirred at RT for 1 h. The mixture was then diluted with water and extracted with EA (3×100 mL). The combined organic layer was dried with Na₂SO₄, and then concentrated to give crude 47-6 (260 mg, 973 μmol, 97.28%), which was used directly in the next step.

To a solution of 47-6 (260 mg, 973 μmol) in THF (4 mL) at 0° C., MeMgBr (1.5 mmol) was added dropwise. The mixture was stirred at RT for 1 h. The reaction was quenched with sat. NH₄Cl, and the mixture was extracted with EA (3×100 mL). The combined organic layer was dried over Na₂SO₄, and then concentrated to give the crude product. The crude product was purified by silica gel (PE:EA=5:1 to 3:1) to give 47-7 (90 mg, 318 μmol, 32.66%).

To a solution of 47-7 (85 mg, 300. μmol) in NMP (1 mL), Mg(OtBu)₂ (205 mg, 1.2 mmol) was added. The mixture was stirred at 80° C. for 30 mins. Then 47-7a (193 mg, 600 μmol) was added, and the mixture was stirred at 100° C. for overnight. The mixture was cooled to RT, diluted with water and extracted with EA (3×100 mL). The combined organic layer was dried over Na₂SO₄, and then concentrated to give the crude product. The crude was purified by prep-TLC (PE:EA=1:2) to obtain 47-8 (55 mg, 127 μmol, 42.30%).

To a solution of 47-8 (50 mg, 115 μmol) in EtOH (1 mL) was added Pd(OH)₂/C (5 mg) under H₂. The mixture was stirred at 50° C. for overnight. The mixture was then filtered and concentrated to give the crude product. The crude was purified by silica gel (DCM:MeOH=200:1 to 100:1) to obtain 47-9 (30 mg, 87 μmol, 75.8%).

To a solution of 47-9 (180 mg, 524.31 μmol) in DCM (2 mL), TMSBr (1.51 g, 13.1 mmol) was added. The mixture was stirred at RT for 2 h. The mixture was then concentrated to give the crude product which was purified by MPLC to give 47 (66 mg, 229 μmol, 43.83%) as a white solid. LCMS m/z=288.1 [M+H]⁺.

Example 14

(((1-(2-amino-4-oxo-3,4-dihydroimidazo[2,1-f][1,2,4]triazin-7-yl)propan-2-1)oxy)methyl)phosphonic acid (Compound 48)

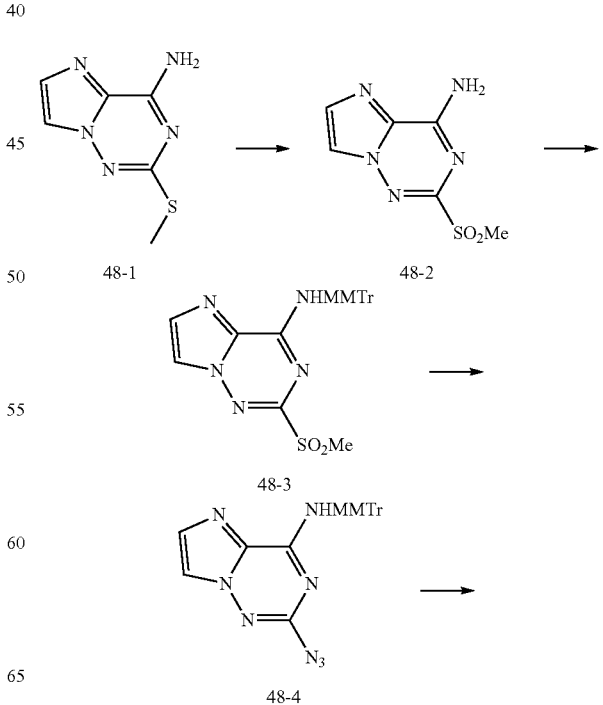

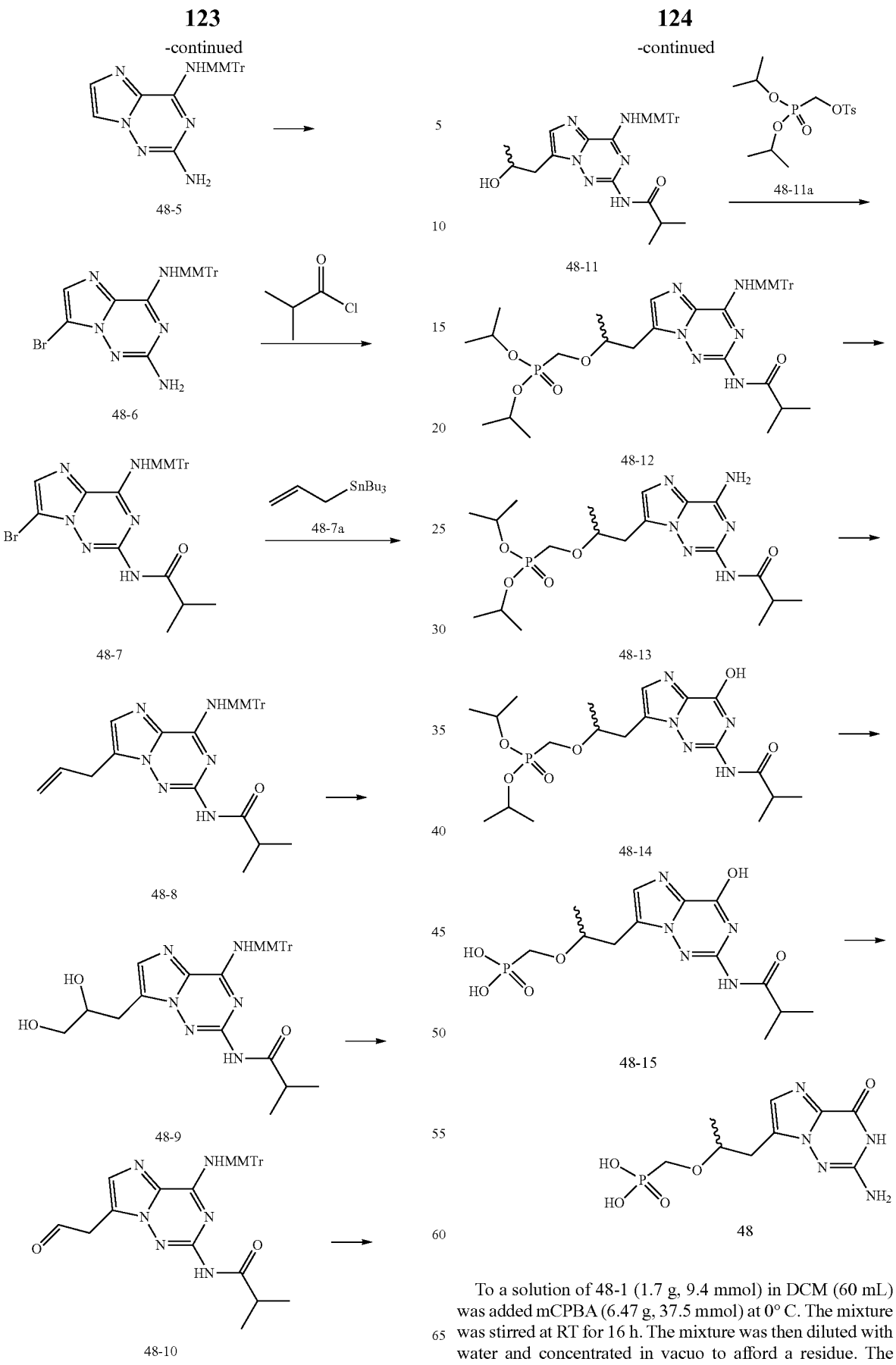
To a solution of 48-1 (1.7 g, 9.4 mmol) in DCM (60 mL) was added mCPBA (6.47 g, 37.5 mmol) at 0° C. The mixture was stirred at RT for 16 h. The mixture was then diluted with water and concentrated in vacuo to afford a residue. The mixture was basified with saturated $Na_2CO_3$ to pH=10 and filtered. The filter cake was washed with water and petroleum ether to give 48-2 (1.70 g, 8 mmol, 85%) as a white solid.

To a solution of 48-2 (777 mg, 3.6 mmol) in DMF (20 mL) was added NaH (437 mg, 10.9 mmol, 60% dispersion in mineral oil) at 0° C. The mixture was stirred at RT for 0.5 h, and then MMTrCl (1.46 g, 4.7 mmol) was added at RT. The mixture was stirred at RT for 16 h. The reaction was quenched with water, and the mixture was extracted with EA (2×50 mL). The combined organic layer was washed with brine, dried over anhydrous sodium sulfate, filtered and concentrated in vacuo to give the crude product. The crude was purified by chromatography column (silica gel, EA:PE=1:3 to 1:2) to give 48-3 (1.40 g, 2.9 mmol, 79.2%) as a white solid.

To a solution of 48-3 (485 mg, 1 μmol) in DMF (10 mL) was added NaN$_3$ (325 mg, 5 mmol) at RT. The mixture was stirred at 100° C. for 16 h, and then cooled to RT. The mixture was diluted with water and extracted with EA (2×50 mL). The combined organic layers were washed with brine, dried over anhydrous sodium sulfate, filtered and concentrated in vacuo to give the crude product which was purified by chromatography column (silica gel, EA:PE=1:20) to give 48-4 (315 mg, 702 μmol, 70.3%) as a white solid.

To a solution of 48-4 (6.60 g, 14.7 mmol) in THF (30 mL) and MeOH (100 mL) was added Raney Ni (1.0 g, 14.7 mmol) at RT. The mixture was stirred at RT under H$_2$ for 16 h. The mixture was filtered, and the filter cake was washed with THF (2×200 mL) by ultrasonic cleaner. The filtrate was concentrated in vacuo to give 48-5 (5.10 g, 12.1 mmol, 82%) as a white solid.

To a solution of 48-5 (5.10 g, 12.1 mmol) in DMF (100 mL) was added NBS (2.15 g, 12.1 mmol) at 0° C., and the mixture was stirred at RT for 1 h. The mixture was diluted with water (400 mL) and filtered. The filter cake was washed with water (4×100 mL). The filter cake was then dissolved in EA (300 mL). The combined organic layer was washed with brine, dried over anhydrous sodium sulfate and filtered. The filtrate was concentrated in vacuo to give 48-6 (5.70 g, 11.4 mmol, 94.2%) as a yellow solid.

To a solution of 48-6 (3.90 g, 7.8 mmol) in pyridine (80 mL) was added isobutyl chloride (3.32 g, 31.1 mmol) at 0° C. The mixture was stirred at 0° C. for 2 h, and then stirred at RT for 15 h. The reaction was quenched using MeOH, and the mixture was concentrated in vacuo to give a residue. The residue was dissolved in THF (150 mL) and MeOH (150 mL). Ammonium hydroxide (20 mL) was added at 0° C. The mixture was stirred for 1 h, and then acidified with citric acid to pH=5. The mixture was diluted with water (300 mL) and extracted with EA (2×200 mL). The combined organic layer was washed with brine, dried over anhydrous sodium sulfate, filtered and concentrated in vacuo to afford the crude product. The crude product was purified by chromatography column (silica gel, EA:PE=1:10) to give 48-7 (3.70 g, 6.5 mmol, 83.2%) as a white solid.

To a solution of 48-7 (5.50 g, 9.6 mmol) and 48-7a (3.19 g, 9.6 mmol) in DMF (550 mL), Pd(PPh$_3$)$_4$ (2.17 g, 1.9 mmol) and LiCl (530 mg, 12.5 mmol) were added. The mixture was stirred at 100° C. for 1 h, and then cooled to RT. The mixture was diluted with water and extracted with EA (3×50 mL). The combined organic layer was dried over Na$_2$SO$_4$ and concentrated to give the crude product. The crude was purified by silica gel to give 48-8 (2.80 g, 5.3 mmol, 54.7%).

To a solution of 48-8 (1.10 g, 2.1 mmol) in 1,4-dioxane (15 mL) and H$_2$O (2 mL) was added K$_2$OsO$_4$·2H$_2$O (23 mg, 62 μmol) and NMO (730 mg, 6.2 mmol) at RT. The mixture was stirred at RT for 1.5 h. The reaction was diluted with water and extracted with EA (3×30 mL). The organic layer was dried over Na$_2$SO$_4$ and concentrated to give the crude product. The crude product was purified by silica gel (PE:EA=2:1 to DCM:MeOH=80:1) to give 48-9 (800 mg, 1.4 mmol, 68.2%) as a white solid.

To a solution of 48-9 (2.0 g, 3.5 mmol) in 1,4-dioxane (40.2 mL) was added NaIO$_4$ (1.89 g, 8.8 mmol) dissolved in H$_2$O (19.8 mL) at 0° C. The mixture was stirred at RT for 1.5 h. The reaction was diluted with water and extracted with EA (3×100 mL). The combined organic layer was dried over Na$_2$SO$_4$ and concentrated to give crude 48-10 (1.89 g, 3.5 mmol, 100%) as a colorless oil.

To a solution of 48-10 (5.70 g, 10.7 mmol) dissolved in THF (100 mL), MeMgBr (1.4 M, 30.5 mL) was added at 0° C. The mixture was stirred at RT for 2 h. The reaction was quenched with sat. NH$_4$Cl (aq) and extracted with EA (3×100 mL). The combined organic layer was dried with Na$_2$SO$_4$ and concentrated to give the crude product. The crude product was purified by silica gel (PE:EA=1:2) to give 48-11 (900 mg, 1.6 mmol, 15.3%).

To a solution of 48-11 (1.20 g, 2.2 mmol) in DMF (10 mL) was added NaH (261.6 mg, 10.9 mmol) at 0° C. The mixture was stirred at RT for 0.5 h. Then 48-11a (764 mg, 2.2 mmol) dissolved in DMF (2 mL) was added. The mixture was stirred at RT for 6 h. The reaction was quenched with sat. NH$_4$Cl (aq) and extracted with EA (3×150 mL). The combined organic layer was dried with Na$_2$SO$_4$ and concentrated to give the crude product which was purified by silica gel to give 48-12 (520 mg, 714 μmol, 82% purity 26.8%) as a yellow oil.

To 48-12 (400 mg, 550 μmol) was added 3% TCA/DCM (10 mL). The solution was stirred at RT for 15 mins. Sat. NaHCO$_3$(aq.) was added, and the mixture was extracted with EA (3×30 mL). The combined organic layer was dried with Na$_2$SO$_4$ and concentrated to give the crude product. The crude product was purified by silica gel (DCM:MeOH=150:1 to 100:1) to give 48-13 (230 mg, 504 μmol, 91.8%) as a yellow oil.

To a solution of 48-13 (200 mg, 440 μmol) in AcOH (8 mL) and H$_2$O (4 mL), was added NaNO$_2$ (3.03 g, 43.8 mmol). The mixture was stirred at RT for 3 d. The mixture was concentrated to give a residue. The residue was diluted with EA (50 mL) and washed with NaHCO$_3$ (aq). The organic layer was concentrated to give the crude product which was purified with prep-TLC to give 48-14 (130 mg, 285 μmol, 64.9%) as a white solid.

To a solution of 48-14 (25 mg, 55 μmol) in MeOH (1 mL), 33 wt. % methylamine in absolute ethanol (1 mL) was added. The solution stirred at 40° C. for 24 h. The reaction was then concentrated to give crude 48-15 (10 mg, 26 μmol, 47.2%) as a white solid.

To a solution of 48-15 (40 mg, 103 μmol) in DCM (500 μL) was added TMSBr (594 mg, 5.2 mmol). The mixture was stirred at RT for 4 h. The mixture was then concentrated to give the crude product, which was purified by prep-HPLC to give 48 (17 mg, 56 μmol, 54.3%). LCMS m/z=304.1 [M+H]$^+$. Compounds 10c and 10d may be similarly obtained by treating 10a and 10b, respectively, with TMSBr in DCM.

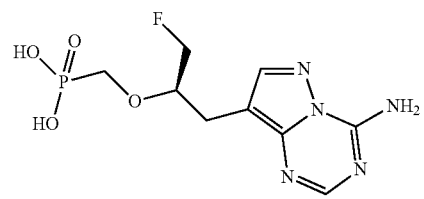

10c

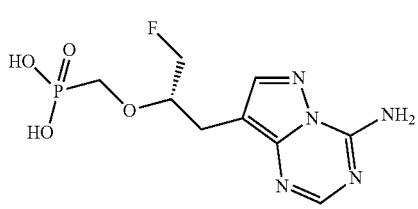

48-1 may be obtained by adding 2,4-bis(methylthio)imidazo[2,1-f][1,2,4]triazine (8.0 g, 37.7 mmol, *J. Chem. Soc. Perkin Trans.* 1, No. 20, p. 2929-2936 (1999)) to 7M NH$_3$/MeOH (60 mL) and stirring in a Par reactor at 80° C. overnight followed by concentration under reduced pressure to provide 48-1 (6.5 g, 95% yield) as a yellow solid. LCMS m/z=182.0 [M+H]$^+$.

Example 15

(S)-(((1-(4-aminopyrrolo[2,1-f][1,2,4]triazin-7-yl)-3-fluoropropan-2-yl)oxy)methyl)phosphonic acid (Compound 49)

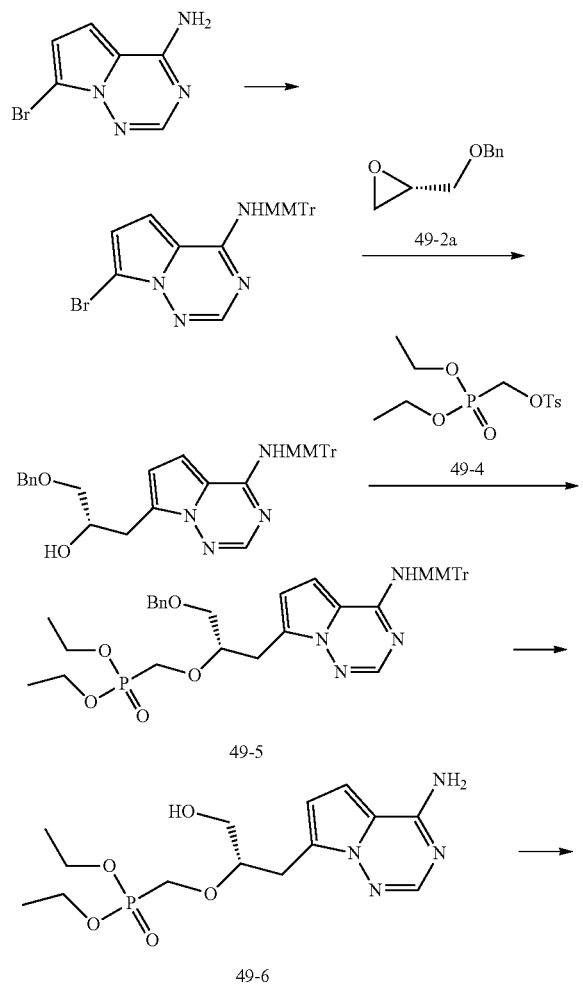

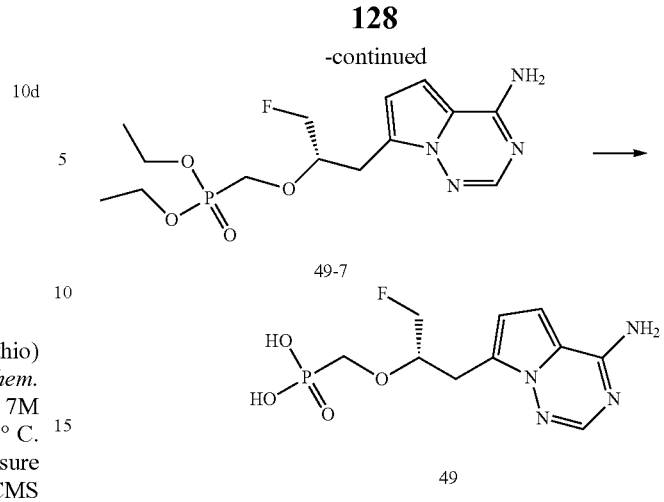

A solution of 49-1 (8.73 g, 41.2 mmol, prepared according to the procedures provided in WO 2007/56170) and NaH (2.47 g, 61.8 mmol) in anhydrous DMF (100 mL) was stirred at 0° C. under nitrogen for 0.5 h. MMTrCl (12.7 g, 41.2 mmol) was added under nitrogen. The mixture was stirred at RT for 2.0 h. Water and EtOAc were added. The water layer was extracted with EtOAc (3×). The organic phases were combined, washed with water and dried over Na$_2$SO$_4$. The product was purified by column chromatograph (PE:EA=20:1) to give 49-2 (16.2 g, 81%).

To a solution of 49-2 (5.18 g, 10.7 mmol) in dry THF (35 mL) were added n-BuLi (12.84 mL, 32.1 mmol, 2.5 M) dropwise at −78° C. under nitrogen for 20 mins. The mixture was stirred at −78° C. for 30 mins and then 49-2a (5.26 g, 32.1 mmol) was added. The mixture was warmed to RT slowly, and the stirred for 2 h under nitrogen. NH$_4$Cl (aq.) and EtOAc was added. The water layer was extracted by EtOAc. The organic layer was washed with brine and concentrated to give the crude product. The crude product was purified by column chromatograph (PE:EA=3:1) to give 49-3 (1.74 g, 28.6%).

To the solution of 49-3 (3.42 g, 6.0 mmol) in NMP (18 mL) was added Mg(O$^t$Bu)$_2$ (4.08 g, 24.0 mmol). The mixture was stirred at 90° C. under N$_2$ atmosphere for 1 h. Then 49-4 (3.86 g, 12.0 mmol) in NMP (5 mL) was added under N$_2$ atmosphere. The mixture was stirred at 90° C. overnight, and then cooled to RT. Water and EtOAc were added to the mixture. The mixture was acidified to pH=8.0 with 2 N HCl (aq.). The water layer was extracted with EtOAc, and the organic layer was washed with brine. The organic layer was concentrated and purified by column chromatograph (PE:EA=1:1) to give 49-5 (3.23 g, 74.8%).

To the solution of 49-5 (3.23 g, 4.6 mmol) in EtOH (80 mL) was added Pd/C (0.33 g). The mixture was stirred at 60° C. under H$_2$ atmosphere overnight, and then filtered. The filtrate was concentrated and purified by silica gel column (DCM:MeOH=10:1) to give 49-6 (0.92 g, 57.5%).

To the solution of 49-6 (93 mg, 0.3 mmol) in toluene (1.5 mL) was added DBU (79 mg, 0.5 mmol) and CF$_3$(CF$_2$)$_3$SO$_2$F (157 mg, 0.5 mmol). The mixture was stirred at 0° C. under N$_2$ atmosphere for 2 h. Sat. NH$_4$Cl (aq.) and EtOAc were added. The organic layer was concentrated to give the crude product which was purified by silica gel column (DCM:MeOH=10:1) to give 49-7 (17 mg, 18.2%).

To the solution of 49-7 (80 mg, 0.2 mmol) in acetonitrile (1.5 mL) was added TMSBr (0.85 g, 5.6 mmol) at 0° C. The mixture was stirred at RT for 1.0. Another portion of TMSBr (0.85 g, 5.6 mmol) was added at 0° C. The mixture was stirred at RT for 2 h. The mixture was concentrated and purified by HPLC to give 49 (23 mg, 33%). LCMS: m/z=305.1 [M+H]+.

Example 16

(((1-(2-amino-4-oxo-3,4-dihydropyrrolo[2,1-f][1,2,4]triazin-7-yl)propan-2-yl)oxy)methyl)phosphonic acid (Compound 50)

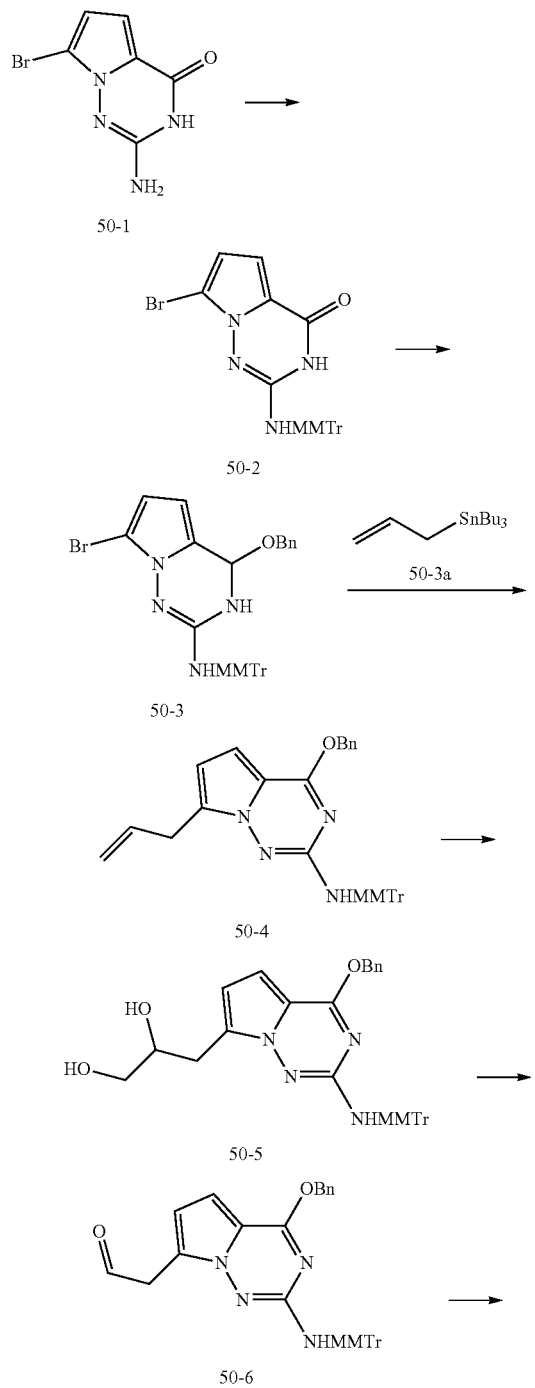

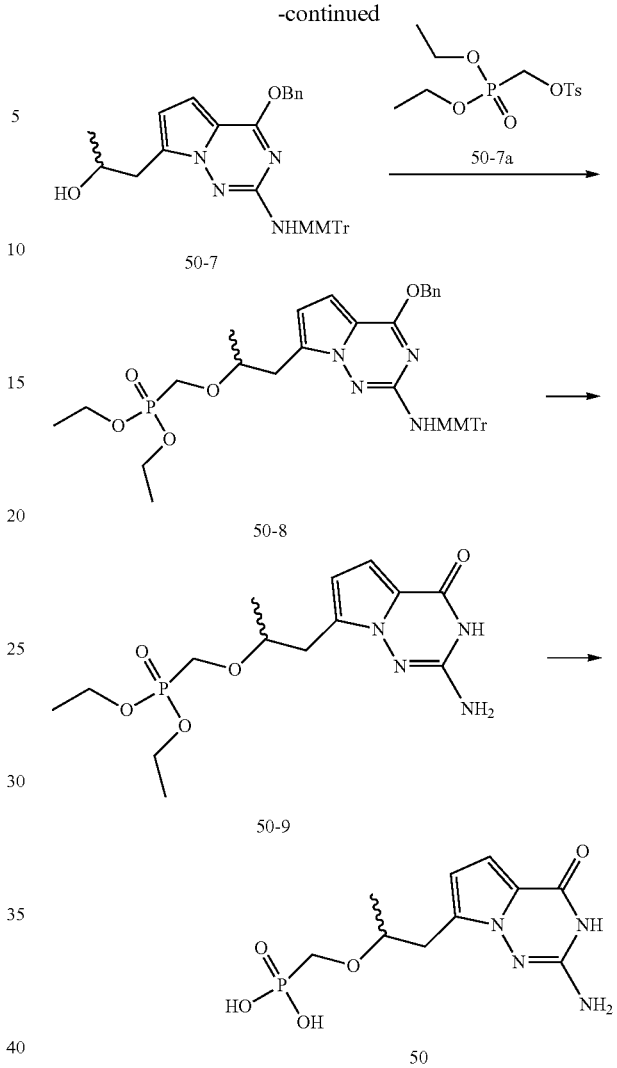

A solution of 50-1 (4.45 g, 19.4 mmol) and NaH (2.0 g, 50 mmol) in anhydrous DMF (45 mL) was stirred at 0° C. under nitrogen for 0.5 h. MMTrCl (6.7 g, 22.0 mmol) was added under nitrogen. The mixture was stirred at ambient temperature for 2 h. Water and EtOAc were added. The water layer was extracted by EtOAc (3×). The organic phase was combined, washed with water and dried over Na2SO4. The product was purified by column chromatograph (PE:EA=4:1) to give 50-2 (5.7 g, 58.8%).

To the solution of 50-2 (5.50 g, 11.0 mmol) in DMF (55 mL) was added K2CO3 (3.04 g, 22.0 mmol) and BnBr (2.82 g, 16.5 mmol). The mixture was stirred at 80° C. for 1.5 h. Water and EtOAc were added. The water layer was extracted with EtOAc, and the organic layer was washed with brine. The organic layer was concentrated and purified by column chromatograph (PE:EA=6:1) to give 50-3 (4.74 g, 8 mmol, 73%).

To the solution of 50-3 (4.72 g, 8.0 mmol) in DMF (48 mL) was added 50-3a (3.18 g, 9.6 mmol), Pd(PPh3)4 (1.85 g, 1.6 mmol) and LiCl (0.44 g, 10.4 mmol). The mixture was stirred at 100° C. for 1.5 h. The mixture was then cooled to RT. Water and EtOAc were added to the mixture. The water layer was extracted with EtOAc, and the organic layer was washed with brine. The organic layer was concentrated and purified by column chromatograph (PE:EA=10:1) to give 50-4 (4.3 g, 7.8 mmol, 97.4%).

To the solution of 50-4 (4.3 g, 7.8 mmol) in 1,4-dioxane (60 mL) and water (9 mL), NMO (3.26 g, 27.9 mmol) and K$_2$OsO$_4$.2H$_2$O (0.1 g, 0.28 mmol) were added. The mixture was stirred at ambient temperature for 1 h. The mixture was then diluted with water and extracted with EA. The organic layer was washed with brine, concentrated and then purified by column chromatograph (DCM:MeOH=30:1) to give 50-5 (3.92 g, 6.6 mmol, 84.3%).

To the solution of 50-6 (1.76 g, 3.0 mmol) in THF (18 mL) and water (3.6 mL) was added NaIO$_4$ (1.28 g, 6.0 mmol). The mixture was stirred at ambient temperature for 1.5 h. The mixture was diluted with water and extracted with EA. The organic layer was washed with brine, dried with Na$_2$SO$_4$ and concentrated to give crude 50-7, which was used directly in the next step.

To the solution of 50-7 (1.66 g, 3.0 mmol) in dry THF (18 mL) was added CH$_3$MgBr (6.5 mL, 690 mmol, 1.4 M) at 0° C. under N$_2$ atmosphere. The mixture was stirred at 0° C. for 2 h. The mixture was diluted with water and extracted with EA. The organic layer was washed with brine, concentrated and purified by column chromatograph (PE:EtOAc=3:1) to give 50-8 (1.03 g, 1.8 mmol, 60.2%).

To the solution of 50-8 (1.03 g, 1.8 mmol) in NMP (6 mL) was added Mg(OtBu)$_2$ (1.22 g, 7.2 mmol). The mixture was stirred at 90° C. under N$_2$ atmosphere for 1 h. Then 50-8a (1.16 g, 3.6 mmol) in NMP (1 mL) was added under N$_2$ atmosphere. The mixture was stirred at 90° C. overnight. The mixture was then cooled to r.t., diluted with water and acidified to pH=8.0 with 2 N HCl aqueous. The water layer was extracted with EtOAc. The organic layer was washed with brine, concentrated and purified by column chromatography (PE:EA=1:1) to give 50-9 (0.92 g, 1.3 mmol, 71%).

To the solution of 50-9 (0.89 g, 1.2 mmol) in EtOH (30 mL) was added Pd/C. The mixture was stirred at 60° C. under H$_2$ atmosphere overnight. The mixture was then filtered. The filtrate was concentrated and purified by silica gel column (DCM:MeOH=10:1) to give 50-10 (0.24 g, 55%).

To the solution of 50-10 (0.24 mg, 0.7 mmol) in acetonitrile (3.0 mL) was added TMSBr (2.55 g, 16.7 mmol) at 0° C. The mixture was stirred at RT for 1 h. Another portion of TMSBr (2.55 g, 16.7 mmol) was added at 0° C. The mixture was stirred at RT for 2 h. The mixture was concentrated and purified by HPLC to give 50 (40.0 mg, 20%). LCMS: m/z=305.1 [M+H]$^+$.

Example 17

Compound 52

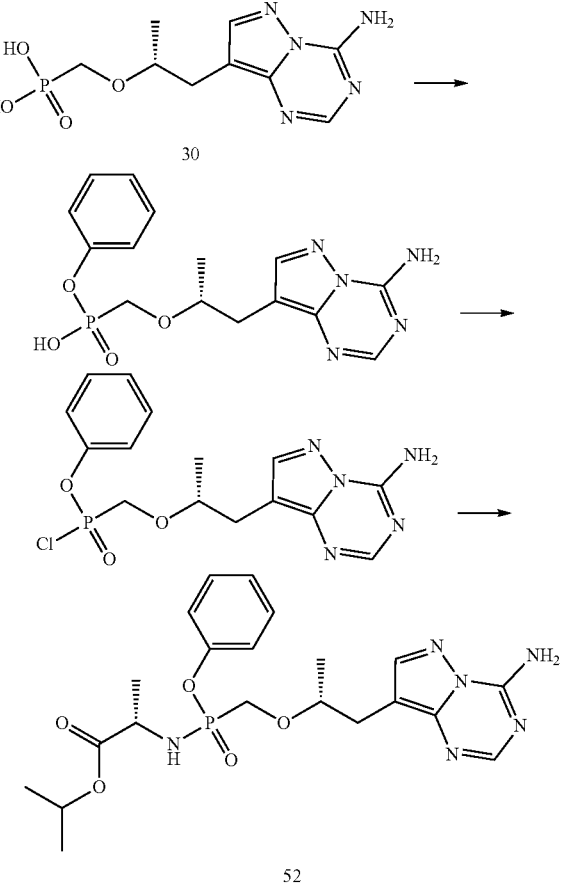

To 30 (30 mg, 0.1 mmol) and DMAP (68 mg, 0.6 mmol) in CH$_3$CN (1.5 mL) at RT was added Et$_3$N (116 mg, 160 µL, 1.1 mmol) and (PhO)$_3$P (260 mg, 220 µL, 0.8 mmol) in a 4 mL vial. The air in the vial was replaced with Ar, and the reaction was then sealed. The mixture was then stirred at 100° C. for 16 h. The mixture was added to the top of a silica gel column (10 g), and the column was dried under high vacuum for 0.5 h. The mixture was then eluted with neat methanol. Fractions with the intermediate product were combined and evaporated until dryness. The intermediate product was recovered as a gel, which was further dried under high vacuum overnight.

The intermediate product was dissolved in CH$_3$CN (2.5 mL), and SOCl$_2$ (123 mg, 75 µL, 1.03 mmol) was added at RT. The mixture in the small vial (4 mL) was stirred at 70° C. for 2 h. The mixture was concentrated at 35° C. under vacuum, and then dried under high vacuum to give chloride product.

The chloride product was dissolved in CH$_3$CN (1.3 mL), and cooled to 0° C., and L-alanine isopropyl ester (0.47 g, 3.6 mmol) was added. The mixture was stirred at 0° C. for 2.5 h. The mixture was stored at −20 OC overnight, and then concentrated until dryness. The resulting residue was separated by prep-HPLC (CH$_3$CN—H$_2$O, 5 to 95%, including 0.1% formic acid). Fractions containing the product were combined, and dried by lyophilization to give 52 as a white fluffy solid. LCMS: m/z=477.1 [M+H]$^+$; $^{31}$P NMR δ ppm 23.20 and 22.33.

Example 18

The following compounds in Table 4 were prepared in a similar manner as 52.

TABLE 4

| # | Compound | $^{31}$P NMR | MS [M + H]$^+$ |
|---|---|---|---|
| 53 | | 22.89, 21.72 | 477.0 |
| 61 | | 24.70, 24.61, 23.97, 23.58 | 493.0 |
| 62 | | 22.36, 21.15 | 495.1 |
| 63 | | 22.26, 21.35 | 495.0 |
| 73 | | 22.78, 21.91 | 489.1 |
| 74 | | 21.58, 20.65 | 513.1 |

TABLE 4-continued
| # | Compound | ³¹P NMR | MS [M + H]⁺ |
|---|---|---|---|
| 75 | | 24.90, 24.77, 23.98 | 507.1 |
| 76 | | 22.26, 21.35 | 495.0 |
| 77 | | 21.89, 20.49 | 513.1 |
| 78 | | 22.00, 20.73 | 495.0 |
Example 19
((1-((4-aminopyrazolo[1,5-a][1,3,5]triazin-8-yl)methyl)cyclopropoxy)methyl) phosphonic acid (Compound 64)
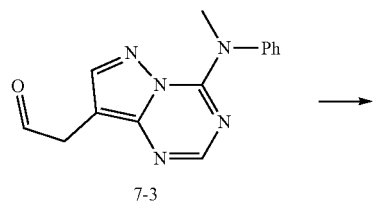
7-3
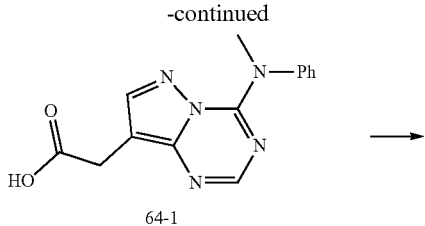
64-1
-continued
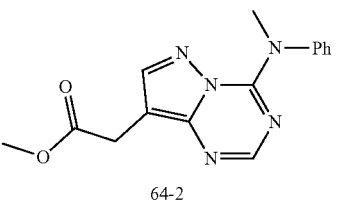
64-2

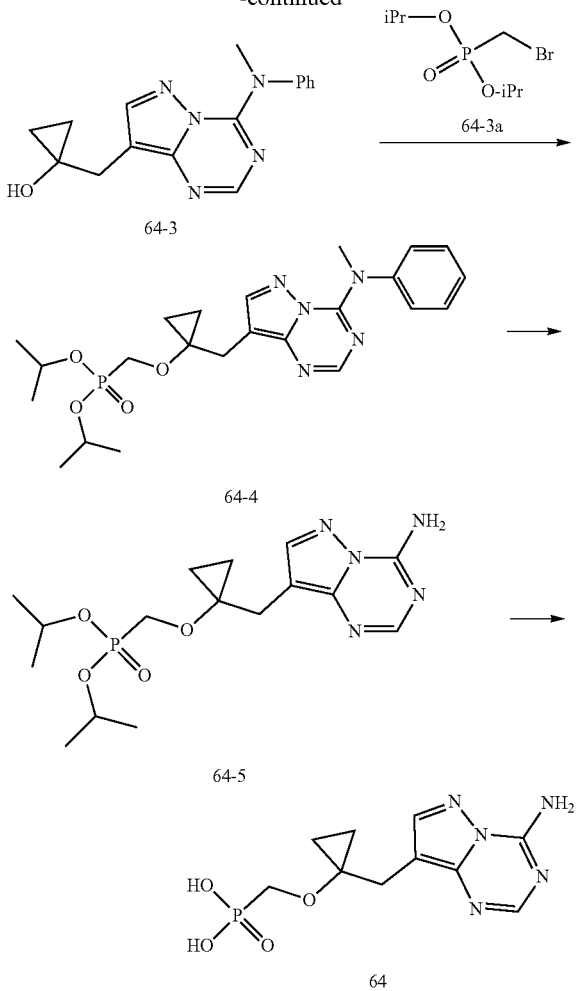

Preparation of (64-3): To a solution of compound 64-2 (6.50 g, 21.9 mmol) in THF (130 mL) was added dropwise Ti(Oi-Pr)$_4$ (12.42 g, 43.7 mmol) at rt. EtMgBr (83 mmol, 83 mL) was added dropwise at r.t over 1 hour and stirred at rt for 2 hrs. 2N H$_2$SO$_4$ (aq) was added, followed by saturated aqueous Na$_2$CO$_3$ was added to adjust pH>7. The mixture was extracted with EA, and the organic layer was collected, washed with brine, dried over Na$_2$SO$_4$ and concentrated in vacuo to give a residue. The residue was purified by silica gel chromatography (PE:EA=5:1-3:1) to give 64-3 (1.73 g, 5.9 mmol, 26.8% yield) as a yellow oil. $^1$HNMR (DMSO-d$_6$, 400 MHz): δ ppm 8.18 (s, 1H), 7.96 (s, 1H), 7.42-7.39 (m, 2H), 7.35-7.30 (m, 3H), 4.54-4.46 (m, 2H), 3.82 (d, J=10.4 Hz, 2H), 3.74 (s, 3H), 2.92 (s, 2H), 1.19 (d, J=6 Hz, 6H), 1.13 (d, J=6 Hz, 6H), 0.74-0.73 (m, 2H), 0.62-0.59 (m, 2H). LCMS m/z=296.2 (M+H)$^+$.

Preparation of (64-4): A solution of compound 64-3 (1.70 g, 5.8 mmol) and LiI (8 mg, 58 µmol) in DMF (5 mL) was heated up to 60° C. Then t-BuOLi (737 mg, 9.2 mmol) in THF (5 mL) and compound 64-3a (2.01 g, 7.8 mmol) in DMF (5 mL) were added slowly and simultaneously to the above solution, and the mixture was stirred at 60° C. for 3 hrs. Water was added, and the resulting mixture was extracted with EA. The organic layer was collected, washed with brine, dried over Na$_2$SO$_4$ and concentrated in vacuo to give a residue, which was purified by silica gel chromatography (DCM:MeOH=300:1-100:1) to give 64-4 (600 mg, 1.3 mmol, 22% yield) as a yellow oil. $^1$H NMR (DMSO-d$_6$, 400 MHz): δ ppm 8.60 (s, 1H), 8.29 (s, 1H), 8.15 (s, 1H), 8.02 (s, 1H), 4.54-4.46 (m, 2H), 7.67 (d, J=10 Hz, 2H), 2.93 (s, 2H), 1.18 (d, J=6 Hz, 6H), 1.13 (d, J=6 Hz, 6H), 0.76-0.73 (m, 2H), 0.64-0.61 (m, 2H). LCMS m/z=474.3 (M+H)$^+$.

Preparation of (64-5): A solution of compound 64-4 (400 mg, 850 µmol) in 7M NH$_3$/MeOH (20 mL) was stirred in a sealed tube at 100° C. overnight. The reaction mixture was concentrated in vacuo and separated by prep-TLC to give 64-5 (160 mg, 420 µmol, 49.4% yield) as a white solid. $^1$HNMR (DMSO-d$_6$, 400 MHz): δ ppm 8.60 (s, 1H), 8.29 (s, 1H), 8.15 (s, 1H), 8.02 (s, 1H), 4.54-4.46 (m, 2H), 7.67 (d, J=10 Hz, 2H), 2.93 (s, 2H), 1.18 (d, J=6 Hz, 6H), 1.13 (d, J=6 Hz, 6H), 0.76-0.73 (m, 2H), 0.64-0.61 (m, 2H). LCMS m/z=384.2 (M+H)$^+$.

Preparation of (64): To a solution of compound 64-5 (200 mg, 520 µmol) in ACN (2 mL) was added TMSBr (1.60 g, 10.4 mmol) at 0° C. The mixture was stirred at rt for 10 hrs. The reaction mixture was concentrated in vacuo and separated by prep-HPLC to give 64 (50 mg, 170 µmol, 32% yield) as a white solid. $^1$HNMR (DMSO-d$_6$, 400 MHz): δ ppm 8.63 (s, 1H), 8.30 (s, 1H), 8.19 (s, 1H), 8.03 (s, 1H), 3.66 (d, J=10 Hz, 2H), 2.92 (s, 2H), 0.75 (s, 2H), 0.57 (s, 2H). $^{31}$PNMR (DMSO-d$_6$, 162 MHz): δ 16.11 (s). LCMS m/z=300.1 (M+H)$^+$.

Preparation of (64-1): To a solution of compound 7-3 (21.2 g, 79.3 mmol) in acetonitrile (500 mL) were added dropwise NaH$_2$PO$_4$.2H$_2$O (37.1 g, 238 mmol) in H$_2$O (125 mL), 30% H$_2$O$_2$ (44.94 g, 397 mmol, 30% purity) and NaClO$_2$ (21.41 g, 238 mmol) in H$_2$O (125 mL) at 0° C. The mixture was stirred at rt overnight. Water was added, and the mixture was extracted with ethyl acetate, the organic layer was washed with brine, dried over Na$_2$SO$_4$ and concentrated under reduced pressure to give 64-1 (13.60 g, 48 mmol, 60.5% yield) as a yellow oil. $^1$HNMR (DMSO-d$_6$, 400 MHz): δ ppm 8.19 (s, 1H), 7.90 (s, 1H), 7.43-7.39 (m, 2H), 7.35-7.32 (m, 3H), 3.75 (s, 3H), 3.69 (s, 2H), 3.62 (s, 3H). LCMS m/z=284.2 (M+H)$^+$.

Preparation of (64-2): To a solution of compound 64-1 (12.60 g, 44.5 mmol) in DMF (200 mL) was added MeI (12.6 g, 89 mmol) and K$_2$CO$_3$ (18.4 g, 133.4 mmol). The mixture was stirred at rt for 2 hrs. Water was added, and the mixture was extracted with ethyl acetate. The organic layer was collected, washed with brine, dried over Na$_2$SO$_4$ and concentrated in vacuo to give a residue. The residue was purified by silica gel chromatography (PE:EA=5:1) to give 64-2 (6.50 g, 21.9 mmol, 49.2% yield) as a yellow solid. $^1$HNMR (DMSO-d$_6$, 400 MHz): δ ppm 8.16 (s, 1H), 7.88 (s, 1H), 7.42-7.39 (m, 2H), 7.34-7.30 (m, 3H), 5.26 (s, 1H), 3.74 (s, 3H), 2.83 (s, 2H), 0.55-0.50 (m, 2H), 0.48-0.44 (m, 2H). LCMS m/z=298.2 (M+H)$^+$.

Example 20
(S) (((3-(4-aminopyrazolo[1,5-a][1,3,5]triazin-8-yl)-1,1-difluoropropan-2-yl)oxy)methyl)phosphonic acid (Compound 65)
(R)-(((3-(4-aminopyrazolo[1,5-a][1,3,5]triazin-8-yl)-1,1-difluoropropan-2-yl)oxy)methyl)phosphonic acid (Compound 66)
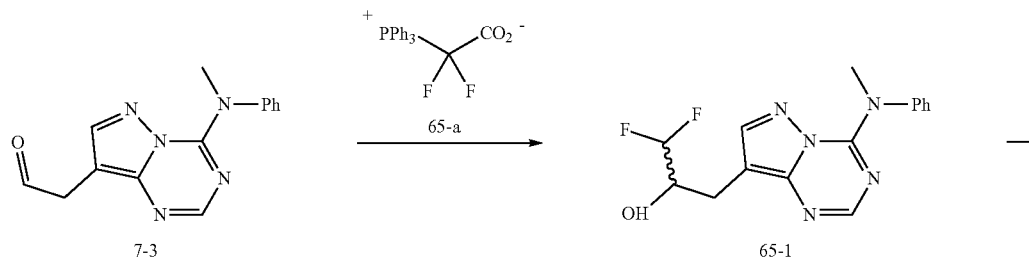
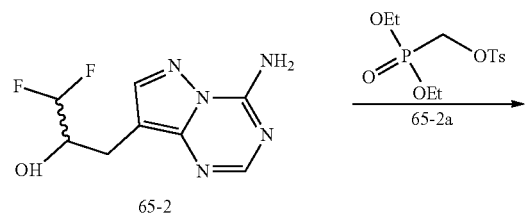
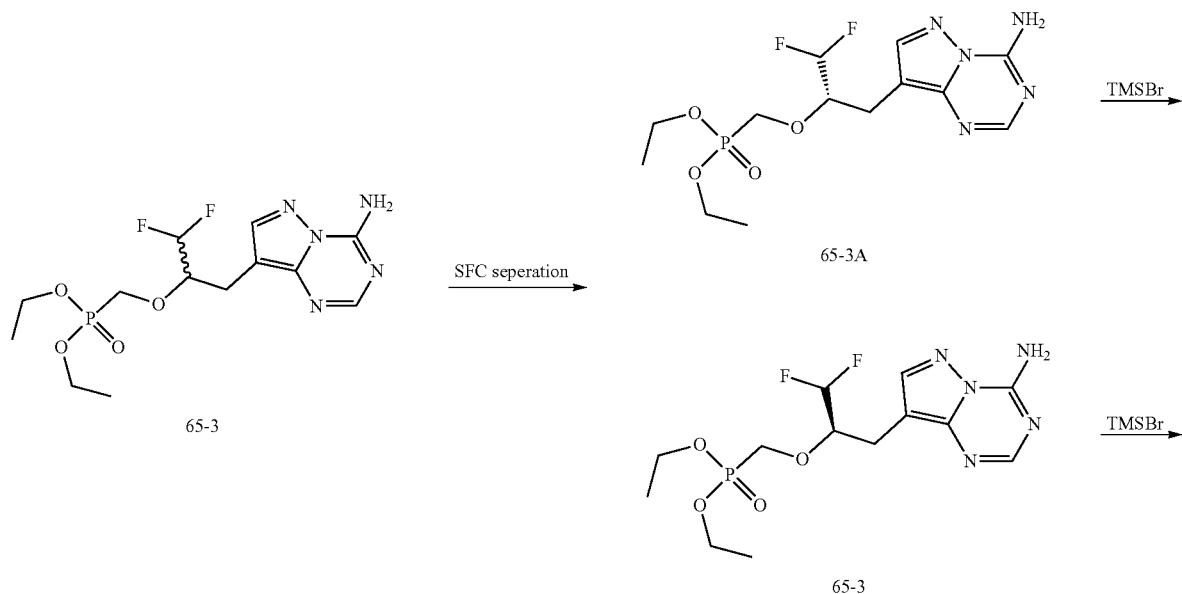

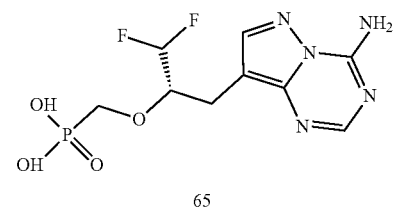

65

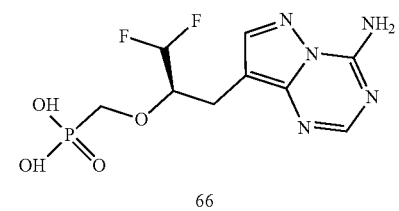

66

Preparation of (65-1): To a solution of 7-3 and 65-a (3.10 g, 11.6 mmol, dx.doi.org/10.1021/ol503225s) in DCE (13 mL), TMSCl (2.68 g, 2.2 mL) was added at room temperature, under N₂ atmosphere. The reaction was stirred at 50° C. for about 1 h. KF (3.28 g, 11.6 mmol) was slowly added to the reaction mixture, which was stirred at 50° C. for 4 h. The reaction mixture was extracted with EA, and the organic layers were combined and washed with brine, dried with Na₂SO₄ and concentrated in vacuo to give a residue which was further purified by silica gel chromatography to give 65-1 (1.57 g, 4.9 mmol, 42.4% yield) as a colorless oil. ESI-LCMS: m/z 320.2 [M+H]⁺.

Preparation of (65-2): A solution of 65-1 (980 mg, 3.1 mmol) in NH₃/MeOH (40 mL) was stirred at 100° C. for about 6 h. The reaction mixture was then concentrated in vacuo to give a residue which was further purified by TLC to give 65-2 (407 mg, 1.8 mmol, 57.8% yield) as white solid. ¹H-NMR (400 MHz, DMSO-d₆): δ 8.63 (s, 1H), 8.38 (s, 1H), 8.08 (s, 1H), 8.04 (s, 1H), 6.04-5.75 (m, 1H), 5.66 (d, J=4.8 Hz, 1H), 3.94-3.93 (m, 1H), 2.91-2.69 (m, 2H). ESI-LCMS: m/z 230.1 [M+H]⁺.

Preparation of (65-3): To a solution of 65-2 (100 mg, 440 μmol) in NMP (1 mL), Mg(t-BuO)₂ (298 mg, 440 μmol) was added at room temperature under N₂ atmosphere. The reaction mixture was stirred at 70° C. for about 0.5 h. 65-2a (281 mg, 870 mol) was slowly added to the reaction mixture, which was stirred at this temperature for about 5 h. The reaction mixture was extracted with EA and the organic layer washed with brine, dried with Na₂SO₄ and concentrated in vacuo to give a residue which was purified by silica gel chromatography to give 65-3 (82 mg, 220 μmol, 49.6% yield) as a white solid. The two enantiomers were separated through supercritical fluid chromatography to give compound 65-3A (212.4 mg, retention time: 7.21 min) and compound 65-3 (208 mg, retention time: 8.68 min). (SFC, CHIRALPAK AD-H column, Column size: 0.46 cm I.D.×25 cm L, Injection: 1.0 ul, Mobile phase: Hexane/EtOH/DEA=70/30/0.1 (V/V/V), Flow rate: 1.0 ml/min, retention time: 7.211 min, 8.677 min)¹H-NMR (400 MHz, D₂O): δ ppm 8.65 (s, 1H), 8.33 (s, 1H), 8.12 (s, 1H), 8.05 (s, 1H), 6.28-6.00 (m, 1H), 4.06-3.90 (m, 7H), 3.00-2.82 (m, 2H), 1.20-1.12 (m, 6H). ESI-LCMS: m/z 380.2 [M+H]⁺.

Preparation of (65): To a solution of compound 65-3A (196 mg, 780 μmol) in ACN (3.0 mL) was added TMSBr (2.50 g, 780 μmol, 3 mL) at 0° C. The mixture was stirred at rt for 5 hrs, then concentrated in vacuo to give a residue. The residue was purified by MPLC to give 65 (70 mg, 217 μmol, 27.8% yield) as a white solid. ¹H-NMR (400 MHz, D₂O): δ ppm 8.64 (s, 1H), 8.32 (s, 1H), 8.20 (s, 1H). 8.04 (s, 1H), 6.22-5.93 (m, 1H), 3.96-3.90 (m, 1H), 3.80-3.65 (m, 2H), 3.00-2.96 (m, 1H), 2.86-2.80 (m, 1H), ³¹P-NMR (162 MHz, DMSO-d₆): δ 15.57 (s). ESI-LCMS: m/z 324.1 [M+H]⁺.

Preparation of (66): To a solution of compound 65-3 (200 mg, 530 μmol) in ACN (2.1 mL) was added TMSBr (1.69 g, 530 μmol, 2 mL) at 0° C. The mixture was stirred at rt for 5 hrs, then concentrated in vacuo to give a residue. The residue was purified by MPLC to give 66 (65 mg, 200 μmol, 38.1% yield) as a white solid. ¹H-NMR (400 MHz, D₂O): δ ppm 8.65 (s, 1H), 8.33 (s, 1H), 8.20 (s, 1H), 8.04 (s, 1H), 6.22-5.93 (m, 1H), 3.97-3.90 (m, 1H), 3.80-3.65 (m, 2H), 3.01-2.96 (m, 1H), 2.86-2.80 (m, 1H). ³¹P-NMR (162 MHz, DMSO-d₆): δ 15.49 (s). ESI-LCMS: m/z 324.1 [M+H]⁺.

Example 21
(S)-(((1-(4-aminoimidazo[2,1-f][1,2,4]triazin-7-yl)-3-fluoropropan-2-yl)oxy) methyl) phosphonic acid
(Compound 67)
(R)-(((1-(4-aminoimidazo[2,1-f][1,2,4]triazin-7-yl)-3-fluoropropan-2-yl)oxy) methyl)phosphonic acid
(Compound 68)
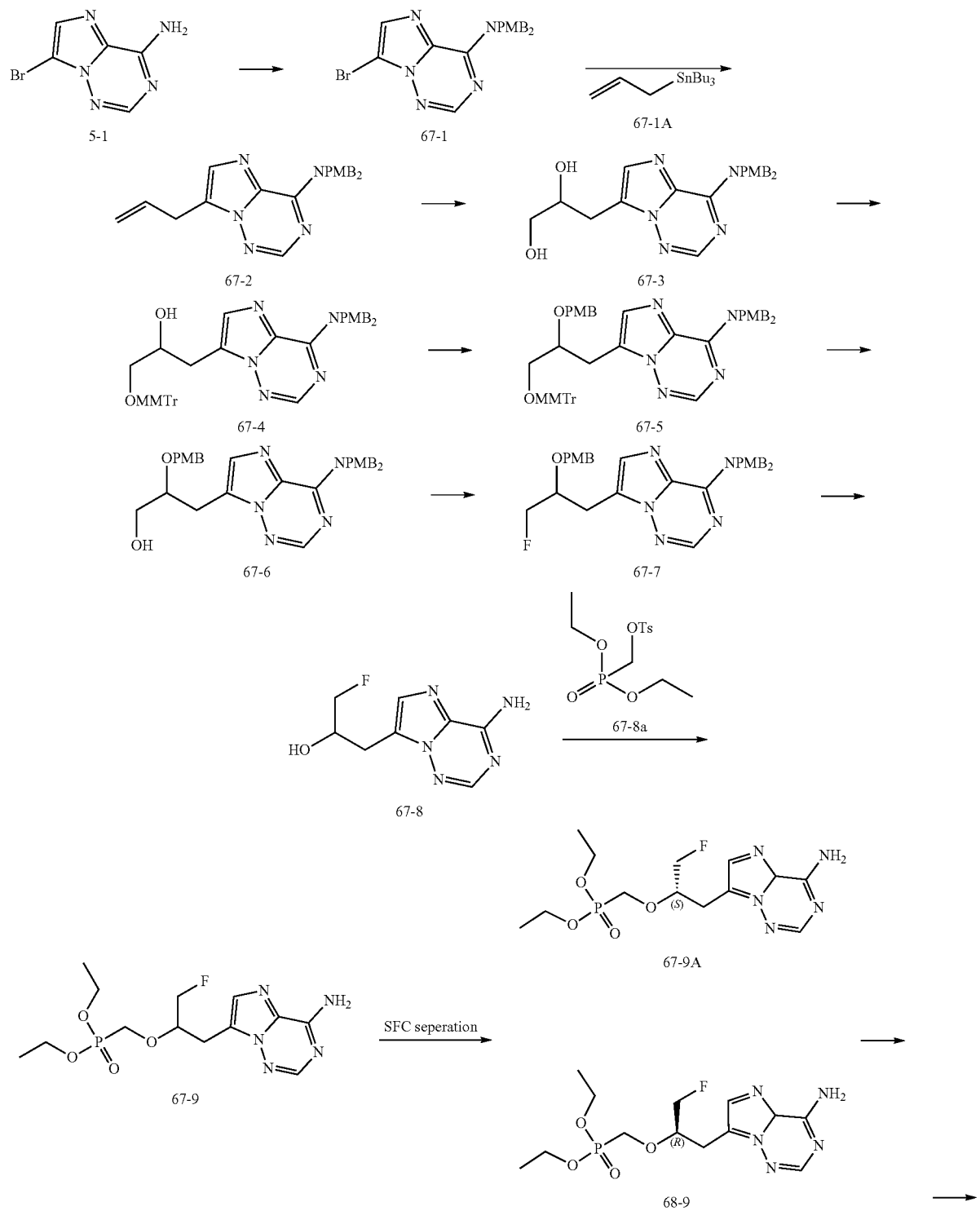

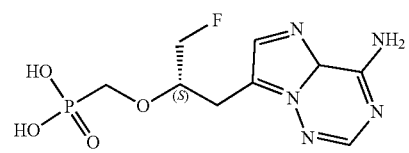

67

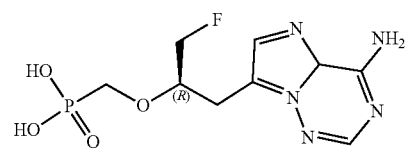

68

Preparation of (67-1): To a pre-cooled solution of compound 5-1 (15 g, 70 mmol) in DMF (150 mL) in an ice bath was added NaH (10 g, 420 mmol) in three batches. The mixture was stirred at 0° C. for 1 hour. PMBCl (54.9 g, 350 mmol) was added and the resultant solution was then stirred at room temperature for 4 hours. Water (200 mL) was slowly added at 0° C. to quench the reactions. The resultant solution was then extracted with EA (500 mL×3). The combined organic layer was washed with brine, dried over anhydrous $Na_2SO_4$ and then concentrated in vacuo to give a residue. The residue was finally purified by silica gel column to give 67-1 (12 g, 38% yield) as a colorless oil. LCMS m/z=454.1 $(M+H)^+$.

Preparation of (67-2): 67-1 (15.2 g, 33.2 mmol), 67-1A (14.3 g, 43.2 mmol), LiCl (1.83 g, 43.2 mmol) and $Pd(PPh_3)_4$ (3.84 g, 3.32 mmol) were dissolved in DMF (150 mL). The resultant solution was then stirred under nitrogen gas atmosphere at 100° C. for 1 hour. Water was then added to quench the reaction. The resultant solution was extracted with EA (500 mL×3), and the organic layer was washed with brine, dried over anhydrous $Na_2SO_4$ and finally concentrated in vacuo to give a residue. The residue was purified by silica gel chromatography (PE:EA=10:1) to give 67-2 (12.1 g, 87.6% yield) as a yellow oil. LCMS m/z=416.2 $(M+H)^+$.

Preparation of (67-3): To a solution of 67-2 (12.1 g, 29.1 mmol) in mixed solvents of THF (200 mL) and water (20 mL) were added NMO (10.2 g, 87.4 mmol) and $K_2OsO_4.2H_2O$ (193 mg, 0.6 mmol). The mixture was stirred at room temperature for 5 hours. Saturated $Na_2SO_3$ aqueous solution was then added to quench the reaction. The resultant solution was extracted with EA (500 mL×3). The organic layer was washed with brine, dried over anhydrous $Na_2SO_4$ and then concentrated in vacuo to give a residue. The residue was purified by silica gel chromatography (DCM:MeOH=70:1) to give 67-3 (12 g, 92% yield) as a yellow oil. LCMS m/z=450.3 $(M+H)^+$.

Preparation of (67-4): To a solution of 67-3 (12 g, 26.7 mmol) in dry DCM (200 mL) in an ice bath were sequentially added triethyl amine (11.1 mL, 80.1 mmol), MMTrCl (12.4 g, 40 mmol) and DMAP (0.65 g, 5.4 mmol). The mixture was stirred at room temperature overnight. Water (100 mL) was added to quench the reaction. The resultant solution was then extracted with EA (500 mL×3). The combined organic layer was further washed with brine, dried over anhydrous $Na_2SO_4$ and finally concentrated in vacuo to give a residue. The residue was purified by silica gel chromatography to give 67-4 (15.1 g, 78% yield) as a white solid. LCMS m/z=722.4.4 $(M+H)^+$.

Preparation of (67-5): To a solution of 67-4 (15.1 g, 20.9 mmol) in DMF (150 mL) in an ice bath were added NaH (1.51 g, 62.7 mmol) and NaI (0.31 g, 2.1 mmol). The mixture was further stirred at 0° C. for 1 hour. After PMBCl (6.55 g, 41.8 mmol) was added, the solution was stirred at room temperature overnight. Water (200 mL) was then added, and the solution was extracted with EA (500 mL×3). The combined organic layer was washed with brine, dried over anhydrous $Na_2SO_4$ and finally concentrated in vacuo to give a residue. The residue was purified by silica gel chromatography (PE:EA=5:1) to give 67-5 (17.2 g, 97% yield) as a colorless oil. LCMS m/z=842.4 $(M+H)^+$.

Preparation of (67-6): To a solution of 67-5 (17.2 g, 20.43 mmol) in DCM (1000 mL) in an ice bath was slowly added trichloroacetic acid (49.6 g, 306.45 mmol). The mixture was stirred at room temperature for 10 min. Sat. $NaHCO_3$ solution (300 mL) was then slowly at 0° C. The resultant solution was then extracted with DCM and the combined organic layer was washed with brine, dried over anhydrous $Na_2SO_4$ and finally concentrated in vacuo to give a residue. The residue was purified by silica gel chromatography (DCM:MeOH=100:1) to give 67-6 (9.8 g, 84% yield) as a colorless oil. LCMS m/z=570.3 $(M+H)^+$.

Preparation of (67-7): To a solution of 67-6 (4.90 g, 8.60 mmol) in THF (500 mL) under ice bath were sequentially added DBU (8.67 g, 34.40 mmol) and $CF_3(CF_2)_3SO_2F$ (10.39 g, 34.40 mmol) in dropwise manner. The mixture was then stirred at room temperature overnight. Water (200 mL) was then added to quench the reaction. The resultant solution was then extracted with EA (200 mL×3). The combined organic layer was washed with brine, dried over anhydrous $Na_2SO_4$ and finally concentrated in vacuo to give a residue. The residue was purified by silica gel chromatography (PE:EA=5:1) to give 67-7 (1.50 g, 30% yield) as a colorless oil. $^1$HNMR (DMSO-$d_6$, 400 MHz): δ ppm 8.18 (s, 1H), 7.53 (s, 1H), 7.25 (d, J=8.7 Hz, 4H), 7.06 (d, J=8.6 Hz, 2H), 6.90 (d, J=8.4 Hz, 4H), 6.79-6.77 (m, 2H), 5.73-5.57 (m, 2H), 4.88-4.41 (m, 6H), 4.14-4.05 (m, 1H), 3.74 (s, 6H), 3.70 (s, 3H), 3.15 (d, J=6.4 Hz, 2H). LCMS m/z=572.3 $(M+H)^+$.

Preparation of (67-8): Compound 67-7 (2.0 g, 3.5 mmol) was dissolved in TFA (50 mL) and the solution was refluxed overnight. The reaction mixture was then concentrated in vacuo to give a residue. The residue was dissolved with THF, then sat. Na$_2$CO$_3$ solution (1-2 mL) was added to adjust pH to 10. Silica gel was added into the mixture which was further concentrated in vacuo. The sample was purified by silica gel chromatography (DCM:MeOH=20:1) to give 67-8 (0.67 g, 90% yield) as a white solid. $^1$HNMR (DMSO-d$_6$, 400 MHz): δ ppm 8.15-8.07 (m, 3H), 7.45 (s, 1H), 5.31 (d, J=5.6 Hz, 1H), 4.46-4.09 (m, 3H), 3.07-2.91 (m, 2H). LCMS m/z=212.1 (M+H)$^+$.

Preparation of (67-9): A solution of 67-8 (0.67 g, 3.2 mmol) and magnesium tert-butoxide (1.62 g, 9.5 mmol) in NMP (7 mL) was stirred at 70° C. for 30 min. Then compound 67-8a (1.53 g, 4.8 mmol) was added and the resultant solution was further stirred at 70° C. overnight. Water (50 mL) was added, and the resultant solution was then extracted with EA (100 mL×3). The combined organic layer was washed with brine, dried over Na$_2$SO$_4$ and concentrated in vacuo to give a residue. The residue was purified by silica gel chromatography (DCM:MeOH=50:1) to give 67-9 (400 mg, 35% yield) as a white solid. Two enantiomers were separated through supercritical fluid chromatography (SFC) to give 67-9A (212 mg, retention time: 4.201 min) and 68-9 (198 mg, retention time: 6.133 min). (SFC separation conditions: CHIRALPAK AD-H chromatography, Chromatography size: 0.46 cm I.D.×15 cm L, Injection: 1.0 ul, Mobile phase: Hexane/IPA=60/40 (V/V), Flow rate: 1.0 ml/min, retention time: 4.201 min, 6.133 min)$^1$HNMR (DMSO-d$_6$, 400 MHz): δ ppm 8.18-8.09 (m, 3H), 7.51 (s, 1H), 7.09-4.36 (m, 2H), 4.13-3.87 (m, 7H), 3.13 (d, J=6.4 Hz, 2H), 1.20-1.14 (mz, 6H). LCMS m/z=362.1 (M+H)$^+$.

Preparation of (67): To a solution of compound 67-9A (210 mg, 580 μmol) in CH$_3$CN (2.10 mL) was added TMSBr (2.22 g, 14.5 mmol) at 0° C. The mixture was stirred at room temperature for 4 hours. The reaction mixture was then concentrated in vacuo to give a residue. The residue was purified by MPLC to give 67 (132 mg, 74% yield) as a white solid. $^1$HNMR (DMSO-d$_6$, 400 MHz): δ ppm 8.17-8.09 (m, 3H), 7.55 (s, 1H), 4.64-4.61 (m, 0.5H), 4.52-4.45 (m, 1H), 4.37-4.33 (m, 0.5H), 4.01-3.00 (m, 1H), 3.74-3.64 (m, 2H), 3.14 (d, J=6.4 Hz, 2H). $^{31}$PNMR (DMSO-d$_6$, 162 MHz): δ 16.34 (s). $^{19}$FNMR (DMSO-d$_6$, 376 MHz): δ −228.58 (s). LCMS m/z=306.1 (M+H)$^+$.

Preparation of (68): To a solution of compound 68-9 (140 mg, 390 μmol) in CH$_3$CN (1.40 mL) was added TMSBr (1.48 g, 9.7 mmol) at 0° C. The mixture was stirred at r.t for 4 hours. The reaction mixture was concentrated in vacuo to give a residue. The residue was purified by MPLC to give 68 (95 mg, 80% yield) as a white solid. $^1$HNMR (DMSO-d$_6$, 400 MHz): δ ppm 8.17-8.09 (m, 3H), 7.55 (s, 1H), 4.64-4.61 (m, 0.5H), 4.52-4.45 (m, 1H), 4.37-4.33 (m, 0.5H), 4.01-3.00 (m, 1H), 3.74-3.64 (m, 2H), 3.14 (d, J=6.4 Hz, 2H). $^{31}$PNMR (DMSO-d$_6$, 162 MHz): δ 16.33 (s). $^{19}$FNMR (DMSO-d$_6$, 376 MHz): δ −228.58 (s). LCMS m/z=306.1 (M+H)$^+$.

Example 22

((1-((2-amino-4-oxo-3,4-dihydropyrazolo[1,5-a][1,3,5]triazin-8-yl)methyl)cyclopropoxy)methyl)phosphonic acid (22)

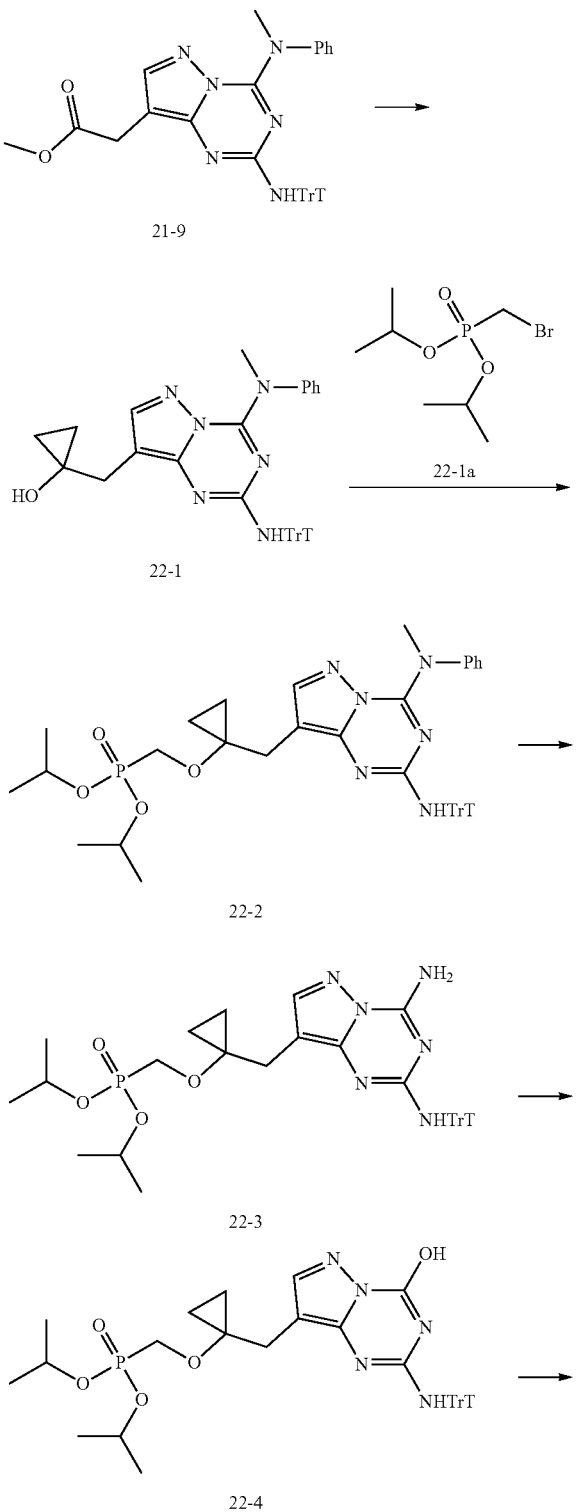

-continued

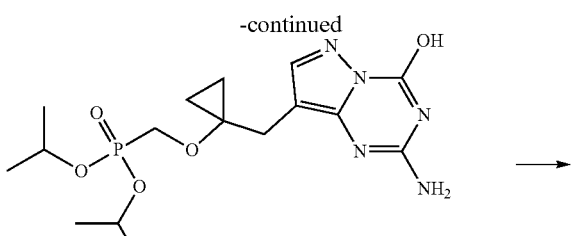

22-5

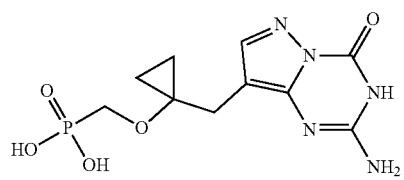

22

Preparation of (85-1): To a solution of 84-9 (14.0 g, 25.2 mmol) in THF (140 mL) was added Ti(OiPr)₄ (21.52 g, 75.7 mmol). The mixture was stirred at room temperature for 15 minutes. EtMgBr (1 M, 146 mL) was then added to the mixture dropwise over 1 hour. The resultant mixture was further stirred at room temperature for 1 hour. After the reaction was finished, the mixture was quenched with saturated aqueous NH₄Cl (200 mL). The solution was extracted with EA (200 mL×2), and the combined organic layer was dried over anhydrous Na₂SO₄. After filtration, the solution was concentrated in vacuo to give a residue which was purified by column chromatography (PE:EA=5:1) to give 85-1 (8.30 g, 15. mmol, 59% yield) as a white solid. ESI-LCMS: m/z=553.4 [M+H]⁺.

Preparation of (85-2): To a solution of 85-1 (8.00 g, 14.5 mmol) in DMF (80 mL) was added LiI (193 mg, 1.5 mmol) and t-BuOLi (5.79 g, 72.4 mmol). After heating to 50° C., the solution of 85-1a (18.75 g, 72.4 mmol) in THF (10 mL) was added dropwise over 0.5 hour. The resulting mixture was stirred at 50° C. for 2 hours. The mixture was then quenched with water (100 mL). The solution was then extracted with EA (100 mL×2). The combined organic layer was dried over anhydrous Na₂SO₄. After filtration, the solution was concentrated in vacuo to give a residue which was purified by column chromatography (PE:EA=8:1) to give 85-2 (7.10 g, 9.7 mmol, 67% yield) as a brown solid. ESI-LCMS: m/z 731.5 [M+H]⁺.

Preparation of (85-3): A solution of NH₃/MeOH (7 M, 45 mL) was added to a solution of 85-2 (6.10 g, 8.4 mmol) in MeOH (5 mL) in a sealed tube. The mixture was stirred at 120° C. for 40 hours. The solution was concentrated in vacuo to give a residue which was purified by column chromatography (PE:EA=1:1) to give 85-3 (3.60 g, 5.6 mmol, 67% yield) as a yellow solid. ESI-LCMS: m/z 641.4 [M+H]⁺.

Preparation of (85-4): To a solution of 85-3 (1.01 g, 1.6 mmol) in CH₃CN (6 mL) were added H₂O (3 mL), AcOH (3 mL) and NaNO₂ (3.27 g, 47.4 mmol) sequentially. The mixture was stirred at 45° C. for 24 hours. Saturated aqueous NaHCO₃ was added until pH value is close to 8. The solution was then extracted with EA (20 mL×3). The combined organic layer was dried over anhydrous Na₂SO₄. After filtration, the solution was concentrated in vacuo to give a residue which was purified by column chromatography (DCM:MeOH=160:1) to give 85-4 (351 mg, 0.6 mmol, 35% yield) as a yellow solid. ESI-LCMS: m/z 642.5 [M+H]⁺.

Preparation of (85-5): To a solution of 85-4 (270 mg, 0.4 mmol) in DCM (5 mL) was added trichloroacetic acid (0.5 mL). The solution was stirred at room temperature for 3 hours. The mixture was then concentrated in vacuo to give a residue which was purified by MPLC to give 85-5 (133 mg, 0.3 mmol, 79% yield) as a white solid. ESI-LCMS: m/z 400.2 [M+H]⁺.

Preparation of (85): To a solution of 85-5 (133 mg, 0.3 mmol) in dichloroethane (3 mL) was added TMSBr (3.09 g, 26.6 mmol) at room temperature. The mixture was stirred at 70° C. for 3 hours. 3 mL water was then added. The mixture was concentrated directly in vacuo to give a residue which was purified by MPLC to give 22 (35 mg, 0.1 mmol, 33% yield) as a white solid. ¹HNMR (400 MHz, DMSO-d₆): δ 11.11 (s, 2H), 7.81 (s, 1H), 6.66 (s, 2H), 3.61 (d, J=10.2 Hz, 2H), 2.72 (s, 2H), 0.73 (q, J=4.7 Hz, 2H), 0.53-0.47 (m, 2H). ESI-LCMS: m/z 316.1 [M+H]⁺.

Example 23

(((1-(2-amino-4-oxo-3,4-dihydropyrazolo[1,5-a][1,3,5]triazin-8-yl)-2-methylpropan-2-yl)oxy)methyl) phosphonic acid (84)

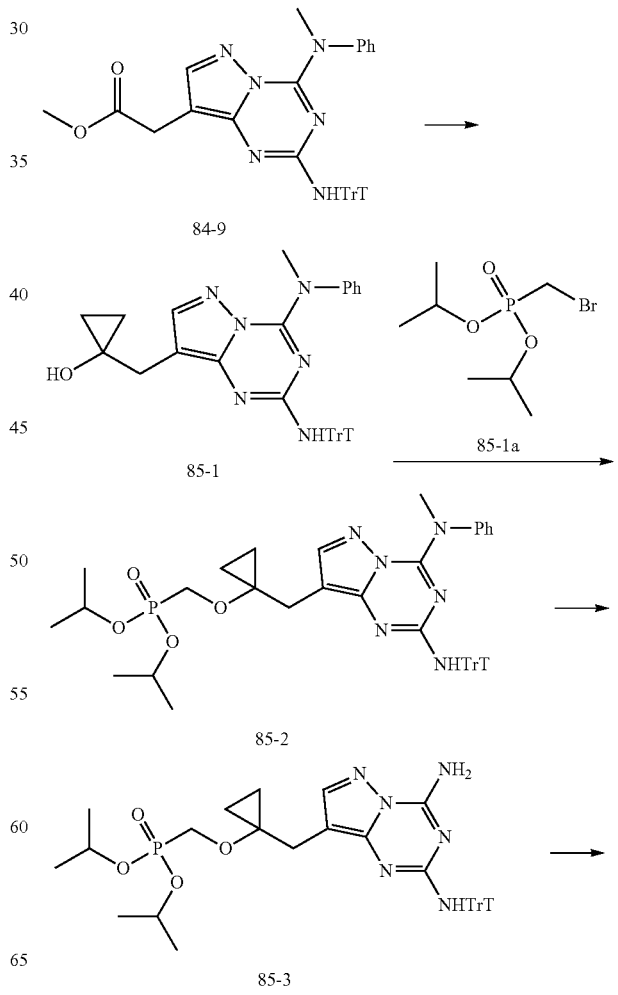

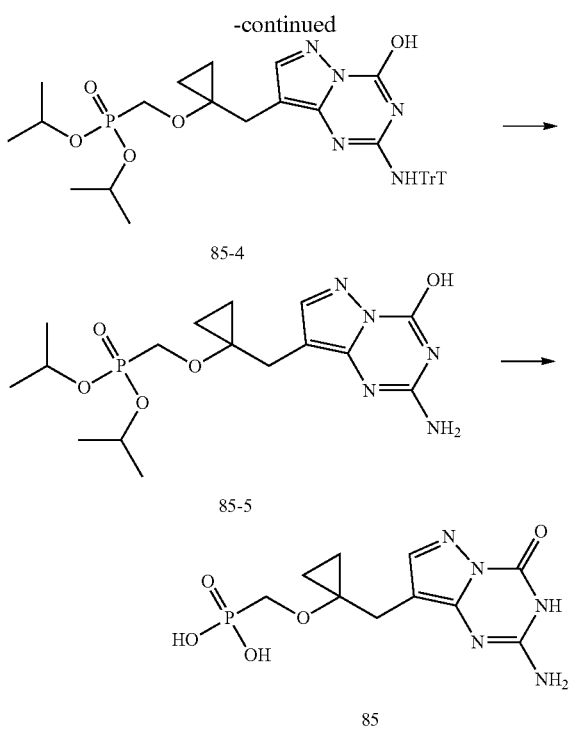

Preparation of (84-2): To a solution of 84-1 (840 mg, 2.1 mmol, J. Med. Chem. 2009, 52, 655-663), LiCl (116 mg, 2.7 mmol) and Pd(PPh$_3$)$_4$ (472 mg, 0.4 mmol) in DMF (6 mL) was added 84-1a (908 mg, 2.7 mmol) under N$_2$. The resultant mixture was stirred at 100° C. for 1 hour. After the reaction was finished, water (30 mL) was added and the solution was then extracted with EA (50 mL×3). The combined organic layer was dried over anhydrous Na$_2$SO$_4$. The solution was then concentrated in vacuo to give a residue which was purified by column chromatography (PE:EA=40:1) to give 84-2 (320 mg, 1 mmol, 49% yield) as a white solid. LCMS m/z=312.1 (M+H)$^+$.

Preparation of (84-3): To a solution of 84-2 (4.1 g, 13.2 mmol) in mixed solvents of dioxane (40 mL) and H$_2$O (10 mL) were added K$_2$OsO$_4$.2H$_2$O (145 mg, 0.4 mmol) and NMO (3.27 g, 105.4 mmol) at rt. The mixture was stirred at room temperature for 1.5 h. After the reaction was finished, water (50 mL) was added and the solution was then extracted with EA (150 mL×3). The combined organic layer was dried over anhydrous Na$_2$SO$_4$. After filtration, the solution was concentrated to give a residue which was purified by column chromatography (DCM:MeOH=80:1) to give 84-3 (3.10 g, 9 mmol, 68% yield) as a light yellow oil. LCMS m/z=346.2 (M+H)$^+$.

Preparation of (84-4): To a solution of 84-3 (3.10 g, 9.0 mmol) in dioxane (50 mL) was added the solution of NaIO$_4$ (4.80 g, 22.4 mmol) in H$_2$O (10 mL) at 0° C. The mixture was stirred at room temperature for 1.5 hours. After the reaction was finished, water (50 mL) was added and the solution was then extracted with EA (100 mL×3). The combined solution was dried over Na$_2$SO$_4$. After filtration, the solution was concentrated in vacuo to give crude 84-4 (2.80 g, 8.9 mmol, 99% yield) as a light yellow oil. The crude 84-4 was used directly for the next step.

Preparation of (84-5): To a solution of 84-4 (2.80 g, 8.93 mmol) in MeCN (40 mL) were added NaH$_2$PO$_4$ (3.80 g, 26.8 mmol), H$_2$O$_2$ (1.52 g, 44.7 mmol) and NaClO$_2$ (2.40 g, 26.8 mmol) sequentially at 0° C. The mixture was stirred at room temperature for 16 h. After the reaction was finished, the reaction was quenched with saturated aqueous Na$_2$SO$_3$ (20 mL). The resultant solution was extracted with EA (100 mL×3). The combined organic layer was then dried over anhydrous Na$_2$SO$_4$. After filtration, the solution was concentrated to give crude 84-5 (3.00 g, 8.3 mmol, 93% yield) as a yellow oil which was used directly for the next step. LCMS m/z=362.2 (M+H)$^+$.

Preparation of (84-6): To a solution of 84-5 (1.00 g, 2.8 mmol) in DMF (10 mL) were added K$_2$CO$_3$ (1.15 g, 8.3 mmol) and MeI (3.60 mmol, 0.22 mL) at 0° C. After the reaction was finished, water (20 mL) was added and the solution was then extracted with EA (50 mL×3). The combined organic layer was dried over Na$_2$SO$_4$. After filtration, the solution was concentrated in vacuo to give a residue which was purified by column chromatography (PE:EA=3:1) to give 84-6 (520 mg, 0.3 mmol, 50% yield) as a light yellow oil. LCMS m/z=376.1 (M+H)$^+$. $^1$HNMR (400 MHz, CDCl$_3$): δ 7.90 (s, 1H), 7.49-7.42 (m, 3H), 7.27-7.22 (m, 2H), 3.89 (s, 3H), 3.78 (s, 2H), 3.72 (s, 3H), 3.33 (s, 3H).

Preparation of (84-7): To a solution of 84-6 (3.80 g, 10.1 mmol) in DMSO (100 mL) was added NaN$_3$ (3.29 g, 50.6 mmol). The mixture was stirred at room temperature for 3 hours. After the reaction was finished, water (50 mL) was added and the solution was then extracted with EA (50 mL×3). The combined organic layer was dried over anhydrous Na$_2$SO$_4$. After filtration, the solution was then concentrated in vacuo to give a residue which was purified by column chromatography (PE:EA=3:1) to give 84-7 (3.20 g, 9.5 mmol, 93% yield) as a white solid. LCMS m/z=339.2 (M+H)$^+$.

Preparation of (84-8): To a solution of 84-7 (2.00 g, 5.9 mmol) in MeOH (20 mL) was added Pd/C (72 mg, 0.6 mmol) at room temperature. The mixture was stirred under H$_2$ atmosphere (2-3 atm) at room temperature for 2.5 hours. After the reaction was finished, Pd/C was filtered out. The resultant filtrate was finally concentrated in vacuo to give crude 84-8 (1.80 g, 5.8 mmol, 97% yield) as a light yellow oil.

Preparation of (84-9): To a solution of 84-8 (12.0 g, 38.4 mmol) in pyridine (200 mL) was added TrtCl (16.00 g, 57.6 mmol) at room temperature. The mixture was stirred at 50° C. for 16 hours. After the reaction was finished, the reaction was quenched with MeOH (10 mL). The solution was then concentrated in vacuo to give a residue which was purified by column chromatography (PE:EA=8:1) to give 84-9 (18.30 g, 33 mmol, 86% yield) as a light yellow solid. LCMS m/z=555.4 (M+H)$^+$.

Preparation of (84-10): To a solution of 84-9 (2.80 g, 5.1 mmol) in THF (30 mL) was added MeMgBr (1.4 M, 18.0 mL) dropwise at 0° C. The mixture was then stirred at room temperature for 4 hours. After the reaction was finished, it was quenched with saturated aqueous NH$_4$Cl (10 mL) at 0° C. The resultant mixture was then extracted with EA (50 mL×3). The combined organic layer was dried over anhydrous Na$_2$SO$_4$. After filtration, the solution was concentrated in vacuo to give a residue which was purified by column chromatography (PE:EA=3:1) to give 84-10 (1.15 g, 2.1 mmol, 41% yield) as a light yellow solid. LCMS m/z=555.4 (M+H)$^+$.

Preparation of (84-11): To a solution of 84-10 (1.40 g, 2.52 mmol) in DMF (10 mL) was added LiOtBu solution (1.20 g, 15 mmol) in THF (0.3 mL). After heating to 50° C., 84-10a (6.53 g, 25.2 mmol) was added dropwise. The mixture was stirred at 50° C. for 2 hours. After the mixture was cooled to room temperature, water (30 mL) was added and the solution was extracted with EA (100 mL×3). The combined organic layer was dried over anhydrous Na$_2$SO$_4$. After filtration, the solution was then concentrated to give a residue which was purified by column chromatography (PE:EA=2:1) to give 84-11 (1.20 g, 1.6 mmol, 65% yield) as a light yellow oil. LCMS m/z=733.5 (M+H)$^+$.

Preparation of (84-12): A solution of NH$_3$/MeOH (7 M, 45 mL) was added to a solution of 84-11 (1.20 g, 1.6 mmol) in MeOH (5 mL) in a sealed tube. The mixture was then stirred at 100° C. for 72 hours. After the reaction was finished, the solution was concentrated in vacuo to give a residue which was purified by column chromatography (DCM:MeOH=150:1) to give 84-12 (820 mg, 1.3 mmol, 78% yield) as a light yellow solid. LCMS m/z=643.4 (M+H)$^+$. $^1$H NMR (400 MHz, DMSO-d$_6$): δ 7.74 (s, 2H), 7.63 (s, 1H), 7.40-7.33 (m, 6H), 7.29-7.20 (m, 6H), 7.19-7.05 (m, 4H), 4.58 (m, 2H), 3.50 (s, 2H), 2.21 (s, 2H), 1.24 (dd, J=9.9, 6.2 Hz, 12H), 0.76 (s, 6H).

Preparation of (84-13): To a solution of 84-12 (820 mg, 1.3 mmol) in mixed solvents of AcOH (10 mL) and H$_2$O (5 mL) was added NaNO$_2$ (2.64 g, 38.3 mmol) at room temperature. The mixture was then stirred at 50° C. for 24 hours. After the reaction was done, the solution was then concentrated in vacuo to give a residue. The residue was dissolved in EA (50 mL) and then washed with saturated aqueous NaHCO$_3$ (20 mL). The organic layer was dried over anhydrous Na$_2$SO$_4$. After filtration, the solution was concentrated in vacuo to give a residue which was purified by column chromatography (DCM:MeOH=120:1) to give 84-13 (262 mg, 0.7 mmol, 51% yield) as a yellow solid. LCMS m/z=644.4 (M+H)$^+$. $^1$H NMR (400 MHz, DMSO-d$_6$): δ 10.88 (s, 1H), 7.61 (d, J=3.9 Hz, 2H), 7.47-7.13 (m, 15H), 4.58 (dd, J=6.2, 1.5 Hz, 2H), 3.49 (d, J=11.1 Hz, 2H), 2.09 (s, 2H), 1.24 (dd, J=11.5, 6.2 Hz, 12H), 0.73 (s, 6H).

Preparation of (84-14): To a solution of 84-13 (650 mg, 1.0 mmol) in DCM (10 mL) was added trichloroacetic acid (750 mg). The solution was stirred at room temperature for 1.5 hours. After the reaction was done, saturated aqueous NaHCO$_3$ (30 mL) was added and the solution was extracted with EA (100 mL×3). The organic layer was dried over anhydrous Na$_2$SO$_4$. After filtration, the solution was concentrated in vacuo to give a residue which was purified by MPLC to give 84-14 (350 mg, 0.9 mmol, 86% yield) as a yellow solid. LCMS m/z=402.2 (M+H)$^+$.

Preparation of (84): To a solution of 84-14 (240 mg, 0.6 mmol) in dichloroethane (10 mL) was added TMSBr (0.78 mL, 6 mmol) at room temperature. The mixture was stirred under reflux for 2.5 hours. After the reaction was done, water (2 mL) was added. The final solution was concentrated in vacuo to give a residue which was purified by MPLC to give 84 (152 mg, 0.5 mmol, 80% yield) as a white solid. LCMS m/z=318.2 (M+H)$^+$. $^1$H NMR (400 MHz, DMSO-d$_6$): δ 7.80 (s, 1H), 3.51 (d, J=11.4 Hz, 2H), 2.58 (s, 2H), 1.08 (s, 6H). $^{31}$P NMR (162 MHz, DMSO-d$_6$) δ 18.62.

Example 24

Diphosphates

Acyclonucleoside phosphonate (0.05 mmol) was converted to triethylammonium salt by addition of 0.5 M TEAB buffer to its aqueous suspension. The resulting clear solution was concentrated to a solid residue, which was rendered anhydrous by coevaporating several times with anhydrous acetonitrile and keeping under high vacuum. Solid material was dissolved in DMF (1.0 mL) and CDI (40 mg; 0.25 mmol) was added. The mixture was stirred at RT for 7 h and then a solution of tetrabutylammonium pyrophosphate (0.25 g; ~0.25 mmol) in DMF (0.2 mL) was added. The mixture was stirred for 2 d at RT and then quenched with triethylammonium acetate buffer, diluted with water (10 mL) and loaded on HiPrep Q HP 16/10 column. Separation was done in a linear gradient of NaCl from 0 to 1N in 50 mM TRIS-buffer (pH 7.5). Corresponding fractions were concentrated. Desalting was achieved by RP HPLC on Synergy 4 p Hydro-RP column (Phenomenex). A linear gradient of acetonitrile from 0 to 30% in 50 mM triethylammonium acetate buffer (pH 7.5) was used for elution. The corresponding fractions were combined, concentrated and lyophilized to remove excess of buffer. Phosphono diphosphates obtained are provided in Table 5.

TABLE 5

| # | Structure | m/z [M − 1] | $^{31}$P-NMR [δ] |
|---|---|---|---|
| 19 | 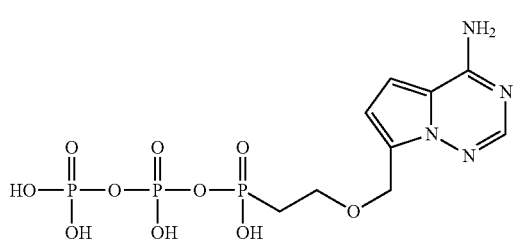 [SMILES: Nc1ncnn2c(COCCP(=O)(O)OP(=O)(O)OP(=O)(O)O)ccc12] | 431.1 | +15.11 (br s), −9.57 (br s), −21.58 (br s) |
| 20 | 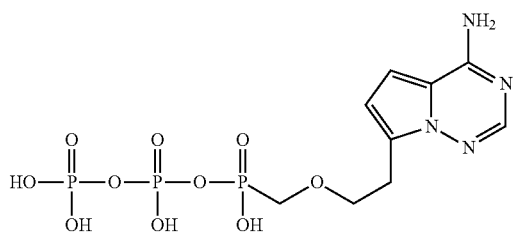 [SMILES: Nc1ncnn2c(CCOCP(=O)(O)OP(=O)(O)OP(=O)(O)O)ccc12] | 431.0 | +9.75 (br s), −5.97 (br s), −19.59 (br s) |

TABLE 5-continued

| # | Structure | m/z [M − 1] | $^{31}$P-NMR [δ] |
|---|---|---|---|
| 21 | 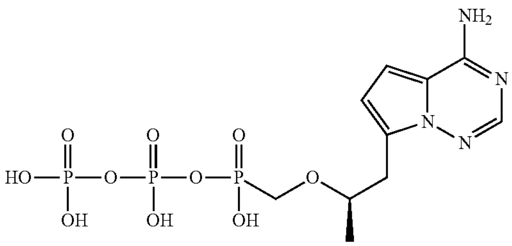 [SMILES: C[C@H](Cc1ccc2c(N)ncnn12)OCP(=O)(O)OP(=O)(O)OP(=O)(O)O] | 445.3 | +10.06 (d, J = 23.5 Hz), −7.49 (br s), −20.32 (br s) |
| 22 | 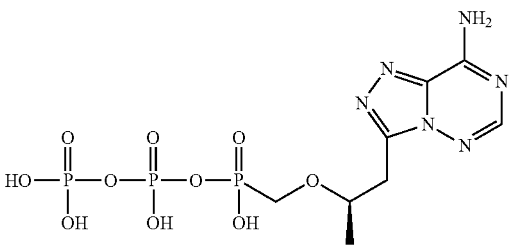 [SMILES: C[C@H](Cc1nnc2c(N)ncnn12)OCP(=O)(O)OP(=O)(O)OP(=O)(O)O] | 447.2 | +8.55 (d, J = 24.6 Hz), −6.77 (br s), −22.03 (br s) |
| 23 | 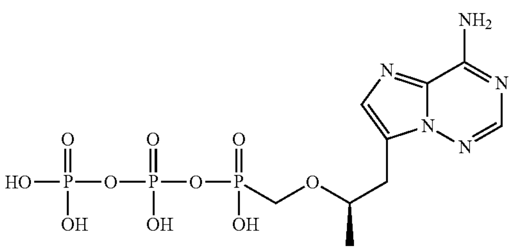 [SMILES: C[C@H](Cc1cnc2c(N)ncnn12)OCP(=O)(O)OP(=O)(O)OP(=O)(O)O] | 446.2 | +8.82 (d, J = 22.1 Hz), −7.02 (br s), −22.12 (br s) |
| 24 | 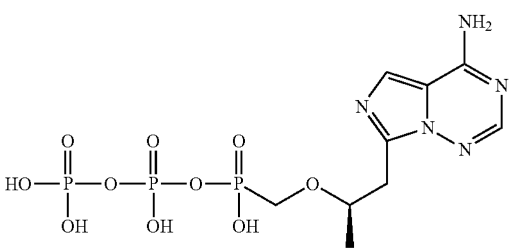 [SMILES: C[C@H](Cc1ncc2c(N)ncnn12)OCP(=O)(O)OP(=O)(O)OP(=O)(O)O] | 445.8 | +9.27 (d, J = 25.9 Hz), −10.88 (d, J = 25.9 Hz), −23.18 (br s) |
| 25 | 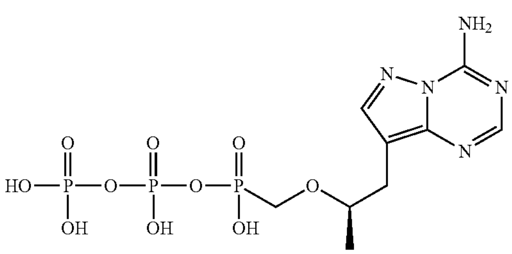 [SMILES: C[C@H](Cc1cnn2c(N)ncnc12)OCP(=O)(O)OP(=O)(O)OP(=O)(O)O] | 445.7 | +9.30 (d, J = 27.1 Hz), −11.01 (d, J = 20.9 Hz), −23.39 (dd, J = 19.7, 27.1 Hz) |
| 26 | 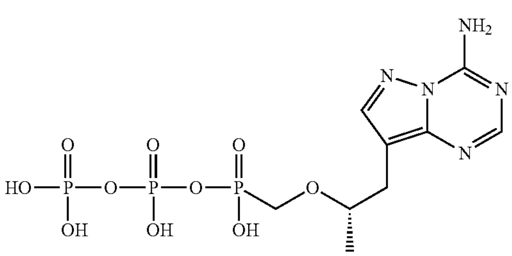 [SMILES: C[C@@H](Cc1cnn2c(N)ncnc12)OCP(=O)(O)OP(=O)(O)OP(=O)(O)O] | 445.8 | +9.20 (d, J = 27.1 Hz), −11.04 (d, J = 19.7 Hz), −23.46 (dd, J = 20.3, 26.5 Hz) |

TABLE 5-continued

| # | Structure | m/z [M − 1] | $^{31}$P-NMR [δ] |
|---|---|---|---|
| 27 | 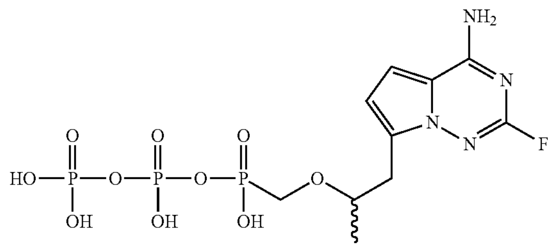 [SMILES: CC(Cc1ccc2c(N)nc(F)nn12)OCP(=O)(O)OP(=O)(O)OP(=O)(O)O] | 462.8 | +9.10 (d, J = 25.8 Hz), −11.06 (d, J = 19.3 Hz), −23.42 (dd, J = 20.3, 27.4 Hz) |
| 28 | 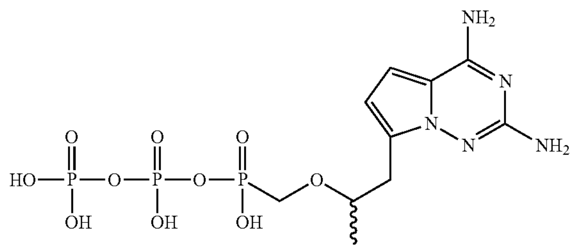 [SMILES: CC(Cc1ccc2c(N)nc(N)nn12)OCP(=O)(O)OP(=O)(O)OP(=O)(O)O] | — | +8.72 (d, J = 25.8 Hz), −6.23 (d, J = 19.3 Hz), −22.16 (br s) |
| 55 | 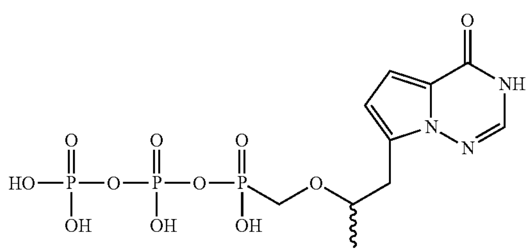 [SMILES: CC(Cc1ccc2c(=O)[nH]cnn12)OCP(=O)(O)OP(=O)(O)OP(=O)(O)O] | 445.9 | +8.50 (d, J = 27.1 Hz), −7.64 (br s), −22.82 ('t', J = 24.0 Hz) |
| 56 | 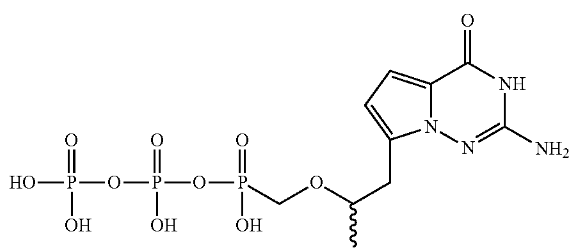 [SMILES: CC(Cc1ccc2c(=O)[nH]c(N)nn12)OCP(=O)(O)OP(=O)(O)OP(=O)(O)O] | 460.7 | +8.43 (d, J = 25.9 Hz), −6.78 (d, J = 19.8 Hz), −22.64 ('t', J = 21.5 Hz) |
| 57 | 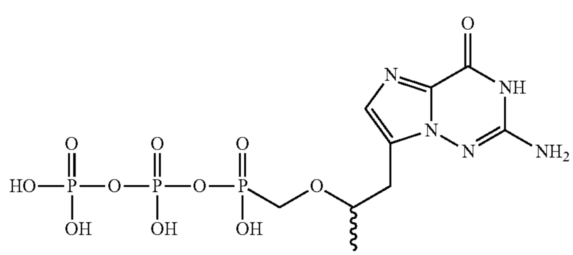 [SMILES: CC(Cc1cnc2c(=O)[nH]c(N)nn12)OCP(=O)(O)OP(=O)(O)OP(=O)(O)O] | 462.1 | +8.65 (d, J = 25.8 Hz), −7.80 (br s), −22.75 ('t', J = 23.3 Hz) |
| 58 | 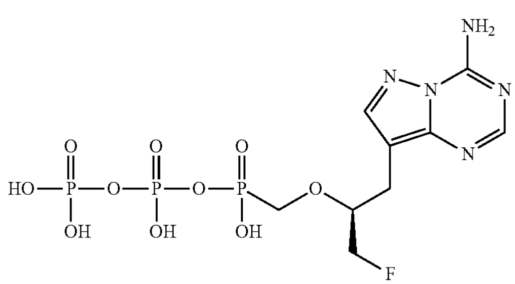 [SMILES: Nc1ncnc2c(C[C@@H](CF)OCP(=O)(O)OP(=O)(O)OP(=O)(O)O)cnn12] | 463.9 | +8.25 (d, J = 27.5 Hz), −11.06 (d, J = 19.4 Hz), −23.49 ('t', J = 21.0 Hz) |

TABLE 5-continued

| # | Structure | m/z [M − 1] | $^{31}$P-NMR [δ] |
|---|---|---|---|
| 59 | 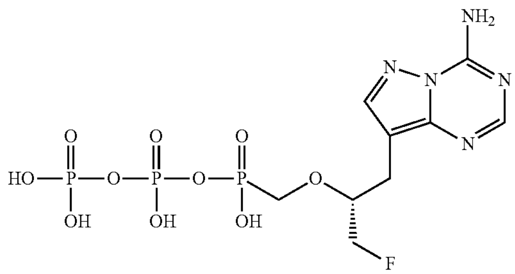 [SMILES: Nc1ncnc2c(C[C@H](CF)OCP(=O)(O)OP(=O)(O)OP(=O)(O)O)cnn12] | 463.8 | +8.24 (d, J = 25.9 Hz), −11.06 (d, J = 19.4 Hz), −23.52 ('t', J = 22.7 Hz) |
| 60 | 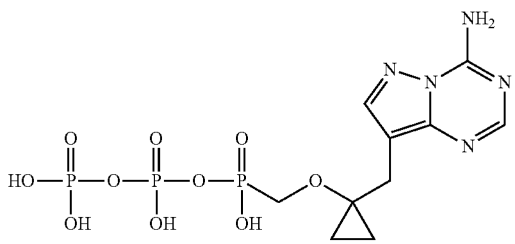 [SMILES: Nc1ncnc2c(CC3(OCP(=O)(O)OP(=O)(O)OP(=O)(O)O)CC3)cnn12] | 458.5 | +8.78 (d, J = 25.9 Hz), −10.46 (d, J = 19.4 Hz), −23.27 ('t', J = 22.7 Hz) |
| 79 | 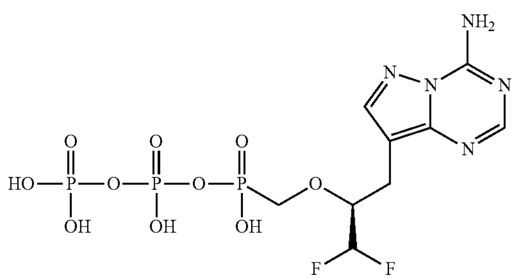 [SMILES: Nc1ncnc2c(C[C@H](OCP(=O)(O)OP(=O)(O)OP(=O)(O)O)C(F)F)cnn12] | 481.8 | +7.53 (d, J = 27.1 Hz), −10.95 (d, J = 18.5 Hz), −22.36 ('t', J = 22.7 Hz) |
| 80 | 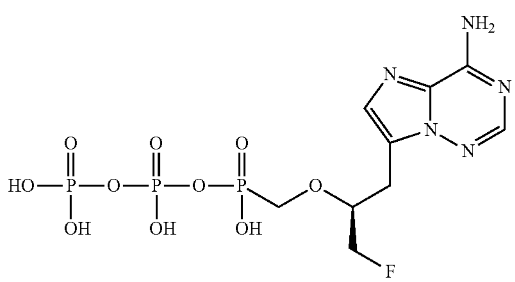 [SMILES: Nc1ncnn2c(C[C@@H](CF)OCP(=O)(O)OP(=O)(O)OP(=O)(O)O)cnc12] | 463.7 | +7.98 (d, J = 27.0 Hz), −10.91 (d, J = 19.8 Hz), −23.43 ('t', J = 23.5 Hz) |
| 81 | 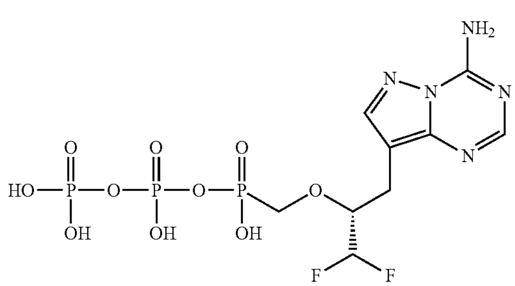 [SMILES: Nc1ncnc2c(C[C@@H](OCP(=O)(O)OP(=O)(O)OP(=O)(O)O)C(F)F)cnn12] | 482.0 | +7.43 (d, J = 27.2 Hz), −10.97 (d, J = 18.5 Hz), −23.44 ('t', J = 22.8 Hz) |

TABLE 5-continued

| # | Structure | m/z [M − 1] | $^{31}$P-NMR [δ] |
|---|---|---|---|
| 82 | 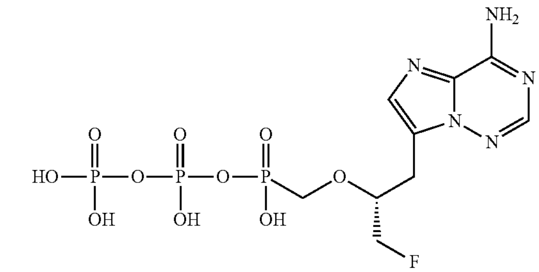 [SMILES: Nc1ncnn2c(C[C@H](CF)OCP(=O)(O)OP(=O)(O)OP(=O)(O)O)cnc12] | 463.9 | +8.02 (d, J = 21.0 Hz), −10.90 (br s), −23.39 (br s) |
| 83 | 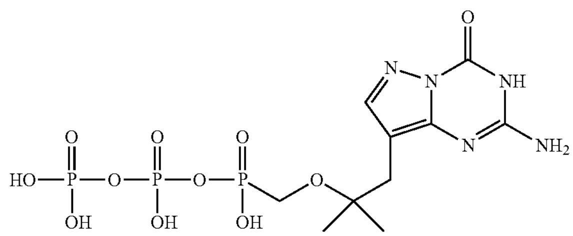 [SMILES: CC(C)(Cc1cnn2c(=O)[nH]c(N)nc12)OCP(=O)(O)OP(=O)(O)OP(=O)(O)O] | 476.3 | +11.06 (d, J = 29.0 Hz), −10.95 (d, J = 19.8 Hz), −23.09 ('t', J = 21.5 Hz) |

Example 25

Compounds of Formula (I)

For some compounds, the foregoing syntheses are exemplary and can be used as a starting point to prepare additional compounds of Formula (I). Examples of additional compounds of Formula (I) are shown below. These compounds can be prepared in various ways, including those synthetic schemes shown and described herein. Those skilled in the art will be able to recognize modifications of the disclosed syntheses and to devise routes based on the disclosures herein; all such modifications and alternate routes are within the scope of the claims.

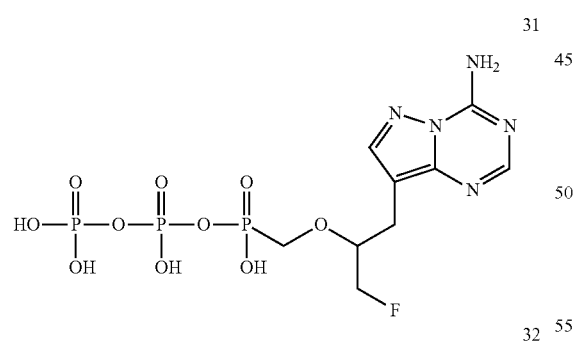

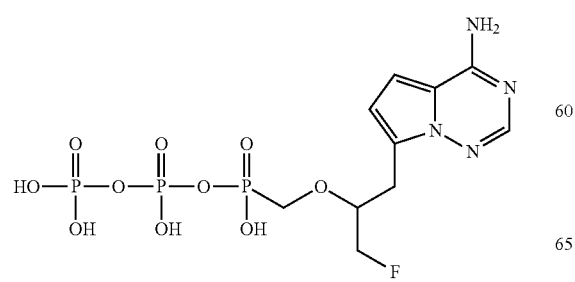

-continued

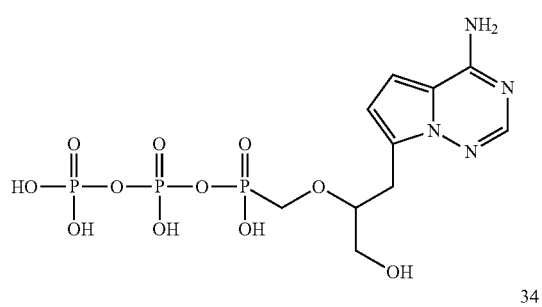

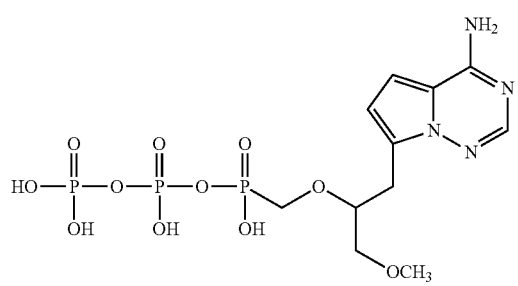

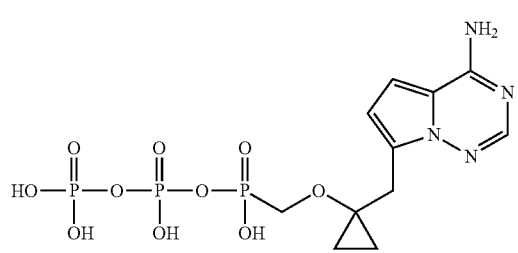

36
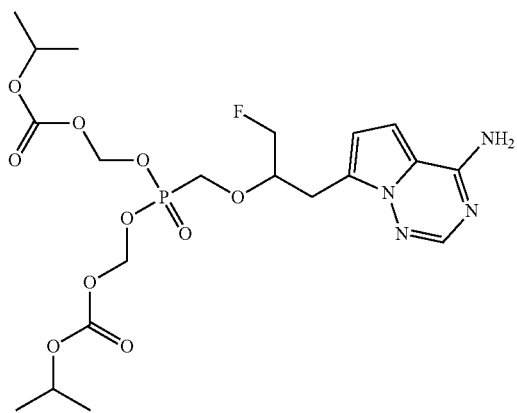
37
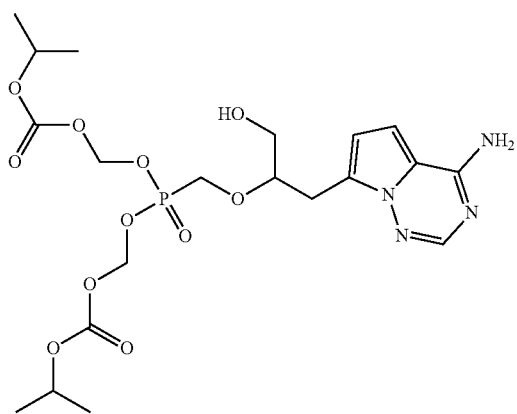
38
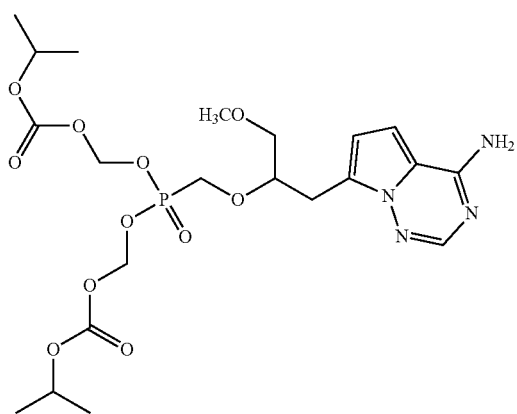
39
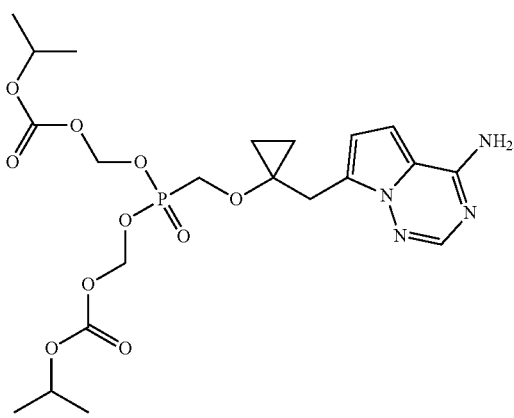
40
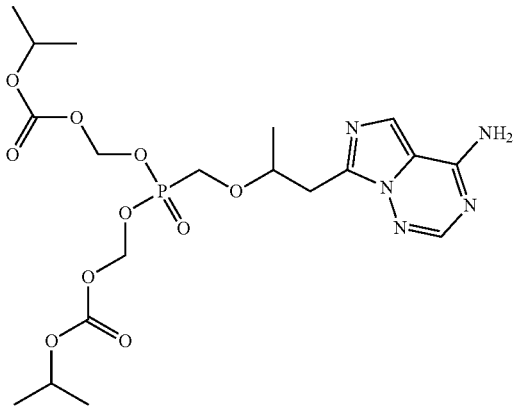
41
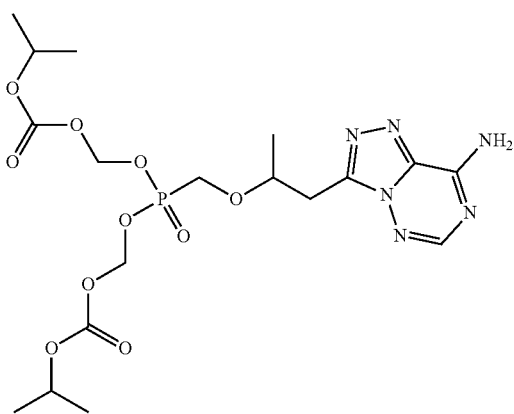

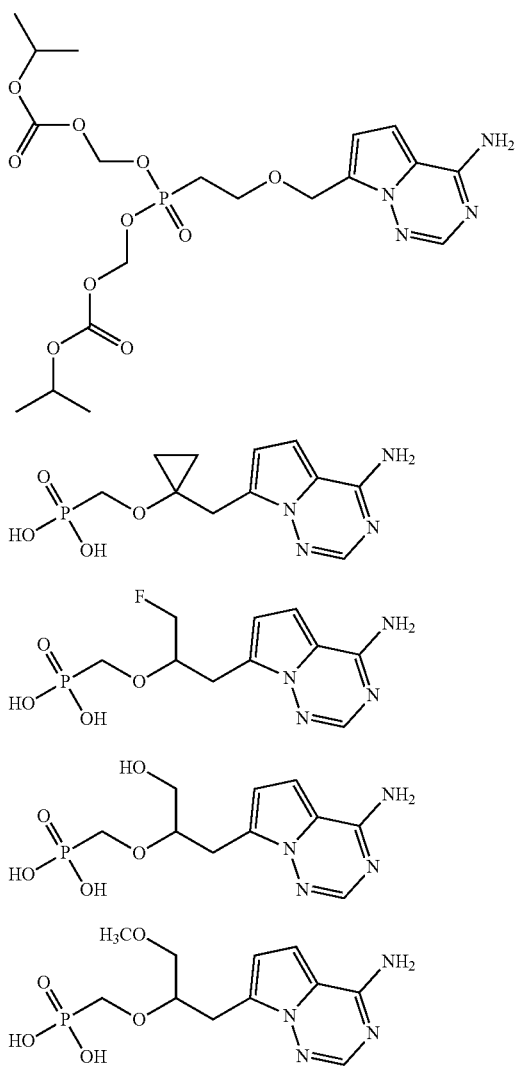

Example A

HIV Single-Cycle Assay 24 hours prior to infection, CEM human T lymphoblast cells (ATCC, Manassas, Va.) were plated in assay media (MEM supplemented with 10% FBS, 1% penicillin/streptomycin (all Mediatech, Manassas, Va.) and 1% DMSO (Sigma-Aldrich, St Louis, Mo.)) were plated at a density of $5 \times 10^5$ cells/mL ($5 \times 10^4$ cells/well) in white 96-well plates. Serially diluted compounds were added to cells and incubated overnight at 37° C., 5% $CO_2$. The following day, cells were infected with VSV-G pseudotyped HIV NL4-3, in which parts of the env and nef were genes replaced with Renilla-luciferase, and infected cells were incubated for 72 h at 37° C., 5% $CO_2$. Viral inoculum was titrated to achieve a Renilla-luciferase signal of approximately 100× fold over background. Antiviral activity was measured by addition of 100 ul of Renilla-Glo® reagent (Promega, Madison, Wis.) to infected cells. After a 10 min incubation at RT, luminescence was measured on a Victor X3 multi-label plate reader (Perkin Elmer, Waltham, Mass.). Cytotoxicity of uninfected parallel cultures was determined by addition of 100 μl CellTiter-Glo® reagent (Promega, Madison, Wis.), and incubation for 10 mins at RT. Luminescence was measured on a Victor X3 multi-label plate reader.

Compounds of Formula (I) are active in the assay as noted in Table 6, where 'A' indicates an $EC_{50} < 20$ μM, 'B' indicates an $EC_{50}$ of $\geq 20$ μM and $<100$ μM and 'C' indicates an $EC_{50} \geq 100$ μM.

Table 6.

| # | $EC_{50}$ (nM) |
|---|---|
| 1 | C |
| 2 | B |
| 3 | C |
| 4 | C |
| 5 | A |
| 6 | C |
| 7 | A |
| 8 | B |
| 9 | A |
| 10 | A |
| 11 | A |
| 12 | A |
| 13 | A |
| 14 | A |
| 29 | B |
| 30 | A |

Example B

Inhibition of HIV Reverse Transcriptase

Recombinant full length HIV-1 Reverse Transcriptase (HIVrt) was purchased from Abcam, catalog # ab63979. The last 385 nucleotide region of the HCV anti-genome complementary to the 5' untranslated region (c5'UTR) was synthesized using T7 RNA polymerase Megascript kit from Ambion (Cat # AM1333). A DNA oligo served as an internal initiation primer and was purchased from IDT. Unless otherwise specified, reaction samples consisted of 20 nM c5'UTR RNA, 100 nM DNA primer, and 1 nM HIVrt, mixed together in a buffer containing 50 mM Tris pH 7.5, 100 mM KCl, 4 mM dithiothreitol (DTT), and 12.5 mM $MgCl_2$. Reactions were initiated at 30° C. by adding 0.1 μM adenosine triphosphate (dATP), 0.1 μM cytosine triphosphate (dCTP), 1 μM guanosine triphosphate (dGTP), and 0.32 μM $^3$H-thymidine triphosphate ($^3$H-TTP), in a final volume of 50 μL. After 40-mins incubation, the reaction was terminated by adding 60 μl of chilled 20% (w/v) trichloroacetic acid with 500 M ATP to precipitate nucleic acids. After incubation at 4° C. for 1 h, the sample underwent filtration on a multiscreen BV 1.2-μm 96-well plate (Millipore). 40 μL Microscint-20 (Perkin Elmer) was added to the well and the counts in the sample were determined by a Trilux Microbeta microplate scintillation reader (Wallac).

All data were analyzed with GraphPad Prism. The compound concentration at which the enzyme-catalyzed rate was reduced by 50% ($IC_{50}$) was calculated by fitting the data to the equation Y=% Min+(% Max−% Min)/(1+X/$IC_{50}$), where Y corresponds to the percent relative enzyme activity, % Min is the residual relative activity at saturating compound concentration, % Max is the relative maximum enzyme activity, and X corresponds to the compound concentration. The $K_i$ was calculated using the Cheng-Prusoff equation assuming competitive inhibition relative to natural dNTP incorporation: $K_i=IC_{50}/(1+[dNTP]/K_m)$, where [dNTP] is the concentration of natural dNTP and $K_m$ is the apparent $K_m$ for dNTP. The standard HIVrt RNA-dependent DNA polymerization (RdDp) assay was used to determine the $IC_{50}$ values.

Compounds of Formula (I) are active in the assay as noted in Table 7, where 'A' indicates an $IC_{50}$<50 nM, 'B' indicates an $IC_{50}$ of ≥50 nM and <250 nM and 'C' indicates an $IC_{50}$≥250 nM.

TABLE 7

| # | $IC_{50}$ (nM) |
|---|---|
| 19 | C |
| 20 | A |
| 21 | A |
| 22 | C |
| 23 | A |
| 24 | C |
| 25 | B |
| 26 | A |
| 27 | A |
| 28 | C |
| 55 | C |
| 56 | A |
| 57 | B |
| 58 | A |
| 59 | A |
| 60 | B |
| 79 | C |
| 80 | B |
| 81 | B |
| 82 | B |
| 83 | C |

Example C

Inhibition of HBV

HepG2.117 cells (with fewer than 25 passages) were cultured in DMEM/F12 50/50 medium (Corning, REF 10-092-CM) with 10% FBS (Coning REF 35-011-CV), 250 ug/ml G418 Sulfate (Corning, REF 30-234-CI), 2 ug/ml Tetracycline (TEKNOVA, cat # T3325) and 1×P/S (Corning, 30-002-CI). For each assay, cells were plated in assay medium: DMEM/F12 50/50 (Corning, REF 10-092-CM), 2% Tet-system approved FBS (Clontech, Cat #631106) and 1×P/S (Corning, 30-002-CI).

Determination of Anti-HBV Activity

Determination of 50% inhibitory concentration ($EC_{50}$) of compounds in HCV replicon cells were performed by the following procedure. On the first day, cells were seeded at 30,000 cells per 100 µL well in Biocoat collage coated flat bottom 96 well plates. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in assay media. The final DMSO concentration was 1%. The cells were incubated at 37° C. for 72 hours.

The antiviral activity was measured using a quantitative kinetic reverse transcription-polymerase chain reaction (RT-PCR) assay directly measuring the HBV viral copy numbers from the supernatant of HepG2.117 cells. $EC_{50}$ was defined as the concentration of compound at which the HBV viral copy numbers from the HepG2.117 cells was reduced 50% relative to its level in the absence of compound. HBV viral copy numbers are normalized to the level observed in the absence of inhibitor, which was defined as 100%. Results for selected compounds are shown in Table 8.

Compounds of Formula (I) are active in the assay as noted in Table 8, where 'A' indicates an $EC_{50}$<1 µM, 'B' indicates an $EC_{50}$ of ≥1 µM and <10 µM, 'C' indicates an $EC_{50}$≥10 µM and <100 µM, and 'D' indicates an $EC_{50}$≥100 µM.

TABLE 8

| # | $EC_{50}$ (µM) |
|---|---|
| 1 | A |
| 2 | C |
| 8 | C |
| 9 | B |
| 10 | B |
| 10c | B |
| 10d | B |
| 11 | A |
| 12 | A |
| 13 | D |
| 14 | A |
| 15 | B |
| 16 | A |
| 18 | B |
| 48 | A |
| 51 | A |
| 52 | A |
| 53 | A |
| 61 | A |
| 62 | A |
| 63 | A |
| 64 | C |
| 65 | B |
| 66 | B |
| 67 | C |
| 68 | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

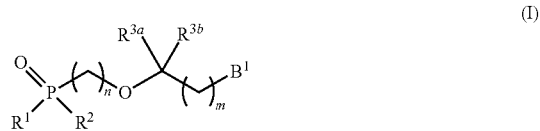

wherein:

$B^1$ is selected from the group consisting of: an optionally substituted

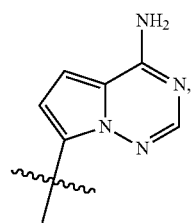 [SMILES: *c1ccc2c(N)ncnn12]

an optionally substituted

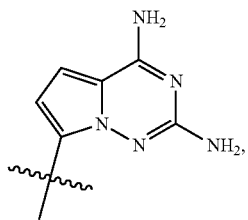 [SMILES: *c1ccc2c(N)nc(N)nn12]

an optionally substituted

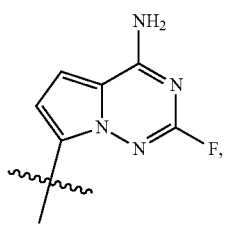 [SMILES: *c1ccc2c(N)nc(F)nn12]

an optionally substituted

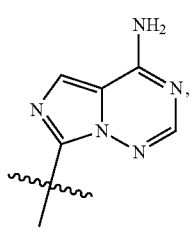 [SMILES: *c1ncc2c(N)ncnn12]

an optionally substituted

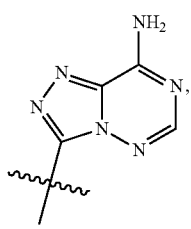 [SMILES: *c1nnc2c(N)ncnn12]

an optionally substituted

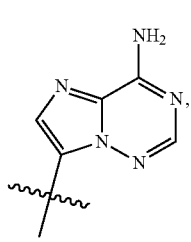 [SMILES: *c1cnc2c(N)ncnn12]

an optionally substituted

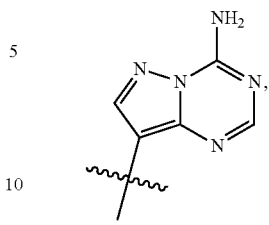

an optionally substituted

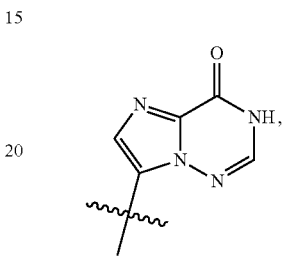

an optionally substituted

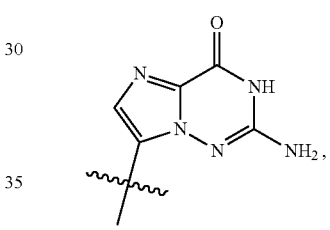

an optionally substituted

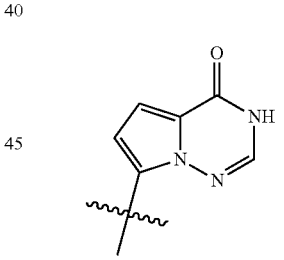

and an optionally substituted

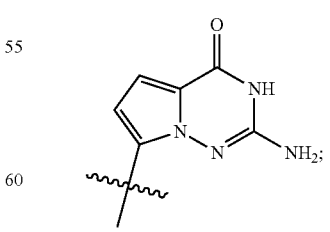

$R^1$ and $R^2$ are each independently selected from the group consisting of $O^-$, —OH, an optionally substituted —O—$C_{1-24}$ alkyl, an optionally substituted —O—$C_{2-24}$ alkenyl, an optionally substituted —O—$C_{2-24}$ alkynyl, an optionally substituted —O—$C_{3-6}$ cycloalkyl, an optionally substituted —O—$C_{3-6}$ cycloalkenyl, an optionally substituted —O-aryl, an optionally substituted —O-heteroaryl, an optionally substituted —O-aryl($C_{1-6}$ alkyl), an optionally substituted —O—$(CR^4R^5)_p$—O—$C_{1-24}$ alkyl, an optionally substituted —O—$(CR^6R^7)_q$—O—$C_{1-24}$ alkenyl,

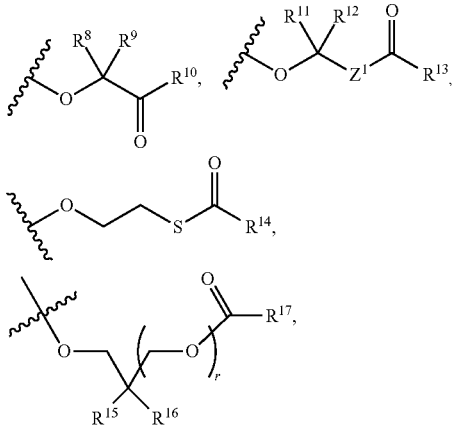

an optionally substituted N-linked amino acid and an optionally substituted N-linked amino acid ester derivative; or $R^1$ is

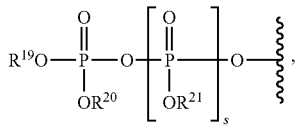

and $R^2$ is O⁻ or OH; or $R^1$ and $R^2$ are taken together to form a moiety selected from the group consisting of an optionally substituted

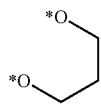

and an optionally substituted

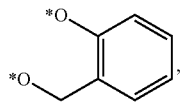

wherein the phosphorus and the moiety form a six-membered or ten-membered ring system;

$R^{3a}$ and $R^{3b}$ are each independently selected from the group consisting of hydrogen, halogen, an unsubstituted $C_{1-4}$ alkyl, an unsubstituted $C_{3-6}$ cycloalkyl, cyano, halogen($C_{1-4}$ alkyl), hydroxy($C_{1-4}$ alkyl), alkoxy($C_{1-4}$ alkyl), acyl($C_{1-4}$ alkyl) and cyano($C_{1-4}$ alkyl); or $R^{3a}$ and $R^{3b}$ are taken together with the carbon to which they are connected to form an optionally substituted $C_{3-6}$ cycloalkyl;

each $R^4$, each $R^5$, each $R^6$ and each $R^7$ are independently hydrogen, an optionally substituted $C_{1-24}$ alkyl or alkoxy;

$R^8$, $R^9$, $R^{11}$ and $R^{12}$ are each independently selected from the group consisting of hydrogen, an optionally substituted $C_{1-24}$ alkyl and an optionally substituted aryl;

$R^{10}$ and $R^{13}$ are each independently selected from the group consisting of hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl and an optionally substituted —O-monocyclic heterocyclyl;

$R^{14}$ is selected from the group consisting of hydrogen, an optionally substituted $C_{1-24}$ alkyl and an optionally substituted aryl;

$R^{15}$ and $R^{16}$ are each independently selected from the group consisting of —C≡N, an optionally substituted $C_{2-8}$ organylcarbonyl, an optionally substituted $C_{2-8}$ alkoxycarbonyl and an optionally substituted $C_{2-8}$ organylaminocarbonyl;

$R^{17}$ is selected from the group consisting of hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

$R^{19}$, $R^{20}$ and $R^{21}$ are each independently absent or hydrogen;

m is 0 or 1;

n is 1 or 2;

p and q are each independently selected from the group consisting of 1, 2 and 3;

r is 1 or 2;

s is 0 or 1;

$Z^1$ is oxygen (O) or sulfur (S).

2. The compound of claim 1, wherein $B^1$ is selected from the group consisting of: an unsubstituted

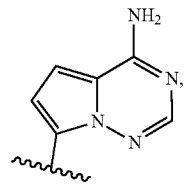 [SMILES: *c1ccc2c(N)ncnn12]

an unsubstituted

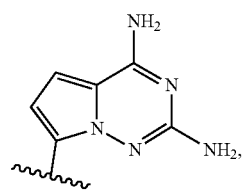 [SMILES: *c1ccc2c(N)nc(N)nn12]

an unsubstituted

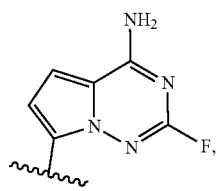 [SMILES: *c1ccc2c(N)nc(F)nn12]

an unsubstituted

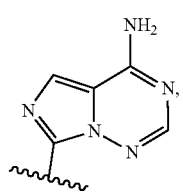 [SMILES: *c1ncc2c(N)ncnn12]

an unsubstituted

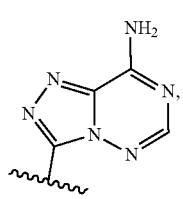 [SMILES: *c1nnc2c(N)ncnn12]

an unsubstituted

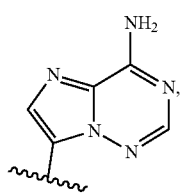 [SMILES: *c1cnc2c(N)ncnn12]

an unsubstituted

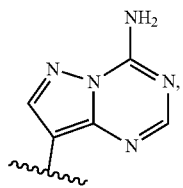 [SMILES: *c1cnn2c(N)ncnc12]

an unsubstituted

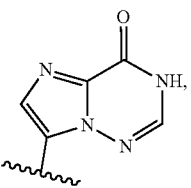 [SMILES: *c1cnc2c(=O)[nH]cnn12]

an unsubstituted

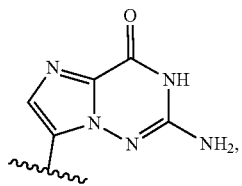 [SMILES: *c1cnc2c(=O)[nH]c(N)nn12]

an unsubstituted

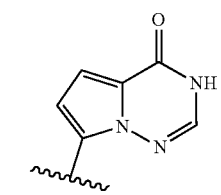 [SMILES: *c1ccc2c(=O)[nH]cnn12]

and an unsubstituted

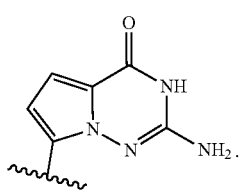 [SMILES: *c1ccc2c(=O)[nH]c(N)nn12]

3. The compound of claim 1, wherein $R^1$ and $R^2$ are each independently selected from the group consisting of $O^-$, —OH, an optionally substituted —O-aryl, an optionally substituted —O-heteroaryl, an optionally substituted N-linked amino acid and an optionally substituted N-linked amino acid ester derivative.

4. The compound of claim 1, wherein the optionally substituted N-linked amino acid ester derivative of $R^1$ and $R^2$ is independently selected from the group consisting of:

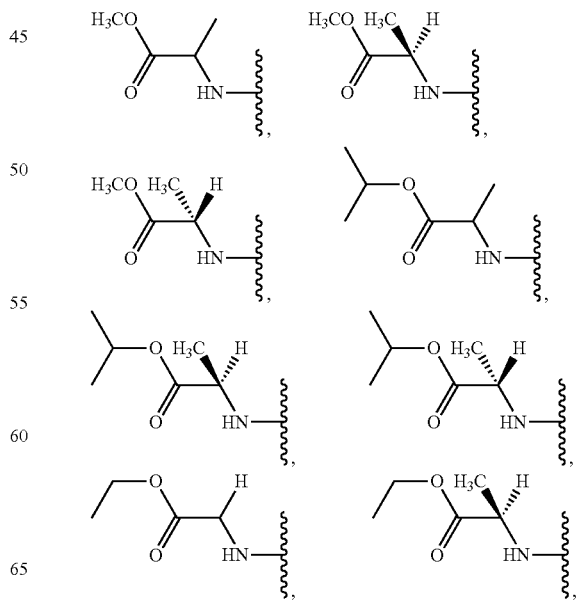

-continued

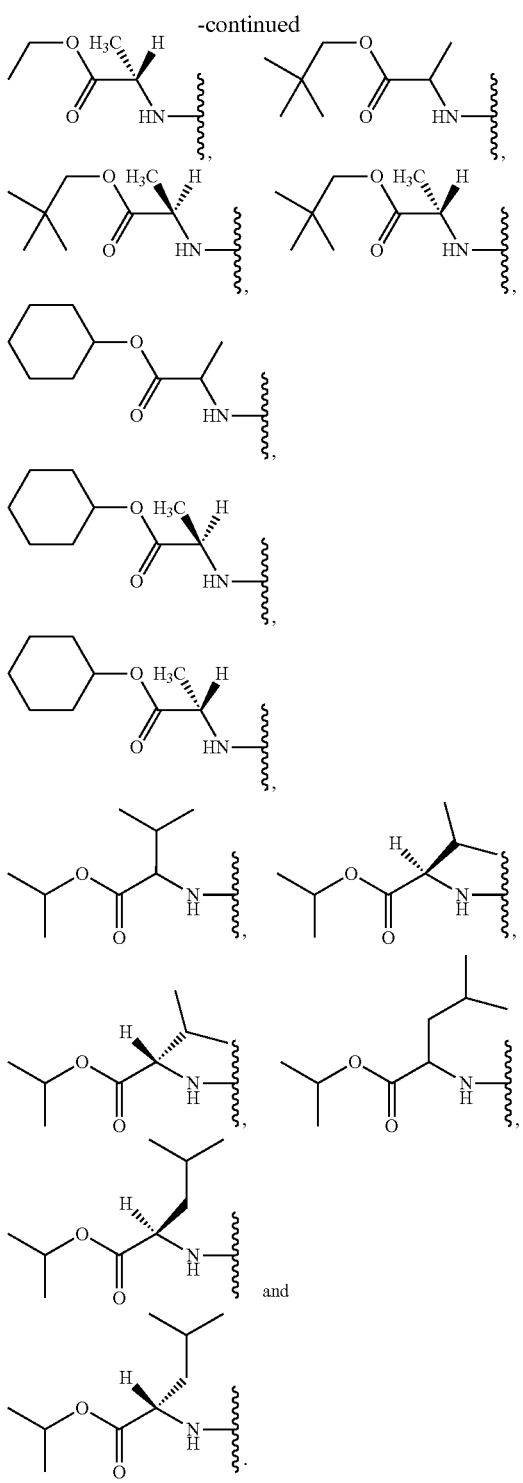

and

5. The compound of claim 1, wherein $R^{3a}$ and $R^{3b}$ are each hydrogen.

6. The compound of claim 1, wherein at least one of $R^{3a}$ and $R^{3b}$ is an unsubstituted $C_{1-4}$ alkyl.

7. The compound of claim 1, wherein one of $R^{3a}$ and $R^{3b}$ is hydrogen; and other of $R^{3a}$ and $R^{3b}$ is halogen($C_{1-4}$ alkyl).

8. The compound of claim 1, wherein one of $R^{3a}$ and $R^{3b}$ is hydrogen; and other of $R^{3a}$ and $R^{3b}$ is hydroxy($C_{1-4}$ alkyl).

9. The compound of claim 1, wherein one of $R^{3a}$ and $R^{3b}$ is hydrogen; and other of $R^{3a}$ and $R^{3b}$ is alkoxy($C_{1-4}$ alkyl).

10. The compound of claim 1, wherein $R^{3a}$ and $R^{3b}$ are each independently selected from the group consisting of hydrogen, fluoro, $CH_3$, $CH_2F$, $CHF_2$, $CH_2OH$ and $CH_2$—O—$CH_3$, or wherein $R^{3a}$ and $R^{3b}$ are taken together with the carbon to which they are connected form an optionally substituted cyclopropyl.

11. The compound of claim 1, wherein n is 1.

12. The compound of claim 1, wherein m is 1.

13. The compound of claim 1 selected from the group consisting of:

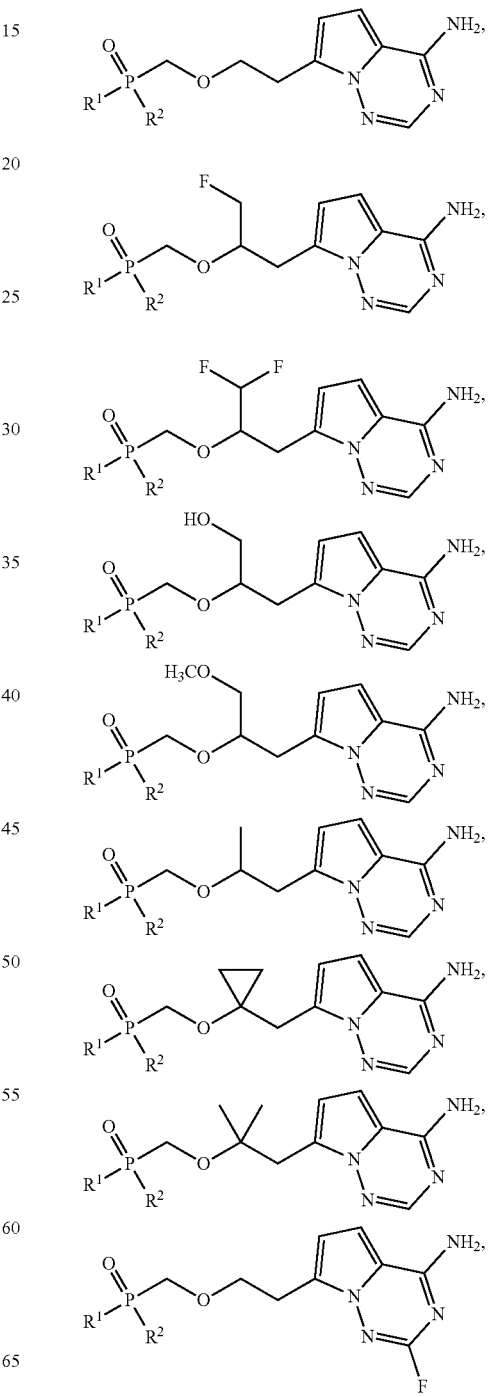

177
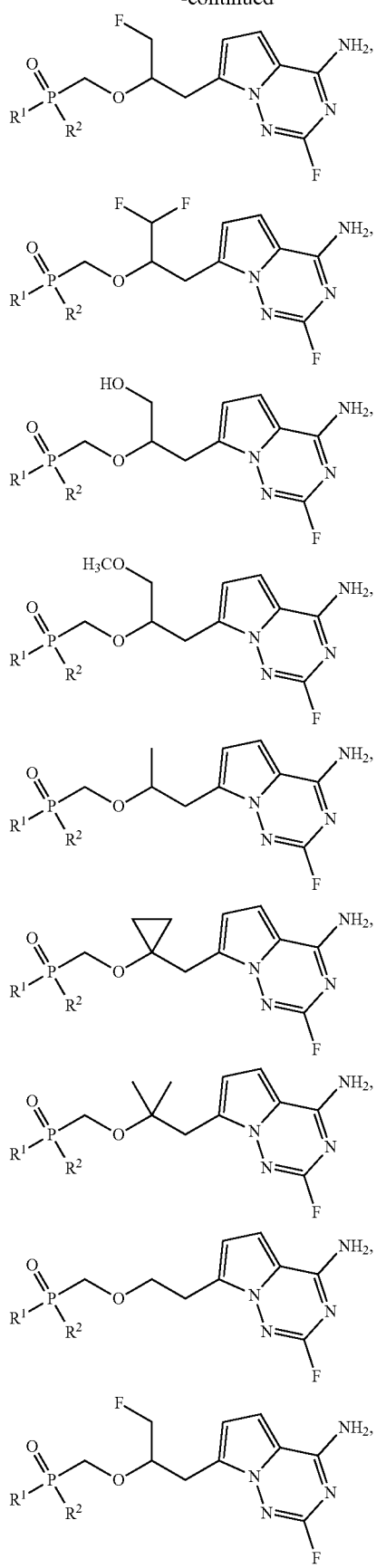
178
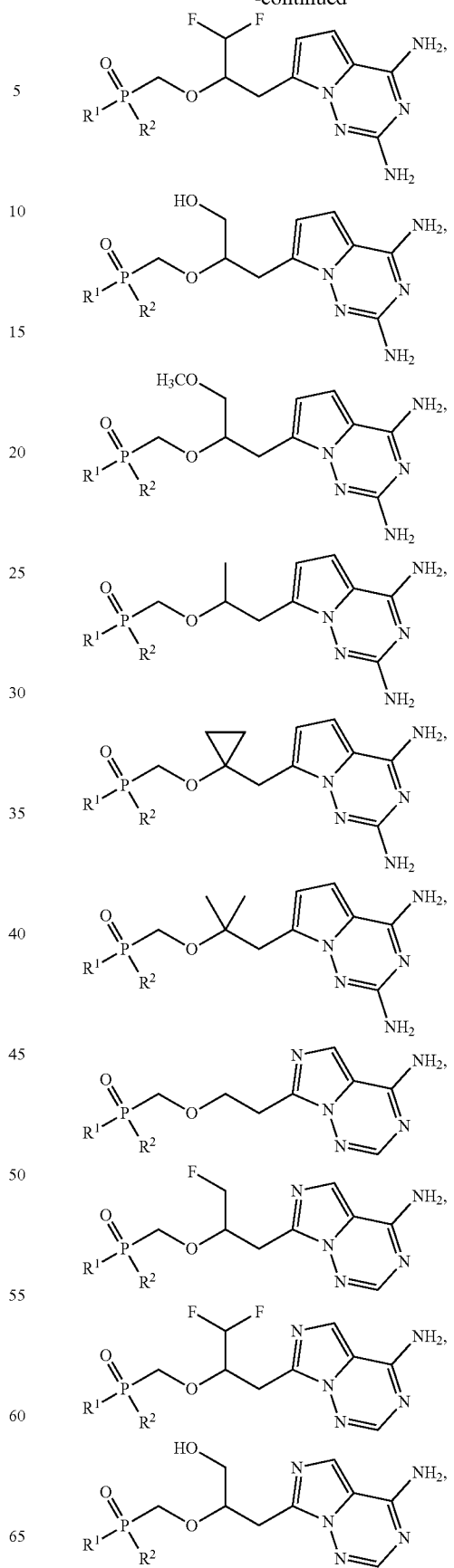

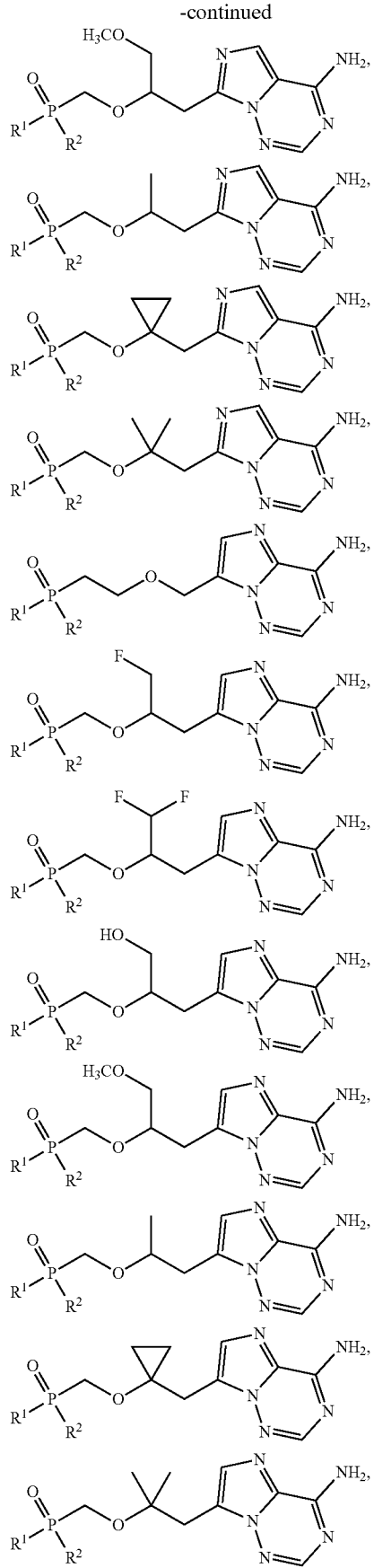
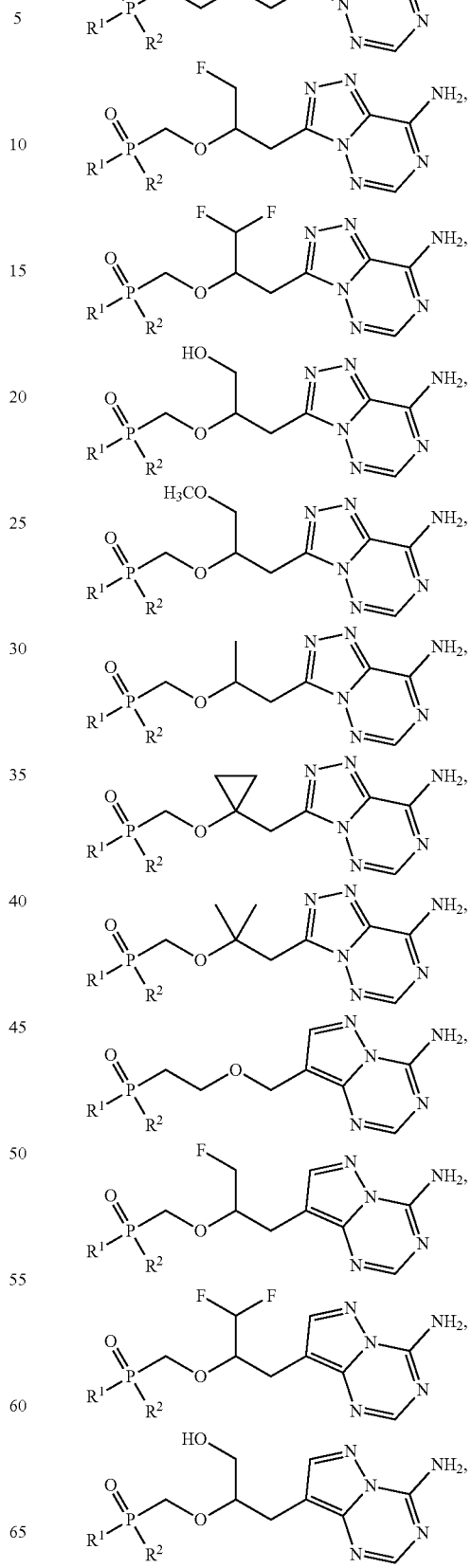

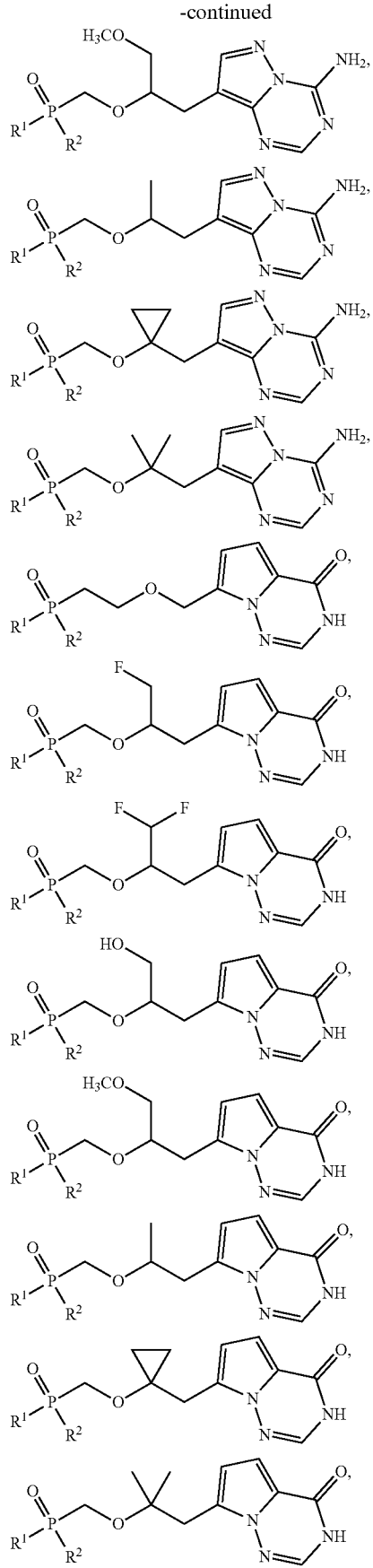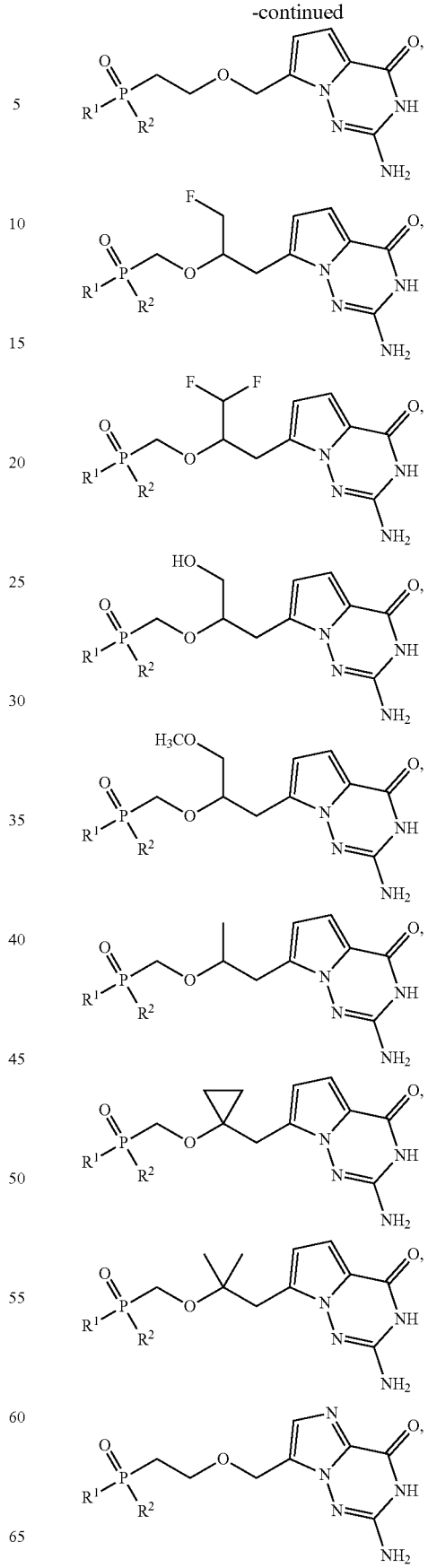

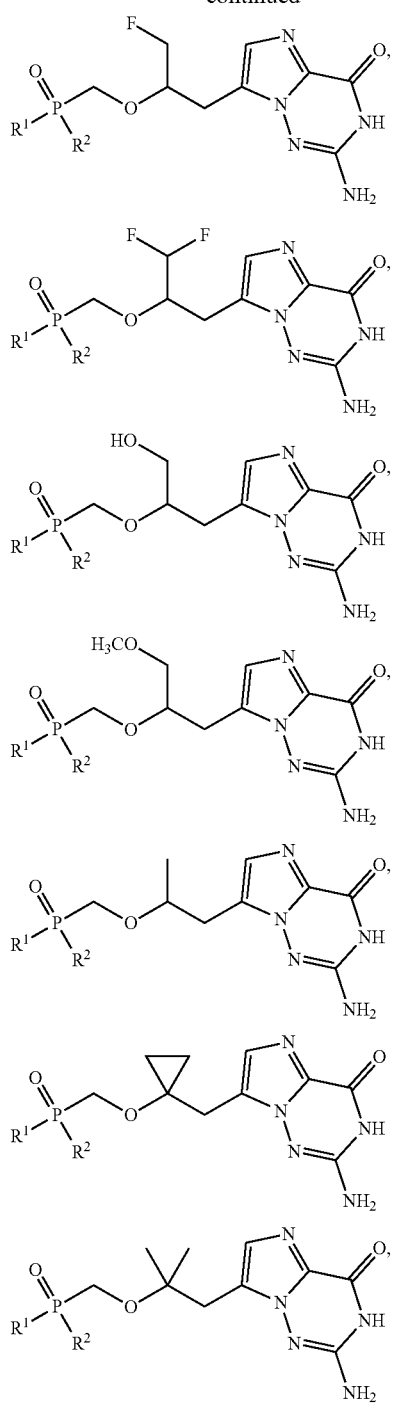
or a pharmaceutically acceptable salt of any of the foregoing.
14. A compound selected from the group consisting of:
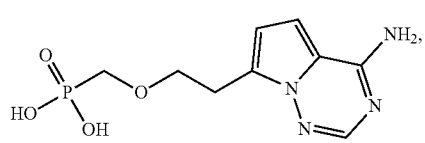
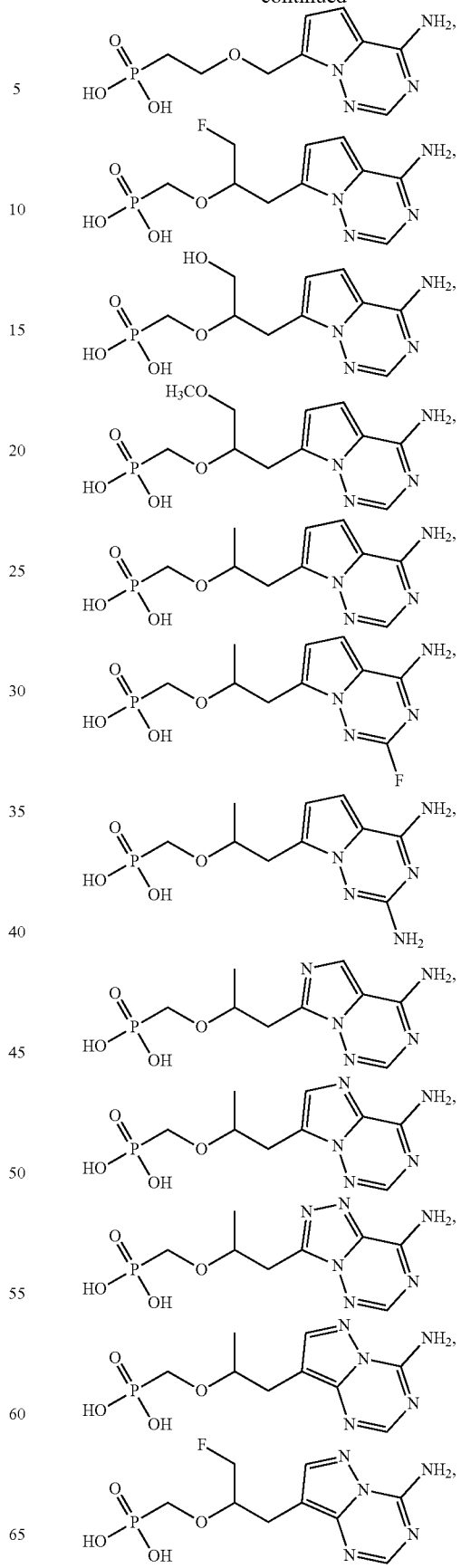

-continued
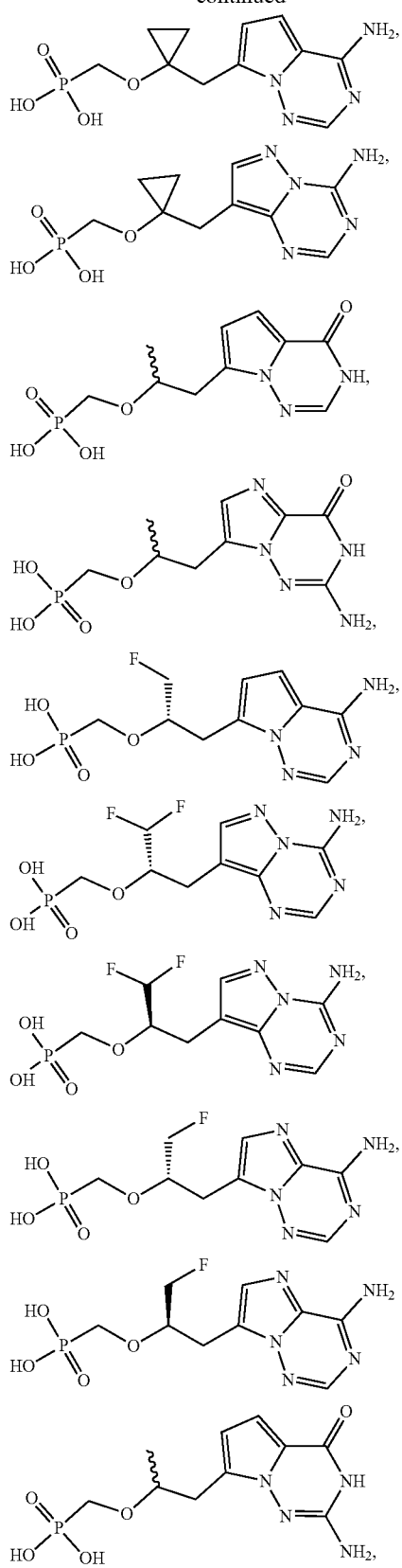
or a pharmaceutically acceptable salt of any of the foregoing.
15. The compound of claim 1 selected from the group consisting of:
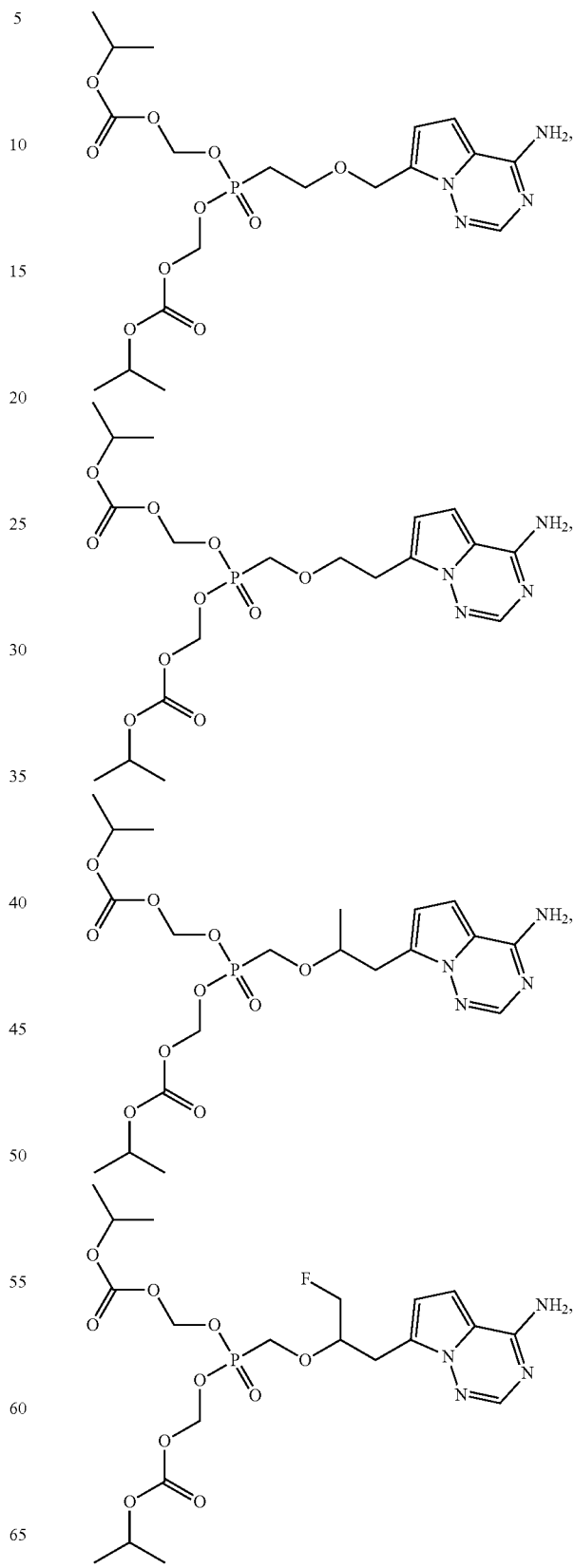

187
-continued
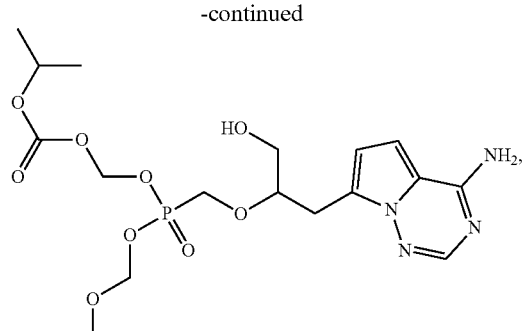
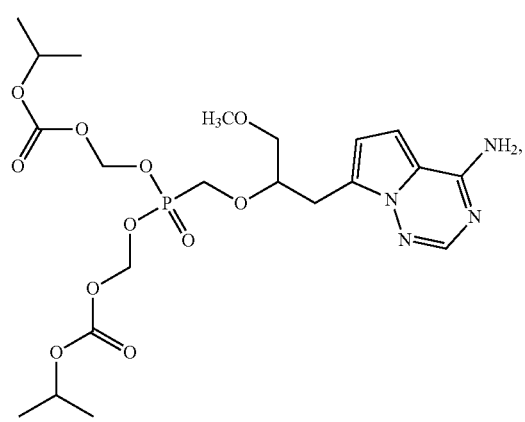
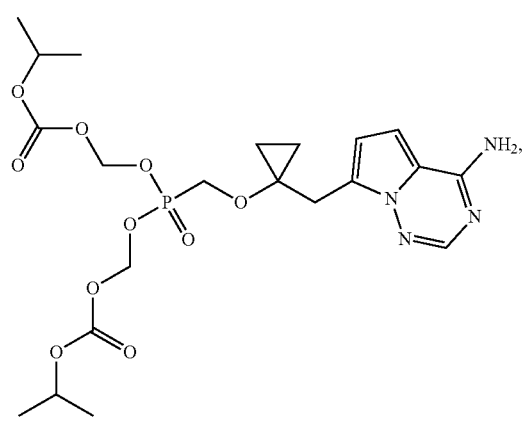
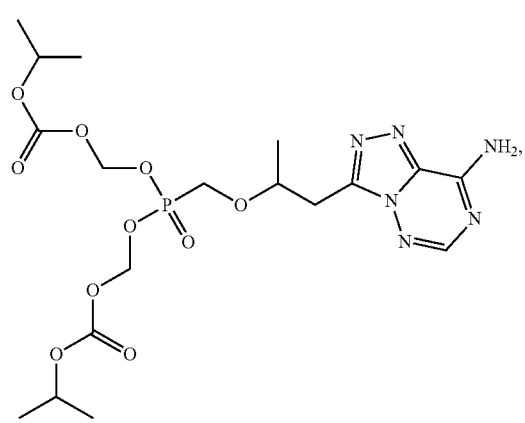
188
-continued
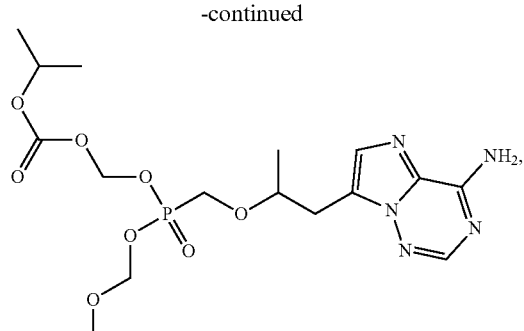
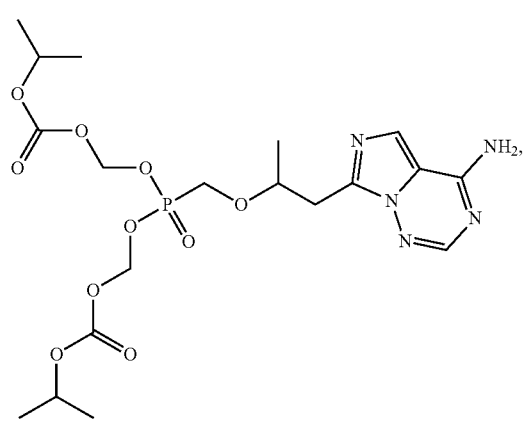
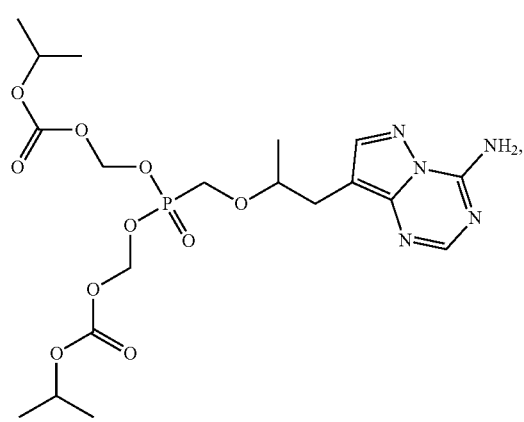
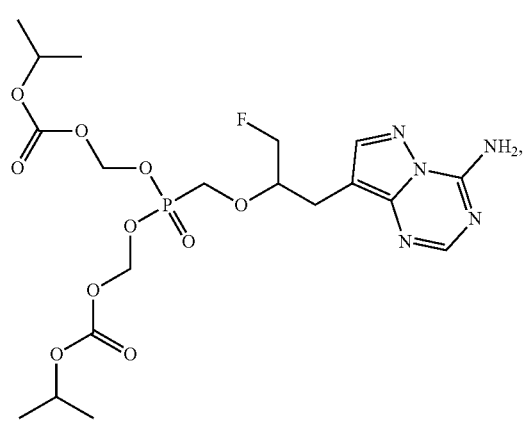

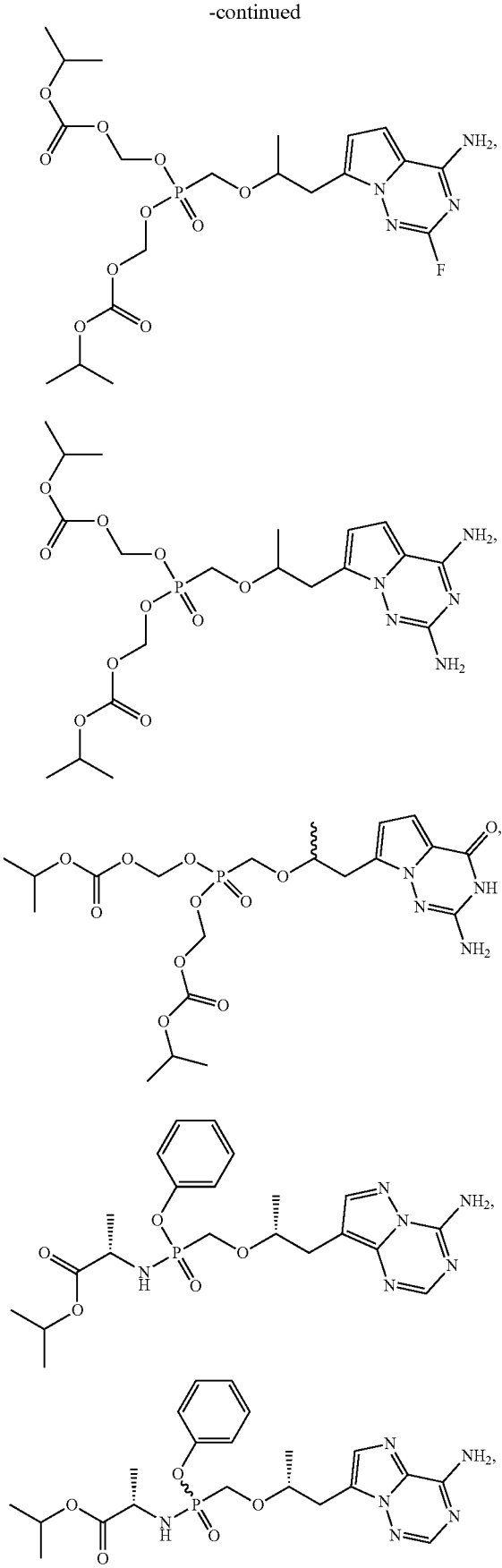

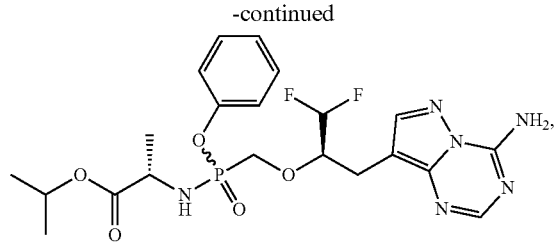
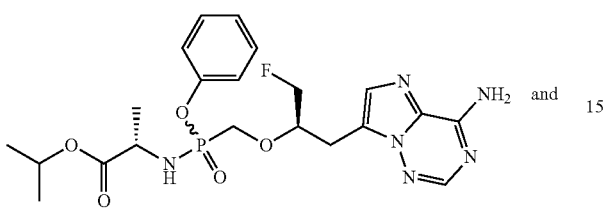 and
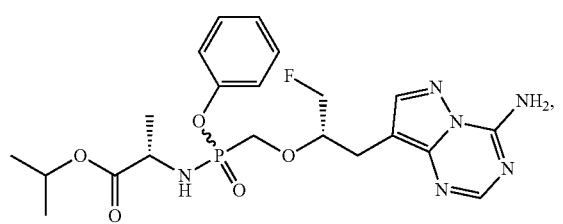
or a pharmaceutically acceptable salt of any of the foregoing.
16. The compound of claim 1 selected from the group consisting of:
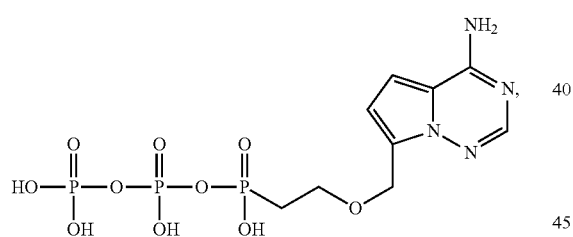
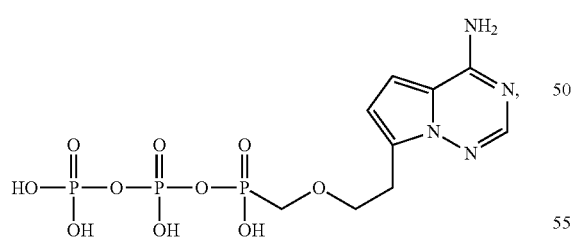
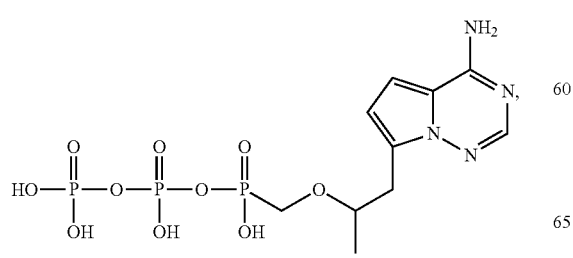
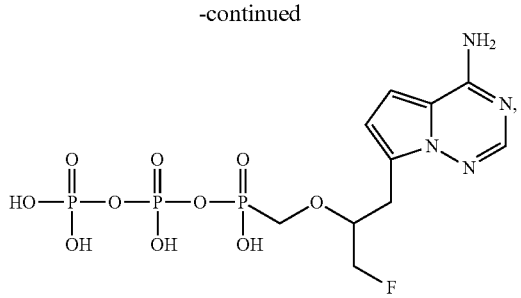
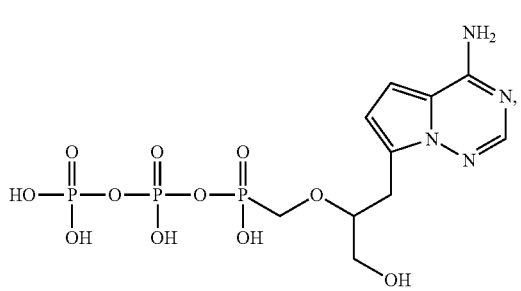
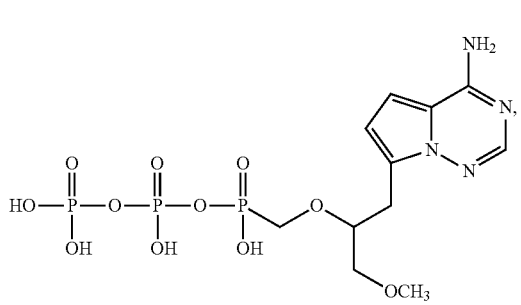
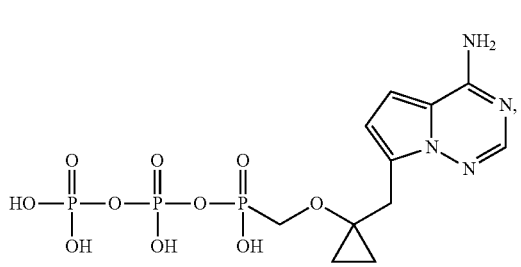
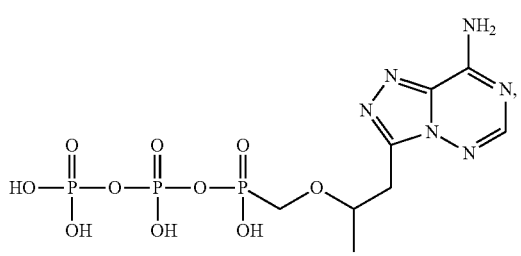
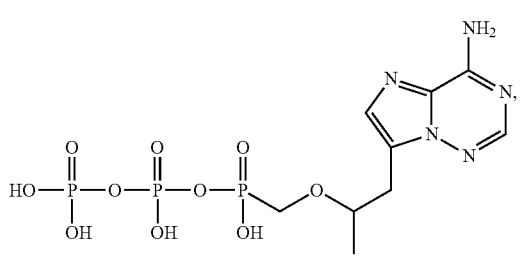

-continued
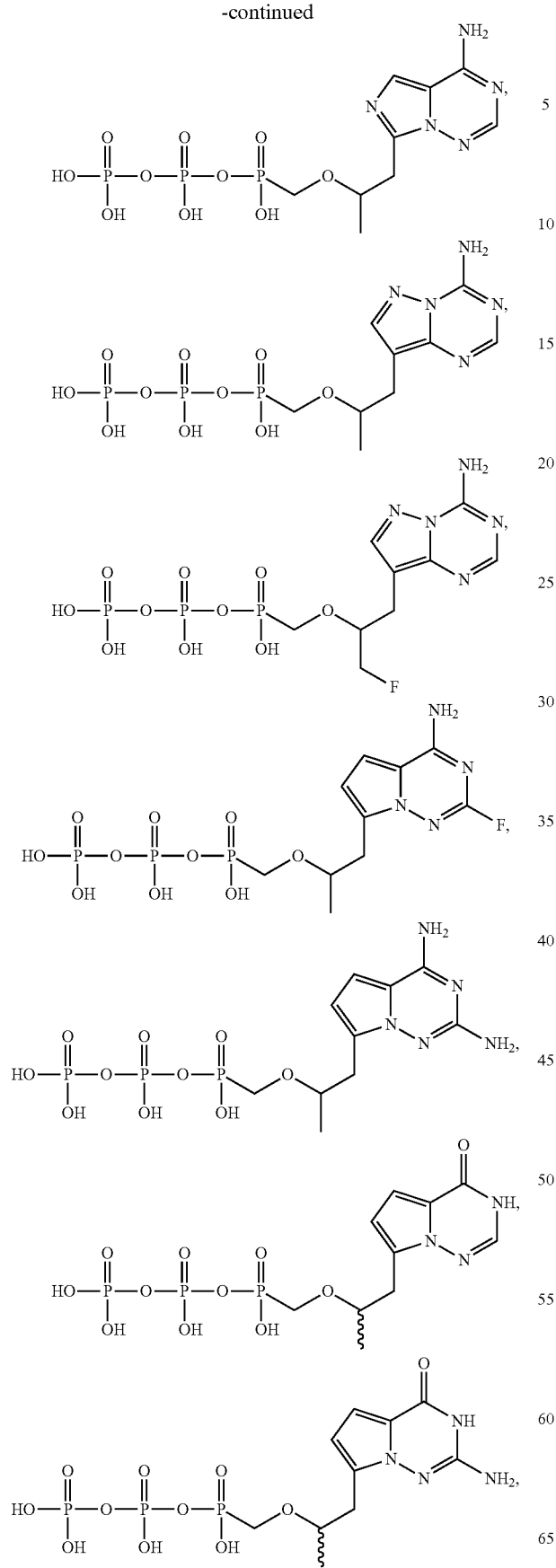
-continued
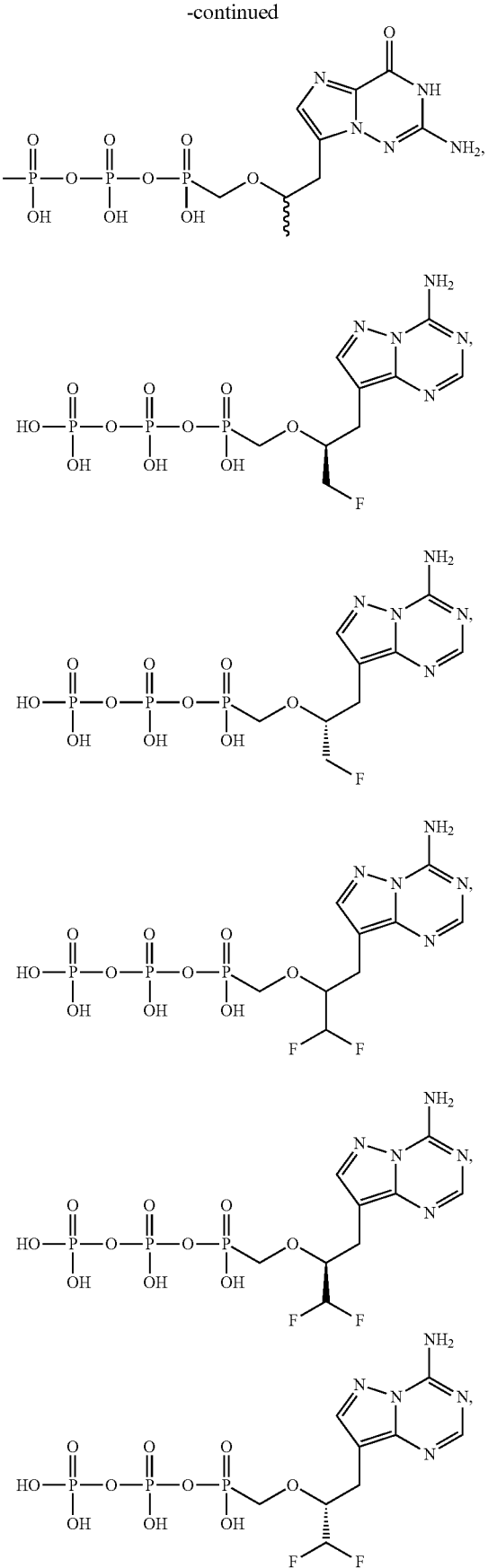

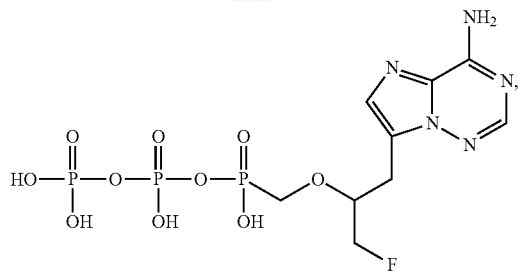

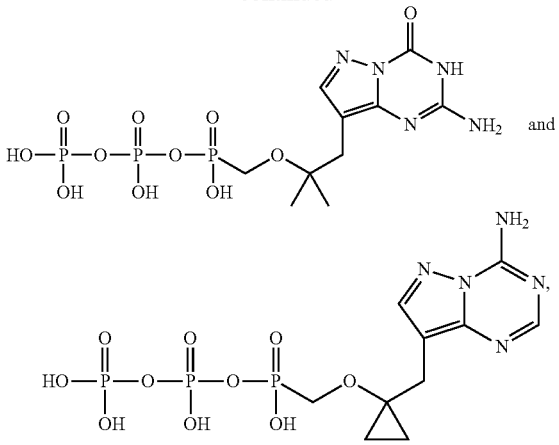

or a pharmaceutically acceptable salt of any of the foregoing.

17. A pharmaceutical composition comprising an effective amount of a compound of claim 1, or a pharmaceutically acceptable salt thereof, and a pharmaceutically acceptable carrier, diluent, excipient or combination thereof.

18. A method of ameliorating or treating an HBV and/or HDV infection, comprising administering to a subject suffering from the HBV and/or HDV infection an effective amount of a compound of claim 1, or a pharmaceutically acceptable salt thereof, or the pharmaceutical composition of claim 17.

19. A method of ameliorating or treating an HIV infection comprising administering to a subject suffering from the HIV infection an effective amount of a compound of claim 1, or a pharmaceutically acceptable salt thereof, or the pharmaceutical composition of claim 17.

* * * * *